(12) United States Patent
Ryder et al.

(10) Patent No.: US 6,218,393 B1
(45) Date of Patent: Apr. 17, 2001

(54) ANTHRANILIC ACID DERIVATIVES AS MULTI DRUG RESISTANCE MODULATORS

(75) Inventors: Hamish Ryder; Philip Anthony Ashworth; Michael Bryan Roe; Julie Elizabeth Brumwell; Sukhjit Hunjan; Adrian John Folkes; Jason Terry Sanderson; Susannah Williams; Levi Michael Maximen, all of Slough (GB)

(73) Assignee: Xenova Limited, Berkshire (GB)

( * ) Notice: Subject to any disclaimer, the term of this patent is extended or adjusted under 35 U.S.C. 154(b) by 0 days.

(21) Appl. No.: 09/284,642

(22) PCT Filed: Oct. 17, 1997

(86) PCT No.: PCT/GB97/02885

§ 371 Date: Jun. 9, 1999

§ 102(e) Date: Jun. 9, 1999

(87) PCT Pub. No.: WO98/17648

PCT Pub. Date: Apr. 30, 1998

(30) Foreign Application Priority Data

Aug. 19, 1997 (GB) .................................................. 9717576

(51) Int. Cl.$^7$ ......................... C07D 217/04; A61K 31/47
(52) U.S. Cl. ................... 514/249; 514/255.05; 514/307; 514/308; 514/311; 514/314; 544/353; 544/405; 546/146; 546/152
(58) Field of Search ..................................... 546/146, 152; 514/307, 249, 255.05, 308, 311, 314; 544/353, 405

(56) References Cited

FOREIGN PATENT DOCUMENTS

| 0 529 395 | 3/1993 | (EP) . |
|---|---|---|
| 2 286 394 | 8/1995 | (GB) . |
| WO 94 01408 | 1/1994 | (WO) . |
| WO 94 14809 | 7/1994 | (WO) . |
| WO 94 22842 | 10/1994 | (WO) . |
| WO 96 20190 | 7/1996 | (WO) . |

*Primary Examiner*—Zinna Northington Davis
(74) *Attorney, Agent, or Firm*—Nixon & Vanderhye

(57) ABSTRACT

Anthranilic acids of formula (I):

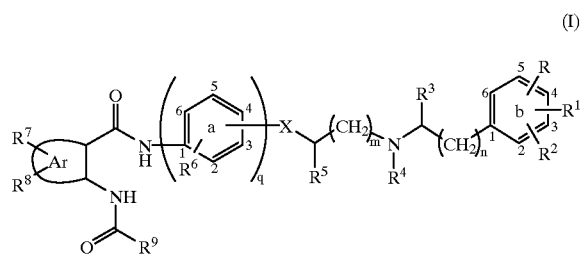

wherein each of R to $R^9$ is an organic substituent, n is 0 or 1, m is 0 or an integer of 1 to 6, q is 0 or 1, X is a direct bond, O, S, —S—$(CH_2)_p$ or —O—$(CHO_2)_p$— wherein p is from 1 to 6 and Ar is an unsaturated carbocyclic or heterocyclic group, and the pharmaceutically acceptable salts thereof, have activity as inhibitors of P-glycoprotein and may thus be used, inter alia, as modulators of multidrug resistance in the treatment of multidrug resistant cancers, for example to potentiate the cytotoxicity of a cancer drug.

23 Claims, No Drawings

ANTHRANILIC ACID DERIVATIVES AS MULTI DRUG RESISTANCE MODULATORS

This application is a 35 U.S.C. § 371 national phase entry application of PCT/GB97/02885 filed Oct. 17, 1997.

The present invention relates to compounds useful as modulators of multi-drug resistance (MDR), in particular MDR caused by over-production of P-glycoprotein (P-gp), to their preparation and to pharmaceutical and veterinary compositions containing them.

The resistance of tumours to treatment with certain cytotoxic agents is an obstacle to the successful chemotherapeutic treatment of cancer patients. A tumour may acquire resistance to a cytotoxic agent used in a previous treatment. A tumour may also manifest intrinsic resistance, or cross-resistance, to a cytotoxic agent to which it has not previously been exposed, that agent being unrelated by structure or mechanism of action to any agent used in previous treatments of the tumour.

Analogously, certain pathogens may acquire resistance to pharmaceutical agents used in previous treatments of the diseases or disorders to which those pathogens give rise. Pathogens may also manifest intrinsic resistance, or cross resistance, to pharmaceutical agents to which they have not previously been exposed. Examples of this effect include multi-drug resistant forms of malaria, tuberculosis, leishmaniasis and amoebic dysentery. These phenomena are referred to collectively as multi-drug resistance (MDR).

The most common form of MDR is caused by over-production in the cell membrane of P-gp, a protein which is able to reduce the accumulation of drugs in cells by pumping them out. This protein has been shown to be a major cause of multidrug resistance in tumour cells (Beck, W. T. *Biochem. Pharmacol*, 1987, 36,2879–2887).

In addition to cancer cells, p-glycoprotein has been found in many normal human tissues including the liver, small intestine, kidney, and blood-brain endothelium. P-gps are localised to the secretory domains of the cells in all these tissues. This localisation suggests that P-gp may play a role in limiting the absorption of foreign toxic substances across biological barriers.

Consequently, in addition to their ability to increase the sensitivity of cancer cells to cytotoxic agents, P-gp inhibitors are expected to increase the net oral absorption of certain drugs and improve the transport of drugs through the blood-brain barrier. Indeed, administration of cyclosporin, a P-gp inhibitor, has been shown to increase the intestinal absorption of acebutolol and vinblastine in rats by 2.6 and 2.2-fold respectively (Tereo, T. et al. *J. Pharm. Pharmacol*, 1996, 48, 1083–1089), while mice deficient in mdr la P-gp gene exhibit up to 100-fold increased senstivity to the centrally neurotoxic pesticide ivermectin (Schinkel, A. H. et al *Cell* 1994, 77, 491–502). Besides increased drug levels in the brain, the P-gp deficient mice were shown to have elevated drug levels in many tissues and decreased drug elimination.

Disadvantages of drugs which have so far been used to modulate MDR, termed resistance modifying agents or RMAs, are that they frequently possess a poor pharmacokinetic profile and/or are toxic at the concentrations required for MDR modulation.

It has now been found that a series of anthranilic acid derivatives have activity as inhibitors of P-gp and may therefore be used in overcoming the multi-drug resistance of tumours and pathogens. They also have potential utility in improving the absorption, distribution, metabolism and elimination characteristics of certain drugs.

The present invention therefore provides a compound which is an anthranilic acid derivative of formula (I):

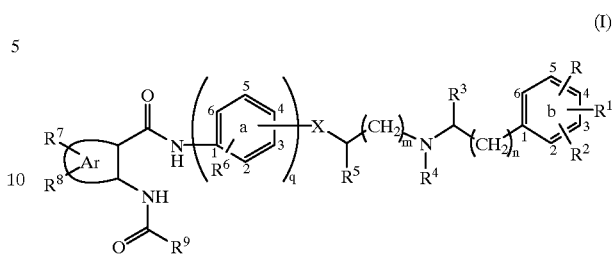

wherein
each of R, $R^1$ and $R^2$, which are the same or different, is H, $C_1$–$C_6$ alkyl, OH, $C_1$–$C_6$ alkoxy, halogen, nitro, or $N(R^{10}R^{11})$ wherein each of $R^{10}$ and $R^{11}$, which are the same or different, is H or $C_1$–$C_6$ alkyl, or $R^1$ and $R^2$, being attached to adjacent positions of ring b, together form a methylenedioxy or ethylenedioxy group;

$R^3$ is H or $C_1$–$C_6$ alkyl $R^4$ is $C_1$–$C_6$ alkyl or $R^4$ represents —$CH_2$— or —$CH_2CH_2$— which is attached either (i) to position 2 of ring b to complete a saturated 5- or 6-membered nitrogen-containing ring fused to ring b, or (ii) to the position in ring a adjacent to that to which X, being a single bond, is linked, thereby completing a saturated 5- or 6-membered nitrogen-containing ring fused to ring a;

$R^5$ is H, OH or $C_1$–$C_6$ alkyl;

X is a direct bond, O, S, —S—$(CH_2)_p$— or —O—$(CH_2)_p$— wherein p is an integer of 1 to 6;

$R^6$ is H, $C_1$–$C_6$ alkyl or $C_1$–$C_6$ alkoxy;

q is 0 or 1;

Ar is an unsaturated carbocyclic or heterocyclic group;

each of $R^7$ and $R^8$, which are the same or different, is H, $C_1$–$C_6$ alkyl which is unsubstituted or substituted, $C_1$–$C_6$ alkoxy, hydroxy, halogen, phenyl, —NHOH, nitro, a group $N(R^{10}R^{11})$ as defined above or a group $SR^{12}$ wherein $R^{12}$ is H or $C_1$–$C_6$ alkyl or $R^7$ and $R^8$, when situated on adjacent carbon atoms, form together with the carbon atoms to which they are attached a benzene ring or a methylenedioxy substituent;

$R^9$ is phenyl or an unsaturated heterocyclic group, either of which is unsubstituted or substituted by $C_1$–$C_6$ alkyl, OH, $C_1$–$C_6$ alkoxy, halogen, $C_3$–$C_6$ cycloalkyl, phenyl, benzyl, trifluoromethyl, nitro, acetyl, benzoyl or $N(R^{10}R^{11})$ as defined above, or two substituents on adjacent ring positions of the said phenyl or heterocyclic group together complete a saturated or unsaturated 6-membered ring, or form a methylenedioxy group;

n is 0 or 1; and m is 0 or an integer of 1 to 6;

or a pharmaceutically acceptable salt thereof.

The group X is linked to any one of the positions 2 to 6 in ring a which are not occupied by $R^6$. Preferably it is linked to position 3 or 4. In a preferred series of compounds $R^6$ is at position 2 and X is at position 3 or 4 in ring a. When X is at position 3 or 4 in ring a $R^6$ may alternatively occupy position 5. Owing to the free rotation of ring a, position 6 is equivalent to position 2.

The value of m is preferably 0 or an integer of 1 to 3, more preferably 1 or 2. The value of q is preferably 1.

A $C_1$–$C_6$ alkyl group may be linear or branched. A $C_1$–$C_6$ alkyl group is typically a $C_1$–$C_4$ alkyl group, for example a methyl, ethyl, propyl, i-propyl, n-butyl, sec-butyl or tert-butyl group. A halogen is F, Cl, Br or I. Preferably it is F, Cl or Br. A $C_1$–$C_6$ alkyl group which is substituted is typically substituted by one or more halogen atoms, for instance by 1, 2 or 3 halogen atoms. It may be a perhaloalkyl group, for instance trifluoromethyl.

A $C_1$–$C_6$ alkoxy group may be linear or branched. It is typically a $C_1$–$C_4$ alkoxy group, for example a methoxy, ethoxy, propoxy, i-propoxy, n-propoxy, n-butoxy, sec-butoxy or tert-butoxy group. The integer m is from 1 to 6 and is typically 1, 2 or 3.

An unsaturated carbocyclic group is typically a $C_5$–$C_{10}$ carbocyclic group which contains at least one unsaturated bond, for instance a $C_6$–$C_{10}$ aryl group such as a phenyl or naphthyl group. An unsaturated heterocyclic group is typically a 5 or 6-membered heterocyclic ring with at least one unsaturated bond, which contains one or more heteroatoms selected from N, S and O and which is optionally fused to a benzene ring or to a second such 5 or 6-membered heterocyclic ring.

An unsaturated heterocyclic group may be, for example, a furan, thiophene, pyrrole, indole, isoindole, pyrazole, imidazole, isoxazole, oxazole, isothiazole, thiazole, pyridine, quinoline, quinoxaline, isoquinoline, thienopyrazine, pyran, pyrimidine, pyridazine, pyrazine, purine or triazine group. The aforesaid heterocyclic ring may be unsubstituted or substituted by one or more substituents, for instance one or more substituents selected from OH, halogen, $C_1$–$C_6$ alkyl which is unsubstituted or substituted, for example by halogen, such as $CF_3$, $C_1$–$C_6$ alkoxy, nitro and an amino group $N(R^{10}R^{11})$ as defined above.

Preferably the heterocyclic group represented by $R^9$ includes at least one nitrogen atom and the heterocyclic group represented by Ar includes at least one nitrogen or sulphur atom.

In a preferred series of compounds n is 0 and $R^4$ represents —$CH_2CH_2$— which is attached to position 2 or 6 of ring b to complete, with ring b, a tetrahydroisoquinoline group. Alternatively, n is 1 and $R^4$ is —$CH_2$— which is attached to position 2 or 6 of ring b to complete, with ring b, a tetrahydroisoquinoline group.

In another preferred series of compounds m is 1, X is a single bond attached to position 3 or 4 of ring a and $R^4$ represents —$CH_2$— which is attached to a ring position adjacent to position 3 or 4, respectively, of ring a to complete with ring a a tetrahydroisoquinoline group. Alternatively m is 0, X is a single bond attached to position 3 or 4 of ring a and $R^4$ is —$CH_2CH_2$— which is attached to a ring position adjacent to position 3 or 4, respectively, of ring a to complete with ring a a tetrahydroisoquinoline group.

The moiety Ar is preferably a benzene, naphthalene, thiophene, thienopyrazine, pyridine, pyrazine, indole or furan ring.

The group $R^9$ is preferably a quinoline, isoquinoline, quinoxaline, pyridine, pyrazine, oxazole, isoxazole, thiazole or isothiazole group. More preferably $R^9$ is a quinolin-3-yl, quinoxalin-2-yl, pyrazin-2-yl, pyridin-2-yl, pyridin-3-yl, oxazol-4-yl or thiazol-4-yl group.

R, $R^1$ and $R^2$ are preferably independently selected from H, OH, $C_1$–$C_6$ alkoxy and nitro, or R is H and $R^1$ and $R^2$, being attached to positions 2 and 3, 3 and 4, 4 and 5 or 5 and 6 of ring b, together form a methylenedioxy or ethylenedioxy group.

In a preferred aspect, the anthranilic acid of the invention has the following formula (Ia):

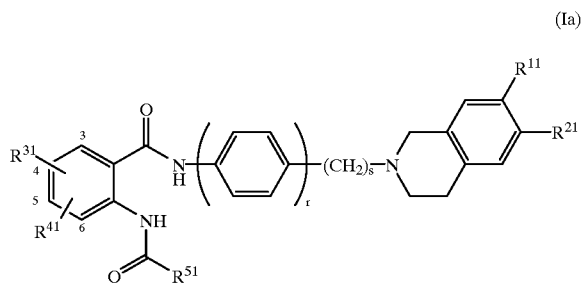

wherein $R^{11}$ and $R^{21}$, which may be the same or different, are each hydrogen or methoxy;

$R^{31}$ and $R^{41}$, which may be the same or different, are each independently selected from H, $CH_3$, $CF_3$, F, Cl, Br, $NH_2$, $NO_2$, NHOH, methoxy, hydroxy and phenyl; or $R^{31}$ and $R^{41}$, when situated on adjacent carbon atoms, form together with the carbon atoms to which they are attached a benzene ring or a methylenedioxy substituent, $R^{51}$ is 2-furanyl, 3-furanyl, 2-thiophene, 3-thiophene, 2-indolyl or 2-benzofuranyl or a ring of one of the following formulae (II'), (III') or (IV'):

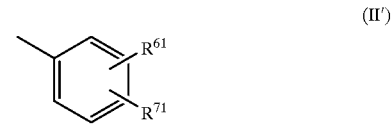

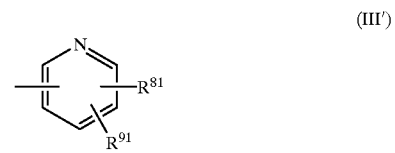

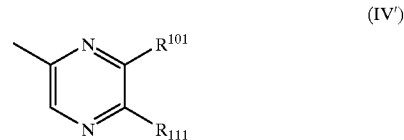

wherein $R^{61}$ and $R^{71}$, which may be the same or different, are selected from hydrogen, $C_1$–$C_6$ alkyl which is linear or branched, $C_3$–$C_6$ cycloalkyl, phenyl, benzyl, trifluoromethyl, F, Cl, Br, $OR^{12}$, $NO_2$, dimethylamino, diethylamino, acetyl and benzoyl, or $R^{61}$ and $R^{71}$ when situated on adjacent carbon atoms, form together with the carbon atoms to which they are attached a benzene ring or a methylenedioxy substituent;

$R^{81}$ and $R^{91}$, which may be the same or different are each hydrogen, methyl or methoxy, or $R^{81}$ and $R^{91}$, when situated on adjacent carbons, form together with the pyridine ring to which they are attached a quinoline or 5,6,7,8-tetrahydroquinoline ring system; $R^{101}$ and $R^{111}$, which may be the same or different, are each hydrogen, methyl or propionyl; or $R^{101}$ and $R^{111}$, when on adjacent carbon atoms, form together with the carbon atoms to which they are attached a benzene ring, $R^{121}$ is H, $C_1$–$C_6$ alkyl, or $C_3$–$C_6$ cycloalkyl, phenyl, benzyl or acetyl;

r is 0 or 1, and s is 1, 2 or 3;

or a pharmaceutically acceptable salt thereof.

The integer s is from 1 to 3, and is preferably 1 or 2. In a preferred series of compounds of formula (Ia) r is 1, s is 2, $R^{11}$ and $R^{21}$ are both methoxy and $R^{51}$ is a 2-quinoxaline group, a 3-quinoline group, a 2-pyrazine group or a 3-pyridine group, all of which groups may be unsubstituted or substituted.

In another aspect, the anthranilic acid of the invention has the following structure (A)

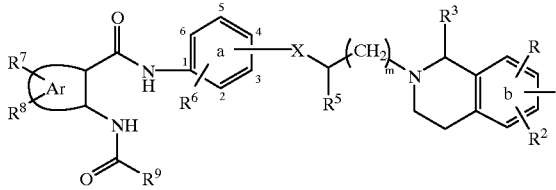

(A)

wherein (a) each of R, $R^1$ and $R^2$, which are the same or different, is H, OH, $NO_2$, $N(R^{10}R^{11})$, halogen or $C_2$–$C_6$ alkoxy, or R is H and $R^1$ and $R^2$ form, together with the carbon atoms to which they are attached, a methylenedioxy or ethylenedioxy group, provided R, $R^1$ and $R^2$ are not all H; and each of $R^3$, $R^5$, $R^6$, $R^7$, $R^8$, $R^9$, Ar, X and m is as defined for formula (I) above; or (b) each of R, $R^1$ and $R^2$, which are the same or different, is H or OMe and each of $R^3$, $R^5$, $R^6$, $R^7$, $R^8$, $R^9$, Ar, X and m is as defined above.

In another aspect the anthranilic acid of the invention has the following structure (B):

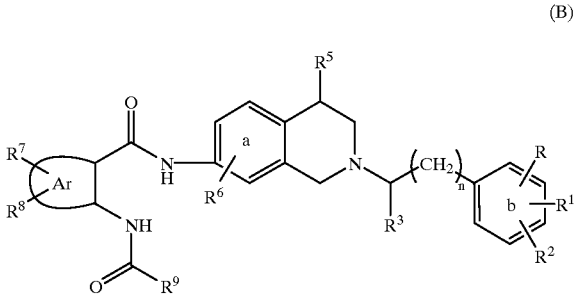

(B)

wherein R, $R^1$ to $R^3$, $R^5$ to $R^9$, Ar and n are as defined above for formula (I)

In a further aspect, the anthranilic acid of the invention has the following structure (C):

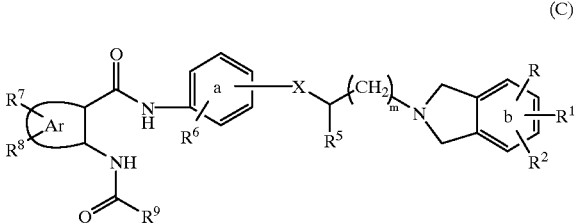

(C)

wherein R, $R^1$ to $R^3$, $R^5$ to $R^9$, Ar, X and m are as defined above for formula (I).

In a further aspect, the anthranilic acid of the invention has the following structure (D):

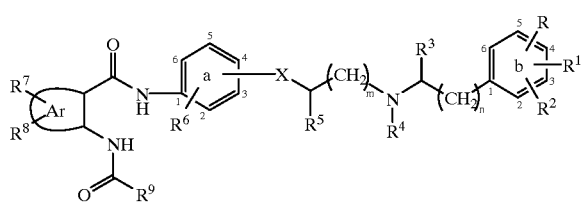

(D)

wherein R, $R^1$ to $R^9$, Ar, m and n are as defined above for formula (I) and X, which is at position 3 or 4 in ring a, is as defined above for formula (I).

In a preferred series of compounds of formula (I), $R^4$ is $C_1$–$C_6$ alkyl. Preferably R, $R^1$ and $R^2$ are each H, OH or methoxy.

In ring a, $R^6$ is linked to any one of positions 2 to 6. Typically $R^6$ is linked to position 2 in ring a.

Examples of preferred compounds of the invention are as follows.

| Chemical Name | Compound No. |
|---|---|
| 2-Chloro-quinoline-3-carboxylic acid (2-{4-[2-(6,7-dimethoxy-3,4-dihydro-1H-isoquinolin-2-yl)-ethyl]-phenylcarbamoyl}-phenyl)-amide | 9591 |
| 4-Hydroxy-7-trifluoromethyl-quinoline-3-carboxylic acid (2-{4-[2-(6,7-dimethoxy-3,4-dihydro-1H-isoquinolin-2-yl)-ethyl]-phenylcarbamoyl}-phenyl)-amide | 9592 |
| Quinoline-3-carboxylic acid (2-{4-[2-(6,7-dimethoxy-3,4-dihydro-1H-isoquinolin-2-yl)-ethyl]-phenylcarbamoyl}-thiophen-3-yl)-amide | 9594 |
| Quinoline-3-carboxylic acid (2-{4-[2-(6,7-dimethoxy-3,4-dihydro-1H-isoquinolin-2-yl)-ethyl]-phenylcarbamoyl}-4-dimethylamino-phenyl)-amide | 9595 |
| Quinoxaline-2-carboxylic acid (2-{4-[2-(6,7-dimethoxy-3,4-dihydro-1H-isoquinolin-2-yl)-ethyl]-phenylcarbamoyl}-4-dimethylamino-phenyl)-amide | 9596 |
| Quinoxaline-2-carboxylic acid (2-{4-[2-(6,7-dimethoxy-3,4-dihydro-1H-isoquinolin-2-yl)-ethyl]-phenylcarbamoyl}-thiophen-3-yl)-amide | 9597 |
| Quinoxaline-2-carboxylic acid (3-{4-[2-(6,7-dimethoxy-3,4-dihydro-1H-isoquinolin-2-yl)-ethyl]-phenylcarbamoyl}-pyridin-2-yl)-amide | 9600 |
| 4-Hydroxy-quinoline-3-carboxylic acid (2-{4-[2-(6,7-dimethoxy-3,4-dihydro-1H-isoquinolin-2-yl)-ethyl]-phenylcarbamoyl}-phenyl)-amide | 9606 |
| Quinoxaline-2-carboxylic acid (3-{4-[2-(6,7-dimethoxy-3,4-dihydro-1H-isoquinolin-2-yl)-ethyl]-phenylcarbamoyl}-4-methyl-thiophen-2-yl)-amide | 9608 |
| Quinoline-3-carboxylic acid (3-{4-[2-(6,7-dimethoxy-3,4-dihydro-1H-isoquinolin-2-yl)-ethyl]-phenylcarbamoyl}-4-methyl-thiophen-2-yl)-amide | 9609 |
| Quinoxaline-2-carboxylic acid [2-(4-{2-[(3,4-dimethoxy-benzyl)-methyl-amino]-ethyl}-phenylcarbamoyl)-phenyl]-amide | 9612 |
| Quinoline-3-carboxylic acid [2-(4-{2-[(3,4-dimethoxy-benzyl)-methyl-amino]-ethyl}-phenylcarbamoyl)-phenyl]-amide | 9613 |
| Quinoxaline-2-carboxylic acid {2-[2-(3,4-dimethoxy-benzyl)-1,2,3,4-tetrahydro-isoquinolin-7-ylcarbamoyl]-phenyl}-amide | 9614 |
| Quinoline-3-carboxylic acid (2-{4-[2-(6,7-dimethoxy-3,4-dihydro-1H-isoquinolin-2-yl)-ethyl]-phenylcarbamoyl}-4-methylsulfanyl-phenyl)-amide | 9615 |

| Chemical Name | Compound No. |
|---|---|
| Quinoline-3-carboxylic acid (4-{4-[2-(6,7-dimethoxy-3,4-dihydro-1H-isoquinolin-2-yl)-ethyl]-phenylcarbamoyl}-thiophen-3-yl)-amide | 9616 |
| N-(4-{4-[2-(6,7-Dimethoxy-3,4-dihydro-1H isoquinolin-2-yl)-ethyl]-phenylcarbamoyl}-thiophen-3-yl)-6-methyl-nicotinamide | 9617 |
| Quinoline-3-carboxylic acid (2-{4-[2-(6,7-dimethoxy-3,4-dihydro-1H-isoquinolin-2-yl)-ethylsulfanyl]-phenylcarbamoyl}-phenyl)-amide | 9621 |
| Quinoline-3-carboxylic acid (3-{4-[2-(6,7-dimethoxy-3,4-dihydro-1H-isoquinolin-2-yl)-ethyl]-phenylcarbamoyl}-pyrazin-2-yl)-amide | 9622 |
| Quinoline-3-carboxylic acid (2-{4-[2-(6,7-dimethoxy-3,4-dihydro-1H-isoquinolin-2-yl)-ethoxy]-phenylcarbamoyl}-phenyl)-amide | 9623 |
| Quinoline-3-carboxylic acid (2-{4-[2-(6,7-dimethoxy-1-methyl-3,4-dihydro-1H-isoquinolin 2-yl)-ethyl]-phenylcarbamoyl}-phenyl)-amide | 9625 |
| Quinoline-3-carboxylic acid (2-{4-[2-(1,3-dihydro-isoindol-2-yl)-ethyl]-phenylcarbamoyl}-phenyl)-amide | 9626 |
| Quinoline-3-carboxylic acid (2-{4-[2-(6,7-dichloro-3,4-dihydro-1H-isoquinolin-2-yl)-ethyl]-phenylcarbamoyl}-phenyl)-amide | 9628 |
| Quinoline-3-carboxylic acid (2-{4-[2-(7,8-dichloro-3,4-dihydro-1H-isoquinolin-2-yl)-ethyl]-phenylcarbamoyl}-phenyl)-amide | 9629 |
| Quinoline-3-carboxylic acid {2-[4-(2-{[2-(3,4-dimethoxy-phenyl)-ethyl]-methyl-amino}-ethyl)-phenylcarbamoyl]-phenyl}-amide | 9630 |
| Quinoline-3-carboxylic acid [2-(4-{2-[(3,4-dimethyl-benzyl)-methyl-amino]-ethyl}-phenylcarbatnoyl)-phenyl]-amide | 9631 |
| Quinoxaline-2-carboxylic acid (2-{4-[2-(6,7-dimethoxy-3,4-dihydro-1H-isoquinolin-2-yl)-ethoxy]-phenylcarbamoyl}-phenyl)-amide | 9632 |
| Quinoline-3-carboxylic acid (2-{3-[2-(6,7-dimethoxy-3,4-dihydro-1H-isoquinolin-2-yl)-ethyl]-phenylcarbamoyl}-phenyl)-amide | 9633 |
| Quinoline-3-carboxylic acid (2-{4-[2-(7-nitro-3,4-dihydro-1H-isoquinolin-2-yl)-ethyl]-phenylcarbamoyl}-phenyl)-amide | 9634 |
| 2-Methyl-thiazole-4-carboxylic acid (2-{4-[2-(6,7-dimethoxy-3,4-dihydro-1H-isoquinolin-2-yl)-ethyl]-phenylcarbamoyl}-phenyl)-amide | 9635 |
| Quinoline-3-carboxylic acid [2-(4-{2-[(3,4-dimethoxy-benzyl)-ethyl-amino]-ethyl}-phenylcarbamoyl)-phenyl]-amide | 9636 |
| 2-Methyl-oxazole-4-carboxylic acid (2-{4-[2-(6,7-dimethoxy-3,4-dihydro-1H-isoquinolin-2-yl)-ethyl]-phenylcarbamoyl}-phenyl)-amide | 9638 |
| Quinoline-3-carboxylic acid [2-(4-{2-[(3-isopropoxy-4-methoxy-benzyl)-methyl-amino]-ethyl}-phenylcarbamoyl)-phenyl]-amide | 9639 |
| Quinoline-3-carboxylic acid [2-(4-{2-[methyl-(3,4,5-trimethoxy-benzyl)-amino]-ethyl}-phenylcarbamoyl)-phenyl]-amide | 9640 |
| Quinoline-3-carboxylic acid [2-(4-{2-[butyl-(3,4-dimethoxy-benzyl)-amino]-ethyl}-phenylcarbamoyl)-phenyl]-amide | 9641 |
| Quinoline-3-carboxylic acid [2-(4-{2-[(4-butoxy-3-methoxy-benzyl)-methyl-amino]-ethyl}-phenylcarbamoyl)-phenyl]-amide | 9642 |
| Quinoline-3-carboxylic acid [2-(4-{2-[(3,4-difluoro-benzyl)-methyl-amino]-ethyl}-phenylcarbamoyl)-phenyl]-amide | 9643 |
| Quinoline-3-carboxylic acid [2-(4-{2-[(2,3-dihydro-benzo [1,4]dioxin-6-ylmethyl)-methyl-amino]-ethyl}-phenylcarbamoyl)-phenyl]-amide | 9645 |
| Quinoline-3-carboxylic acid [2-(4-{2-[(4-isopropoxy-3-methoxy-benzyl)-methyl-amino]-ethyl}-phenylcarbamoyl)-phenyl]-amide | 9646 |
| Quinoline-3-carboxylic acid [2-(4-{2-[(3-hydroxy-4-methoxy-benzyl)-methyl-amino]-ethyl}-phenylcarbamoyl)-phenyl]-amide | 9647 |
| Quinoline-3-carboxylic acid (2-{4-[3-(6,7-dimethoxy-3,4-dihydro-1H-isoquinolin-2-yl)-2-hydroxy-propoxy]-phenylcarbamoyl}-phenyl)-amide | 9648 |
| Quinoline-3-carboxylic acid [2-(4-{2-[(4-hydroxy-3-methoxy-benzyl)-methyl-amino]-ethyl} phenylcarbamoyl)-phenyl]-amide | 9649 |
| Quinoline-3-carboxylic acid (2-{4-[2-(6,7-dimethoxy-3,4-dihydro-1H-isoquinolin-2-yl)-ethyl]-2-methyl-phenylcarbamoyl}-phenyl)-amide | 9650 |
| Quinoline-3-carboxylic acid (2-{4-[2-(6,7-dimethoxy-3,4-dihydro-1H-isoquinolin-2-yl)-ethyl]-2-methoxy-phenylcarbamoyl}-phenyl)-amide | 9651 |
| Quinoline-3-carboxylic acid [2-(4-{[(3-isopropoxy-4-methoxy-benzyl)-methyl-amino]-methyl}-phenylcarbamoyl)-phenyl]-amide | 9652 |
| 5-Methyl-pyrazine-2-carboxylic acid (2-{3-[2-(6,7-dimethoxy-3,4-dihydro-1H-isoquinolin-2-yl)-ethyl]-phenylcarbamoyl}-phenyl)-amide | 9653 |
| Quinoline-3-carboxylic acid (2-{4-[2-(6,7-dimethoxy-3,4-dihydro-1H-isoquinolin-2-yl)-1-methyl-ethyl]-phenylcarbamoyl}-phenyl)-amide | 9654 |
| Quinoline-3-carboxylic acid [2-(4-{2-[(4-dimethylamino-benzyl)-methyl-amino]-ethyl}-phenylcarbamoyl)-phenyl]-amide | 9655 |
| Quinoline-3-carboxylic acid [2-(4-{2-[(3-butoxy-4-methoxy-benzyl)-methyl-amino]-ethyl}-phenylcarbamoyl)-4,5-dimethoxy-phenyl]-amide | 9656 |
| 5-Methyl-pyrazine-2-carboxylic acid (2-{4-[2-(6,7-dimethoxy-3,4-dihydro-1H-isoquinolin-2-yl)-ethyl]-2-methoxy-phenylcarbamoyl}-phenyl)-amide | 9657 |
| Pyrazine-2-carboxylic acid (2-{4-[2-(6,7-dimethoxy-3,4-dihydro-1H-isoquinolin-2-yl)-ethyl]2-methyl-phenylcarbamoyl}-phenyl)-amide | 9658 |
| Pyrazine-2-carboxylic acid (2-{4-[2-(6,7-dimethoxy-3,4-dihydro-1H-isoquinolin-2-yl)-ethyl]-2-methoxy-phenylcarbamoyl}-phenyl)-amide | 9659 |
| Quinoline-3-carboxylic acid (2-{3-[2-(6,7-dimethoxy-31 4-dihydro-1H-isoquinolin-2-yi)-propyl]-phenyicarbamoyi}-phenyi)-atnide | 9660 |
| N-[2-(4-{[(3-Isopropoxy-4-methoxy-benzyl)-methyl-amino]-methyl}-phenylcarbamoyl)-phenyl]-nicotinamide | 9661 |
| Quinoline-3-carboxylic acid [5-chloro-2-(4-{2-[(3-4-dimethoxy-benzyl)-methyl-amino]-ethyl}-phenylcarbamoyl)-phenyl]-amide | 9663 |
| Quinoline-3-carboxylic acid (2-{4-[2-(7,8-dihydro-5H-[1,3]dioxolo[4,5-g]isoquinolin-6-yl)-ethyl]-phenylcarbamoyl}-phenyl)-amide | 9664 |
| Quinoline-3-carboxylic acid (2-{4-[2-(6,7-diethoxy-3,4-dihydro-1H-isoquinolin-2-yl)-ethyl]-phenylcarbamoyl}-phenyl)-amide | 9665 |
| Quinoline-3-carboxylic acid (6-{4-[2-(6,7-dimethoxy-3,4-dihydro-1H-isoquinolin-2-yl)-ethyl]-phenylcarbamoyl}-thieno[2,3-b]pyrazin-7-yl)-amide | 9666 |
| Quinoline-3-carboxylic acid [2-(4-{2-[(3,4-dimethoxy-benzyl)-methyl-amino]-ethyl}-phenylcarbamoyl)-4,5-dif uoro-phenyl]-amide | 9667 |
| Quinoline-3-carboxylic acid [2-(4-{2-[(3,4-dimethoxy-benzyl)-methyl-amino]-ethyl}-phenylcarbamoyl)-5-methyl-phenyll-amide | 9668 |
| Quinoline-3-carboxylic acid [2-(4-{2-[(3,4-dimethoxy-benzyl)-isopropyl-amino]-ethyl}-phenylcarbamoyl)-phenyl]-amide | 9669 |
| Quinoline-3-carboxylic acid [2-(4-{2-[(3,4-dimethoxy-benzyl)-methyl-amino]-ethyl}-phenylcarbamoyl)-5-nitro-phenyl]-amide | 9677 |
| 2-(4-Isopropyl-benzoylamino)-N-[2-(6,7-dimethoxy-3,4-dihydro-1H-isoquinolin02-yl)-ethyl]-benzamide | 9304 |
| 2-(4-Isopropyl-benzoylamino)-N-[2-(6,7-dimethoxy-3,4-dihydro-1H-isoquinolin-2-yl)-ethyl]-6-chloro-benzamide | 9405 |
| 2-(4-Isopropyl-benzoylamino)-N-[2-(6,7-dimethoxy-3,4-dihydro-1H-isoquinolin-2-yl)-ethyl]-5-chioro-benzamide | 9354 |

| Chemical Name | Compound No. |
|---|---|
| 2-(4-Isopropyl-benzoylamino)-N-[2-(6,7-dimethoxy-3,4-dihydro-1H-isoquinolin-2-yl)-ethyl]-4-chloro-benzamide | 9350 |
| 2-(4-Isopropyl-benzoylamino)-N-[2-(6,7-dimethoxy-3,dihydro-1H-isoquinolin-2-yl)-ethyl]-3-chloro-benzamide | 9401 |
| 2-(4-Isopropyl-benzoylamino)-N-[2-(6,7-dimethoxy-3,4-dihydro-1H-isoquinolin-2-yl)-ethyl]-5-bromo-benzamide | 9394 |
| 2-(4-Isopropyl-benzoylamino)-N-[2-(6,7-dimethoxy-3,4-dihydro-1H-isoquinolin-2-yl)-ethyl]-4-fluoro-benzamide | 9349 |
| 2-(4-Isopropyl-benzoylamino)-N-[2-(6,7-dimethoxy-3,4-dihydro-1H-isoquinolin-2-yl)-ethyl]-3-methyl-benzamide | 9398 |
| 2-(4-Isopropyl-benzoylamino)-N-[2-(6,7-dimethoxy-3,4-dihydro-1H-isoquinolin-2-yl)-ethyl]-3-methoxy-benzamide | 9399 |
| 2-(4-Isopropyl-benzoylamino)-N-[2-(6,7-dimethoxy-3,4-dihydro-1H-isoquinolin-2-yl)-ethyl]-3-hydroxy-benzamide | 9424 |
| 2-(4-Isopropyl-benzoylamino)-N-[2-(6,7-dimethoxy-3,4-dihydro-1H-isoquinolin-2-yl)-ethyl]-4-nitro-benzamide | 9420 |
| 2-(4-Isopropyl-benzoylamino)-N-[2-(6,7-dimethoxy-3,4-dihydro-1H-isoquinolin-2-yl)-ethyl]-4-amino-benzamide | 9435 |
| 2-(4-Isopropyl-benzoylamino)-N-[2-(6,7-dimethoxy-3,4-dihydro-1H-isoquinolin-2-yl)-ethyl]-5-phenyl-benzamide | 9432 |
| 3-(4-Isopropyl-benzoylamino)-naphthalene-2-carboxylic acid [2-(6,7-dimethoxy-3,4-dihydro-1H-isoquinolin-2-yl)-ethyl]-amide | 9410 |
| 2-(4-Dimethylamino-benzoylamino)-N-L2-(6,7-dimethoxy-3,4-dihydro-1H-isoquinolin-2-yl)-ethyl]-benzamide | 9256 |
| 2-(4-Propyl-benzoylamino)-N-[2-(6,7-dimethoxy-3,4-dihydro-1H-isoquinolin-2-yl)-ethyl]-benzamide | 9297 |
| 2-(4-Pentyl-benzoylamino)-N-[2-(6,7-dimethoxy-3,4-dihydro-1H-isoquinolin-2-yl)-ethyl]-benzamide | 9395 |
| 2-(4-Cyclohexyl-benzoylamino)-N-[2-(6,7-dimethoxy-3,4-dihydro-1H-isoquinolin-2-yl)-ethyl]-benzamide | 9331 |
| Biphenyl-4-carboxylic acid {2-[2-(6,7-dimethoxy-3,4-dihydro-1H-isoquinolin-2-yl)-ethylcarbamoyl]-phenyl}-amide | 9294 |
| Naphthalene-2-carboxylic acid {2-[2-(6,7-dimethoxy-3,4-dihydro-1H-isoquinolin-2-yl)-ethylcarbamoyl]-phenyl}-amide | 9295 |
| Benzo[1,3]dioxole-5-carboxylic acid {2-[2-(6,7-dimethoxy-3,4-dihydro-1H-isoquinolin-2-yl)-ethylcarbamoyl]-phenyl}-amide | 9302 |
| 2-(4-Diethylamino-benzoylamino)-N-[2-(6,7-dimethoxy-3,4-dihydro-1H-isoquinolin-2-yl)-ethyl]-benzamide | 9310 |
| 2-(4-tert-Butyl-benzoylamino)-N-[2-(6,7-dimethoxy-3,4-dihydro-1H-isoquinolin-2-yl)-ethyl]-benzamide | 9334 |
| 2-Benzoylamino-N-[2-(6,7-dimethoxy-3,4-dihydro-1H-isoquinolin-2-yl)-ethyl]-benzamide | 9351 |
| 2-(4-Bromo-benzoylamino)-N-[2-(6,7-dimethoxy-3,4-dihydro-1H-isoquinolin-2-yl)-ethyl]-benzamide | 9380 |
| 2-(4-Nitro-benzoylamino)-N-[2-(6,7-dimethoxy-3,4-dihydro-1H-isoquinolin-2-yl)-ethyl]-benzamide | 9381 |
| 2-(4-Phenoxy-benzoylamino)-N-[2-(6,7-dimethoxy-3,4-dihydro-1H-isoquinolin-2-yl)-ethyl]-benzamide | 9426 |
| 2-(4-Benzoyl-benzoylamino)-N-[2-(6,7-dimethoxy-3,4-dihydro-1H-isoquinolin-2-yl)-ethyl]-benzamide | 9427 |
| 2-(4-Benzyl-benzoylamino)-N-[2-(6,7-dimethoxy-3,4-dihydro-1H-isoquinolin-2-yl)-ethyl]-benzamide | 9442 |
| 2-(4-Cyclohexyloxy-benzoylamino)-N-[2-(6,7-dimethoxy-3,4-dihydro-1H-isoquinolin-2-yl)-ethyl]-benzamide | 9459 |
| 2-(4-Benzyloxy-benzoylamino)-N-[2-(6,7-dimethoxy-3,4-dihydro-1H-isoquinolin-2-yl)-ethyl]-benzamide | 9460 |
| Pyridine-2-carboxylic acid {2-[2-(6,7-dimethoxy-3,4-dihydro-1H-isoquinolin-2-yl)-ethylcarbamoyl]-phenyl}-amide | 9377 |
| N-{2-[2-(6,7-Dimethoxy-3,4-dihydro-1H-isoquinolin-2-yl)-ethylcarbamoyl]-phenyl}-nicotinamide | 9359 |
| N-{2-[2-(6,7-Dimethoxy-3,4-dihydro-1H-isoquinolin-2-yl)-ethylcarbamoyl]-phenyl}-isonicotinamide | 9384 |
| Pyrazine-2-carboxylic acid {2-[2-(6,7-dimethoxy-3,4-dihydro-1H-isoquinolin-2-yl)-ethylcarbamoyl]-phenyl}-amide | 9391 |
| Quinoxaline-2-carboxylic acid {2-[2-(6,7-dimethoxy-3,4-dihydro-1H-isoquinolin-2-yl)-ethylcarbamoyl]-phenyl}-amide | 9347 |
| Isoquinoline-1-carboxylic acid {2-[2-(6,7-dimethoxy-3,4-dihydro-1H-isoquinolin-2-yl)-ethylcarbamoyl]-phenyl}-amide | 9383 |
| Quinoline-2-carboxylic acid {2-[2-(6,7-dimethoxy-3,4-dihydro-1H-isoquinolin-2-yl)-ethylcarbamoyl]-phenyl}-amide | 9385 |
| Isoquinoline-3-carboxylic acid {2-[2-(6,7-dimethoxy-3,4-dihydro-1H-isoquinolin-2-yl)-ethylcarbamoyl]-phenyl}-amide | 9389 |
| Quinoline-3-carboxylic acid {2-[2-(6,7-dimethoxy-3,4-dihydro-1H-isoquinolin-2-yl)-ethylcarbamoyl]-phenyl}-amide | 9397 |
| Thiophene-3-carboxylic acid {2-[2-(6,7-dimethoxy-3,4-dihydro-1H-isoquinolin-2-yl)-ethylcarbamoyl]-phenyl}-amide | 9365 |
| 1H-Indole-2-carboxylic acid {2-[2-(6,7-dimethoxy-3,4-dihydro-1H-isoquinolin-2-yl)-ethylcarbamoyl]-phenyl-amide | 9367 |
| Quinoxaline-2-carboxylic. acid (2-{4-[2-(6,7-dimethoxy-3,4-dihydro-1H-isoquinolin-2-yl)-ethyl]-phenylcarbamoyl}-phenyl)-amide | 9531 |
| Quinoxaline-2-carboxylic acid (2-{4-[2-(6,7-dimethoxy-3,4-dihydro-1H-isoquinolin-2-yl)-ethyl]-phenylcarbamoyl}-5-hydroxyamino-phenyl)-amide | 9542 |
| Quinoxaline-2-carboxylic acid (2-{4-[2-(6,7-dimethoxy-3,4-dihydro-1H-isoquinolin-2-yl)-ethyl]-phenylcarbamoyl}-4-methyl-phenyl)-amide | 9543 |
| Quinoxaline-2-carboxylic acid (2-{4-[2-(6,7-dimethoxy-3,4-dihydro-1H-isoquinolin-2-yl)-ethyl]-phenylcarbamoyl}-4-hydroxy-phenyl)-amide | 9554 |
| Quinoxaline-2-carboxylic acid (2-{4-(2-(6,7-dimethoxy-3,4-dihydro-1H-isoquinolin-2-yl)-ethyl]-phenylcarbamoyl}-5-nitro-phenyl)-amide | 9541 |
| Quinoxaline-2-carboxylic acid (2-{4-[2-(6,7-dimethoxy-3,4-dihydro-1H-isoquinolin-2-yl)-ethyl]-phenylcarbamoyl}-5-trifluoromethyl-phenyl)-amide | 9561 |
| Quinoxaline-2-carboxylic acid (2-{4-[2-(6,7-dimethoxy-3,4-dihydro-1H-isoquinolin-2-yl)-ethyl]-phenylcarbamoyl}-3-fluoro-phenyl)-amide | 9562 |
| Quinoxaline-2-carboxylic acid (2-{4-[2-(6,7-dimethoxy-3,4-dihydro-1H-isoquinolin-2-yl)-ethyl]-phenylcarbamoyl}-3-fluoro-phenyl)-amide | 9564 |
| Quinoxaline-2-carboxylic acid. (2-{4-[2-(6,7-dimethoxy-3,4-dihydro-1H-isoquinolin-2-yl)-ethyl]-phenylcarbamoyl}-4-fluoro-phenyl)-amide | 9568 |
| Quinoxaline-2-carboxylic acid (2-{4-[2-(6,7-dimethoxy-3,4-dihydro-1H-isoquinolin-2-yl)-ethyl]-phenylcarbamoyl}-4,5-dimethoxy-phenyl)-amide | 9573 |
| Quinoline-3-carboxylic acid (2-{4-[2-(6,7-dimethoxy-3,4-dihydro-1H-isoquinolin-2-yl)-ethyl]-phenylcarbamoyl}-phenyl)-amide | 9544 |

-continued

| Chemical Name | Compound No. |
|---|---|
| Quinoline-3-carboxylic acid (2-{4-[2-(6,7-dimethoxy-3,4-dihydro-1H-isoquinolin-2-yl)-ethyl]-phenylcarbamoyl}-5-fluoro-phenyl)-amide | 9571 |
| Quinoline-3-carboxylic acid (2-{4-[2-(6,7-dimethoxy-3,4-dihydro-1H-isoquinolin-2-yl)-ethyl]-phenylcarbamoyl}-4-fluoro-phenyl)-amide | 9574 |
| Quinoline-3-carboxylic acid (2-{4-[2-(6,7-dimethoxy-3,4-dihydro-1H-isoquinolin-2-yl)-ethyl]-phenylcarbamoyl}-4,5-dimethoxy-phenyl)-amide | 9576 |
| Quinoline-3-carboxylic acid (6-{4-[2-(6,7-dimethoxy-3,4-dihydro-1H-isoquinolin-2-yl)-ethyl]-phenylcarbamoyl}-benzo[1,3]dioxoi-5-yl)-amide | 9578 |
| Quinoline-3-carboxylic acid (2-{4-[2-(6,7-dimethoxy-3,4-dihydro-1H-isoquinolin-2-yl)-ethyl]-phenylcarbamoyl}-5-nitro-phenyl)-amide | 9581 |
| Quinoline-3-carboxylic acid (2,-{4-[2-(6,7-dimethoxy-3,4-dihydro-1H-isoquinolin-2-yl)-ethyl]-phenylcarbamoyl}-4-methyl-phenyl)-amide | 9584 |
| Quinoline-3-carboxylic acid (2-{4-[2-(6,7-dimethoxy-3,4-dihydro-1H-isoquinolin-2-yl)-ethyl]-phenylcarbamoyl}-5-methyl-phenyl)-amide | 9588 |
| Quinoline-3-carboxylic acid (2-{4-[2-(6,7-dimethoxy-3,4-dihydro-1H-isoquinolin-2-yl)-ethyl]-phenylcarbamoyl}-4-chloro-phenyl)-amide | 9593 |
| Quinoline-3-carboxylic acid (2-{4-[2-(6,7-dimethoxy-3,4-dihydro-1H-isoquinolin-2-yl)-ethyl]-phenylcarbamoyl}-5-chloro-phenyl)-amide | 9586 |
| Quinoline-3-carboxylic acid (2-{4-[2-(6,7-dimethoxy-3,4-dihydro-1H-isoquinolin-2-yl)-ethyl]-phenylcarbamoyl}-5-amino-phenyl)-amide | 9589 |
| Quinoline-3-carboxylic acid (2-{4.-[2-(6,7-dimethoxy-3,4-dihydro-1H-isoquinolin-2-yl)-ethyl]-phenylcarbamoyl}-phenyl)-amide | 9545 |
| 5,6,7,8-Tetrahydroquinoline-3-carboxylic acid (2-{4-[2-(6,7-dimethoxy-3,4-dihydro-1H-isoquinolin-2-yl)-ethyl]-phenylcarbamoyl}-phenyl)-amide | 9590 |
| Pyridine-2-carboxylic acid (2-{4-[2-(6,7-dimethoxy-3,4-dihydro-1H-isoquinolin-2-yl)-ethyl]-phenylcarbamoyl}-phenyl)-amide | 9472 |
| N-(2-{4-[2-(6,7-Dimethoxy-3,4-dihydro-1H-isoquinolin-2-yl)-ethyl]-phenylcarbamoyl}-phenyl)-nicotinamide | 9482 |
| N-(2-{4-[2-(6,7-Dimethoxy-3,4-dihydro-1H-isoquinolin-2-yl)-ethyl]-phenylcarbamoyl}-phenyl}-isonicotinamide | 9483 |
| Pyrazine-2-carboxylic acid (2-{4-[2-(6,7-dimethoxy-3,4-dihydro-1H-isoquinolin-2-yl)-ethyl]-phenylcarbamoyl}-phenyl)-amide | 9493 |
| 5-Methyl-pyrazine-2-carboxylic acid (2-{4-[2-(6,7-dimethoxy-3,4-dihydro-1H-isoquinolin-2-yl)-ethyl]-phenylcarbamoyl}-phenyl)-amide | 9527 |
| N-(2-{4-[2-(6,7-Dimethoxy-3,4-dihydro-1H isoquinolin-2-yl)-ethyl]-phenylcarbamoyl} phenyl)-6-methyl-nicotinamide | 9557 |
| N-(2-{4-[2-(6,7-Dimethoxy-3,4-dihydro-1H-isoquinolin-2-yl)-ethyl]-phenylcarbamoyl}-phenyl)-6-methoxy-nicotinamide | 9582 |
| 5-Propionyl-pyrazine-2-carboxylic acid (2-{4-[2-(6,7-dimethoxy-3,4-dihydro-1H-isoquinolin-2-yl)-ethyl]-phenylcarbamoyl}-phenyl)-amide | 9569 |
| 2-Benzoylamino-N-{4-[2-(6,7-dimethoxy-3,4-dihydro-1H-isoquinolin-2-yl)-ethyl]-phenyl}-benzamide | 9456 |
| 2-Benzoylamino-N-{4-[2-(6,7-dimethoxy-3,4-dihydro-1H-isoquinolin-2-yl)-ethyl]-phenyl}-4-methyl-benzamide | 9511 |
| 2-Benzoylamino-N-{4-[2-(6,7-dimethoxy-3,4-dihydro-1H-isoquinolin-2-yl)-ethyl-phenyl}-5-methyl-benzamide | 9510 |
| 2-Benzoylamino-N-{4-[2-(617-dimethoxy-3,4-dihydro-1H-isoquinolin-2-yl)-ethyl]-phenyl}-6-methyl-benzamide | 9512 |
| 2-(2-Fluoro-benzoylamino)-N-{4-[2-(6,7-dimethoxy-3,4-dihydro-1H-isoquinolin-2-yl)-ethyl]-phenyl}-benzamide | 9489 |
| 2-(3-Fluoro-benzoylamino)-N-{4-[2-(6,7-dimethoxy-3,4-dihydro-1H-isoquinolin-2-yl)-ethyl]-phenyl}-benzamide | 9500 |
| 2-(4-Fluoro-benzoylamino)-N-{4-[2-(6,7-dimethoxy-3,4-dihydro-1H-isoquinolin-2-yl)-ethyl]-phenyl}-benzamide | 9501 |
| 2-(2,4-Difluoro-benzoylamino)-N-{4-[2-(6,7-dimethoxy-3,4-dihydro-1H-isoquinolin-2-yl)-ethyl]-phenyl}-benzamide | 9513 |
| 2-(2,6-Difluoro-benzoylamino)-N-{4-[2-(6,7-dimethoxy-3,4-dihydro-1H-isoquinolin-2-yl)-ethyl]-phenyl}-benzamide | 9514 |
| 2-(2-chloro-benzoylamino)-N-{4-[2-(6,7-dimethoxy-3,4-dihydro-1H-isoquinolin-2-yl)-ethyl]-phenyl-benzamide | 9494 |
| 2-(3-chloro-benzoylamino)-N-{4-[2-(617-dimethoxy-3,4-dihydro-1H-isoquinolin-2-yl)-ethyl]-phenyl}-benzamide | 9495 |
| 2-(4-chloro-benzoylamino)-N-{4-[2-(6,7-dimethoxy-3,4-dihydro-1H-isoquinolin-2-yl)-ethyl]-phenyl}-benzamide | 9496 |
| 2-(2-Methyl-benzoylamino)-N-{4-[2-(6,7-dimethoxy-3,4-dihydro-1H-isoquinolin-2-yl}-ethyl]-phenyl}-benzamide | 9497 |
| 2-(3-Methyl-benzoylamino)-N-{4-[2-(6,7-dimethoxy-3,4-dihydro-1H-isoquinolin-2-yl)-ethyl]-phenyl}-benzamide | 9503 |
| 2-(4-Methyl-benzoylamino)-N-{4-[2-(6,7-dimethoxy-3,4-dihydro-1H-isoquinolin-2-yl)-ethyl]-phenyl}-benzamide | 9504 |
| 2-(2-Methoxy-benzoylamino)-N-{4-[2-(617-dimethoxy-3,4-dihydro-1H-isoquinolin-2-yl)-ethyl]-phenyl}-benzamide | 9477 |
| 2-(3-Methoxy-benzoclamino)-N-{4-[2-(6,7-dimethoxy-3,4-dihydro-1H-isoquinolin-2-yl)-ethyl]-phenyl}-benzamide | 9517 |
| 2-(4-Methoxy-benzoylamino)-N-{4-[2-(6,7-dimethoxy-3,4-dihydro-1H-isoquinolin-2-yl)-ethyl]-phenyl}-benzamide | 9518 |
| 2-(2-Hydroxy-benzoylamino)-N-{4-[2-(6,7-dimethoxy-3,4-dihydro-1H-isoquinolin-2-yl)-ethyl]-phenyl-benzamide | 9535 |
| 2-(3-Hydroxy-benzoylamino)-N-{4-[2-(6,7-dimethoxy-3,4-dihydro-1H-isoquinolin-2-yl)-ethyl]-phenyl}-benzanlide | 9549 |
| 2-(4-Hydroxy-benzoylamino)-N-{4-[2-(6,7-dimethoxy-3,4-dihydro-1H-isoquinolin-2-yl)-ethyl]-phenyl}-benzamide | 9559 |
| Acetic acid 2-(2-{4-[2-(6,7-dimethoxy-3,4-dihydro-1H-isoquinolin-2-yl)-ethyl]-phenylcarbamoyl)-phenylcarbamoyl)-phenyl ester | 9534 |
| Acetic acid 3-(2-{4-[2-(6,7-dimethoxy-3,4-dihydro-1H-isoquinolin-2-yl)-ethyl]-phenylcarbamoyl)-phenylcarbamoyl)-phenyl ester | 9540 |
| Acetic acid 4-(2-{4-[2-(6,7-dimethoxy-3,4-dihydro-1H-isoquinolin-2-yl)-ethyl]-phenylcarbamoyl)-phenylcarbamoyl)-phenyl ester | 9548 |
| 2-(2-Trifluoromethyl-benzoylamino)-N-{4-[2-(6,7-dimethoxy-3,4-dihydro-1H-isoquinolin-2-yl)-ethyl]-phenyl}-benzamide | 9523 |
| 2-(3-Trifluoromethyl-benzoylamino)-N-{4-[2-(6,7-dimethoxy-3,4-dihydro-1H-isoquinolin-2-yl)-ethyl]-phenyl-benzamide | 9524 |
| 2-(3-Dimethylamino-benzoylamino)-N-{4-[2-(6,7-dimethoxy-3,4-dihydro-1H-isoquinolin-2-yl)-ethyl]-phenyl}-benzamide | 9556 |
| 2-(4-Isopropyl-benzoylamino)-N-{4-[2-(6,7-dimethoxy-3,4-dihydro-1H-isoquinolin-2-yl)-ethyl]-phenyl}-benzamide | 9447 |
| 2-(4-Cyclohexyl-benzoylamino)-N-{4-[2-(6,7-dimethoxy-3,4-dihydro-1H-isoquinolin-2-yl)-ethyl]-phenyl}-benzamide | 9461 |
| Naphthalene-1-carboxylic acid (2-{4-02-(6,7-dimethoxy-3,4-dihydro-1H-isoquinolin-2-yl)- | 9470 |

-continued

| Chemical Name | Compound No. |
|---|---|
| ethyl]-phenylcarbamoyl}-phenyl)-amide | |
| Naphthaiene-2-carboxylic acid (2-{4-[2-(6,7-dimethoxy-3,4-dihydro-1H-isoquinolin-2-yl)-ethyl]-phenylcarbamoyl}-phenyl)-amide | 9476 |
| 2-(3,4-Dichloro-benzoylamino)-N-{4-[2-(6,7-dimethoxy-3,4-dihydro-1H-isoquinolin-2-yl)-ethyl]-phenyl}-benzamide | 9536 |
| 2-(3,4-Dimethyl-benzoylamino)-N-{4-[2-(6,7-dimethoxy-3,4-dihydro-1H-isoquinolin-2-yl)-ethyl]-phenyl}-benzamide | 9538 |
| Thiophene-2-carboxylic acid (2-{4-[2-(6,7-dimethoxy-3,4-dihydro-1H-isoquinolin-2-yl)-ethyl]-phenylcarbamoyl}-phenyl)-amide | 9471 |
| Thiophene-3-carboxylic acid (2-{4-[2-(6,7-dimethoxy-3,4-dihydro-1H-isoquinolin-2-yl)-ethyl]-phenylcarbamoyl}-phenyl)-amide | 9492 |
| Furan-3-carboxylic acid (2-{4-[2-(6,7-dimethoxy-3,4-dihydro-1H-isoquinolin-2-yl)-ethyl]-phenylcarbamoyl}-phenyl)-amide | 9526 |
| 1H-Indole-2-carboxylic acid (2-{4-[2-(6,7-dimethoxy-3,4-dihydro-1H-isoquinolin-2-yl)-ethyl]-phenylcarbamoyl}-phenyl)-amide | 9515 |
| Benzofuran-2-carboxylic acid (2-{4-[2-(6,7-dimethoxy-3,4-dihydro-1H-isoquinolin-2-yl)-ethyl]-phenylcarbamoyl}-phenyl)-amide | 9539 |
| 2-(4-cyclohexyl-benzoylamino)-N-[3-(6,7-dimethoxy-3,4-dihydro-1H-isoquinolin-2-yl)-propyl-benzamide | 9466 |
| 2-(4-Cyclohexyl-benzoylamino)-N-[2-(3,4-dihydro-1H-isoquinolin-2-yl)-ethyl]-benzamide | 9479 |
| Quinoxaline-2-carboxyXic acid (2-{4-[3-(6,7-dimethoxy-3,4-dihydro-1H-isoquinolin-2-yl)-propyl]-phenylcarbamoyl}-phenyl)-amide | 9567 |
| Quinoxaline-2-carboxylic acid {2-[4-(6,7-dimethoxy-3,4-dihydro-1H-isoquinolin-2-ylmethyl)-phenylcarbamoyl]-phenyl}-amide | 9572 |
| Quinoline-3-carboxylic acid (2-{4-[2-(3,4-dihydro-1H-isoquinolin-2-yl)-ethyl]-phenylcarbamoyl}-phenyl)-amide | 9577 |
| Quinoline-3-carboxylic acid {2-[4-(6,7-dimethoxy-3,4-dihydro-1H-isoquinolin-2-ylmethyl)-phenylcarbamoyl]-phenyl}-amide | 9585 |

Compounds of formula (I) may be produced by a process which comprises:

(a) treating an aminobenzamide of formula (VI)

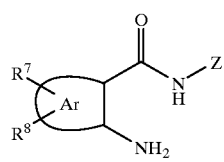

(VI)

wherein Ar, $R^7$ and $R^8$ are as defined above and Z is the moiety:

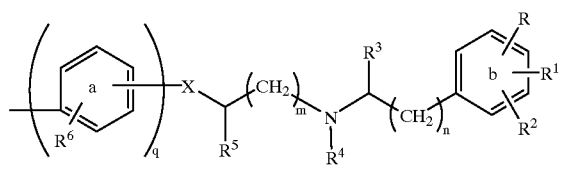

wherein m, n, q, R, $R^1$ to $R^6$ and X are as defined above, with a carboxylic acid of formula $R^9$—COOH, or an activated derivative thereof, wherein $R^9$ is as defined above; or (b) treating a compound of formula XII:

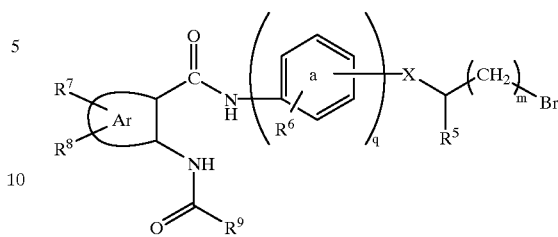

(XII)

wherein Ar, $R^5$, $R^6$ to $R^9$, X, q, and m are as defined above, with an amine of formula XX:

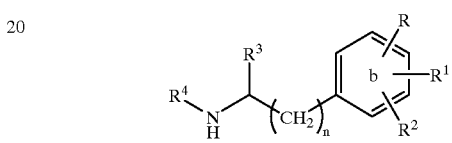

(XX)

wherein R, $R^1$ to $R^4$ and n are as defined above; and, if desired, removing any optional protecting groups present, and/or if desired, converting one compound of formula (I) into another compound of formula (I) and/or, if desired, converting one compound of formula (I) into a pharmaceutically acceptable salt thereof and/or, if desired, converting a salt into a free compound of formula (I).

In process variant (a) the carboxylic acid $R^9$—COOH is commercially available or may be prepared as described in Reference Example 6A which follows. The acid may be activated as the corresponding acid chloride $R^9$—COCl. This may be obtained commercially or prepared by treating the free carboxylic acid $R^9$—COOH with thionyl chloride. Alternatively the carboxylic acid $R^9$—COOH can be activated with cyclohexyl-N-(2-morpholinoethyl)-carbodiimide methyl-p-toluene sulphonate and 1-hydroxybenzotriazole, or with 2-chloro-1-methylpyridinium iodide.

Amino benzamides of general formula VI may be obtained by one of three routes, illustrated below in scheme 1 in which each of Z, $R^7$, $R^8$ and Ar is as defined above. The first route comprises the direct coupling of the appropriately substituted, commercially available anthranilic acid IV with an amine of formula IX (step iii), and is described in more detail in Reference Example 4A which follows. The starting amine of formula IX may be prepared as described in Reference Example 1A which follows.

The second route comprises coupling of the appropriately substituted, commercially available, nitrobenzoic acid III and subsequent reduction of the nitro group to an amino group (steps 1 and ii). These steps are described in more detail in Reference Examples 2A and 3A, respectively, which follow. The third route involves 4 steps, starting from a commercially available amino ester VII. This route is described in more detail in Reference Example 5 which follows.

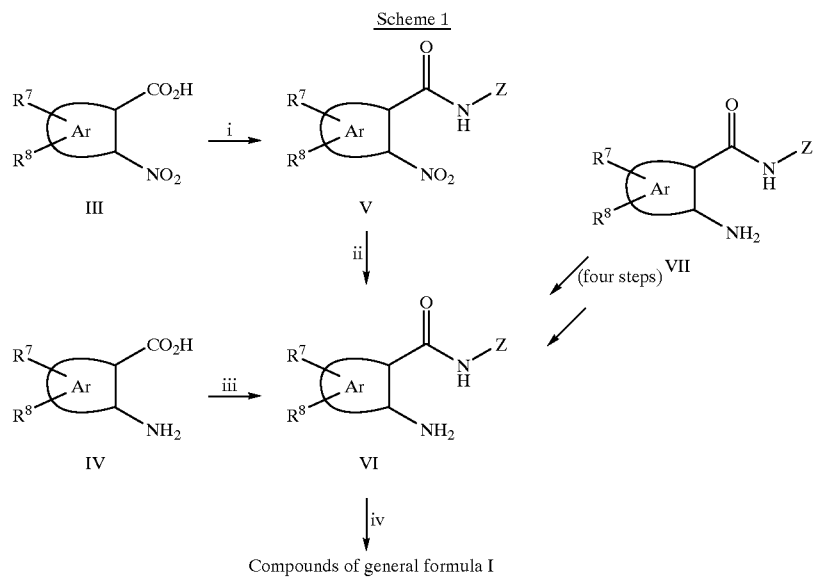

In process variant (b), the amines of formula XX are known compounds or can be prepared from known starting materials using conventional techniques in organic chemistry, for instance as described in Example 3. The intermediate bromide of formula XII is prepared by treatment of the corresponding hydroxy compound of formula XVII with a brominating agent. Suitable brominating agents include N-bromosuccinimide. The hydroxy compound of formula XVII may be prepared as illustrated in scheme 2. The reactions of scheme 2 are described in more detail in Reference Example 7 which follows.

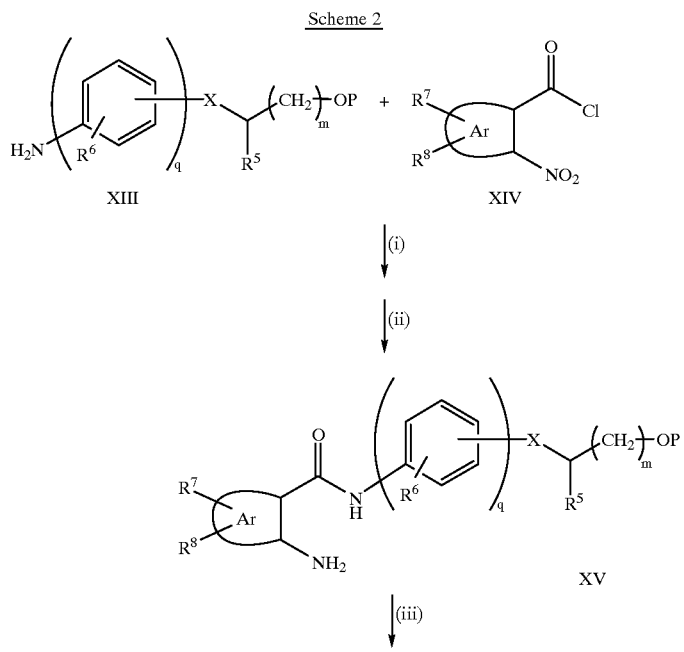

-continued

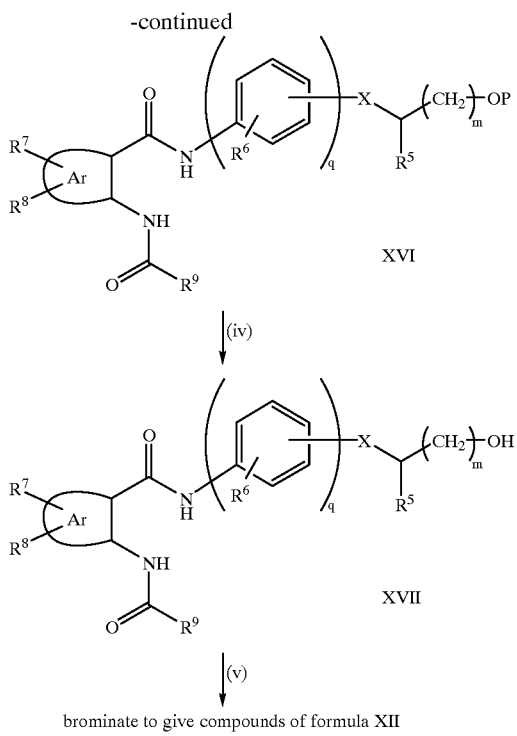

XVI

↓(iv)

XVII

↓(v)

brominate to give compounds of formula XII

The starting amino derivative of formula XIII, in which P is a hydroxy protecting group, is prepared from the corresponding protected nitro derivative by reduction, for instance by treatment with $H_2$ in EtOH in the presence of $PtO_2$. The protected nitro derivative is in turn obtained by treating the unprotected nitro derivative with a protecting group that affords the group P.

Step (i) is typically carried out by reacting together the compounds of formulae XIII and XIV in the presence of a base, for instance triethylamine. The resulting compound is reduced in step (ii), for instance under the conditions described above for the preparation of compound XIII, to give the intermediate compound of formula XV.

Step (iii) involves the treatment of the compound of formula XV with a compound $R^9$—COCl in an organic solvent in the presence of a base to give the compound of formula XVI. The latter compound is deprotected in step (iv), and the resulting deprotected derivative of formula XVII is treated with a brominating agent in step (v) to give the desired compound of formula XII.

Compounds of formula (Ia) may be produced by a process which comprises:

(a') treating an aminobenzamide of formula VIII'

(VIII')

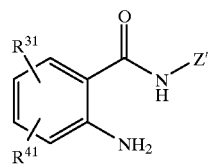

wherein $R^{31}$ and $R^{41}$ are as defined above and, if required, are optionally protected, and Z' is the moiety wherein r, s, $R^{11}$ and $R^{21}$ are as defined above, with a carboxylic acid of formula $R^{51}$—COOH, or an activated derivative thereof, wherein $R^{51}$ is as defined above; or (b') treating a compound of formula XII':

(XII')

wherein $R^{51}$ is as defined above, with an amine of formula IX':

(IX')

wherein r, s, $R^{11}$ and $R^{21}$ are as defined above, to produce a compound of formula (Ia) wherein $R^{31}$ and $R^{41}$ are both hydrogen; or (c') treating an azalactone of formula XIII':

(XIII')

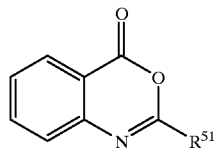

wherein $R^{51}$ is as defined above, with an amine of formula (IX')

(IX')

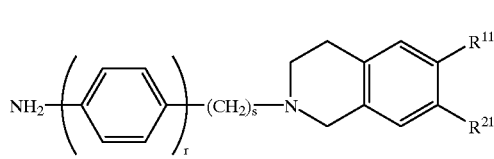

wherein r, s, $R^{11}$ and $R^{21}$ are as defined above, to produce a compound of formula (Ia) wherein $R^{31}$ and $R^{41}$ are both hydrogen; and, if desired, removing any optional protecting groups present, and/or if desired, converting one compound of formula (Ia) into another compound of formula (Ia) and/or, if desired, converting one compound of formula (Ia) into a pharmaceutically acceptable salt thereof and/or, if desired, converting a salt into a free compound of formula (Ia).

In process variant (a') the carboxylic acid $R^{51}$—COOH is commercially available or may be prepared as described in Reference Example 6B which follows. The acid may be activated as the corresponding acid chloride $R^{51}$—COCl. This may be obtained commercially or prepared by treating the free carboxylic acid $R^{51}$—COOH with thionyl chloride. Alternatively the carboxylic acid $R^{51}$—COOH can be activated with cyclohexyl-N-(2-morpholinoethyl)-carbodiimide methyl-p-toluene sulphonate and 1-hydroxybenzotriazole, or with 2-chloro-1-methylpyridinium iodide.

The 2-aminobenzamides of formula VIII' are produced by one of two routes. The first comprises reduction of the corresponding 2-nitrobenzamides, for instance by treatment with hydrogen in the presence of a $PtO_2$ catalyst. The 2-nitrobenzamide in turn may be produced by treatment of the corresponding 2-nitrobenzoic acid, which is optionally activated, with an amine of formula IX' as defined above. The preparation of amines of formula IX' is described in Reference Example 1B which follows. The steps to intermediate VIII' are illustrated in the following Scheme 3. Steps (i), (ii) and (iii) in the scheme are described in Reference Examples 2B, 3B and 4B respectively, which follow and step (iii) is described in Reference Example 4B. Production of the amine IX' is described in Reference Example 1B.

Scheme 3

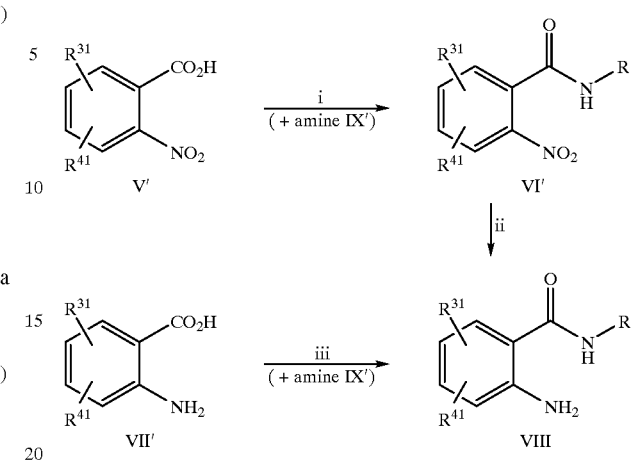

In process variant (b') the intermediate of formula XII' is prepared by hydrolysis of the corresponding methyl ester which, in turn, is prepared by treatment of commercially available methyl anthranilate with an acid chloride in the presence of triethylamine in dichloromethane. These steps are described in Reference Example 6 which follows.

In process variant (c') the azalactone of formula XIII' is prepared by treating commercially available anthranilic acid with an acid chloride of general formula $R^{51}$—COCl in pyridine or a pyridine/dichloromethane mixture at 0° C. for 3–8 hours.

Compounds of formula (I) may be converted into pharmaceutically acceptable salts, and salts may be converted into the free compound, by conventional methods. Salts may be mono- or bis-salts. Bis-salts, or double salts, can be formed when there are two basic nitrogen atoms in the structure of the compound of formula (1). Suitable salts include salts with pharmaceutically acceptable inorganic or organic acids. Examples of inorganic acids include hydrochloric acid, sulphuric acid and orthophosphoric acid. Examples of organic acids include p-toluenesulphonic acid, methanesulphonic acid, mucic acid and succinic acid. Bis-salts may include, in particular, bis-hydrochlorides and bis-mesylates.

The optional conversion of a compound of formula (I) into another compound of formula (I) may be carried out by conventional methods. For instance, a compound of formula (I) containing an esterified hydroxy group such as —OCOMe may be converted into a compound of formula (I) containing a free hydroxy group by hydrolysis, for instance alkaline hydrolysis. A compound of formula (I) containing a free hydroxy group may be converted into a compound of formula (I) containing an esterified hydroxy group by esterification, for instance by reaction with a suitable carboxylic acid, acid halide or acid anhydride.

A compound containing a halogen may be converted into a compound containing an aryl group by Suzuki coupling (Miyaura M, Yanagi T and Suzuki, A, Synth. Commun. 1981 vol 11, p.513). A compound of formula (I) containing a nitro group may be converted into a compound of formula (I) containing an amino group by reduction, for instance by treatment with hydrogen gas in the presence of a $PtO_2$ catalyst. Similarly, a compound of formula (I) containing a nitro group may be converted into a compound of formula (I) containing a hydroxyamino group —NHOH by reduction, for instance by treatment with hydrogen gas in the presence of a PtO$_2$ catalyst under suitably controlled conditions.

Cancer cells which exhibit multi-drug resistance, referred to as MDR cells, display a reduction in intracellular drug accumulation compared with the corresponding drug-sensitive cells. As discussed above, studies using in vitro derived MDR cell lines have shown that MDR is often associated with increased expression of a plasma membrane glycoprotein (P-gp) which has drug binding properties. P-gp is thought to function as an efflux pump for many hydrophobic compounds, and transfection studies using cloned P-gp have shown that its overexpression can confer the MDR phenotype on cells: see, for example, Ann. Rev. Biochem 58 137–171 (1989).

A major function of P-gp in normal tissues is to export intracellular toxins from the cell. There is evidence to suggest that overexpression of P-gp may play a clinical role in multi-drug resistance. Increased levels of P-gp mRNA or protein have been detected in many forms of human cancers—leukaemias, lymphomas, sarcomas and carcinomas. Indeed, in some cases P-gp levels have been found to be increased in tumour biopsies obtained after relapse from chemotherapy.

Inhibition of P-gp function in P-gp mediated MDR has been shown to lead to a net accumulation of anti-cancer agent in the cells. For example, Verapamil a known calcium channel blocker was shown to sensitise MDR cells to Vinca alkaloids in vitro and in vivo: *Cancer Res.,* 41, 1967–1972 (1981). The proposed mechanism of action involves competition with the anti-cancer agent for binding to the P-gp. A range of structurally unrelated resistance-modifying agents acting by this mechanism have been described such as tamoxifen (Nolvadex:ICI) and related compounds, and cyclosporin A and derivatives.

Anthranilic acid derivatives of formula I and their pharmaceutically acceptable salts (hereinafter referred to as "the present compounds") have been found in biological tests to have activity as inhibitors of P-gp. They can be used to modulate MDR, in particular P-gp mediated MDR. The results are set out in Example 1 which follows. As P-gp inhibitors the present compounds may be used as multi-drug resistance modifying agents, also termed resistance-modifying agents, or RMAs. The present compounds can modulate, e.g. reduce, or eliminate multi-drug resistance, especially that which is P-gp mediated.

The present compounds can therefore be used in a method of potentiating the cytotoxicity of an agent which is cytotoxic to a tumour cell. Such a method comprises, for instance, administering one of the present compounds to the tumour cell whilst the tumour cell is exposed to the cytotoxic agent in question. The therapeutic effect of a chemotherapeutic, or antineoplastic, agent may thus be enhanced. The multi-drug resistance of a tumour cell to a cytotoxic agent during chemotherapy may be reduced or eliminated.

The present compounds can also be used in a method of treating a disease in which the responsible pathogen exhibits multi-drug resistance, especially P-gp mediated multi-drug resistance for instance multi-drug resistant forms of malaria (*Plasmodium falciparum*), tuberculosis, leishmaniasis and amoebic dysentery. Such a method comprises, for instance, administering one of the present compounds with (separately, simultaneously or sequentially) the drug to which the pathogen concerned exhibits multi-drug resistance. The therapeutic effect of a drug directed against a multidrug resistant pathogen may thus be potentiated.

A human or animal patient harbouring a tumour may be treated for resistance to a chemotherapeutic agent by a method comprising the administration thereto of one of the present compounds. The present compound is administered in an amount effective to potentiate the cytotoxicity of the said chemotherapeutic agent. Examples of chemotherapeutic or antineoplastic agents which are preferred in the context of the present invention include Vinca alkaloids such as vincristine and vinblastine; anthracycline antibiotics such as daunorubicin and doxorubicin; mitoxantrone; actinomycin D; taxanes e.g. taxol; epipodophyllotoxins e.g. etoposide and plicamycin.

The present compounds may also be used in a method of enhancing the absorption, distribution, metabolism and/or elimination characteristics of a therapeutic agent, which method comprises administering to a patient, separately, simultaneously or sequentially, one of the present compounds and the said therapeutic agent. In particular this method may be used to enhance the penetration of the therapeutic agent into the central nervous system, or to enhance the oral absorption of the therapeutic agent.

For instance, the present compounds can be used in a method of facilitating the delivery of drugs across the blood brain barrier, and in the treatment of AIDS or AIDS related complex. A human or animal patient in need of such treatment may be treated by a method comprising the administration thereto of one of the present compounds.

The present compounds can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration when a compound of the invention is administered alone to adult humans is 0.001 to 50 mg/kg, most commonly in the range of 0.01 to 5 mg/kg, body weight. Such a dosage may be given, for example, from 1 to 5 times daily by bolus infusion, infusion over several hours and/or repeated administration.

An anthranilic acid derivative of formula (I) or a pharmaceutically acceptable salt thereof is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. An agent for use as a modulator of multi-drug resistance comprising any one of the present compounds is therefore provided.

The present compounds may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occuring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents;

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspensions.

Daily dosages can vary within wide limits and will be adjusted to the individual requirements in each particular case. In general, for administration to adults, an appropriate daily dosage is in the range of about 5 mg to about 500 mg, although he upper limit may be exceeded if expedient. The daily dosage can be administered as a single dosage or in divided dosages.

The invention will be further illustrated in the Examples which follow.

Example 1

Testing of Compounds of Formula (I) and Their Salts as Modulators of MDR

Materials and Methods

The EMT6 mouse mammary carcinoma cell line and the MDR resistant subline AR 1.0 were cultured in RPMI 1640 medium containing 10% foetal calf serum and 2 mM glutamine at 37° C. in 5% $CO_2$. Cells were passaged between 1 in 200 and 1 in 2000 in the case of the parental cell line and between 1 in 20 and 1 in 200 in the case of the MDR resistant subline, after trypsinisation (0.25% trypsin, 0.2 gl$^{-1}$, EDTA).

1. Drug accumulation assay

AR 1.0 cells were seeded 48 hours prior to assay into 96 well opaque culture plates (Canberra Packard). The assay medium contained a mixture of tritiated Daunorubicin (DNR) (0.3 µCi/Ml), a cytotoxic agent, and unlabelled DNR ((2 µM). Compounds of formula I were serially diluted in assay medium over a range of concentrations from 0.508 nM to 10 µM. The cells were incubated at 37° C. for 1 hr before washing and determination of cell associated radioactivity. Results are expressed as an IC$_{50}$ for accumulation where 100% accumulation is that observed in the presence of the known RMA verapamil at a concentration of 100 µM.

The results are set out in the following Table A.

TABLE A

| Compound No. | IC$_{50}$ (µM) Accumulation |
|---|---|
| 9591 | 0.425 |
| 9592 | >10 |
| 9594 | 0.087 |
| 9595 | 0.37 |
| 9596 | 0.132 |
| 9597 | 0.087 |
| 9600 | 0.199 |
| 9606 | >10 |
| 9608 | 0.224 |
| 9609 | 0.431 |
| 9612 | 0.087 |
| 9613 | 0.098 |
| 9614 | 0.278 |
| 9615 | 0.213 |
| 9616 | 0.113 |
| 9617 | 0.203 |
| 9621 | 0.453 |
| 9622 | 0.207 |
| 9623 | 1.89 |
| 9625 | 0.347 |
| 9626 | 0.278 |
| 9628 | 2.27 |
| 9629 | >10 |
| 9630 | 0.235 |
| 9631 | 0.669 |
| 9632 | 0.431 |
| 9633 | 0.593 |
| 9634 | 6.955 |
| 9635 | 0.669 |
| 9636 | 0.184 |
| 9638 | 0.552 |
| 9639 | 0.108 |
| 9640 | 0.194 |
| 9641 | 0.0019 |
| 9642 | 0.341 |
| 9643 | 0.425 |
| 9645 | 0.179 |
| 9646 | 0.295 |
| 9647 | 0.033 |
| 9648 | 0.038 |
| 9649 | 0.188 |
| 9650 | 0.061 |
| 9651 | 0.071 |
| 9652 | 0.064 |
| 9653 | 0.490 |
| 9654 | 0.135 |
| 9655 | 0.557 |
| 9656 | 0.188 |
| 9657 | 0.343 |
| 9658 | 2.90 |
| 9659 | 1.38 |
| 9660 | 6.424 |
| 9661 | 0.362 |
| 9663 | 0.175 |
| 9664 | 1.679 |

TABLE A-continued

| Compound No. | IC$_{50}$ (µM) Accumulation |
|---|---|
| 9665 | 0.389 |
| 9666 | 8.672 |
| 9667 | 0.076 |
| 9668 | 0.087 |
| 9669 | 0.469 |
| 9677 | 0.169 |
| 9304 | 1.2 |
| 9405 | 0.3 |
| 9354 | 0.6 |
| 9350 | 0.8 |
| 9401 | 3.0 |
| 9394 | 3.4 |
| 9349 | 0.3 |
| 9398 | 1.5 |
| 9399 | 5.0 |
| 9424 | 2.5 |
| 9420 | 1.9 |
| 9435 | 1.9 |
| 9432 | 3.2 |
| 9410 | 3.0 |
| 9256 | 1.7 |
| 9297 | 0.4 |
| 9395 | 1.3 |
| 9331 | 1.3 |
| 9294 | 0.4 |
| 9295 | 0.39 |
| 9302 | 5.0 |
| 9310 | 1.2 |
| 9334 | 1.3 |
| 9351 | 9.0 |
| 9380 | 0.9 |
| 9381 | 3.0 |
| 9426 | 0.69 |
| 9427 | 0.53 |
| 9442 | 1.0 |
| 9459 | 0.65 |
| 9460 | 1.0 |
| 9377 | 5.5 |
| 9359 | >10 |
| 9384 | >10 |
| 9391 | >10 |
| 9347 | 3.0 |
| 9383 | 2.0 |
| 9385 | 1.2 |
| 9389 | 1.8 |
| 9397 | 10 |
| 9365 | 2.0 |
| 9367 | 1.0 |
| 9531 | 0.035 |
| 9542 | 0.13 |
| 9543 | 0.07 |
| 9554 | 0.99 |
| 9541 | 0.02 |
| 9561 | 0.055 |
| 9562 | 0.024 |
| 9564 | 0.2 |
| 9568 | 0.017 |
| 9573 | 0.0095 |
| 9544 | 0.05 |
| 9571 | 0.022 |
| 9574 | 0.019 |
| 9576 | 0.064 |
| 9578 | 0.084 |
| 9581 | 0.015 |
| 9584 | 0.36 |
| 9588 | 0.094 |
| 9593 | 0.014 |
| 9586 | 0.18 |
| 9589 | 1.0 |
| 9545 | 0.8 |
| 9590 | 0.097 |
| 9472 | 0.5 |
| 9482 | 0.54 |
| 9483 | 1.7 |
| 9493 | 0.22 |
| 9527 | 0.052 |

TABLE A-continued

| Compound No. | IC$_{50}$ (μM) Accumulation |
|---|---|
| 9557 | 0.012 |
| 9582 | 1.27 |
| 9569 | 0.93 |
| 9456 | 0.3 |
| 9510 | 0.71 |
| 9511 | 0.37 |
| 9512 | 3.9 |
| 9489 | 0.15 |
| 9500 | 0.19 |
| 9501 | 0.12 |
| 9513 | 0.2 |
| 9514 | 0.25 |
| 9494 | 0.4 |
| 9495 | 0.5 |
| 9496 | 0.48 |
| 9497 | 1.6 |
| 9503 | 2.0 |
| 9504 | 0.26 |
| 9477 | 0.41 |
| 9517 | 0.4 |
| 9518 | 0.3 |
| 9535 | 0.45 |
| 9549 | 4.3 |
| 9559 | 2.06 |
| 9534 | 0.14 |
| 9540 | 1.2 |
| 9548 | 4.9 |
| 9523 | 1.6 |
| 9524 | 1.0 |
| 9556 | 0.86 |
| 9447 | 0.7 |
| 9461 | 1.8 |
| 9470 | 1.3 |
| 9476 | 0.35 |
| 9536 | 0.45 |
| 9538 | 0.22 |
| 9471 | 0.2 |
| 9492 | 1.0 |
| 9526 | 1.4 |
| 9515 | 1.2 |
| 9539 | 0.22 |
| 9466 | 1.4 |
| 9479 | 2.1 |
| 9567 | 0.16 |
| 9572 | 0.053 |
| 9577 | 0.32 |
| 9585 | 0.04 |

2. Potentiation of Doxorubicin toxicity (a) Selected compounds of formula (I) were examined for their ability to potentiate the toxicity of doxorubicin in AR 1.0 cells. In initial proliferation assays compounds were titrated against a fixed concentration of doxorubicin (0.34 μm) which alone is non-toxic to AR 1.0 cells. After a four day incubation with doxorubicin proliferation was measured using the calorimetric sulphorhodamine B assay (Skehan et al; J Natl. Cancer Inst. 82 pp 1107–1112 (1990)). The results are shown in Table B.

(b) Cells were cultured for four days with a titration of doxorubicin (0.263 nM–17.24 μM) in the presence of a fixed concentration of each compound. Proliferation was quantified as described by Skehen et al, loc cit. The IC$_{50}$ (concentration required to reduce proliferation to 50% of the untreated controls) for doxorubicin alone and with each compound were derived and used to calculate the potentiation index (PI):

$$PI = \frac{IC_{50} \text{ for Doxorubicin alone}}{IC_{50} \text{ for Doxorubicin plus } RMA}$$

The results are shown in Tables C1 and C2.

TABLE B

| Compound No. | Compound Toxicity (IC$_{50}$ μM) | Toxicity with Cytotoxic Agent (IC$_{50}$ μM) |
|---|---|---|
| 9304 | 8.0 | 0.15 |
| 9405 | 22 | 0.09 |
| 9354 | 8.0 | 0.15 |
| 9394 | 10 | 0.1 |
| 9349 | 5.5 | 0.14 |
| 9424 | 39 | 2.6 |
| 9420 | 7.0 | 0.4 |
| 9435 | 9.0 | 0.4 |
| 9432 | 35 | 0.2 |
| 9256 | 40 | 0.3 |
| 9297 | 18 | 0.33 |
| 9395 | 9.0 | 0.15 |
| 9331 | 7.0 | 0.04 |
| 9295 | 40 | 0.6 |
| 9310 | 22 | 0.24 |
| 9334 | 8.0 | 0.05 |
| 9351 | 43 | 1.3 |
| 9380 | 40 | 0.5 |
| 9381 | 50 | 1.5 |
| 9426 | 7.0 | 0.06 |
| 9427 | 10 | 0.10 |
| 9442 | 7.2 | 0.05 |
| 9459 | 8.5 | 0.09 |
| 9460 | 7.5 | 0.18 |
| 9347 | 35 | 0.6 |
| 9383 | 40 | 1.0 |
| 9385 | 40 | 0.55 |
| 9389 | 30 | 0.3 |
| 9365 | 42 | 0.8 |
| 9367 | 15 | 0.5 |
| 9531 | 1.1 | 0.005 |
| 9542 | 1.9 | 0.014 |
| 9543 | 0.9 | 0.008 |
| 9554 | 3.0 | 0.05 |
| 9541 | 0.86 | 0.006 |
| 9561 | 13 | 0.01 |
| 9562 | 1.7 | 0.0028 |
| 9564 | 0.4 | 0.008 |
| 9568 | 2.8 | 0.0034 |
| 9573 | 4.0 | 0.0004 |
| 9544 | 1.9 | 0.0077 |
| 9571 | 2.0 | 0.0008 |
| 9574 | 0.32 | 0.005 |
| 9576 | 0.93 | 0.0018 |
| 9578 | 0.9 | 0.0014 |
| 9581 | 0.31 | 0.0038 |
| 9584 | 8.6 | 0.015 |
| 9588 | 6.7 | 0.005 |
| 9593 | 7.0 | 0.005 |
| 9586 | 7.4 | 0.04 |
| 9589 | 36.8 | 4.4 |
| 9545 | 1.7 | 0.07 |
| 9590 | 9.5 | 0.05 |
| 9472 | 6.5 | 0.12 |
| 9482 | 12 | 0.22 |
| 9483 | 8.5 | 0.35 |
| 9493 | 9.0 | 0.05 |
| 9527 | 4.5 | 0.007 |
| 9557 | 9.0 | 0.02 |
| 9569 | 0.19 | 0.008 |
| 9456 | 5.0 | 0.03 |
| 9510 | 2.8 | 0.05 |
| 9511 | 4.0 | 0.06 |
| 9489 | 7.0 | 0.05 |
| 9500 | 5.0 | 0.009 |
| 9501 | 3.0 | 0.04 |
| 9514 | 7.0 | 0.07 |

TABLE B-continued

| Compound No. | Compound Toxicity (IC$_{50}$ μM) | Toxicity with Cytotoxic Agent (IC$_{50}$ μM) |
|---|---|---|
| 9494 | 9.0 | 0.05 |
| 9495 | 4.0 | 0.04 |
| 9496 | 4.0 | 0.03 |
| 9497 | 9.0 | 0.08 |
| 9503 | 3.5 | 0.09 |
| 9504 | 5.0 | 0.06 |
| 9477 | 4.0 | 0.04 |
| 9517 | 2.0 | 0.05 |
| 9518 | 1.5 | 0.019 |
| 9535 | 2.6 | 0.015 |
| 9549 | 5.6 | 0.52 |
| 9534 | 6.6 | 0.0002 |
| 9540 | 6.2 | 1.0 |
| 9548 | 1.8 | 1.0 |
| 9447 | 6.8 | 0.065 |
| 9461 | 7.5 | 0.3 |
| 9470 | 3.5 | 0.075 |
| 9476 | 2.0 | 0.02 |
| 9536 | 2.65 | 0.015 |
| 9538 | 2.3 | 0.014 |
| 9471 | 2.6 | 0.02 |
| 9492 | 3.0 | 0.02 |
| 9539 | 1.7 | 0.011 |
| 9466 | 6.0 | 0.05 |
| 9567 | 1.7 | 0.028 |
| 9572 | 1.7 | 0.014 |
| 9577 | 7.7 | 0.00035 |
| 9585 | 9.2 | 0.022 |

TABLE C1

| Compound No. | Potentiation Index at RMA Concentration | | | | |
|---|---|---|---|---|---|
| | 100 nM | 50 nM | 30 nM | 20 nM | 10 nM |
| 9594 | 601 | 307 | 159 | | 11 |
| 9595 | 45 | 2.99 | 1.93 | | 1.45 |
| 9596 | 354 | 131 | 44 | | 2.68 |
| 9597 | 878 | 551 | 382 | | 80 |
| 9600 | 2.55 | 1.98 | | | |
| 9608 | 178 | 118 | 60 | 31 | 6.7 |
| 9609 | 68 | 19 | 7.4 | 3.4 | 1.4 |
| 9612 | 171 | 149 | 95 | | 11 |
| 9613 | 168 | 97 | 35 | | 3 |
| 9614 | 52 | 32 | 9 | | 2 |
| 9615 | 175 | 85 | 23 | | 2 |
| 9616 | 185 | 143 | 142 | | 13 |
| 9617 | 81 | 15 | 4 | | 1.5 |
| 9621 | 25 | 4.4 | 1.6 | 1.3 | 1.0 |
| 9622 | 79 | 46 | 15 | 8 | 1.8 |
| 9625 | 60 | 7 | 4 | | 1 |
| 9626 | 27 | 8 | 4 | | 1.2 |
| 9630 | 26 | 6 | 2 | | 1 |
| 9631 | 67 | 20 | 9 | | 1 |
| 9632 | 8 | 2.7 | 2.1 | | 1.1 |
| 9633 | 13.7 | 3.4 | 1.3 | | 1.0 |
| 9635 | 7 | 2 | 1.3 | | |
| 9636 | 131 | 46 | 22 | | 2.6 |
| 9638 | 2.6 | 1.5 | 1.1 | | |
| 9639 | 136 | 78 | 34 | | 2.6 |
| 9640 | 23.8 | 4.6 | 2.5 | | 1 |
| 9641 | 162 | 46 | 17 | | 1.5 |
| 9642 | 14 | 2.5 | 1.2 | | 1.0 |
| 9643 | 6.7 | 2.4 | 1.5 | | 1.0 |
| 9645 | 7.2 | 2.1 | 1.3 | | 1.0 |
| 9646 | 4.8 | 1.3 | 1.1 | | 1.0 |
| 9647 | 6 | 1 | | | |
| 9648 | | | 34 | | 16 |
| 9649 | 66 | 60 | 46 | | 53 |
| 9650 | 33 | 14 | 3 | | 3 |

TABLE C1-continued

| Compound No. | Potentiaton Index at RMA Concentration | | | | |
|---|---|---|---|---|---|
| | 100 nM | 50 nM | 30 nM | 20 nM | 10 nM |
| 9651 | 2.2 | 1.1 | | | |
| 9652 | 7.6 | 1.8 | 1.2 | | |
| 9655 | 65 | 37 | 13 | | 1.8 |
| 9660 | 1.4 | 1.2 | 1.1 | | |
| 9661 | 195 | 71 | 38 | | 1.2 |
| 9663 | 82 | 74 | 80 | | 50 |
| 9664 | 116 | 37 | 1.9 | | 1 |
| 9665 | 50 | 28 | 7 | | 1.4 |
| 9667 | | | | | |
| 9668 | | | | | |
| 9669 | | | | | |
| 9677 | | | | | |

TABLE C2

| Compound No. | Potentiation Index at RMA Concentration: | | | | |
|---|---|---|---|---|---|
| | 500 nM | 300 nM | 100 nM | 30 nM | 10 nM |
| 9304 | 30 | | | | |
| 9405 | 8.6 | | | | |
| 9354 | 20 | | | | |
| 9394 | 12 | | | | |
| 9349 | 22 | | | | |
| 9424 | 37 | | | | |
| 9420 | 25 | | | | |
| 9297 | | | 16 | | |
| 9395 | 21 | | | | |
| 9331 | 120 | | 40 | | |
| 9294 | 71 | | 18 | | |
| 9295 | | | 16 | | |
| 9426 | 65 | | | | |
| 9427 | 32 | | 14 | | |
| 9442 | 67 | | 27 | | |
| 9459 | 112 | | 45 | | |
| 9460 | 36 | | 18 | | |
| 9531 | | 160 | 150 | 120 | 30 |
| 9542 | | 160 | 128 | | |
| 9543 | | 150 | 150 | 120 | 24 |
| 9554 | | | 90 | | |
| 9541 | | 160 | 160 | 150 | 75 |
| 9561 | | | 100 | 60 | 14 |
| 9562 | | | 83 | 60 | 40 |
| 9564 | | | 129 | | |
| 9568 | | | 88 | 60 | 23 |
| 9573 | | | 100 | 94 | 83 |
| 9544 | | 150 | 120 | 67 | 15 |
| 9571 | | | 100 | 100 | 38 |
| 9574 | | | 94 | 60 | 16 |
| 9576 | | | 280 | 225 | 78 |
| 9578 | | | | 188 | 43 |
| 9581 | | | | 300 | 90 |
| 9584 | | | | 36 | 2.1 |
| 9588 | | | | 68 | 6 |
| 9593 | | | | 57 | 6 |
| 9586 | | | | 6 | 5 |
| 9589 | | | | 1 | 1 |
| 9590 | | | | 14 | 2 |
| 9483 | 24 | | 14 | | |
| 9493 | 200 | | 85 | 7.6 | |
| 9527 | 120 | | 103 | 50 | 11 | 1.5 |
| 9557 | | | 100 | | 1.2 |
| 9456 | | | 112 | | |
| 9510 | 267 | | 120 | 12 | |
| 9511 | 214 | | 120 | 12 | |
| 9489 | 303 | | 192 | 77 | |
| 9500 | | | 300 | 97 | 5.5 |
| 9501 | | | 183 | 69 | 1.9 |

TABLE C2-continued

| Compound No. | Potentiation Index at RMA Concentration: | | | |
|---|---|---|---|---|
| | 500 nM | 300 nM | 100 nM | 30 nM | 10 nM |
| 9514 | 120 | 40 | | | |
| 9494 | 148 | 38 | | | |
| 9495 | 567 | 261 | 15 | 1.3 | |
| 9496 | 825 | 254 | 19 | 1.6 | |
| 9497 | 200 | 52 | | | |
| 9503 | 77 | 36 | | | |
| 9504 | 267 | 150 | 34 | | |
| 9477 | 63 | 29 | | | |
| 9517 | 120 | 40 | | | |
| 9518 | 240 | 120 | | | |
| 9535 | | | 128 | 32 | |
| 9447 | 340 | 40 | | | |
| 9461 | 30 | 13 | | | |
| 9470 | 90 | 26 | | | |
| 9476 | 136 | 83 | | | |
| 9536 | | | 128 | 32 | |
| 9538 | | | 128 | 43 | |
| 9471 | 230 | 115 | | | |
| 9539 | | | 128 | 32 | |
| 9466 | 60 | 30 | | | |
| 9567 | | | 112 | 8 | 1.7 |
| 9572 | | | 83 | 25 | 2.7 |
| 9577 | | | 112 | 18 | 2.2 |
| 9585 | | | | 7.2 | 1.3 |

3. Potentiation of toxicity of various cytotoxic agents

The potentiation indices of a selection of compounds using a variety of cell lines and a variety of cytotoxics other than doxorubicin were measured following the protocol described above for doxorubicin, and the results are shown in Table D.

TABLE D

| Compound No. | Cell line | Cytotoxic | Potentiaton Index at RMA Concentration | | |
|---|---|---|---|---|---|
| | | | 50 nM | 30 nM | 10 nM |
| 9594 | 2780AD | Taxol | 1126 | 425 | 18 |
| 9594 | H69/LX4 | Vincristine | 356 | 79 | 2 |
| 9594 | AR 1.0 | Taxol | 407 | 308 | 50 |
| 9596 | 2780AD | Taxol | 743 | 160 | 3.5 |
| 9596 | H69/LX4 | Vincristine | 158 | 2 | 1 |
| 9597 | 2780AD | Taxol | 2070 | 1427 | 110 |
| 9597 | H69/LX4 | Vincristine | 44 | 41 | 1 |
| 9608 | H69/LX4 | Taxol | 130 | 17 | 1.6 |
| 9609 | H69/LX4 | Taxol | 9 | 3 | 1 |
| 9612 | H69/LX4 | Taxol | 1329 | 894 | 51 |
| 9613 | H69/LX4 | Taxol | 877 | 236 | 2.2 |
| 9614 | H69/LX4 | Taxol | 11 | 1.1 | |
| 9576 | AR 1.0 | Etoposide | 51 | 45 | 26 |

Reference Example 1A

Preparation of amines of general formula IX

Amines of general formula IX were prepared as shown in the following Table 1

TABLE 1

| Amine IX | Structure | Preparation Reference |
|---|---|---|
| IX.a | [structure: 4-aminophenethyl-6,7-dimethoxy-1,2,3,4-tetrahydroisoquinoline] | see compound 2.2 in Example 2 of WO-A-96/20180 |
| IX.b | [structure: N-methyl-N-(3,4-dimethoxybenzyl)-4-aminophenethylamine] | see Method IX.b below |
| IX.c | [structure: 4-aminophenylthioethyl-6,7-dimethoxy-1,2,3,4-tetrahydroisoquinoline] | see Method IX.c below |
| IX.d | [structure: 4-aminophenoxyethyl-6,7-dimethoxy-1,2,3,4-tetrahydroisoquinoline] | see Method IX.d below |

TABLE 1-continued

| Amine IX | Structure | Preparation Reference |
|---|---|---|
| IX.e | 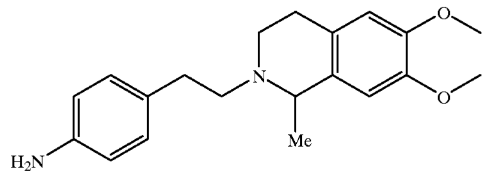 | see Method IX.e below |
| IX.f | 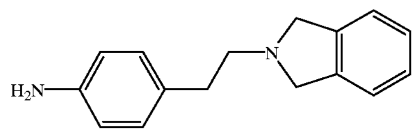 | see Method IX.f below |
| IX.g | 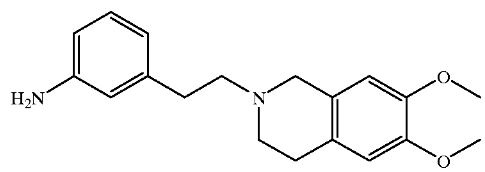 | see Method IX.g below |
| IX.h | 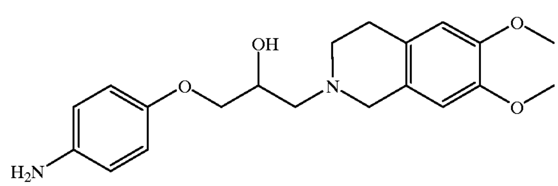 | see Method IX.h below |
| IX.i | 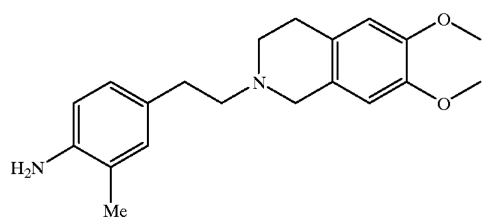 | see Method IX.i below |
| IX.j | 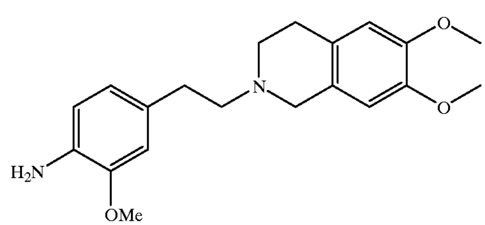 | see Method IX.j below |
| IX.k | 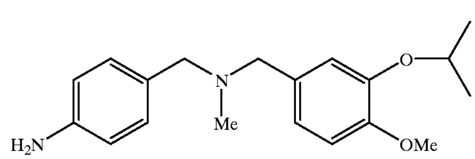 | see Method IX.k below |
| IX.l | 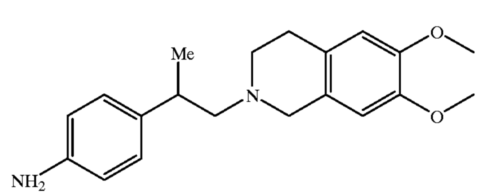 | see Method IX.l below |

TABLE 1-continued

| Amine IX | Structure | Preparation Reference |
|---|---|---|
| IX.m | (structure) | see Method IX.m below |
| IX.n | (structure) | see Method IX.n below |
| IX.o | (structure) | see Method IX.o below |
| IX.p | (structure) | see Method IX.p below |

Method IX.b

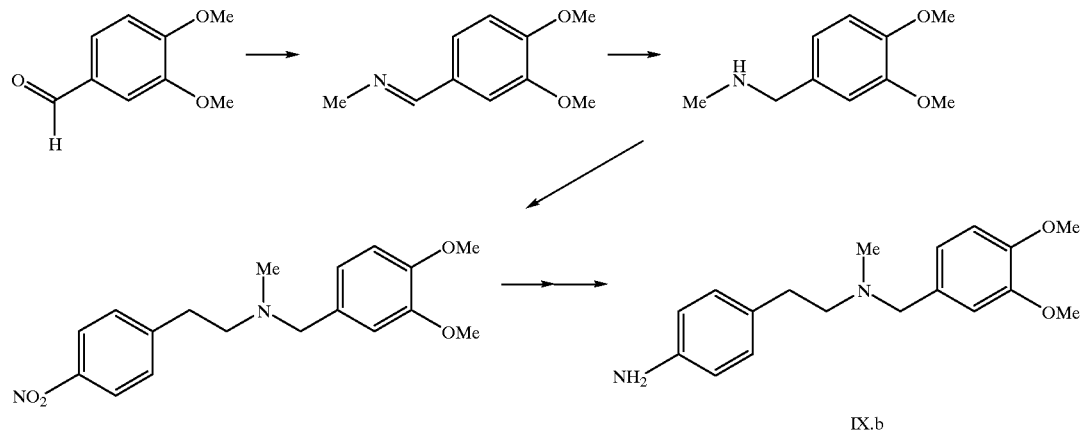

IX.b

Reductive amination of 3,4-dimethoxybenzaldehyde was performed as described in Method 2b(iv) to yield the intermediate secondary amine. Alternatively this amine may be prepared by reaction of veratrylamine with methyl chloroformate, followed by reduction of the carbamate using lithium aluminium hydride. A mixture of the amine (3.76 g), 4-nitrophenethylbromide (4.78 g) and sodium carbonate (3.3 g) in acetonitrile (25 ml) was heated to reflux for 3 hours. After cooling, aqueous work-up yielded an orange oil (1.75 g). The nitro group was reduced under an atmosphere of hydrogen over platinum(IV) dioxide catalyst in ethanol to yield amine IX.b (1.3 g).

Method IX.c

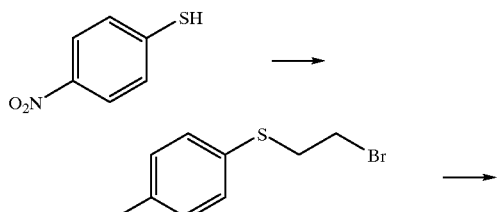

IX.c

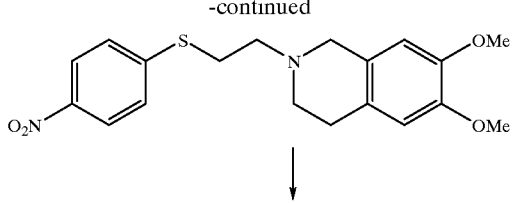

mixture was heated to 80° C. for 2 hours. Aqueous work-up yielded amine IX.c as a gum(195 mg, 90%).

Method IX.d

This was prepared in an analogous method to IX.c using p-nitrophenol as the starting material. Reduction of the nitro group in this case was performed under an atmosphere of hydrogen over platinum(IV) dioxide catalyst in ethanol.

Method IX.e

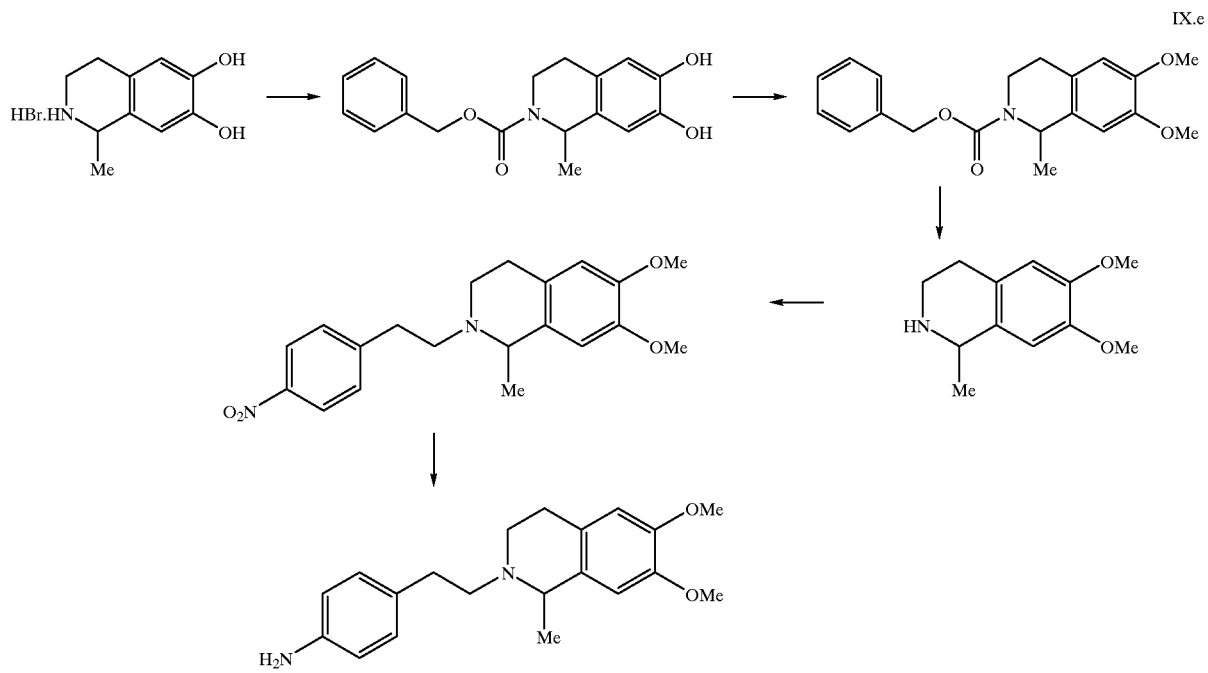

IX.e

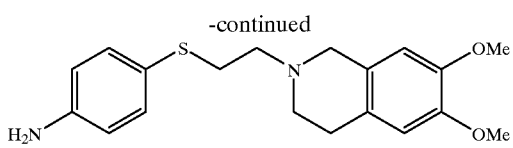

A mixture of 4-nitrothiophenol (1.00 g, 6.44 mmol), 1,2-dibromoethane (1.39 ml, 2.5 equivalents) and potassium carbonate (2.22 g, 2.5 equivalents) in acetonitrile(15 ml) was stirred at room temperature for 30 minutes. Aqueous work-up and fractional crystallisation gave the intermediate bromide(0.8 g, 47%).

A mixture of the bromide (336 mg, 1.28 mmol), 6,7-dimethoxy-1,2,3,4-tetrahydroisoquinoline hydrochloride (294 mg, 1.28 mmol) and potassium carbonate (372 mg, 2.1 equivalents) was heated to reflux in acetonitrile (10 ml) for 3 hours. Aqueous work-up and flash chromatography (ethyl acetate/hexane) yielded the desired tertiary amine(236 mg, 49%). Conc. hydrochloric acid(0.3 ml) was added to a suspension of the tertiary amine (236 mg, 0.63 mmol) in methanol(2 ml), iron(151 mg) was added, and the reaction Sodium carbonate (611 mg, 5.76 mmol) was added to a stirred solution of 1-methyl-6,7-dihydroxy-1,2,3,4-tetrahydroisoquinoline hydrobromide (1.0 g, 3.84 mmol) in acetone-water (25 ml, 4:1). The mixture was cooled to 0° C. before adding benzylchloroformate (0.63 ml, 4.19 mmol). The mixture was allowed to warm up to RT and stirred for 2 days. The reaction mixture was filtered and separated and the filtrate concentrated under vacuum. The resulting aqueous solution was poured into EtOAc (80 ml), and the organic phase was washed with water (3×40 ml), then brine (40 ml), dried (MgSO$_4$) then concentrated under vacuum to afford a brown oil. Purification by flash chromatography (SiO$_2$; hexane:EtOAc, 1:1) afforded the benzyl carbamate (817 mg) as a white foam.

Sodium hydride (60% dispersion; 2.10 g, 0.05 mol) and methyl iodide (27.25 ml, 0.44 mol) were added to a solution of the benzyl carbamate(2.74 g, 8.75 mmol) in THF (100 ml). DMSO (50 ml) was then added and the reaction mixture heated at reflux over night. The reaction mixture was poured into EtOAc (200 ml) and water (100 ml). The organic phase was extracted, washed with water (3×100 ml) and brine (10 ml)), then dried (MgSO$_4$) to give a brown oil. Purification by flash chromatography (SiO$_2$; hexane:EtOAc, 2:1) afforded the dimethoxy intermediate (2.7 g) as a yellow crystalline solid.

The benzyl carbamate group was cleaved by dissolving the intermediate (2.7 g, 8.63 mmol) in MeOH/CH$_2$Cl$_2$ (1:1, 270 ml) and reducing with Pd/activated C (700 mg) for 4 days at atmospheric pressure and at 40 p.s.i for a further 12 hours. Filtration and reduction in vacuo afforded the crude secondary amine(1.89 g) as an orange oil.

The amine was then reacted with 4-nitrophenethylbromide and reduced as in Method IX.b to yield amine IX.e as an orange solid.

Method IX.f

Method IX.f

IX.f

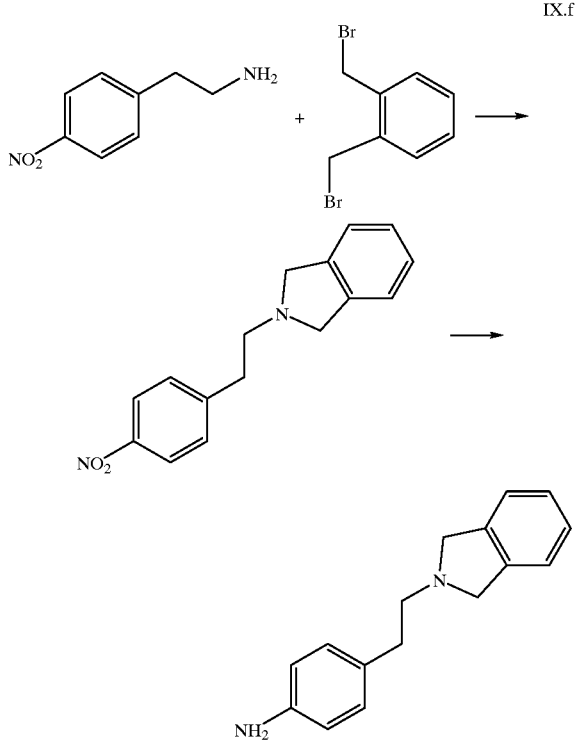

A mixture of 4-nitrophenethylamine hydrochloride (770 mg, 3.8 mmol), α,α-dibromo-o-xylene (1.00 g, 3.8 mmol) and potassium carbonate(1.83 g, 13.3 mmol) was heated to reflux in acetonitrile(20 ml) for 2 hours. Aqueous work-up and flash chromatography (5% methanol in dichloromethane) yielded the desired tertiary amine (297 mg, 29%).

The nitro group was reduced using atmospheric hydrogenation over platinum(IV) dioxide catalyst in a methanol/dichloromethane mixture, and purified using flash chromatography(ethyl acetate/hexane)to yield amine IX.f (187 mg, 71%).

Method IX.g

IX.g

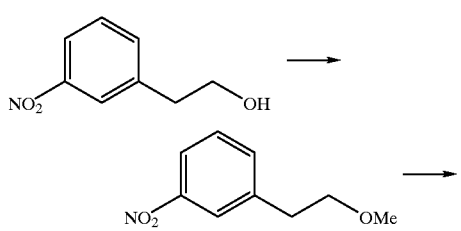

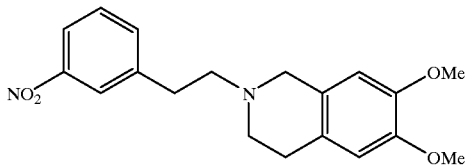

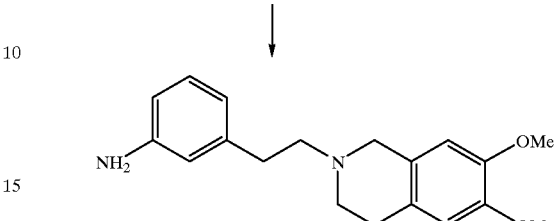

A mixture of 3-nitrophenethyl alcohol (2.11 g), methanesulphonyl chloride (2.44 ml, 2.5 equivalents) and triethylamine (1.76 ml, 2 equivalents) in dichloromethane was stirred at 0° C. for 4.5 hours. Aqueous work-up afforded the desired mesylate as a yellow solid (2.27 g, 73%). To a solution of the mesylate(2.27 g,) in N,N-dimethylformamide (20 ml) was added 6,7-dimethoxy-1,2,3,4-tetrahydroisoquinoline hydrochloride (2.13 g, 1 equiv.) and potassium carbonate(3.2 g, 2.5 equivs.), and the reaction mixture heated to 100° C. for 4 hours. Aqueous work-up yielded the tertiary amine as a yellow oil (1.49 g, 47%).

Reduction of the nitro group in this case was performed under an atmosphere of hydrogen over platinum(IV) dioxide catalyst in ethanol and dichloromethane to yield IX.g (1.11 g).

Method IX.h

Method IX.h

IX.h

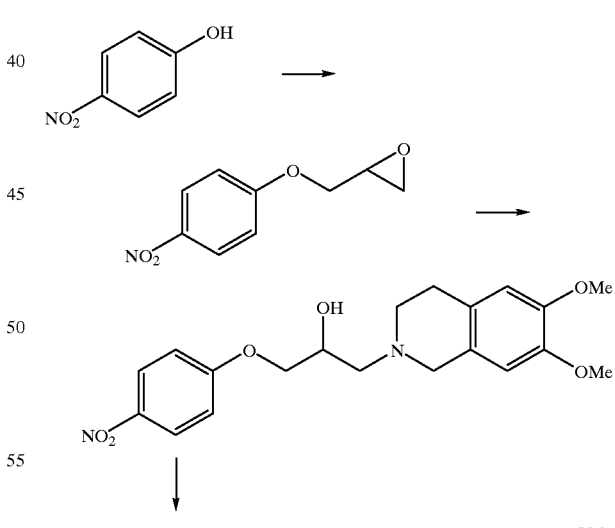

A mixture of 4-nitrophenol(10 g, 72 mmol), epichlorohydrin(11.2 ml, 144 mmol) and potassium carbonate(10 g, 72 mmol) was stirred in N,N-dimethylformamide at room temperature for 18 hours. Aqueous work-up yielded the intermediate epoxide as an off-white crystalline solid (10.8 g, 77%).

A mixture of the epoxide (1.09 g, 5.6 mmol), 6,7-dimethoxy-1,2,3,4-tetrahydroisoquinoline hydochloride (2.1 g, 9.3 mmol) and potassium carbonate (1.3 g, 9.3 mmol) in tetrahydrofuran (20 ml) and water (5 ml) was stirred at room temperature for 72 hours. Aqueous work-up and purification using flash chromatography(ethyl acetate) yielded the desired alcohol as a white solid (390 mg, 50%). Hydrogenation of the nitro group was performed as described in Method IX.b to yield amine IX.h.

Method IX.i before filtrating to afford the diazoketone(2.03 g) as pale brown crystals.

A solution of the diazoketone(2.0 g, 10.0 mmol) in EtOH (13 mmol) was heated at reflux to give a brown solution before adding slowly a solution of silver benzoate (125 mg, 0.54 mmol) in $NEt_3$ (2 ml). The mixture turned black and $N_2$ gas evolved. Further portions of silver benzoate were added until no more gas evolved and the reflux was continued for 55 min. The reaction mixture was filtered through celite, then concentrated under vacuum to afford a brown liquid. Purification by flash chromatography ($SiO_2$; 5% hexane-EtOAc) afforded the desired ethyl ester (1.46 g) as a yellow liquid. The ethyl ester (1.35 g, 6.05 mmol) was dissolved in 1,4-dioxane (50 ml) and water (20 ml) added until turbid. $LiOH.H_2O$ (762 mg, 0.017 mol) was added and the mixture Method IX.i IX.i

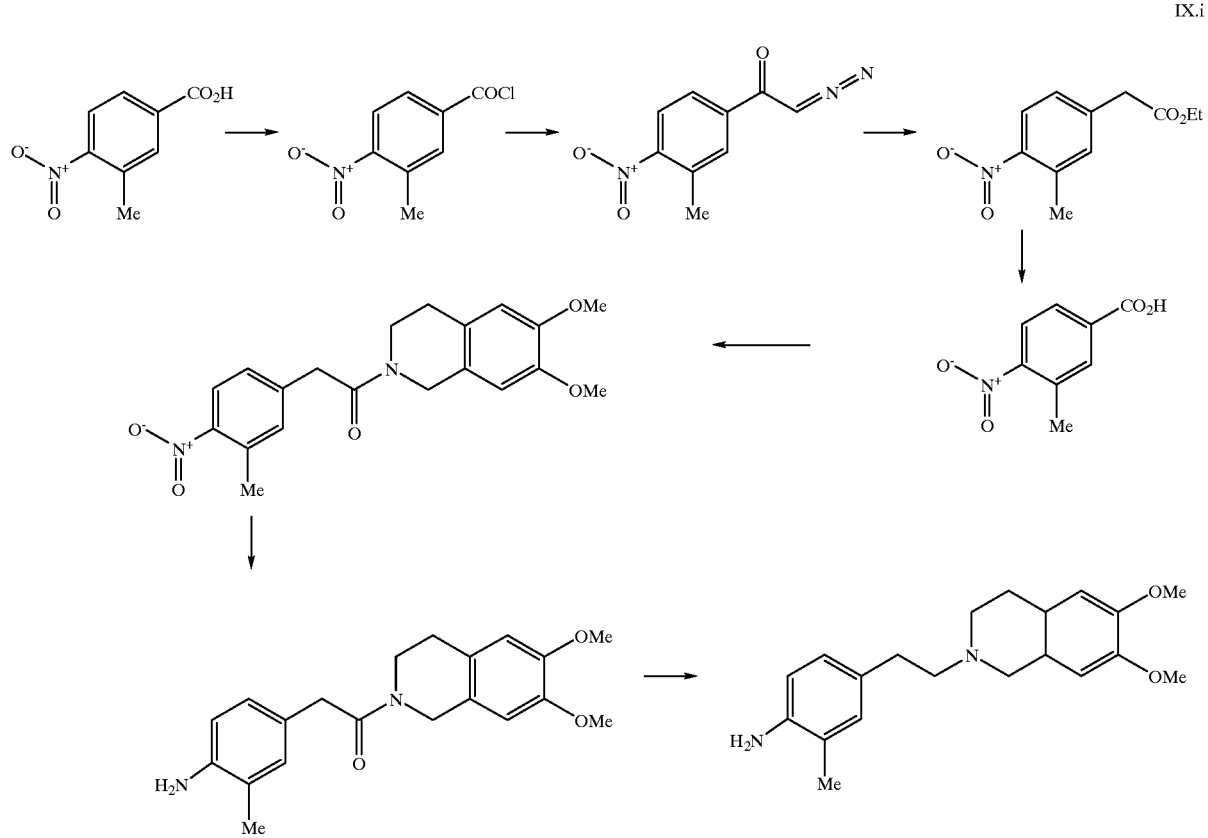

A solution of 3-methyl-4-nitrobenzoic acid (5.0 g, 0.03 mol) and thionyl chloride (10 ml) in toluene 100 ml) was heated at reflux for 3 hrs then allowed to cool over night. The reaction mixture was reduced then azeotroped with toluene and hexanes to afford the acid chloride(quantitative) as an off-white, low melting solid. To diazomethane (prepared from N-methyl-N-nitrosotoluene-p-sulphonamide in excess, as described in Vogel's Practical Organic Chemistry, 4th edition, p 293) was added $NEt_3$ (4 ml). The reaction mixture was cooled (ice-bath) before adding slowly the acid chloride in $Et_2O$. After 2 hrs acetic acid was added until no more $N_2$ gas evolved. The reaction mixture was filtered, concentrated under vacuum, and the residue dissolved in $Et_2O$, washed (sat.$NH_4Cl$, aq. $K_2CO_3$, brine), dried ($Na_2SO_4$) and reduced until crystallisation began. Left to crystallise in the fridge stirred at RT over night. The reaction mixture was made acidic with hydrochloric acid, extracted into $CH_2Cl_2$ (3×80 ml), dried ($MgSO_4$) and concentrated under vacuum to afford the desired acid (633 mg) as orange crystals.

A mixture of the acid (630 mg, 8.23 mmol) and 1-hydroxybenzotriazole hydrate (546 mg, 4.04 mmol) in DMF (30 ml) was stirred at RT for 10 min. 6,7-Dimethoxy-1,2,3,4-tetrahydroisoquinoline (780 mg, 4.04 mmol) was added, followed by dicyclohexyl carbodiimide (667 mg, 3.23 mmol) and the reaction mixture stirred over night. The reaction mixture was filtered and the filtrate concentrated in vacuo, treated with dilute hydrochloric acid, and then dilute sodium hydroxide solution and extracted into $CH_2Cl_2$. The organic phase was washed (water then brine), dried ($Na_2SO_4$). The solvent was evaporated under vacuum to give a yellow residue. Purification by flash chromatography (SiO$_2$; hexane:EtOAc, 1:1) afforded the desired amide (760 mg) as an off-white crystalline solid. The nitro group was reduced using similar conditions as described in Method IX.b with Pd/activated C (50 mg). Purification by flash chromatography(SiO$_2$; hexane:EtOAc, 1:1) afforded the intermediate amine (695 mg) as a white foam. The amide (730 mg, 2.15 mmol) was reduced by adding a solution in tetrahydrofuran (10 ml) to a stirred suspension of lithium aluminium hydride (244 mg, 6.43 mmol) in THF (5 ml) at RT. The reaction mixture was refluxed for 2 hrs, then cooled before carefully adding water (0.5 ml) in CH$_2$Cl$_2$ (20 ml). MgSO$_4$ was added and the reaction mixture stirred for 10 min, filtered and the filtrate evaporated under vacuum to afford the desired amine IX.i (661 mg) as an off-white crystalline solid.

Method IX.j

Using 3-methoxy-4-nitrobenzoic acid as the starting material, amine IX.j was prepared using an analogous method to IX.i.

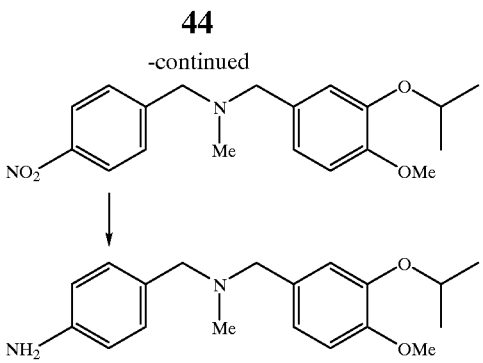

A mixture of the amine (336 mg, 1.61 mmol), 4-nitrobenzyl bromide (289 mg, 1.34 mmol) and potassium carbonate (277 mg, 2.01 mmol) in acetonitrile (50 ml) was stirred at room temperature for 2.5 hours. Aqueous work-up afforded the desired intermediate and the nitro group was then reduced as in Method IX.b to yield IX.k as a yellow oil (380 mg).

Method IX.l

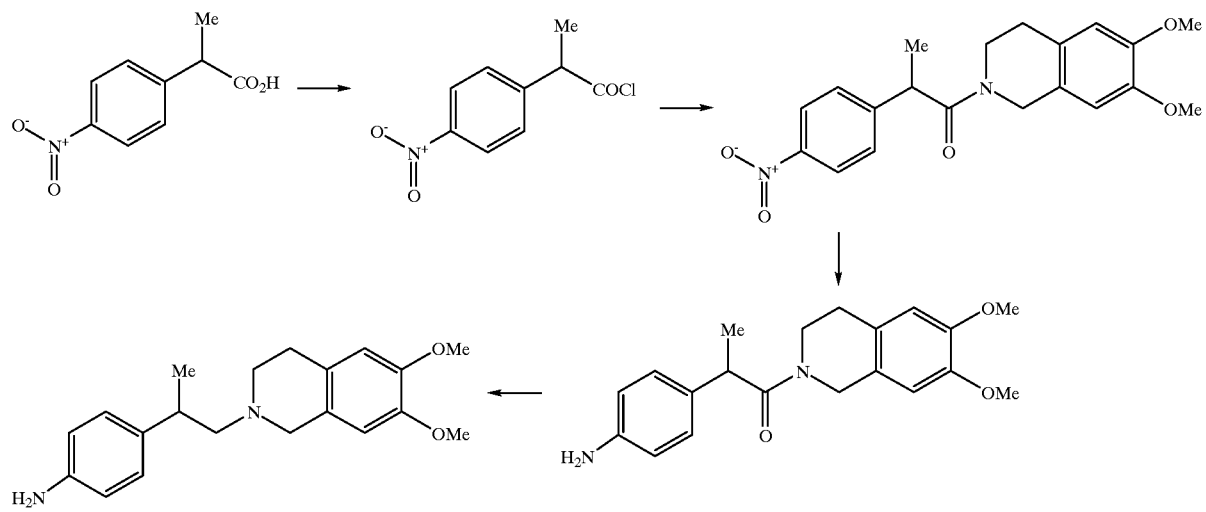

Method IX.k

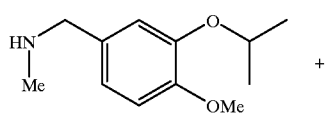

For synthesis of this amine see Method 2b(v)

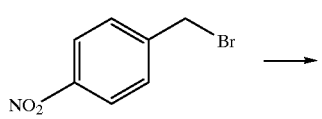

A mixture of 2-(4-nitrophenyl)propionic acid (5.0 g, 26 mmol) and thionyl chloride (3.75 g, 52 mmol) was heated to reflux in toluene (30 ml) for 2 hours before cooling and removing the solvent in vacuo to yield the acid chloride. The acid chloride (5.47 g, 26 mmol) was dissolved in dichloromethane (50 ml) at 0° C. and to this solution was added 6,7-dimethoxy-1,2,3,4-tetrahydroisoquinoline (3.7 g, 24 mmol) and triethylamine (5.4 ml, 39 mmol) and the reaction mixture was stirred for 7 hours. Acid/base work-up and flash chromatography (1% methanol in dichloromethane) yielded the desired amide (4.98 g, 56%).

The nitro group was reduced using atmospheric hydrogenation over palladium on carbon, and the amide was reduced to the desired amine IX.l using lithium aluminium hydride in tetrahydrofuran.

Method IX.m

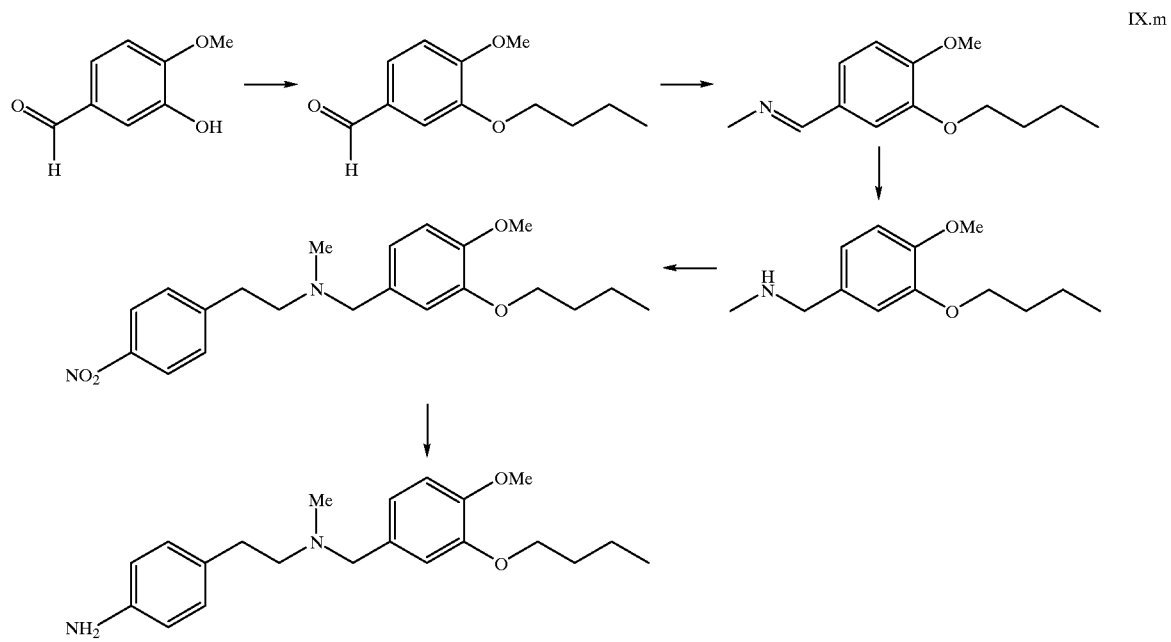

Isovanillin was alkylated with iodobutane and then reductive amination was carried out as described in Method 2b(iv) to yield the intermediate secondary amine. Reaction of this amine with 4-nitrophenethylbromide in acetonitrile, and then hydrogenation of the nitro group under atmospheric hydrogen over platinum(IV) dioxide catalyst yielded the desired amine IX.m.

Method IX.n

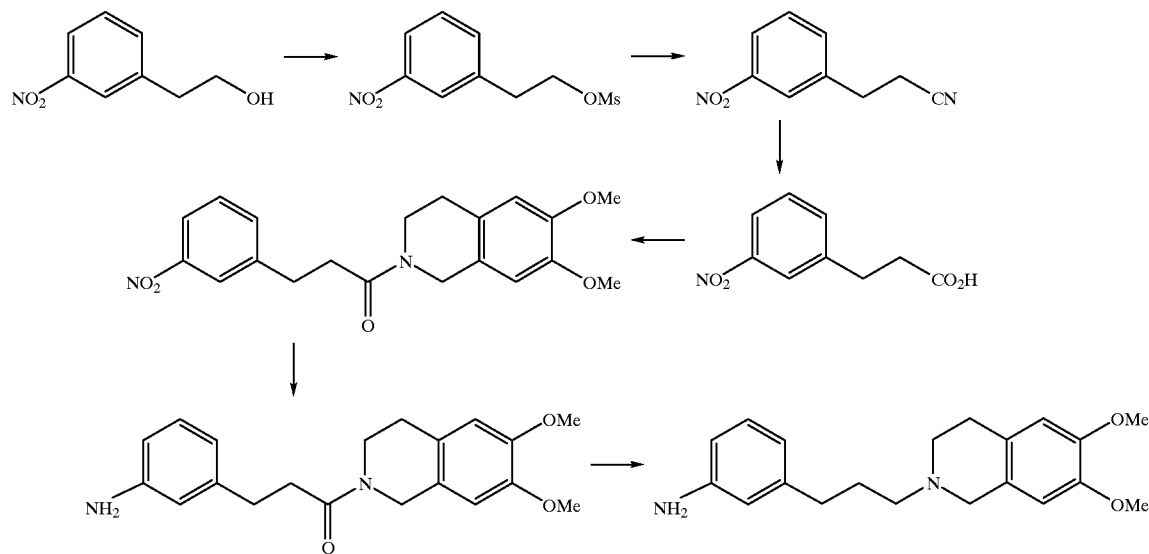

The mesylate was prepared from 3-nitrophenethylbromide as for Method IX.g. A mixture of the mesylate (1.0 g, 4.1 mmol) and sodium cyanide (400 mg, 8.2 mmol) was stirred in dimethylsulphoxide (25 ml) at 90° C. for 7 days. Aqueous work-up yielded the desired nitrile (651 mg, 91%).

The nitrile (615 mg) was heated to reflux in a 1.5M solution of sodium hydroxide (25 ml) for 5 hours. Aqueous work-up afforded the intermediate carboxylic acid (548 mg). This was converted to the acid chloride using thionyl chloride in toluene and then reacted with 6,7-dimethoxy-1, 2,3,4-tetrahydroisoquinoline to yield the amide. The amide and the nitro group were then reduced in an analogous manner to Method IX.i to yield amine IX.n.

Method IX.o

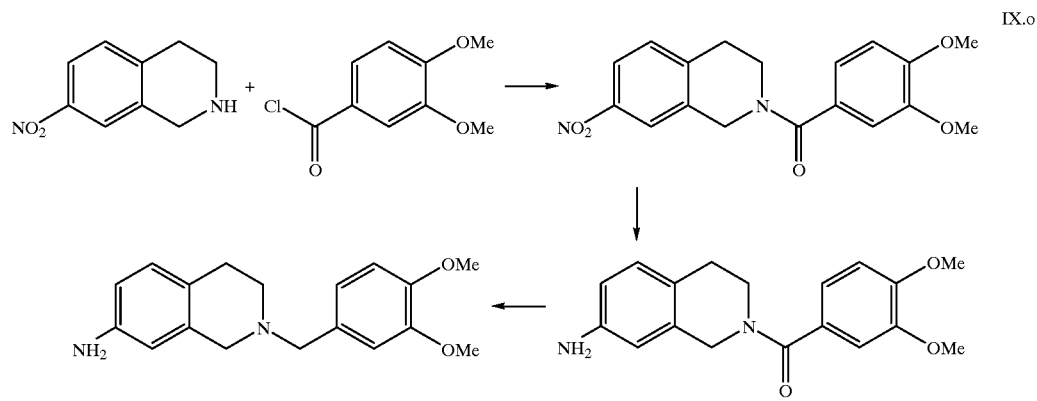

A mixture of 3,4-dimethoxybenzoyl chloride (3.9 g, 19.2 mmol) and 7-nitro-1,2,3,4-tetrahyroisoquinoline (2.81 g, 15.8 mmol) in dichloromethane (200 ml) was stirred for 2 hours and then filtered. The filtrate was collected and after aqueous work-up and flash chromatography (1–10% methanol in dichloromethane) the desired amide was afforded as a yellow oil (3.25 g, 46%). Reduction of the nitro group and the amide is then analogous to Method IX.i. Amine IX.o was obtained as a yellow oil (1.37 g).

Method IX.p

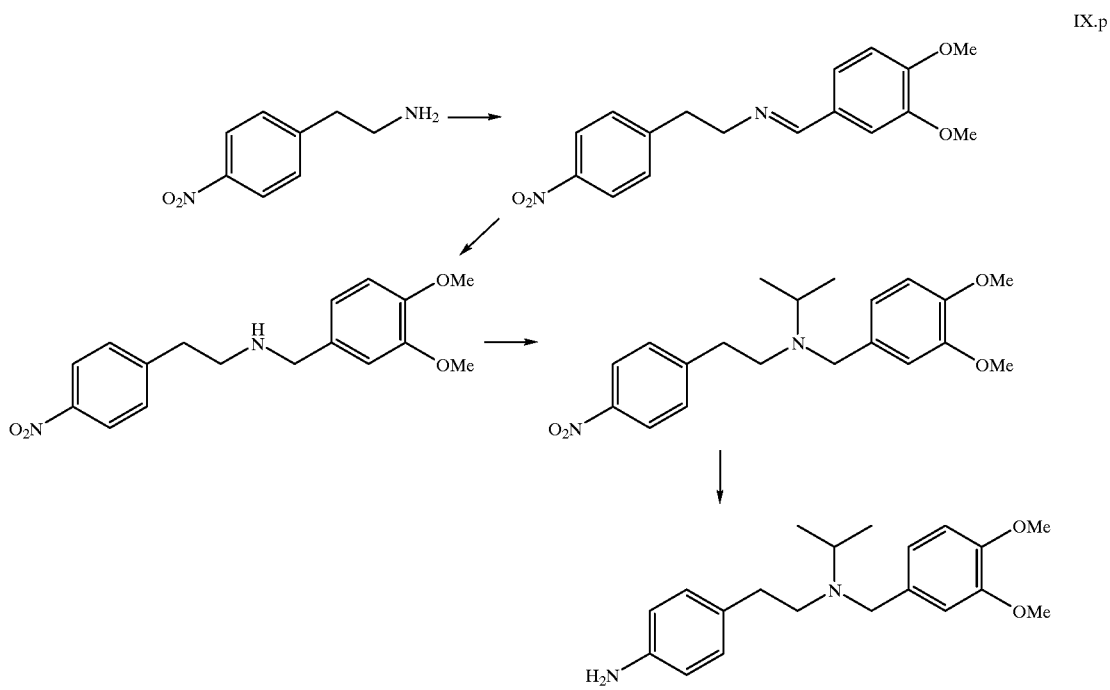

4-Nitrophenethylamine hydrochloride and 3,4-dimethoxybenzaldehyde were stirred in methanol with triethylamine for 3 hours. Hexane was then added to prepicitate the desired imine which was collected by filtration. The imine was reduced to the intermediate secondary amine using sodium borohydride in methanol, and this amine was then alkylated by heating to reflux for 16 hours with 2-iodopropane and potassium carbonate in acetonitrile. Hydrogenation of the nitro group using palladium on carbon under an atmosphere of hydrogen yielded amine IX.p as a yellow gum.

Reference Example 1B

Preparation of Amines of General Formula IX'

Amines of general formula IX' were prepared as shown in the following table 3.

TABLE 3

(IX')

| Amine IX' | r | s | $R^{11}$ | $R^{21}$ | Preparation Reference |
|---|---|---|---|---|---|
| IX'.a | 0 | 2 | OMe | OMe | see compound 3.5 in Example 3 of WO-A-96/20180 |
| IX'.b | 1 | 2 | OMe | OMe | see compound 2.2 in Example 2 of WO-A-96/20180 |
| IX'.c | 0 | 2 | H | H | see compound 3.4 in Example 3 of WO-A-96/20180 |
| IX'.d | 0 | 3 | OMe | OMe | see below |
| IX'.e | 1 | 1 | OMe | OMe | see compound 2.7 in Example 2 of WO-A-96/20180 |
| IX'.f | 1 | 3 | OMe | OMe | see compound 2.10 in Example 2 of WO-A-96/20180 |
| IX'.g | 1 | 2 | H | H | see compound 2.3 in Example 2 of WO-A-96/20180 |

Preparation of 3-(6,7-Dimethoxy-3,4-dihydro-1H-isoquinolin-2-yl)-propylamine (IX'd)

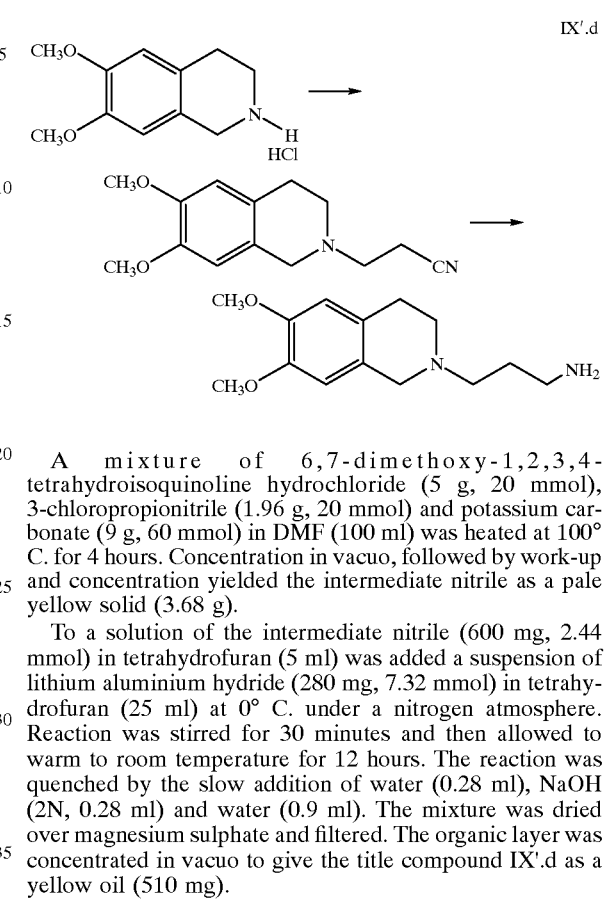

A mixture of 6,7-dimethoxy-1,2,3,4-tetrahydroisoquinoline hydrochloride (5 g, 20 mmol), 3-chloropropionitrile (1.96 g, 20 mmol) and potassium carbonate (9 g, 60 mmol) in DMF (100 ml) was heated at 100° C. for 4 hours. Concentration in vacuo, followed by work-up and concentration yielded the intermediate nitrile as a pale yellow solid (3.68 g).

To a solution of the intermediate nitrile (600 mg, 2.44 mmol) in tetrahydrofuran (5 ml) was added a suspension of lithium aluminium hydride (280 mg, 7.32 mmol) in tetrahydrofuran (25 ml) at 0° C. under a nitrogen atmosphere. Reaction was stirred for 30 minutes and then allowed to warm to room temperature for 12 hours. The reaction was quenched by the slow addition of water (0.28 ml), NaOH (2N, 0.28 ml) and water (0.9 ml). The mixture was dried over magnesium sulphate and filtered. The organic layer was concentrated in vacuo to give the title compound IX'.d as a yellow oil (510 mg).

Reference Example 2A

Preparation of 2-nitrobenzamides of General Formula V

V.13

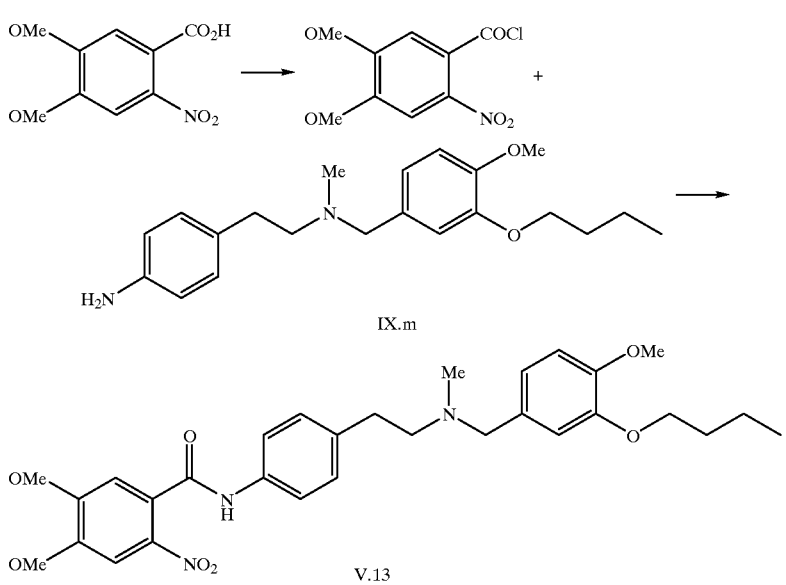

A mixture of 4,5-dimethoxy-2-nitrobenzoic acid (7.0 g, 0.031 mol) and thionyl chloride (4.5 ml, 2 equivalents) was heated to reflux in toluene (140 ml) for 2 hours. After cooling the solvent was removed in vacuo to yield the acid chloride as a yellow solid(quantitative yield).

A mixture of acid chloride (851 mg), amine IX.m (1.09 g), and triethylamine (1 equivalent) in dichloromethane (18 ml) was stirred for 18 hours at room temperature. Aqueous work-up and flash chromatography(ethyl acetate) yielded the desired 2-nitrobenzamide V.13 as a white solid (737 mg).

Following an analogous synthetic route and utilising the appropriately substituted nitrobenzoic acid or nitrobenzoyl chloride and amine IX, the nitro compounds of formula V listed in Table 4 were prepared.

TABLE 4

| Nitrobenzoic Acid or Nitrobenzoyl chloride | Amine IX | Nitrobenzamide V |
|---|---|---|
| 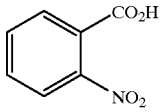 | IX.a | 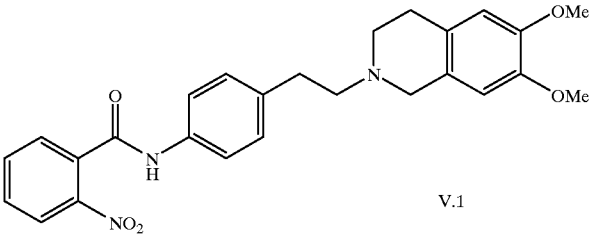 V.1 |
| 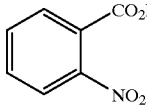 | IX.b | 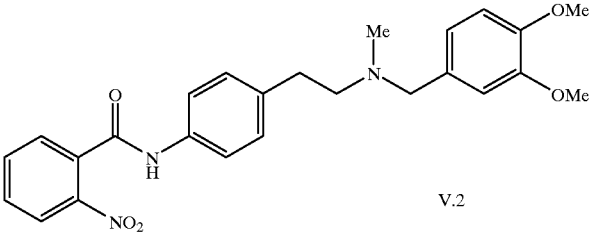 V.2 |
| 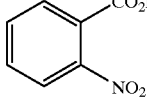 | IX.c | 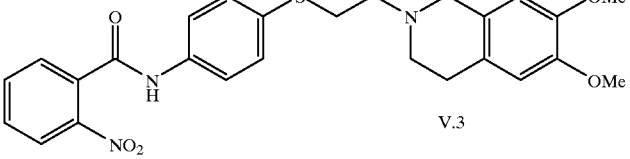 V.3 |
| 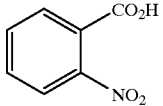 | IX.d | 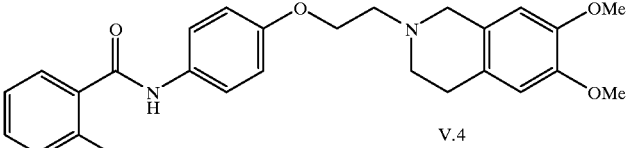 V.4 |
| 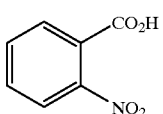 | IX.e | 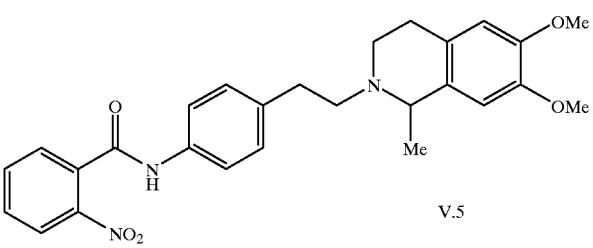 V.5 |

TABLE 4-continued

| Nitrobenzoic Acid or Nitrobenzoyl chloride | Amine IX | Nitrobenzamide V |
| --- | --- | --- |
| 2-nitrobenzoic acid | IX.f | V.6 |
| 2-nitrobenzoic acid | IX.g | V.7 |
| 2-nitrobenzoic acid | IX.h | V.8 |
| 2-nitrobenzoic acid | IX.i | V.9 |
| 2-nitrobenzoic acid | IX.j | V.10 |
| 2-nitrobenzoic acid | IX.k | V.11 |

TABLE 4-continued

| Nitrobenzoic Acid or Nitrobenzoyl chloride | Amine IX | Nitrobenzamide V |
|---|---|---|
| 2-nitrobenzoic acid | IX.l | V.12 |
| 2-nitrobenzoic acid | IX.n | V.14 |
| 2-nitrobenzoic acid | IX.o | V.15 |
| 5-fluoro-2-nitrobenzoic acid | IX.a | V.16 |
| 5-chloro-2-nitrobenzoic acid | IX.a | V.26 |
| 2-nitrobenzoic acid | IX.p | V.28 |

In a variation of the above scheme a 2-nitro-5-halobenzamide such as V.16 or V.26 may be converted into another compound of formula V by the displacement of the halide with a suitable nucleophile such as an amine or a thiol in a suitable solvent such as N.N-dimethylformamide or acetonitrile.

V.18

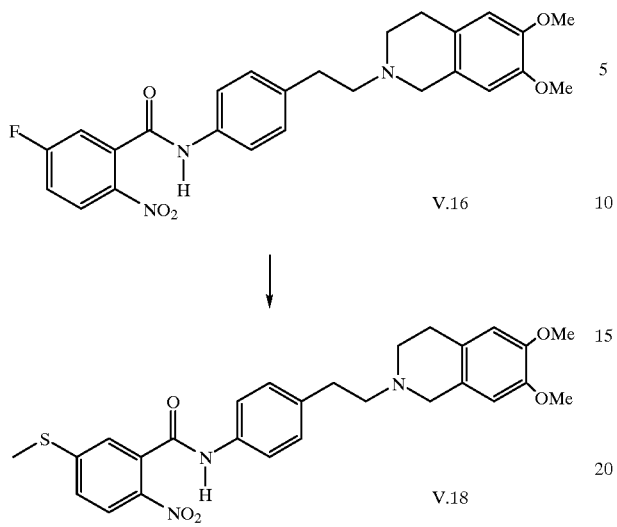

To a solution of V.16 (200 mg, 0.42 mmol) in N,N-dimethylformamide (2 ml) was added sodium thiomethoxide (50 mg, 0.72 mmol) and the reaction mixture was stirred at room temperature for 72 hours. The mixture was then diluted with ethyl acetate, washed with brine, dried over magnesium sulphate and the solvent removed in vacuo to yield V.18 as a yellow solid (190 mg, 89%).

Nitrobenzamide V.17 was prepared by heating to reflux a mixture of V.26 in acetonitrile with excess dimethylamine (40% aqueous solution) for 8 hours.

V.17

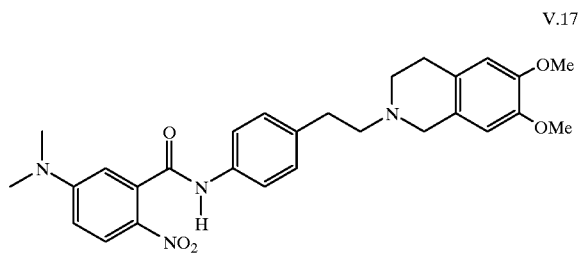

Reference Example 2B

Preparation of 2-nitrobenzamides of General Formula VI'

N-{4-[2-(6,7-Dimethoxy-3,4-dihydro-1H-isoquinolin-2-yl)-ethyl]-phenyl}-2-nitro-4-trifluoromethyl-benzamide (VI'.24)

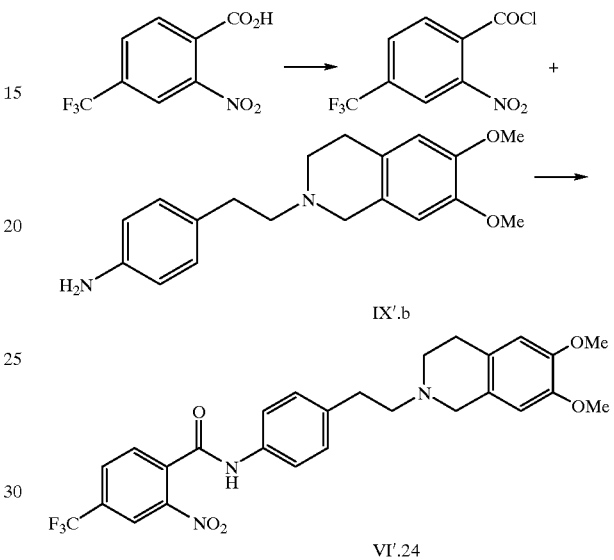

A mixture of 2-nitro-α,α,α-trifluoro-p-toluic acid (0.25 g, 1.06 mmol), thionyl chloride (0.5 ml) and toluene (5.0 ml) was heated at reflux for 4 hours. The solution was concentrated in vacuo and azeotroped with toluene to yield crude acid chloride. This was added to a solution of amine IX'.b (0.28 g, 0.88 mmol) and triethylamine (0.18 ml, 1.33 mmol) in anhydrous CH$_2$Cl$_2$ (10 ml) and stirred at room temperature for 24 hours. Following work-up compound VI'.24 was obtained as an off-white powder (0.44 g) after trituration with ether.

Following an analogous synthetic route and utilising the appropriate nitrobenzoic acid V' and amine IX' the nitro compounds of formula VI' listed in the following Table 5 were prepared.

TABLE 5

| Nitrobenzoic Acid V' | Amine IX' | Nitrobenzamide VI' |
|---|---|---|
| ![structure: 2-nitrobenzoic acid] | IX'.b | ![structure: VI'.23] |

TABLE 5-continued

| Nitrobenzoic Acid V' | Amine IX' | Nitrobenzamide VI' |
|---|---|---|
| IX'.b | | VI'.25 |
| IX'.g | | VI'.26 |
| IX'.b | | VI'.27 |

Reference Example 3A

Preparation of 2-aminobenzamides of General Formula VI from the Corresponding Nitro Compounds

VI.12

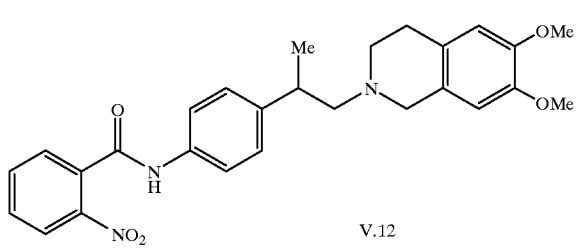

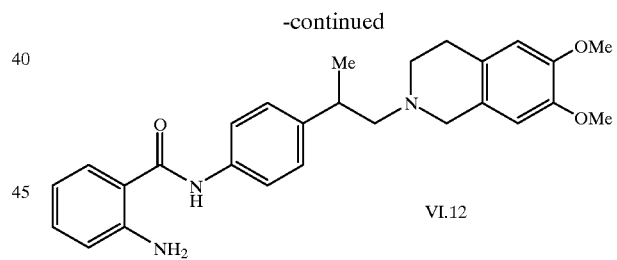

A solution of V.12 (140 mg, 0.30 mmol) in ethanol (5 ml) and $CH_2Cl_2$ (5 ml) was purged with nitrogen and a slurry of platinum (IV) oxide (30 mg) was added. The mixture was stirred under hydrogen at atmospheric pressure for 2 hours, filtered through Celite™ and concentrated in vacuo to yield VI.12 as a white foam (126 mg, 96%).

Following analogous procedures the amino benzamides VI listed in Table 6 were prepared.

TABLE 6

| Nitro Compound V | 2-Aminobenzamide VI |
|---|---|
| V.1 | VI.1 |
| V.2 | VI.2 |
| V.4 | VI.4 |

TABLE 6-continued

| Nitro Compound V | 2-Aminobenzamide VI |
|---|---|
| V.5 | VI.5 |
| V.6 | VI.6 |
| V.7 | VI.7 |
| V.8 | VI.8 |
| V.9 | VI.9 |
| V.10 | VI.10 |
| V.11 | VI.11 |
| V.13 | VI.13 |
| V.14 | VI.14 |
| V.15 | VI.15 |
| V.17 | VI.17 |
| V.28 | VI.28 |

Alternatively for compounds containing a sulphur atom the following method can be used.

Concentrated hydrochloric acid (140 μL) was added to a solution of the nitrobenzamide, V.3 (147 mg, 0.30 mmol) in methanol (2 ml). Iron (72 mg) was added and the reaction mixture was heated to 80° C. for 2 hours, before cooling. The reaction mixture was basified (saturated sodium carbonate solution), extracted into ethyl acetate, dried over magnesium sulphate and the solvent removed in vacuo to yield an off-white solid which was purified using flash chromatography(ethyl acetate) to yield the desired 2-aminobenzamide, VI.3 (47 mg, 34%).

Following an analogous procedure the following 2-aminobenzamide was prepared.

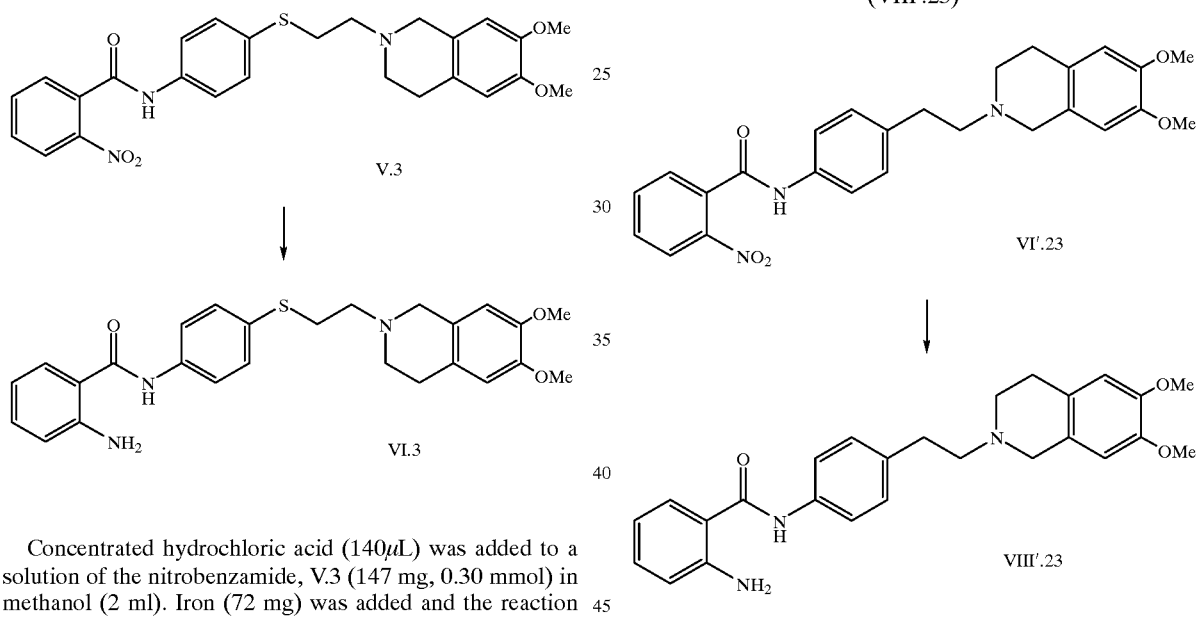

Reference Example 3B

Preparation of 2-aminobenzamides of General Formula VIII' from the Corresponding Nitro Compounds 2-Amino-N-{4-[2-(6,7-Dimethoxy-3,4-dihydro-1H-isoquinolin-2-yl)-ethyl]-phenyl}-benzamide (VIII'.23)

A solution of VI'.23 (12 g, 0.026 mol) in ethanol (200 ml) and CH$_2$Cl$_2$ (160 ml) was purged with nitrogen and a slurry of platinum (IV) oxide (240 mg) was added. The mixture was stirred under hydrogen at atmospheric pressure for 4 hours, filtered through Celite™ and concentrated in vacuo. Recrystallisation from methanol afforded white crystals of VIII'.23 (9.6 g).

Following analogous procedures the aminobenzamides VIII' listed in the following Table 7 were prepared.

TABLE 7

| Nitro Compound | 2-Aminobenzamide VIII' |
|---|---|
| VI'.24 | 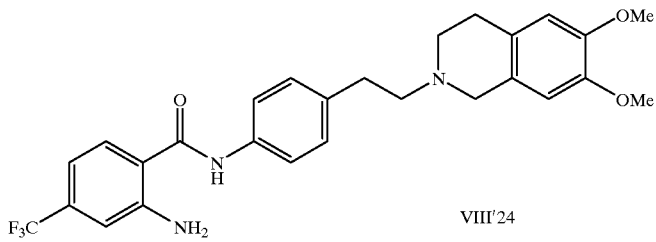 VIII'24 |
| VI'.25 | 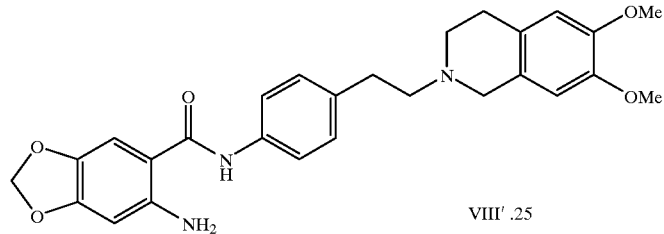 VIII'.25 |
| VI'.26 | 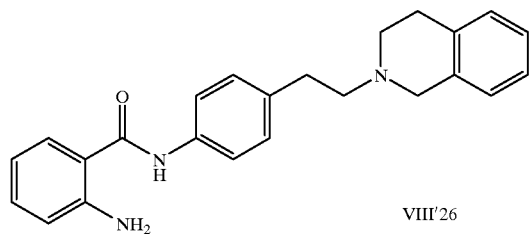 VIII'26 |
| VI'.27 | 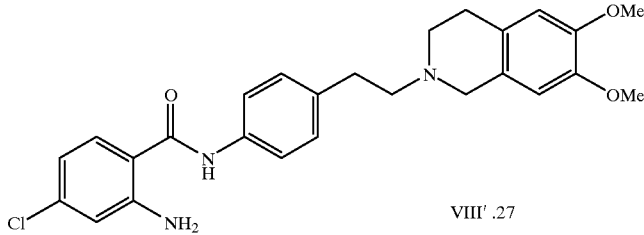 VIII'.27 |

Reference Example 4A

Preparation of 2-aminobenzamides of General Formula VI from the Corresponding Anthranilic Acids

VI.19

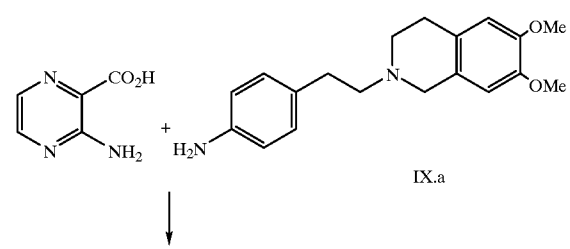

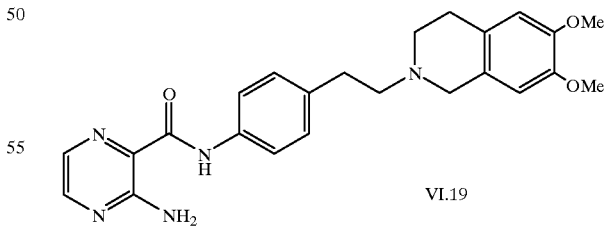

VI.19

A solution of 3-aminopyrazine-2-carboxylic acid (500 mg, 3.60 mmol), amine IX.a (1.12 g, 3.60 mmol), N-cyclohexyl-N-(2-morpholinoethyl)-carbodiimide methyl-p-toluene sulphonate (1.68 g, 3.96 mmol), 1-hydroxybenzotriazole (486 mg, 3.60 mmol) and triethy lamine (501 μL, 3.60 mmol) in anhydrous CH₂Cl₂ (30 ml) was stirred at room temperature for 5 days. Following aqueous work-up and recrystallisation from ethyl acetate the title compound, VI.19 was obtained as a pale yellow solid (733 mg). Following procedures analogous to that described above, the aminobenzamides listed in Table 8 were prepared.

Reference Example 4B

Preparation of 2-aminobenzamides of General Formula VIII' from the Corresponding Anthranilic Acids 2-Amino-N-{4-[2-(6,7-Dimethoxy-3,4-dihydro-1H-isoquinolin-2-yl)-ethyl]-phenyl}-5-methyl-benzamide (VIII'.12)

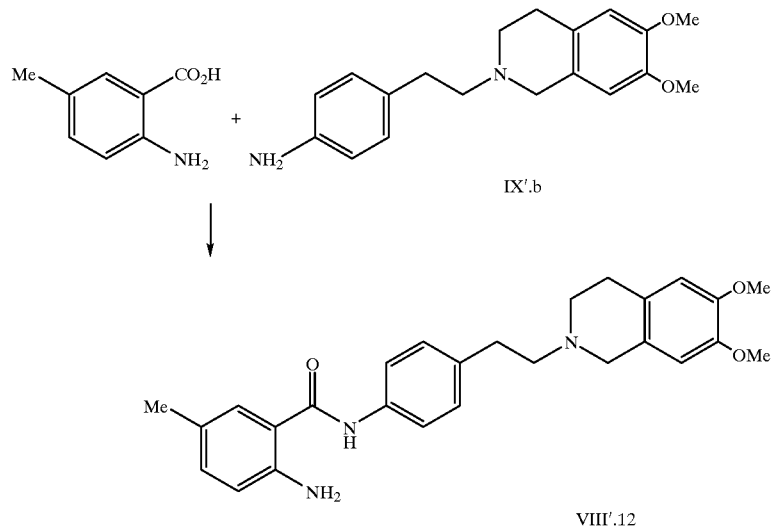

A solution of 2-amino-5-methyl benzoic acid (190 mg, 0.96 mmol), amine IX'.b (300 mg, 0.96 mmol), N-cyclohexyl-N-(2-morpholinoethyl)-carbodiimide methyl-p-toluene sulphonate (449 mg, 1.06 mmol) and 1-hydroxybenzotriazole (143 mg, 1.06 mmol) in anhydrous CH₂Cl₂ (10 ml) was stirred at room temperature for 48 hours. Following work-up and flash chromatography on silica gel in methanol:ethyl acetate (2:98) the title compound, VIII'.12 was obtained as a pale yellow solid (58 mg).

2-Amino-N-[2-(6,7-Dimethoxy-3,4-dihydro-1H-isoquinolin-2-yl)-ethyl]-4-fluoro-benzamide (VIII'.07)

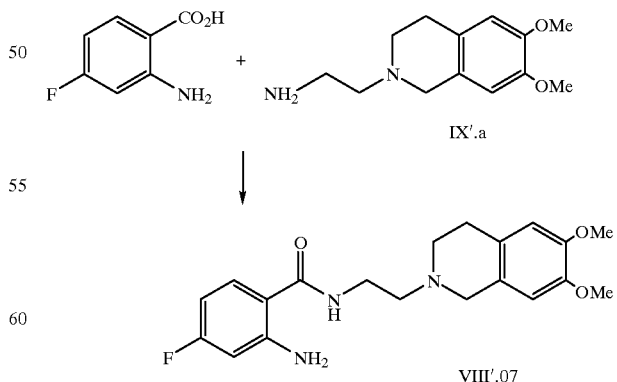

To a stirred solution of N-cyclohexyl-N-(2-morpholinoethyl)-carbodiimide methyl-p-toluene sulphonate (238 mg, 0.56 mmol) and 1-hydroxybenzotriazole (76

TABLE 8

| Anthranilic Acid V | Amine IX | 2-Aminobenzamide VI |
|---|---|---|
| 3-CO₂H, 2-NH₂ pyridine | IX.a | VI.24 |
| 4-Cl, 2-NH₂, CO₂H benzene | IX.b | VI.25 |
| 4,5-diF, 2-NH₂, CO₂H benzene | IX.b | VI.27 |
| 4-Me, 2-NH₂, CO₂H benzene | IX.b | VI.29 |
| 4-O₂N, 2-NH₂, CO₂H benzene | IX.b | VI.30 | mg, 0.56 mmol) in anhydrous CH$_2$Cl$_2$ (10 ml) was added 2-amino-4-fluorobenzoic acid (80 mg, 0.52 mmol) followed by triethylamine (0.08 ml, 0.57 mmol) and amine IX'.a (200 mg, 0.51 mmol). The mixture was stirred at room temperature for 48 hours. Work-up and flash column chromatography over silica gel in methanol:dichloromethane (5:95) gave the aminobenzamide VIII'.07 as a yellow solid (57 mg).

Following procedures analogous to the two described above the aminobenzamides listed in the Table 9 were prepared.

TABLE 9

| Anthrani--lic Acid V' | Amine IX' | 2-Aminobenzamide VIII' |
|---|---|---|
| [2-aminobenzoic acid] | IX'.a | [VIII'01] |
| [3-chloro-2-aminobenzoic acid] | IX'.a | [VIII'.02] |
| [5-chloro-2-aminobenzoic acid] | IX'.a | [VIII'.03] |
| [4-chloro-2-aminobenzoic acid] | IX'.a | [VIII'.04] |
| [3-chloro-2-aminobenzoic acid isomer] | IX'.a | [VIII'.05] |
| [5-bromo-2-aminobenzoic acid] | IX'.a | [VIII'.06] |

TABLE 9-continued

| Anthranilic Acid V' | Amine IX' | 2-Aminobenzamide VIII' |
|---|---|---|
| 3-methyl-2-aminobenzoic acid | IX'.a | VIII'.08 |
| 3-methoxy-2-aminobenzoic acid | IX'.a | VIII'.09 |
| 4-nitro-2-aminobenzoic acid | IX'.a | VIII'.10 |
| 3-amino-2-naphthoic acid | IX'.a | VIII'.11 |
| 4-nitro-2-aminobenzoic acid | IX'.b | VIII'.13 |
| 4-fluoro-2-aminobenzoic acid | IX'.b | VIII'.14 |

TABLE 9-continued

| Anthranilic Acid V' | Amine IX' | 2-Aminobenzamide VIII' |
|---|---|---|
| 2-amino-6-fluorobenzoic acid | IX'.b | VIII'.15 |
| 2-amino-5-fluorobenzoic acid | IX'.b | VIII'.16 |
| 2-amino-4,5-dimethoxybenzoic acid | IX'.b | VIII'.17 |
| 2-amino-6-methylbenzoic acid | IX'.b | VIII'.18 |
| anthranilic acid | IX'.d | VIII'.19 |
| anthranilic acid | IX'.c | VIII'.20 |

TABLE 9-continued
| Anthrani-lic Acid V' | Amine IX' | 2-Aminobenzamide VIII' |
|---|---|---|
| (2-amino benzoic acid) | IX'.f | VIII'.21 |
| (2-amino benzoic acid) | IX'.e | VIII'.22 |
| (4-methyl-2-amino benzoic acid) | IX'.b | VIII'.28 |
| (5-chloro-2-amino benzoic acid) | IX'.b | VIII'.29 |
Reference Example 5
Preparation of 2-aminoamides of General Formula VI from the Corresponding 2-aminoester VII
VI.20
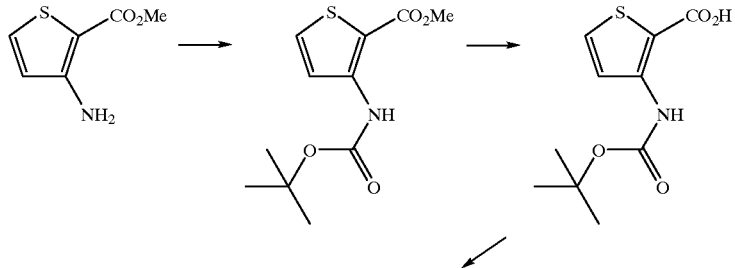

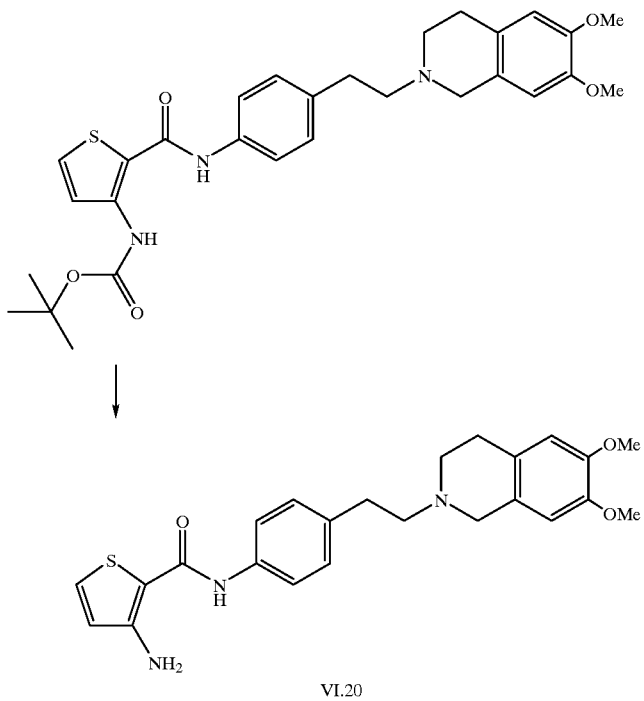

VI.20

To a solution of methyl 3-amino-2-thiophene carboxylate (7.56 g, 48.1 mmol) in dichloromethane (40 ml) was added a solution of di-t-butyl dicarbonate (11.55 g, 52 mmol) in dichloromethane (10 ml) followed by 4-dimethylaminopyridine (600 mg, 4.8 mmol). After stirring for 4 hours at room temperature the reaction mixture was diluted with dichloromethane, washed with water, dried over magnesium sulphate, and the solvent removed in vacuo to yield a gum which was purified using flash chromatography (10% ethyl acetate in hexane) to yield the desired t-butyl carbamate (4.40 g, 36%).

To a solution of the t-butyl carbamate (1.01 g, 3.95 mmol) in tetrahydofuran (4 ml) and methanol (8 ml) was added a solution of sodium hydroxide (316 mg, 7.9 mmol) in water (4 ml). After stirring for 18 hrs at room temperature the reaction mixture was acidified to pH 4, extracted into ethyl acetate, dried over magnesium sulphate, and the solvent removed in vacuo to yield the desired acid as a white solid (800 mg, 83%).

A mixture of the carboxylic acid intermediate (150 mg, 0.62 mmol), N-cyclohexyl-N-(2-morpholinoethyl)-carbodiimide methyl-p-toluene sulphonate (288 mg, 0.68 mmol), 1-hydroxybenzotriazole (92 mg, 0.68 mmol) and IX.a (175 mg, 0.56 mmol) in dry dichloromethane(8 ml) was stirred at room temperature for 3 days. The reaction mixture was then diluted with dichloromethane, washed with water and saturated sodium carbonate solution, dried over magnesium sulphate, and the solvent removed in vacuo to yield a yellow gum which was purified using flash chromatography(silica, ethyl acetate) to yield the desired amide as a white foam (112 mg, 33%).

Anhydrous hydrogen chloride gas was bubbled through a suspension of the amide (202 mg, 0.38 mmol) in 1,4-dioxane for 10 seconds and the reaction mixture stirred for 1 hour. The reaction mixture was then basified(sodium carbonate) and extracted into ethyl acetate, dried over magnesium sulphate and the solvent removed in vacuo to yield aminoamide, VI.20, as a white solid (151 mg, 91%).

Following analogous procedures the following aminoamides were prepared.

TABLE 10

| Starting amino ester VII | Amine IX | Aminoamide VI |
|---|---|---|
| ![structure] Me, thiophene with C(O)OEt and NH2 | IX.a | VI.21 |
| ![structure] thiophene with C(O)OMe and NH2·HCl | IX.a | VI.22 |
| ![structure] thieno-pyridine with C(O)OEt and NH2 | IX.a | VI.23 |

Reference Example 6A

Preparation of Non-commercially Available Acids of General Formula R⁹—CO₂H i)

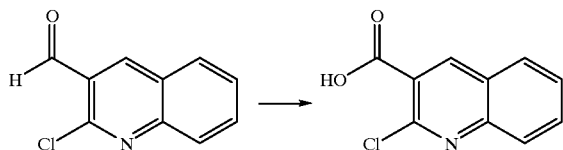

To a hot solution of 2-chloro-3-quinolinecarboxaldehyde (500 mg, 2.61 mmol) in t-butanol (7 ml) and water (12 ml) was added a hot solution of potassium permanganate (580 mg, 3.67 mmol) in water (15 ml) dropwise over a period of 15 minutes. After stirring for 1 hour at reflux, the reaction mixture was allowed to cool, and the MnO₂ precipitate was filtered off and washed with water and t-butanol. The pH of the filtrate was adjusted to pH 5 using 2N hydrochloric acid solution, and was then extracted with chloroform, dried over magnesium sulphate, and the solvent removed in vacuo to yield the acid as a yellow solid (210 mg, 39%).

The desired acid could alternatively be obtained by basic hydrolysis using sodium or lithium hydroxide from the corresponding ester such as 2-methyl-thiazole-4-carboxylic acid ethyl ester or 4-hydroxy-quinoline-3-carboxylic acid ethyl ester in a suitable solvent such as 1,4-dioxane or methanol

Reference Example 6B

Preparation of Acids of General Formula R⁵¹—CO₂H (i) 4-cyclohexyloxybenzoic acid

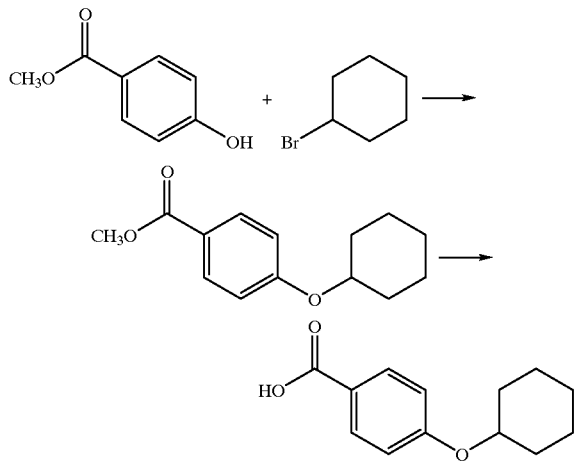

Potassium carbonate (2.26 g, 16.4 mmol) was added to a solution of methyl-4-hydroxybenzoate (1.0 g, 6.6 mmol) and cyclohexyl bromide (1.62 ml, 13.1 mmol) in dimethylformamide (20 ml). The mixture was heated at 100° C. for 24 hours, cooled, filtered and concentrated in vacuo. Work up followed by flash chromatography over silica gel (hexane:ethyl acetate, 5:1) afforded methyl-4-cyclohexylbenzoate (169 mg). This was dissolved (162 mg, 0.69 mmol) in a mixture of 1,4-dioxane (10 ml) and water (5 ml) and lithium hydroxide monohydrate (32 mg, 0.76 mmol) added. The mixture was stirred at room temperature for 18 hours. A further quantity of lithium hydroxide was added (32 mg) and stirring continued for 4 hours. The mixture was added to ethyl acetate, washed with brine and concentrated to yield the title compound as a yellow solid (27 mg).

(ii) 6-methoxy-3-pyridinecarboxylic acid

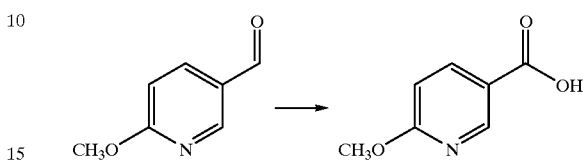

To a solution of 6-methoxy-3-pyridinecarboxaldehyde (50 mg, 0.36 mmol; prepared according to the method of Comins and Killpack, *J. Org. Chem.*, 1990, 55, 69–73) in t-butanol (0.5 ml) was added a solution of potassium permanganate (81 mg) in water (1.0 ml). The mixture was stirred at room temperature for two hours, and then saturated sodium sulphite solution was added until the purple colour disappeared. Reaction mixture was extracted with chloroform several times as it was gradually acidified with dilute HCl (2N). Chloroform extracts were concentrated in vacuo to yield the title compound (42 mg) as a white solid.

(iii) 5-Propionylpyrazinecarboxylic acid

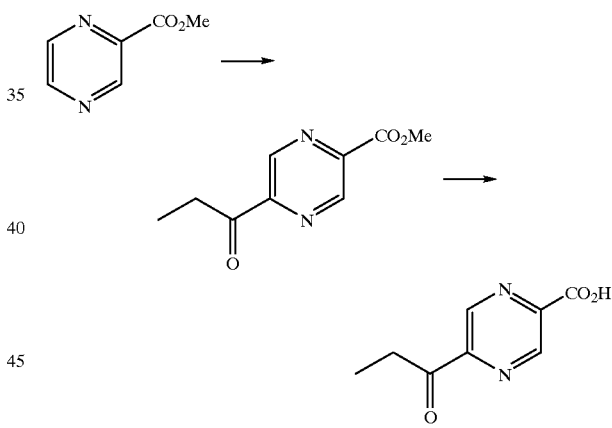

Tert-butyl hydroperoxide (70%, 1.0 ml, 7.25 mmol) and a solution of FeSO₄.7H₂O (3.02 g, 10.9 mmol) in water (8 ml) were added concurrently to a solution of methyl-2-pyrazine carboxylate (250 mg, 1.81 mmol) and propionaldehyde (0.78 ml, 0.9 mmol) in H₂SO₄ (0.75 ml) at 0 C. The reaction was allowed to warm to room temperature and was stirred for 2 hours. Solid Na₂S₂O₅ was added (until starch/iodide test negative) and the mixture extracted with dichloromethane. Concentration in vacuo and flash column chromatography over silica gel in ethyl acetate:hexane (15:85) yielded methyl-5-propionyl-2-pyrazinecarboxylate as a pale yellow solid (106 mg). The methyl ester was treated with LiOH (25 mg, 0.6 mmol) in tetrahydrofuran (15 ml) and water (0.5 ml). After 2 hours at room temperature the mixture was acidified with HCl (2N). Work-up followed by concentration of the organic phase in vacuo gave the title compound (92 mg).

(iv) 5,6,7,8-tetrahydroquinoline-3-carboxylic acid

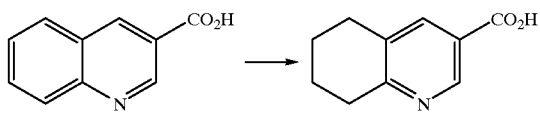

A mixture of 3-quinolinecarboxylic acid (1.73 g, 10.0 mmol) in trifluoroacetic acid (20 ml) with platinum dioxide (200 mg) was shaken in a Parr vessel at 10–15 psi. After 90 minutes the reaction mixture was filtered and the solvent removed in vacuo to yield an oil. The oil was added dropwise onto diethyl ether yielding a white solid which was collected by filtration and then recrystallised from ethyl acetate/hexane to yield the title compound as a white solid (770 mg).

Example 2

Preparation of Compounds of Formula I by Process Variant (a)

Method A

9616

A mixture of 3-quinolinecarboxylic acid (500 mg, 2.89 mmol), thionyl chloride (0.42 ml, 5.8 mmol) and toluene (15 ml) was heated at reflux for two hours. The mixture was cooled and the solvent removed in vacuo to yield the acid chloride as a white solid.

To a solution of amine VI.22 (67 mg, 0.15 mmol) in anhydrous dichloromethane (2 ml) was added acid chloride (41 mg, 1.4 equivalents) while cooling in an ice/water bath. The resulting solution was allowed to warm to room temperature and then stirred for 18 hours. The reaction mixture was diluted with dichloromethane (30 ml), washed with saturated sodium carbonate solution (2×20 ml), dried over magnesium sulphate, and the solvent removed in vacuo to yield a solid which was purified using flash chromatography (silica gel, ethyl acetate) to yield 9616 as a white solid (39 mg, 44%).

Where available the acid chloride, $R^9$—COCl, was purchased directly. Other compounds prepared in an analogous manner are listed in Table 11 below.

Method B

9653

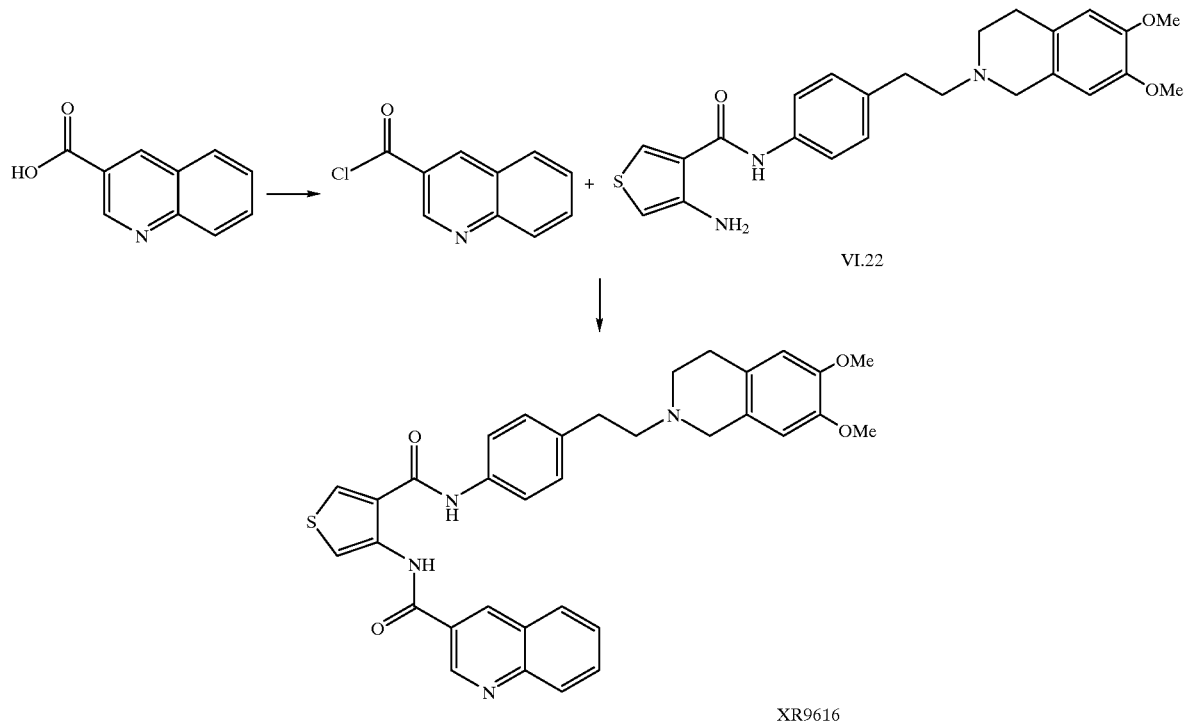

XR9616

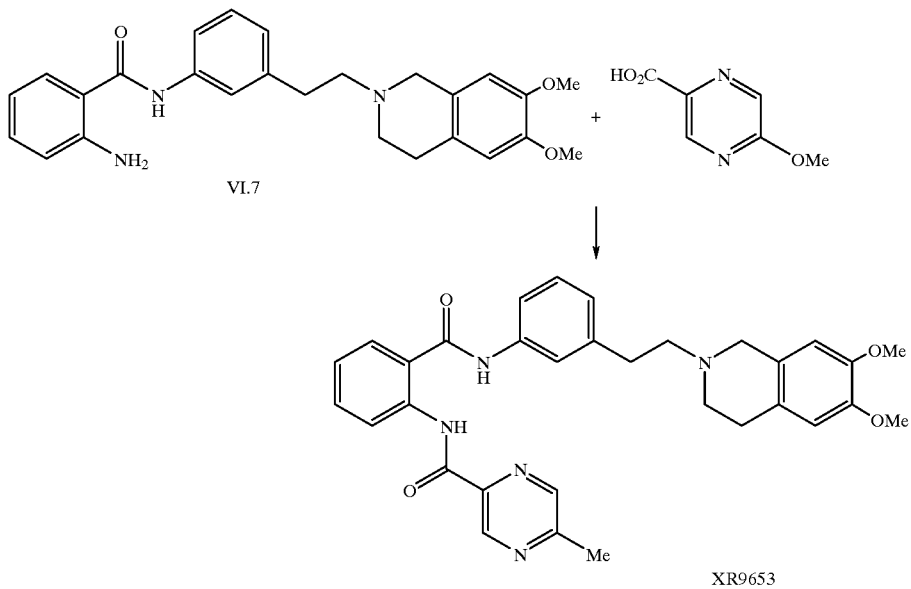

A solution of amine VI.7 (165 mg), 5-methylpyrazine carboxylic acid (63 mg, 1.2 equivalents), cyclohexyl-N-(2-morpholinoethyl)-carbodiimide methyl-p-toluene sulphonate (162 mg, 1.0 equivalent) and 1-hydroxybenzotriazole monohydrate (51 mg, 1.0 equivalent) in dry dichloromethane (15 ml) was stirred at room temperature for 18 hours. The reaction mixture was then diluted with dichloromethane, washed with water and saturated sodium carbonate solution, dried over magnesium sulphate, and the solvent removed in vacuo to yield a solid which was purified using flash chromatography(silica gel, ethyl acetate) to yield 9653 as a white solid (31 mg).

Other compounds prepared in an analogous manner are listed in Table 11 below.

Method C

9617

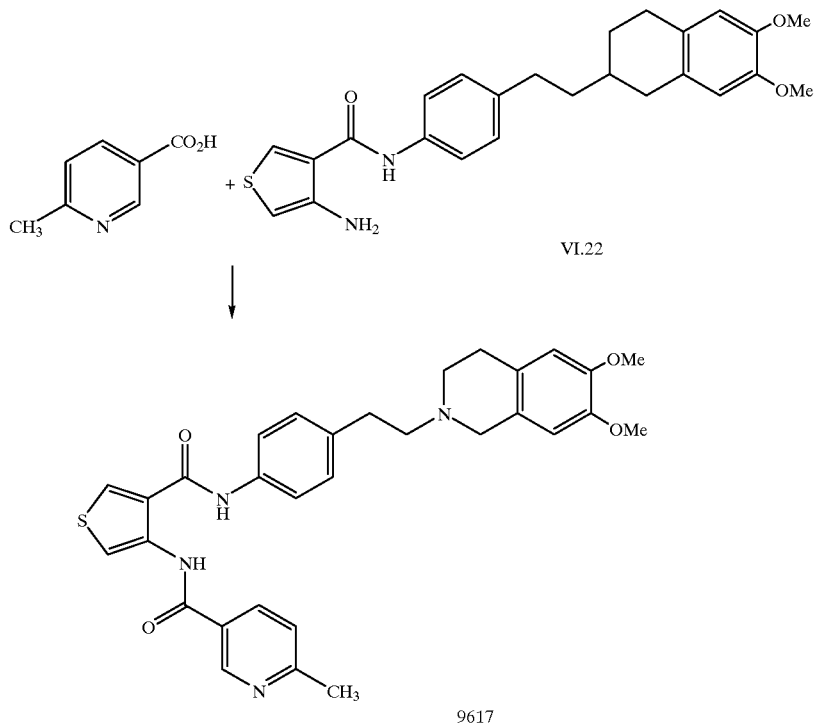

To a solution of 6-methylnicotinic acid (21 mg, 0.15 mmol) and amine VI.22 (50 mg, 0.11 mmol) in anhydrous dichloromethane (2 ml) was added 2-chloro-1-methylpyridinium iodide (41 mg, 0.15 mmol). The mixture was stirred at room temperature for 7 days. Saturated sodium carbonate solution (15 ml) was added and the mixture extracted with dichloromethane (30 ml) twice. The combined organic layers were dried over dry magnesium sulphate and reduced in vacuo. Flash chromatography over silica gel (ethyl acetate) yielded 9617 (11 mg, 18%) as a white solid.

Other compounds prepared in an analogous manner are listed in Table 11 below.

TABLE 11

| Amine of Formula VI | Acid Substituent R⁹ | Method | Compound of Formula I |
|---|---|---|---|
| VI.1 | (2-chloro-3-methylquinoline) | A | 9591 |
| VI.1 | (3-methyl-7-trifluoromethyl-4-hydroxyquinoline) | B | 9592 |
| VI.20 | (3-methylquinoline) | A | 9594 |
| VI.17 | (3-methylquinoline) | A | 9595 |
| VI.17 | (3-methylquinoxaline) | A | 9596 |
| VI.20 | (3-methylquinoxaline) | A | 9597 |
| VI.24 | (3-methylquinoxaline) | A* | 9600 |
| VI.1 | (3-methyl-4-hydroxyquinoline) | A | 9606 |
| VI.21 | (3-methylquinoxaline) | A | 9608 |
| VI.21 | (3-methylquinoline) | A | 9609 |

TABLE 11-continued
| Amine of Formula VI | Acid Substituent R⁹ | Method | Compound of Formula I |
|---|---|---|---|
| VI.2 | 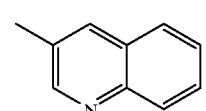 | A | 9612 |
| VI.2 | 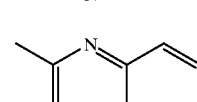 | A | 9613 |
| VI.15 | 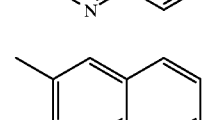 | A | 9614 |
| VI.18 | 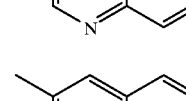 | A | 9615 |
| VI.22 | 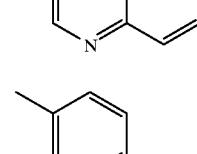 | A | 9616 |
| VI.22 | 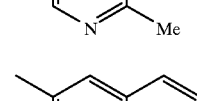 | C | 9617 |
| VI.3 | 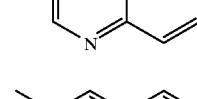 | A | 9621 |
| VI.19 | 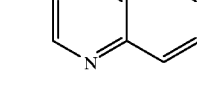 | A* | 9622 |
| VI.4 | 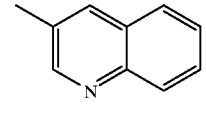 | A | 9623 |
| VI.5 | | A | 9625 |
| VI.6 | 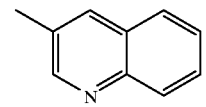 | A | 9626 |
| VI.4 | 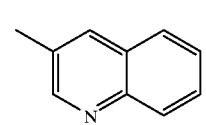 | A | 9632 |

TABLE 11-continued

| Amine of Formula VI | Acid Substituent R⁹ | Method | Compound of Formula I |
|---|---|---|---|
| VI.7 | 3-methylquinoline | A | 9633 |
| VI.1 | 4-methyl-2-methylthiazole | A | 9635 |
| VI.1 | 4-methyl-2-methyloxazole | A | 9638 |
| VI.8 | 3-methylquinoline | A | 9648 |
| VI.9 | 3-methylquinoline | A | 9650 |
| VI.10 | 3-methylquinoline | A | 9651 |
| VI.11 | 3-methylquinoline | A | 9652 |
| VI.7 | 2-methyl-5-methylpyrazine | B | 9653 |
| VI.12 | 3-methylquinoline | A | 9654 |
| VI.13 | 3-methylquinoline | A | 9656 |
| VI.10 | 2-methyl-5-methylpyrazine | B | 9657 |
| VI.9 | 2-methylpyrazine | A | 9658 |

TABLE 11-continued

| Amine of Formula VI | Acid Substituent R⁹ | Method | Compound of Formula I |
|---|---|---|---|
| VI.10 | 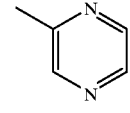 | A | 9659 |
| VI.14 | 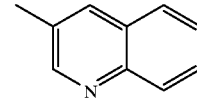 | A | 9660 |
| VI.11 | 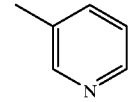 | A | 9661 |
| VI.25 | 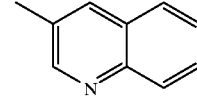 | A | 9663 |
| VI.23 | 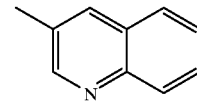 | A* | 9666 |
| VI.27 | 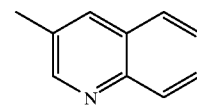 | A | 9667 |
| VI.29 | 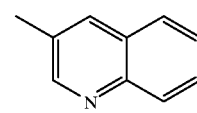 | A | 9668 |
| VI.28 | 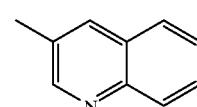 | A | 9669 |
| VI.30 | 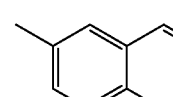 | A* | 9677 |

\* In these examples acetonitrile at a temperature ranging from room temperature to reflux was used instead of dichloromethane.

Reference Example 7

Synthesis of the Intermediate Bromide of Formula XII

A bromide of formula XIIa was prepared as follows:

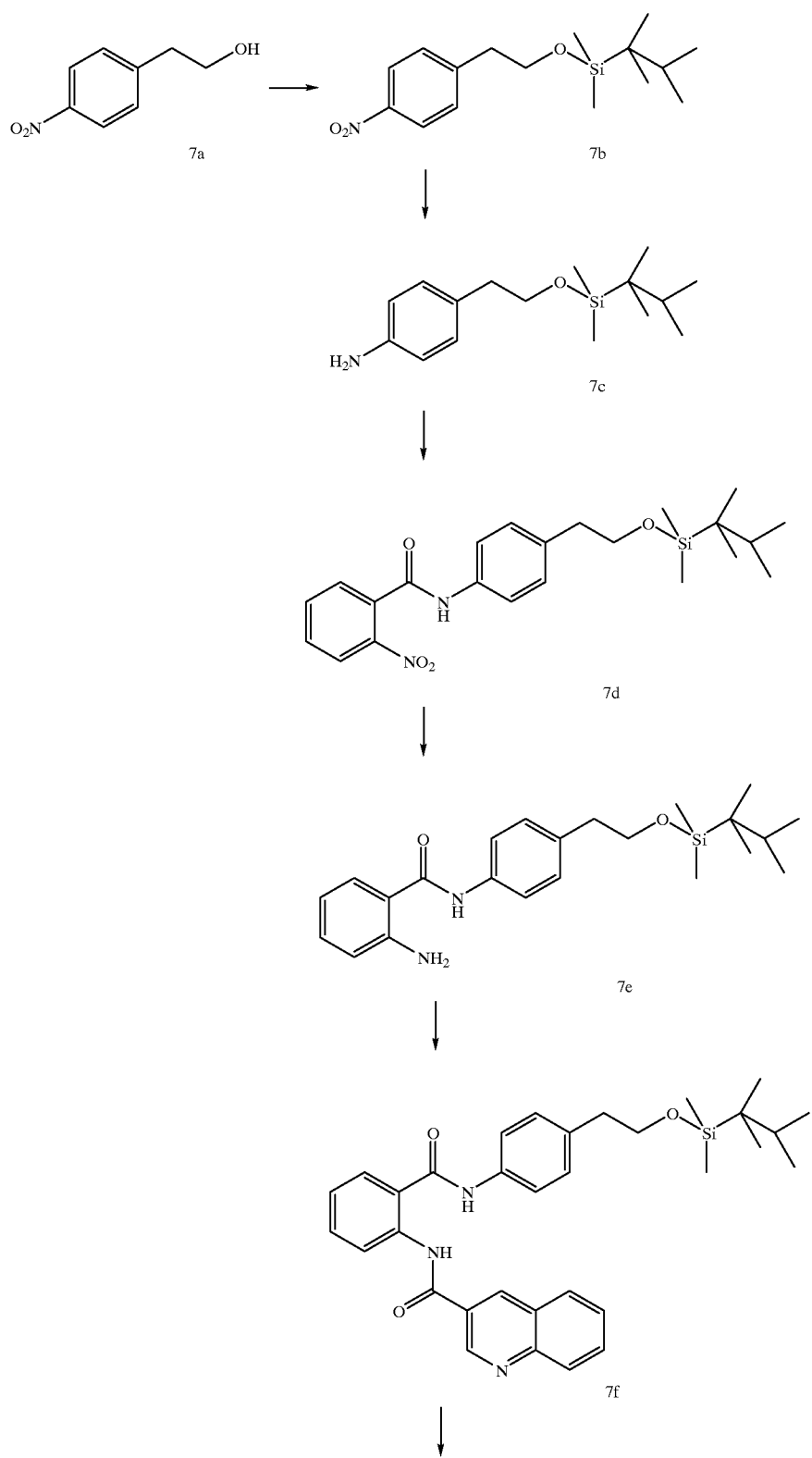

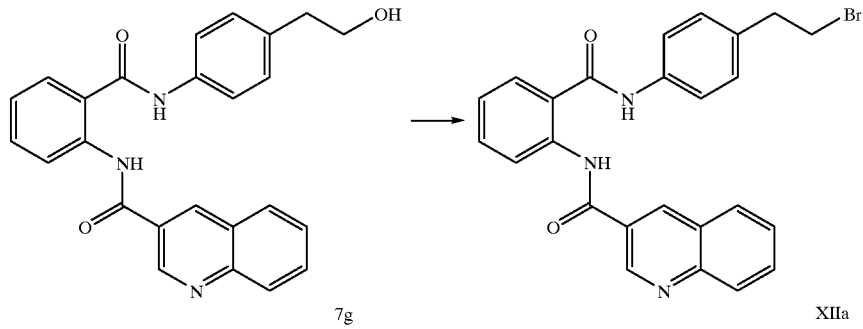

To an ice-cold solution of 7a,4-nitrophenylethyl alcohol (5.0 g, 29.9 mmol) and imidazole (2.25 g, 32.9 mmol) in $CH_2Cl_2$ (200 ml) was added dimethylthexylsilyl chloride (6.5 ml, 33.2 mmol). The reaction mixture was stirred at RT for 16 hrs then diluted with $Et_2O$ (200 ml). The ethereal solution was washed with water (200 ml), 2N HCl (200 ml) and brine (200 ml), dried ($MgSO_4$) and the solvent removed under reduced pressure to afford compound 7b (10 g) as a yellow liquid.

7c

To a solution of 7b (10 g, 32.6 mmol) in EtOH (250 ml) was added $PtO_2$ (400 mg) before introducing $H_2$ gas. The reaction mixture was stirred vigorously for 3 days, filtered through celite and the solvent removed under reduced pressure to afford the compound 7c (9.88 g) as a yellow liquid.

7d

To a cold (0° C.) solution of 7d (8.78 g, 31.75 mmol) and 2-nitrobenzoyl chloride (7.1 g, 38.11 mmol) in $CH_2Cl_2$ (40 ml) was added $NEt_3$ (6.6 ml, 47.64 mmol) and the reaction mixture allowed to warm to RT. After 16 hrs, the reaction mixture was washed with water (40 ml) and the aqueous washings were back-extracted with $CH_2Cl_2$ (2×40 ml). The combined organic phase was dried ($MgSO_4$) and the solvent removed under reduced pressure to give a brown tar-like solid. This solid was stirred in hexane for 2 hrs to give a white solid which was filtered-off then dissolved in $CH_2Cl_2$ and filtered through a plug of flash silica gel. The solvent was removed under reduced pressure to afford the compound 7d (6 g) as a white solid.

7e 7d (5.0 g, 11.7 mmol) was reduced as described for the reduction of 7c, using EtOH (100 ml), and $PtO_2$ (200 mg). The compound 7e (4.42 g) was obtained as a peach coloured solid.

7f

To a solution of 7e (4.75 g, 11.9 mmol) and 3-quinolinecarbonyl chloride (2.7 g, 14.3 mmol) in $CH_2Cl_2$ (70 ml) was added $NEt_3$ (2.5 ml, 17.9 mmol). The reaction mixture was stirred at RT for 16 hrs then poured into dilute sodium carbonate solution (70 ml). The layers were separated, the organic layer washed with water then dried ($MgSO_4$). The solvent was removed under reduced pressure to give the compound 7f (4.9 g) as an off-white solid.

To a solution of 7f (4.78 g, 8.64 mmol) in THF (100 ml) at RT was added tetrabutylammonium fluoride (1M in THF; 19.2 ml, 17.28 mmol) and the solution left to stir for 4 days. The solvent was removed under reduced pressure and the residue dissolved in EtOAc (100 ml) before adding enough water to produce precipitation. The precipitate was filtered and washed with water then $Et_2O$. The residue was azeotroped with toluene and dried in vacuo to give the compound 7g (3 g) as a cream solid.

XIIa

To a solution of 7g (3.0 g, 7.29 mmol) and triphenylphosphine (3.8 g, 14.58 mmol) in DMF (25 ml) was added N-bromosuccinimide (2.6 g, 14.58 mmol). The reaction mixture was heated at 50° C. for 16 hrs, then cooled before adding MeOH (5 ml). After 5 min $Et_2O$ was added until precipitation occurred. The precipitate was filtered and washed with $Et_2O$. The residue was dried in vacuo to give the compound XIIa (2.13 g) as an off-white solid.

Example 3

Preparation of Compounds of Formula (I) by Process Variant (b)

Scheme 3

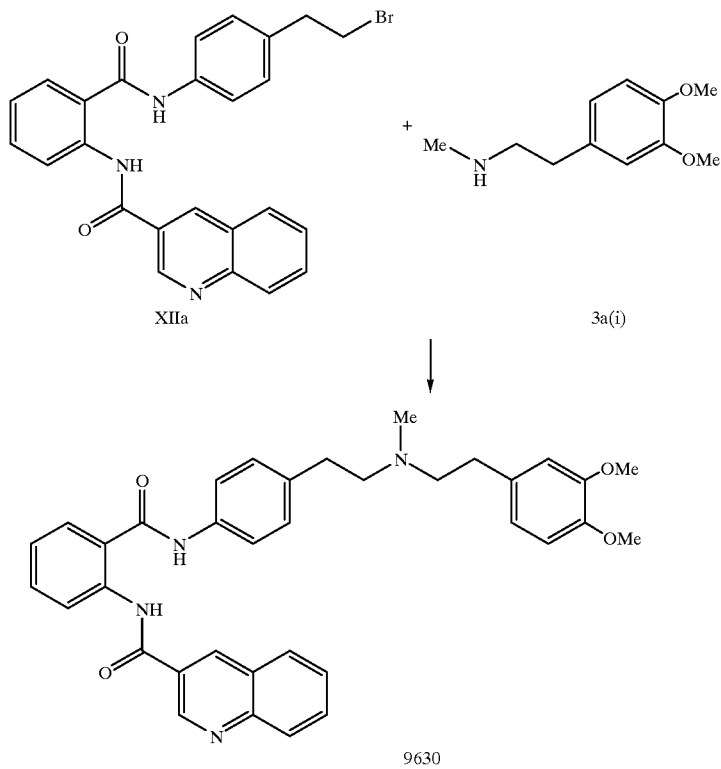

A mixture of 3a(i) (68 mg, 0.35 mmol), which is a compound of formula XX, and was prepared as described below, XIIa (166 mg, 0.35 mmol), potassium carbonate (72 mg, 0.52 mmol) and tetrabutylammonium iodide (0.1 equivalents) in N,N-dimethylformamide(3 ml) was stirred at room temperature for 4 days. The reaction mixture was diluted with ethyl acetate, washed with water, dried over magnesium sulphate and the solvent removed in vacuo to yield a brown gum. Flash chromatography (silica gel, ethyl acetate) and recrystallisation (methanol/dichloromethane) yielded 9630 as a white solid (43 mg, 21%).

Using an analogous method the following compounds of formula (I) were prepared.

| Structure of amine of formula XX | Synthesis of Amine of formula XX | Compound of Formula (I) |
|---|---|---|
| (6,7-dichloro-1,2,3,4-tetrahydroisoquinoline) | see G.E. Stokker, Tetrahedron Letters, 1996,37, 5453–5456 | 9628 |
| (7,8-dichloro-1,2,3,4-tetrahydroisoquinoline) | see G.E. Stokker, Tetrahedron Letters, 1996,37, 5453–5456 | 9629 |
| (N-methyl-3,4-dimethylbenzylamine) | see Method 3a(ii) below | 9631 |
| | see Method 3a(iii) below | 9634 |

-continued

| Structure of amine of formula XX | Synthesis of Amine of formula XX | Compound of Formula (I) |
|---|---|---|
| 3,4-dimethoxybenzyl ethylamine | see Method 3a(iv) below | 9636 |
| 3-isopropoxy-4-methoxybenzyl methylamine | see Method 3a(v) below | 9639 |
| 3,4,5-trimethoxybenzyl methylamine | see Method 3a(vi) below | 9640 |
| 3,4-dimethoxybenzyl butylamine | see Method 3a(vii) below | 9641 |
| 4-butoxy-3-methoxybenzyl methylamine | see Method 3a(viii) below | 9642 |
| 3,4-difluorobenzyl methylamine | see Method 3a(ix) below | 9643 |
| 2,3-dihydro-1,4-benzodioxin-6-ylmethyl methylamine | see Method 3a(x) below | 9645 |
| 4-isopropoxy-3-methoxybenzyl methylamine | see Method 3a(xi) below | 9646 |
| 3-hydroxy-4-methoxybenzyl methylamine | see Method 3a(xii) below | 9647 |
| 4-hydroxy-3-methoxybenzyl methylamine | see Method 3a(xiii) below | 9649 |

| Structure of amine of formula XX | Synthesis of Amine of formula XX | Compound of Formula (I) |
|---|---|---|
| | see Method 3a(xiv) below | 9655 |
| | see Method 3a(xv) below | 9664 |
| | see Method 3a(xvi) below | 9665 |

Method 3a(i)

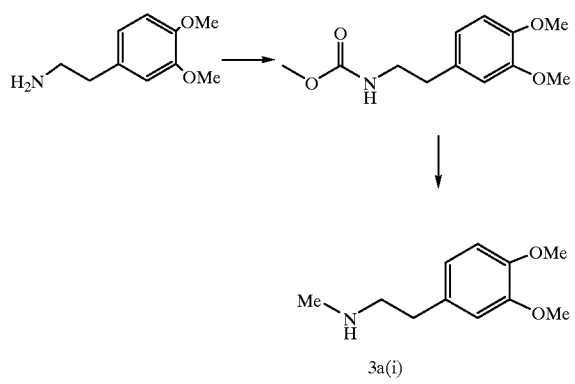

A solution of triethylamine (7.2 ml, 0.052 mol) and homoveratrylamnine (1.92ml, 0.011 mol) in dichloromethane (10 ml) was added to a solution of methyl chloroformate (8 ml, 0.103 mol) in dichloromethane (50 ml) and cooled to −78° C. The reaction mixture was warmed to room temperature and stirred for 18 hours. It was then poured onto saturated sodium carbonate solution, extracted into dichloromethane, dried over magnesium sulphate, and the solvent removed in vacuo to yield a yellow oil which was purified using flash chromatography (1% methanol in ethyl acetate) to yield the methyl carbamate (2.06 g, 78%).

A solution of the methyl carbamate (2.0 g, 8.37 mmol) in tetrahydrofuran (60 ml) was added dropwise to a suspension of lithium aluminium hydride (1.59 g, 41.9 mmol) in tetrahydrofuran (60 ml) and cooled to 0° C. The reaction mixture was allowed to warm to room temperature and stirred for 18 hours. Water (2.2 ml) was added to the reaction mixture, followed by 2N sodium hydroxide solution, further water (2.2 ml) and magnesium sulphate. After stirring for 15 mins the mixture was filtered and the filtrate was reduced in vacuo to yield 3a(i) as a yellow oil (1.61 g, 99%).

Method 3a(ii)

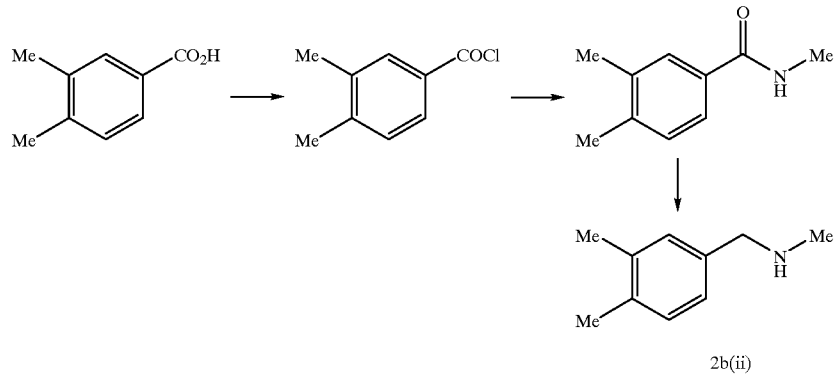

A mixture of 3,4-dimethylbenzoic acid (3.5 g, 23.33 mmol) and thionyl chloride (3.5 ml, 46.7 mmol) was heated to reflux in toluene for 2 hours before cooling and removing the solvent in vacuo to yield the crude acid chloride as an oil. This was dissolved in dichloromethane (50 ml) and a 40% solution of methylamine in water (18 ml, 10 equivalents) was added with ice cooling. After stirring for 48 hours aqueous work-up yielded a yellow solid which was purified using flash chromatography (silica; ethyl acetate/hexane) to yield the desired amide as a white solid (1.84 g, 49%).

To a solution of the amide (1.00 g, 6.13 mmol) in dry tetrahydrofuran(20 ml) was added lithium aluminium hydride (698 mg, 2 equivalents) and the reaction mixture was heated to reflux for 3 hours. After cooling and aqueous work-up a pale oil was obtained which was purified using flash chromatography (silica, ethyl acetate) to yield 3a(ii) as a colourless oil (175 mg, 19%).

Method 3a(iii)

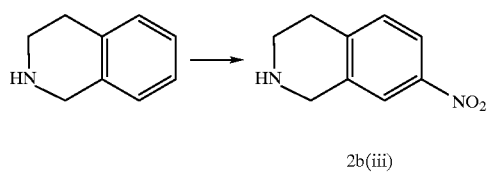

2b(iii)

To concentrated sulphuric acid (80 ml) cooled to 0° C. was added 1,2,3,4-tetrahydroisoquinoline (20.2 ml, 161 mmol) dropwise. Potassium nitrate (17.5 g, 173 mmol) was added in portions carefully. After stirring for 16 hours the reaction mixture was basified with concentrated ammonium hydroxide solution, extracted into chloroform, dried over magnesium sulphate, and the solvent was removed in vacuo to yield a brown oil. This was dissolved in ethanol (120 ml) and conc. hydrochloric acid was added and the resulting precipitate was collected by filtration and recrystallised from methanol to yield the hydrochloride salt of 3a(iii) (11.2 g, 33%).

Methods 3a(iv), 3a(vi), 3a(vii), 3a(ix), 3a(x). 3a(xii), 3a(xiii), and 3a(xiv)

Amines 3a(iv), 3a(vi), 3a(vii), 3a(ix), 3a(x), 3a(xii), 3a(xiii), and 3a(xiv) were all prepared by reductive amination from the appropriate aromatic aldehyde. This involved reaction of the aldehyde with an amine such as methylamine, ethylamine or butylamine in a suitable solvent such as methanol or toluene. The resultant imine was reduced to the desired amine using hydrogenation over platinum(IV) dioxide catalyst in a suitable solvent such as ethanol, or by using lithium aluminium hydride in tetrahydrofuran.

Method 3a(v)

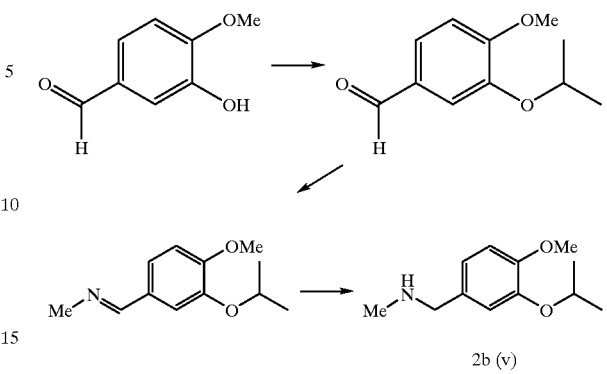

2b (v)

A mixture of 3-hydroxy-4-methoxybenzaldehyde (1.00 g, 6.57 mmol), 2-iodopropane (0.79 ml, 1.2 equivalents) and potassium carbonate (1.09 g, 1.2 equivalents) was heated to reflux in acetonitrile for 5 hours. Aqueous work-up yielded the desired intermediate aldehyde. Reductive amination as described in Method 3a(iv) yielded the desired amine 3a(v). Amines 3a(viii) and 3a[]xi) were prepared in an analogous method using the appropriate commercially available aldehyde and reacting with an alkylating agent such as 1-iodobutane or 2-iodopropane and then reductive amination to the desired amine.

Method 3a(xv)

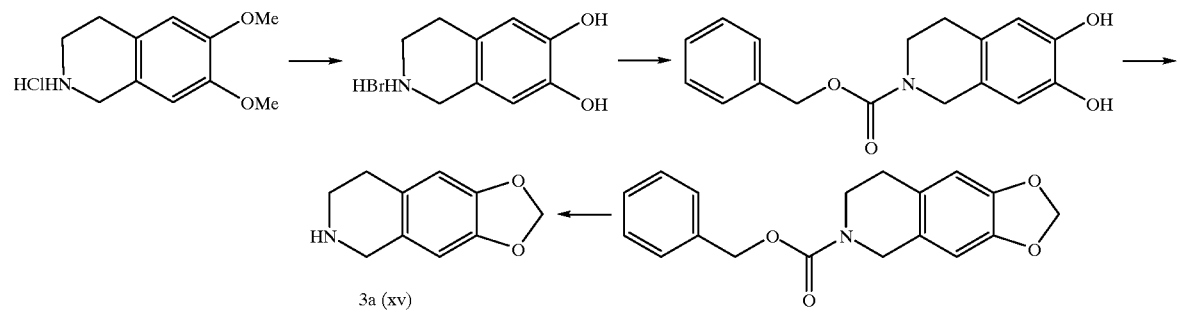

3a (xv)

A solution of 6,7-dimethoxy-1,2,3,4-tetrahydroisoquinoline hydrochloride (5.0 g, 22 mmol) in an excess mixture of 48% hydrobromic acid (80 ml) and 50% hypophosphoric acid (0.4 ml) was heated to reflux for 4 hours. The cooled reaction mixture was filtered and washed with methanol and ether to yield the desired dihydroxylated compound as a white solid (4.75 g, 88%). To a solution of this material (4.75 g) in a 4:1 mixture of acetone:water was added sodium carbonate (3.07 g) and the mixture was cooled in an ice bath. Benzyl chloroformate (3.06 ml) was then added and the reaction mixture was stirred for 18 hours before filtering. The filtrate was collected and aqueous work-up followed by flash chromatography (hexane/ethyl acetate) and trituration with ether yielded the benzyl carbamate (3.6 g, 62%).

To a solution of the benzyl carbamate (1 g, 3.34 mmol) in N,N-dimethylformamide (50 ml) was added dibromomethane (0.28 ml, 3.99 mmol) and potassium carbonate (2.75 g, 19.7 mmol) and the mixture was heated to 100° C. for 1.5 hours. After cooling and filtering, the filtrate was collected and aqueous work-up and flash chromatography (hexane 5:1 ethyl acetate) yielded the desired 1,3 dioxolane (669 mg, 64%).

Atmospheric hydrogenation over palladium-on-carbon in a methanol/dichloromethane mixture cleaved the benzyl carbamate to yield the desired amine 3a(xv).

Method 3a(xvi)

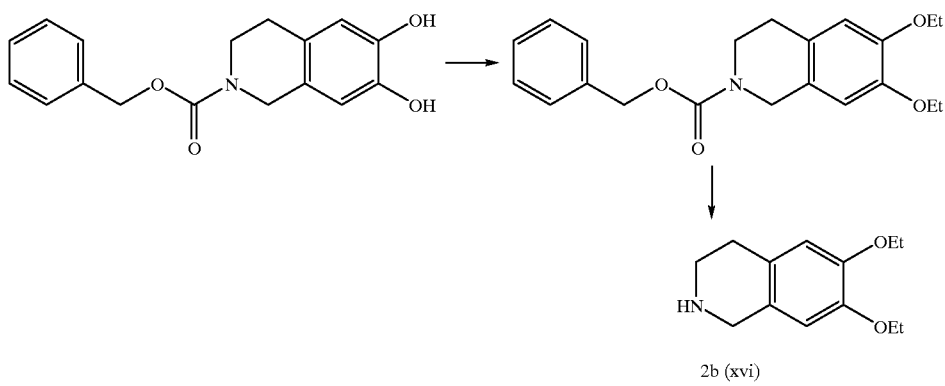

2b (xvi)

To a solution of the intermediate benzyl carbamate (preparation above) (500 mg, 1.67 mmol) in tetrahydrofuran (10 ml) was added sodium hydride (60% dispersion in mineral oil, 385 mg, 10.03 mmol), iodoethane (6.6 ml, 83.6 mmol) and dimethylsulphoxide (5 ml). The reaction mixture was heated to reflux for 18 hours. After aqueous work-up and flash chromatography(hexane 5:1 ethyl acetate) twice, a yellow oil was yielded (549 mg, 92%). The benzyl carbamate was cleaved as above to yield amine 3a(xvi).

Example 4

Preparation of Compounds of Formula Ia by Coupling an Amine of Formula VIII' with an Activated Acid of Formula $R^{51}CO_2H$ (Process Variant (a'))

Method A

Quinoline-3-carboxylic acid (2-{4-[2-(6,7-dimethoxy-3,4-dihydro-1H-isoquinolin-2-yl)-ethyl]-phenylcarbamoyl}-phenyl)-amide (9544)

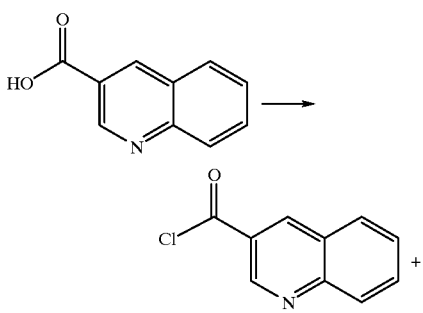

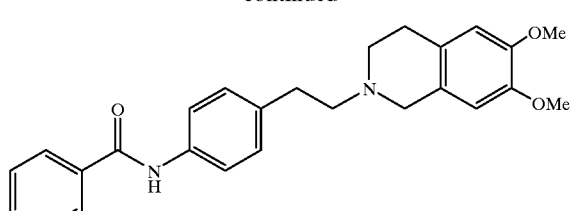

VIII'.23

-continued

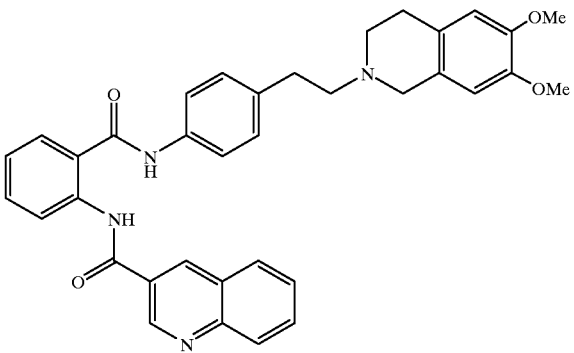

9544

A mixture of 3-quinolinecarboxylic acid (4.0 g, 0.023 mol), thionyl chloride (3.4 ml, 0.046 mol) and toluene (100 ml) was heated at reflux for two hours. The mixture was cooled, reduced in vacuo and triturated in hexanes to afford crude acid chloride (4.15 g) as a white solid. To a suspension of the acid chloride (2.64 g, 14.0 mmol) in anhydrous dichloromethane (100 ml) was added amine VIII.23 (4.0 g, 9.3 mmol) while cooling in an ice/water bath. The resulting solution was allowed to warm to room temperature and then stirred for a further hour. Dilute potassium carbonate solution was added (100 ml) and the mixture extracted with chloroform three times. The combined organic layers were dried over dry magnesium sulphate and evaporated until crystallisation was initiated. An equal volume of diethyl ether was added and the mixture left to crystallise, affording 9544 as a white solid (5.4 g).

Other compounds prepared in an analogous manner are listed in the Table below. Where available the acid chloride, $R^{51}$—COCl, was purchased directly.

Method B

Furan-3-carboxylic acid (2-{4-[2-(6,7-dimethoxy-3,4-dihydro-1H-isoquinolin-2-yl)-ethyl]-phenylcarbamoyl}-phenyl)-amide. (9526)

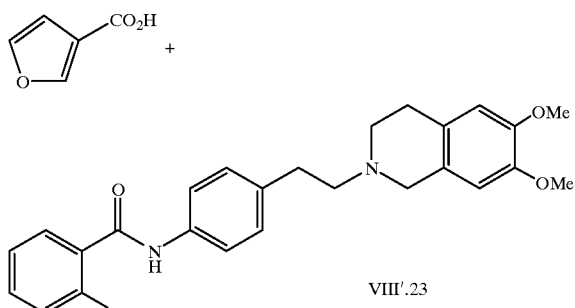

VIII'.23

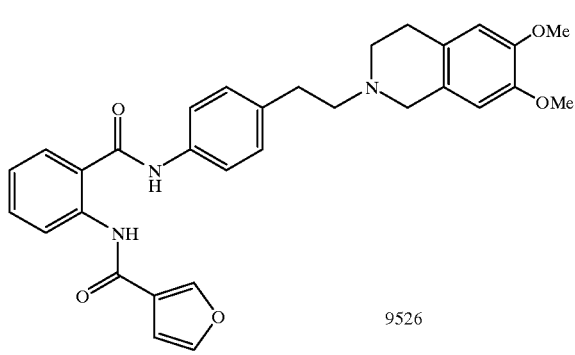

9526

A solution of 3-furoic acid (19 mg, 0.17 mmol), amine VIII'.23 (75 mg, 0.17 mmol), cyclohexyl-N-(2-morpholinoethyl)-carbodiimide methyl-p-toluene sulphonate (79 mg, 0.19 mmol) and 1-hydroxybenzotriazole monohydrate (25 mg, 0.19 mmol) in dry dichloromethane (5.0 ml) was stirred at room temperature for 18 hours. Saturated brine was added and the mixture extracted into dichloromethane (25 ml) twice. The combined organic layers were dried over magnesium sulphate and concentrated in vacuo. Flash chromatography over silica gel (2% methanol, 98% ethyl acetate) followed by recrystallisation from ethyl acetate afforded the title compound 9526 (18 mg) as a yellow crystalline solid. Other compounds prepared in an analogous manner are listed in the Table below.

Method C

N-(2-{4-[2-(6,7-Dimethoxy-3,4-dihydro-1H-isoquinolin-2-yl)-ethyl]-phenylcarbamoyl}-phenyl)-6-methyl-nicotinamide (9557)

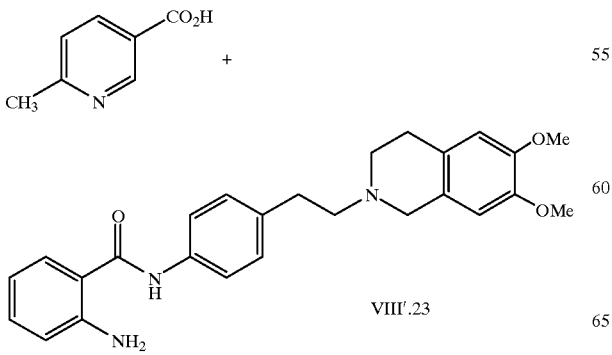

VIII'.23

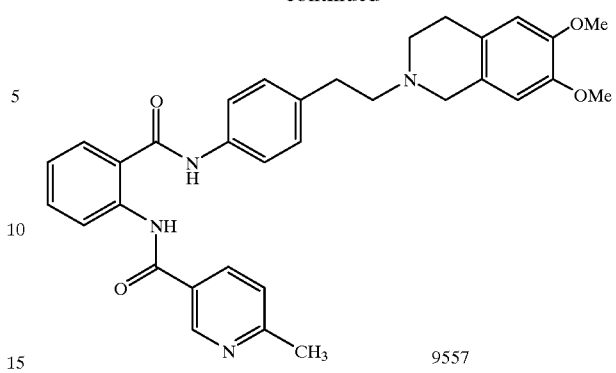

9557

To a solution of 6-methylnicotinic acid (47 mg, 0.34 mmol) and amine VIII'.23 (75 mg, 0.17 mmol) in anhydrous dichloromethane (5.0 ml) was added triethylamine (0.05 ml, 0.34 mmol) followed by 2-chloro-1-methylpyridinium iodide (44 mg, 0.17 mmol). The mixture was stirred at room temperature for 5 days. Saturated sodium carbonate solution (15 ml) was added and the mixture extracted with dichloromethane (30 ml) twice. The combined organic layers were dried over dry magnesium sulphate and reduced in vacuo. Flash chromatography over silica gel (2% methanol, 98% ethyl acetate) followed by trituration in diethyl ether yielded the title compound (9557) (8 mg), as a white solid.

Method D 2-(4-Isopropyl-benzoylamino)-N-[2-(6,7-dimethoxy-3,4-dihydro-1H-isoquinolin-2-yl)-ethyl]-3-methyl-benzamide (9398).

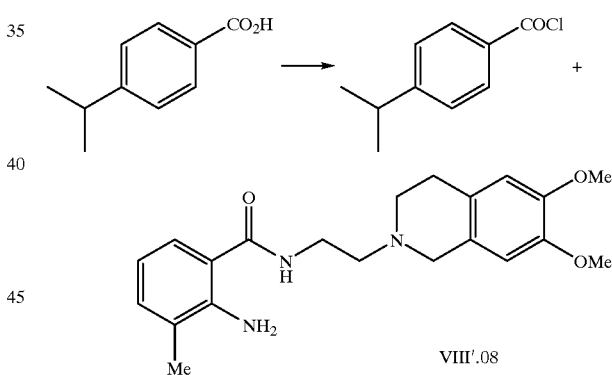

VIII'.08

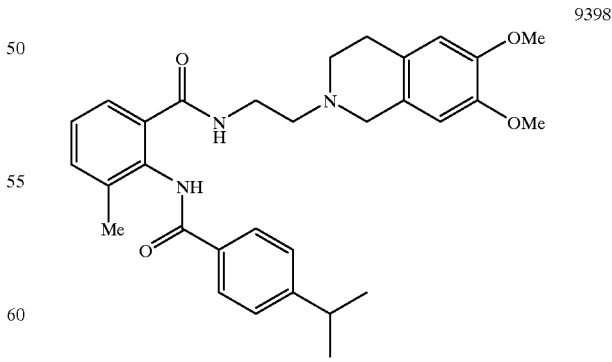

9398

Thionyl chloride (5 ml) was added to a suspension of 4-isopropylbenzoic acid (5.0 g, 0.03 mol) in toluene (50 ml) followed by dimethylformamide (1 drop). The mixture was heated at reflux for 2 hours, cooled and reduced in vacuo to afford the crude acid chloride (5.5 g) as a yellow oil. This acid chloride (68 mg, 0.37 mmol) was added to a mixture of amine VIII'.08 (110 mg, 0.3 mmol) and 2M sodium hydroxide solution while cooling in an ice/water bath. The mixture was allowed to warm to room temperature and stirred vigorously for 5 hours. The mixture was extracted with ethyl acetate (15 ml) twice, brine (15 ml) once, dried over magnesium sulphate and reduced in vacuo. Flash chromatography (2% methanol/98% dichloromethane) over silica gel followed by trituration with diethyl ether afforded 9398 (16 mg) as a white solid. Recrystallisation of the residue of the mother liquors afforded a second crop of title compound (15 mg). Other compounds prepared in an analogous manner are listed below in Table 12.

TABLE 12

| Amine of Formula VIII' | $R_5$ in acid $R^{51}$—COOH | Method | Compound of Formula Ia |
|---|---|---|---|
| VIII'.02 | ⟨structure: p-tolyl-CH(CH₃)₂⟩ | A | 9405 |
| VIII'.03 |  | A | 9354 |
| VIII'.04 |  | A | 9350 |
| VIII'.05 |  | D | 9401 |
| VIII'.06 |  | A | 9394 |
| VIII'.07 |  | A | 9349 |
| VIII'.09 |  | D | 9399 |
| VIII'.10 |  | A | 9420 |
| VIII'.11 |  | A | 9410 |
| VIII'.01 | ⟨structure: p-tolyl-N(CH₃)₂⟩ | A | 9256 |
| VIII'.01 | ⟨structure: p-tolyl-(CH₂)₄CH₃⟩ | A | 9395 |
| VIII'.01 | ⟨structure: p-tolyl-cyclohexyl⟩ | A | 9331 |
| VIII'.01 | ⟨structure: p-tolyl-C(CH₃)₃⟩ | A | 9334 |
| VIII'.01 | ⟨structure: tolyl⟩ | A | 9351 |
| VIII'.01 | ⟨structure: p-tolyl-Br⟩ | A | 9380 |

TABLE 12-continued
| Amine of Formula VIII' | R₅ in acid R⁵¹—COOH | Method | Compound of Formula Ia |
|---|---|---|---|
| VIII'.01 | 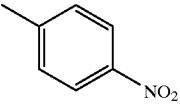 | A | 9381 |
| VIII'.01 | 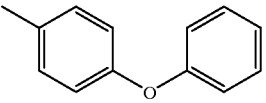 | A | 9426 |
| VIII'.01 | 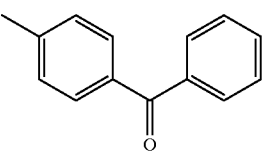 | A | 9427 |
| VIII'.01 | 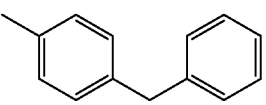 | A | 9442 |
| VIII'.01 | 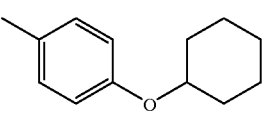 | A | 9459 |
| VIII'.01 | 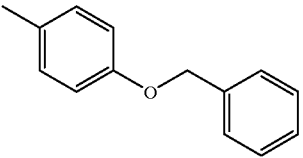 | A | 9460 |
| VIII'.01 | 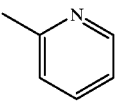 | B | 9377 |
| VIII'.01 | 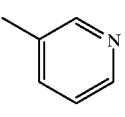 | A | 9359 |
| VIII'.01 | 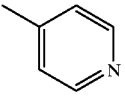 | A | 9384 |
| VIII'.01 | 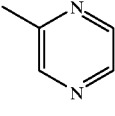 | A | 9391 |
| VIII'.01 | 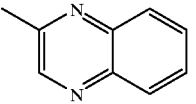 | A | 9347 |

TABLE 12-continued

| Amine of Formula VIII' | R₅ in acid R⁵¹—COOH | Method | Compound of Formula Ia |
|---|---|---|---|
| VIII'.01 | 1-methylisoquinoline | B | 9383 |
| VIII'.01 | 2-methylquinoline | B | 9385 |
| VIII'.01 | 3-methylisoquinoline | B | 9389 |
| VIII'.01 | 3-methylquinoline | A | 9397 |
| VIII'.01 | 3-methylthiophene | A | 9365 |
| VIII'.01 | 2-methylindole | A | 9367 |
| VIII'.23 | 2-methylquinoxaline | A | 9531 |
| VIII'.12 | | A | 9543 |
| VIII'.13 | | A | 9541 |
| VIII'.24 | | A | 9561 |
| VIII'.14 | | A | 9562 |
| VIII'.15 | | A | 9564 |
| VIII'.16 | | A | 9568 |
| VIII'.17 | | A | 9573 |
| VIII'.14 | 3-methylquinoline | A | 9571 |
| VIII'.16 | | A | 9574 |
| VIII'.17 | | A | 9576 |
| VIII'.25 | | A | 9578 |
| VIII'.13 | | A | 9581 |
| VIII'.12 | | A | 9584 |
| VIII'.28 | | A | 9588 |
| VIII'.29 | | A | 9593 |
| VIII'.27 | | A | 9586 |

TABLE 12-continued

| Amine of Formula VIII' | R$_5$ in acid R$^{51}$—COOH | Method | Compound of Formula Ia |
|---|---|---|---|
| VIII'.23 | 2-quinolinyl | A | 9545 |
| VIII'.23 | 5,6,7,8-tetrahydroquinolin-3-yl | A | 9590 |
| VIII'.23 | 2-pyridyl | B | 9472 |
| VIII'.23 | 3-pyridyl | A | 9482 |
| VIII'.23 | 4-pyridyl | A | 9483 |
| VIII'.23 | 2-pyrazinyl | A | 9493 |
| VIII'.23 | 5-methylpyrazin-2-yl | A | 9527 |
| VIII'.23 | 6-methoxypyridin-3-yl | A | 9582 |
| VIII'.23 | 5-propionylpyrazin-2-yl | A | 9569 |
| VIII'.23 | phenyl | A | 9456 |
| VIII'.12 | | A | 9511 |
| VIII'.28 | | A | 9510 |
| VIII'.18 | | A | 9512 |

TABLE 12-continued

| Amine of Formula VIII' | R₅ in acid R⁵¹—COOH | Method | Compound of Formula Ia |
|---|---|---|---|
| VIII'.23 | 2-F-C₆H₄ | A | 9489 |
| VIII'.23 | 3-F-C₆H₄ | A | 9500 |
| VIII'.23 | 4-F-C₆H₄ | A | 9501 |
| VIII'.23 | 2,4-di-F-C₆H₃ | A | 9513 |
| VIII'.23 | 2,6-di-F-C₆H₃ | A | 9514 |
| VIII'.23 | 2-Cl-C₆H₄ | A | 9494 |
| VIII'.23 | 3-Cl-C₆H₄ | A | 9495 |
| VIII'.23 | 4-Cl-C₆H₄ | A | 9496 |
| VIII'.23 | 2-CH₃-C₆H₄ | A | 9497 |
| VIII'.23 | 3-CH₃-C₆H₄ | A | 9503 |

TABLE 12-continued

| Amine of Formula VIII' | R₅ in acid R⁵¹—COOH | Method | Compound of Formula Ia |
|---|---|---|---|
| VIII'.23 | 4-methylphenyl | A | 9504 |
| VIII'.23 | 2-OMe-phenyl | A | 9477 |
| VIII'.23 | 3-OMe-phenyl | A | 9517 |
| VIII'.23 | 4-OMe-phenyl | A | 9518 |
| VIII'.23 | 2-OCOCH₃-phenyl | A | 9534 |
| VIII'.23 | 3-OCOCH₃-phenyl | A | 9540 |
| VIII'.23 | 4-OCOCH₃-phenyl | A | 9548 |
| VIII'.23 | 2-CF₃-phenyl | A | 9523 |
| VIII'.23 | 3-CF₃-phenyl | A | 9524 |
| VIII'.23 | 3-NMe₂-phenyl | A | 9556 |

TABLE 12-continued

| Amine of Formula VIII' | R₅ in acid R⁵¹—COOH | Method | Compound of Formula Ia |
|---|---|---|---|
| VIII'.23 | 4-isopropylphenyl | A | 9447 |
| VIII'.23 | 4-cyclohexylphenyl | A | 9461 |
| VIII'.23 | 1-naphthyl | A | 9470 |
| VIII'.23 | 2-naphthyl | A | 9476 |
| VIII'.23 | 3,4-dichlorophenyl | A | 9536 |
| VIII'.23 | 3,4-dimethylphenyl | A | 9538 |
| VIII'.23 | 2-thienyl | A | 9471 |
| VIII'.23 | 3-thienyl | A | 9492 |
| VIII'.23 | 2-indolyl | A | 9515 |
| VIII'.23 | 2-benzofuranyl | A | 9539 |

TABLE 12-continued

| Amine of Formula VIII' | R₅ in acid R⁵¹—COOH | Method | Compound of Formula Ia |
|---|---|---|---|
| VIII'.19 | 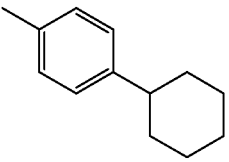 | A | 9466 |
| VIII'.20 | | A | 9479 |
| VIII'.21 | 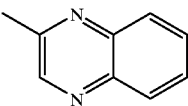 | A | 9567 |
| VIII'.22 | | A | 9572 |
| VIII'.26 | 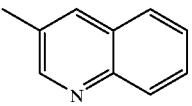 | A | 9577 |
| VIII'.22 | | A | 9585 |

Example 5

Interconversion of Compounds of Formula Ia

Compounds of formula (Ia) prepared as described in Example 4 were converted into other compounds of formula (Ia) as described below.

(i) 2-(2-Hydroxy-benzoylamino)-N-{4-[2-(6,7-dimethoxy-3,4-dihydro-1H-isoquinolin-2-yl)-ethyl]-phenyl}-benzamide (9535).

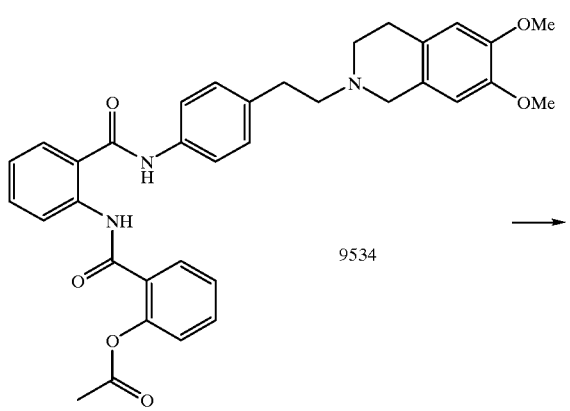

9534

→

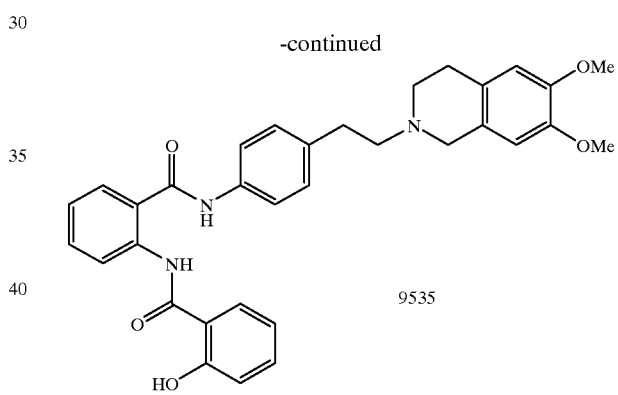

9535

To a solution of 9534 (0.035 g, 0.06 mmol) in methanol (2 ml) was added sodium hydroxide (3 mg, 0.077 mmol) in water (0.5 ml). The mixture was stirred at room temperature for 2 hours then at reflux for a further 3 hours. A further portion of sodium hydroxide (0.18 mmol) was added and reflux continued for 3 hours. The mixture was cooled and acidified (2M HCl) and partially basified with saturated sodium hydrogen carbonate solution. The mixture was extracted with ethyl acetate (2×25 ml), washed with brine solution (30 ml). The organics were dried over magnesium sulphate, filtered and concentrated in vacuo. Chromatography (silica gel, ethyl acetate) gave 9535 as a white solid (19 mg, 58%). Other compounds prepared in an analogous manner were 9549 from 9540 and 9559 from 9548.

(ii) 2-(4-Isopropyl-benzoylamino)-N-[2-(6,7-dimethoxy-3,4-dihydro-1H-isoquinolin-2-yl)-ethyl]-5-phenyl-benzamide (9432).

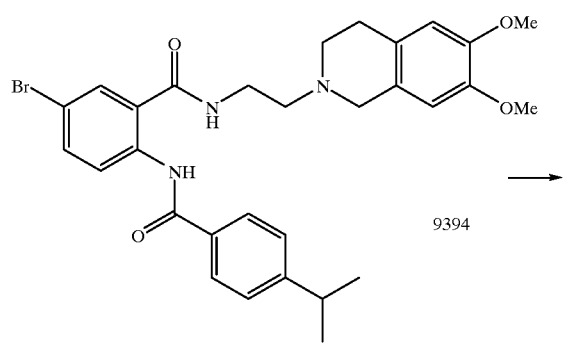

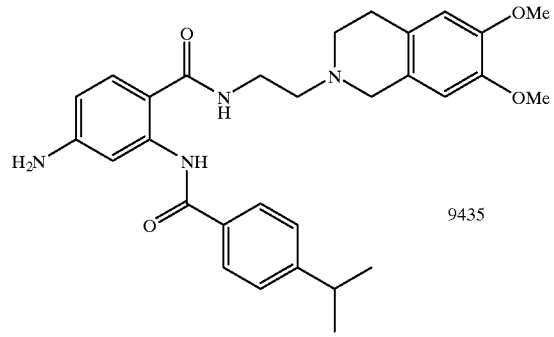

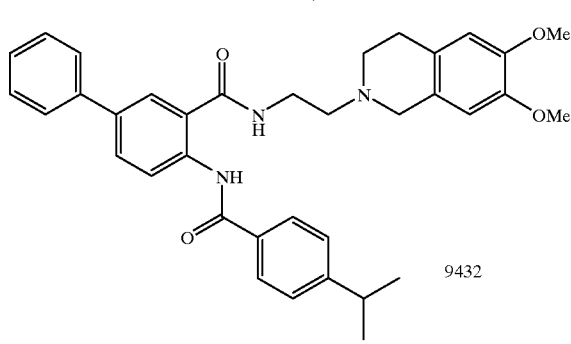

Platinum (IV) oxide (5 mg) was added to a solution of 9420 (47 mg, 0.086 mmol) in methanol (2 ml) and ethyl acetate (2 ml) and the mixture stirred under hydrogen gas at atmospheric pressure for 18 hours. The mixture was filtered through silica gel (10% methanol, 90% ethyl acetate) and concentrated in vacuo to afford 9435 (42 mg, 95%) as a yellow powder.

(iv) Quinoxaline-2-carboxylic acid (2-{4-[2-(6,7-dimethoxy-3,4-dihydro-1H-isoquinolin-2-yl)-ethyl]-phenylcarbamoyl}-5-hydroxyamino-phenyl)-amide (9542).

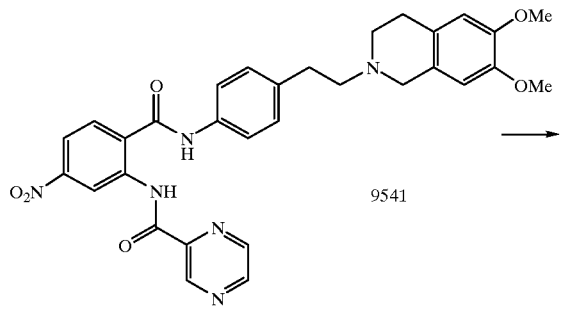

To a solution of 9394 (20 mg, 0.035 mmol) was added phenylboronic acid (5 mg, 0.038 mmol) and tetrakis(triphenylphosphine)palladium (2 mg, 0.00173 mmol) in a mixture of ethylene glycol dimethyl ether (0.5 ml) and sodium carbonate solution (2M, 0.04 ml, 0.08 mmol). The mixture was heated under reflux conditions for 3.5 hours. The mixture was cooled and water (10 ml) was added. The mixture was extracted with ethyl acetate (2×15 ml), washed with water (20 ml) and dried over magnesium sulphate. Filtration and concentration in vacuo, followed by chromatography (silica gel, ethyl acetate) gave 9432 (15 mg, 75%).

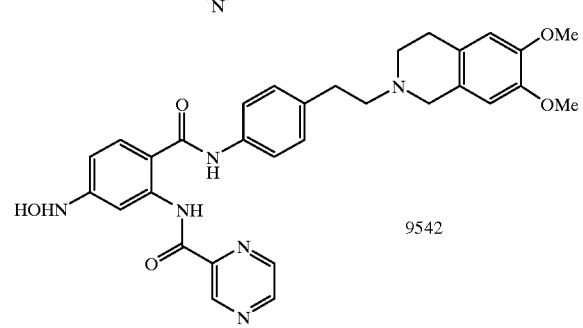

(iii) 2-(4-Isopropyl-benzoylamino)-N-[2-(6,7-dimethoxy-3,4-dihydro-1H-isoquinolin-2-yl)-ethyl]-4-amino-benzamide (9435).

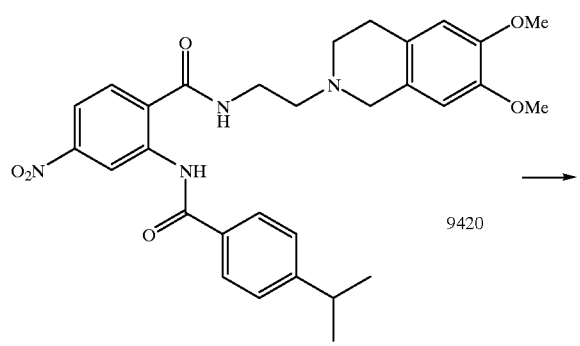

Platinum (IV) oxide (4 mg) was added to a solution of 9541 (38 mg) in ethanol (25 ml) and dichloromethane (25 ml) and the mixture was stirred under hydrogen gas at atmospheric pressure for 18 hours. The mixture was filtered through silica gel and concentrated in vacuo. Trituration with ethyl acetate (x1) then diethyl ether (x3), afforded 9542 (29 mg, 80%) as a yellow solid.

Example 6

Preparation of Compounds of Formula (Ia) Employing Protecting Group Strategy (a) 2-(4-Isopropyl-benzoylamino)-N-[2-(6,7-dimethoxy-3,4-dihydro-1H-isoquinolin-2-yl)-ethyl]-3-hydroxy-benzamide (9424) was prepared as shown in scheme 4:

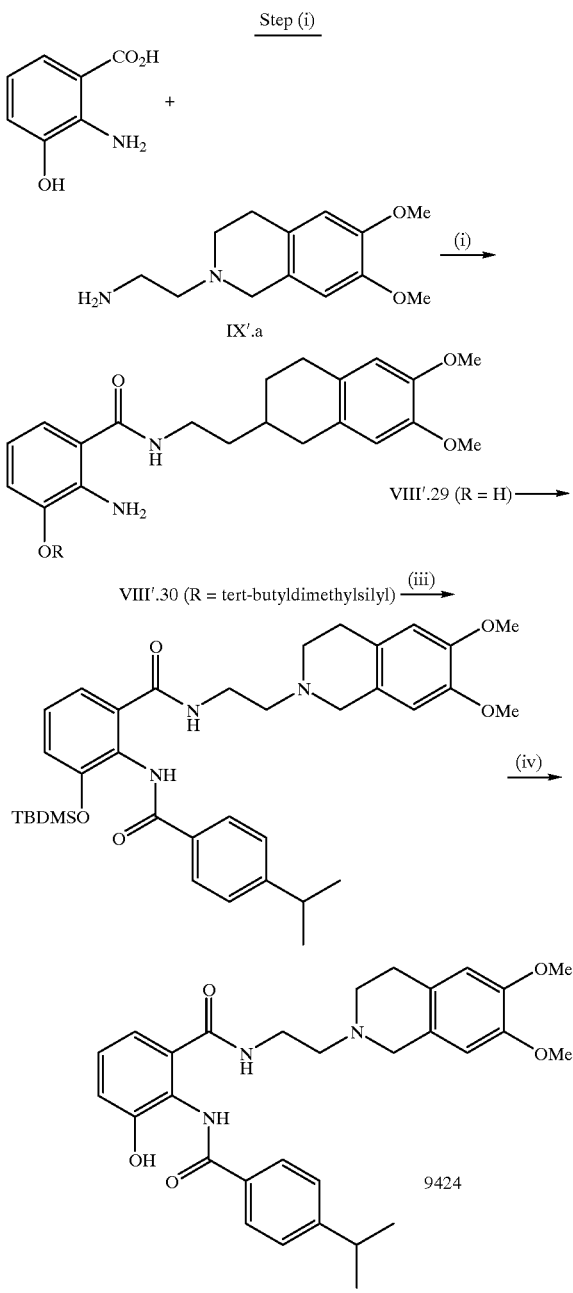

Step (i)

A solution of the commercially available 3-hydroxyanthranilic acid (324 mg, 2.12 mmol), amine IX'.a (500 mg, 2.12 mmol), N-cyclohexyl-N-(2-morpholinoethyl)-carbodiimide-methyl-p-toluene sulphonate (987 mg, 2.33 mmol), 1-hydroxybenzotriazole monohydrate (315 mg, 2.33 mmol) and triethylamine for (0.32 ml, 2.44 ml) in anhydrous dichloromethane (20 ml) was stirred at room temperature 3 days. Aqueous work-up followed by flash chromatography (2% methanol, 98% dichloromethane, silica gel) and trituration (diethyl ether) gave VIII'.29 (174 mg) as an orange solid.

Step (ii)

A solution of VIII'.29 (170 mg, 0.46 mmol), imidazole (34 mg, 0.50 mmol) and tert-butyldimethylsilyl chloride (76 mg, 0.50 mmol) in dimethylformamide (10 ml) was stirred at room temperature for 3 days. A further amount of tert-butyldimethylsilyl chloride (206 mg, 1.37 mmol) and imidazole (93 mg, 1.37 mmol) was added and the mixture stirred for 4 hours. Aqueous work-up followed by flash chromatography (2% methanol, 98% ethyl acetate, silica gel) gave VIII'.30 (142 mg) as a yellow oil.

Step (iii)

Triethylamine (1.12 ml, 8.04 mmol) and amine VIII'.30 (1.57 g, 3.24 mmol) were added to a stirred solution of 4-isopropylbenzoyl chloride (preparation as described for 9398, 738 mg, 4.04 mmol) in anhydrous dichloromethane (20 ml) while cooling in an ice/water bath. The mixture was allowed to warm to room temperature and stirred for 18 hours. The mixture was poured into saturated sodium carbonate solution (50 ml) and extracted with dichloromethane (75 ml) twice. The combined organic extracts were dried over dry magnesium sulphate and reduced in vacuo. Flash chromatography (2% methanol, 98% ethyl acetate, silica gel) gave 2-(4-isopropyl-benzoylamino)-3-(tert-butyl-dimethyl-silanyloxy)-N-[2-(6,7-dimethoxy-1,2,3,4-tetrahydro-naphthalen-2-yl)-ethyl]-benzamide (367 mg) as a cream solid.

Step (iv)

A solution of tetrabutylammonium fluoride (1.0M in tetrahydrofuran, 0.63 ml, 0.63 mmol) was added to a solution of 2-(4-isopropyl-benzoylamino)-3-(tert-butyl-dimethyl-silanyloxy)-N-[2-(6,7-dimethoxy-1,2,3,4-tetrahydro-naphthalen-2-yl)-ethyl]-benzamide (365 mg, 0.58 mmol) in tetrahydrofuran (20 ml) while cooling in an ice/water bath. After stirring for 30 minutes the mixture was poured into saturated ammonium chloride solution (30 ml) and extracted with ethyl acetate (50 ml) twice. The combined organic layers were washed with water (50 ml), brine (50 ml), dried over dry magnesium sulphate and reduced in vacuo. Flash chromatography (2% methanol, 98% ethyl acetate, silica gel) afforded 9424 (220 mg) as a pale yellow solid.

(b) Quinoxaline-2-carboxylic acid (2-{4-[2-(6,7-dimethoxy-3,4-dihydro-1H-isoquinolin-2-yl) -ethyl]-phenylcarbamoyl}-4-hydroxyphenyl)-amide (9554) was prepared as shown in Scheme 5:

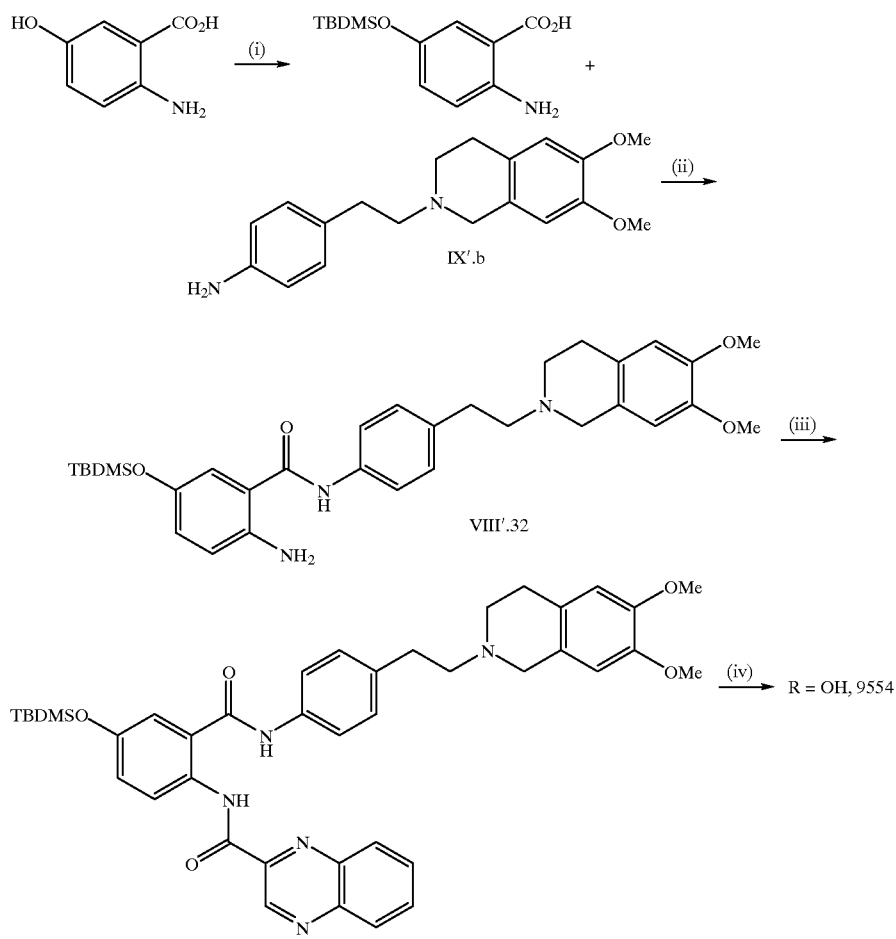

Scheme 5

Step (i)

Imidazole (1.8 g, 26.1 mmol) and tert-butyldimethylsilyl chloride (3.95 g, 26.1 mmol) were added to a solution of the commercially available 5-hydroxyanthranilic acid (1.0 g, 6.54 mmol) in dimethylformamide (40 ml) while cooling in an ice/water bath. The mixture was allowed to warm to room temperature and stirred for 18 hours. Aqueous work-up afforded an impure sample of 2-amino-5-(tert-butyl-dimethyl-silanyloxy)-benzoic acid (1.74 g) that was used in Step (ii) without further purification.

Step (ii)

2-Amino-5-(tert-butyl-dimethyl-silanyloxy)-benzoic acid from Step (i) (1.6 g), amine IX'.b (1.87 g), 6.0 mmol), N-cyclohexyl-N-(2-morpholinoethyl)-carbodiimide-methyl-p-toluene sulphonate (2.79 g, 6.6 mmol) and 1-hydroxybenzotriazole monohydrate (0.89 g, 6.6 mmol) were dissolved in anhydrous dichloromethane (50 ml) and stirred at room temperature for 3 days. Aqueous work-up followed by flash chromatography (silica gel) afforded VIII'.31 (443 mg), as a yellow foam.

Step (iii)

2-Quinoxaloyl chloride (67 mg, 0.35 mmol) was added to a solution of amine VIII'.31 (200 mg, 0.28 mmol) and triethylamine (0.10 ml, 0.72 mmol) in anhydrous dichloromethane (10 ml) while cooling in an ice/water bath. The mixture was allowed to warm to room temperature and stirred for 18 hours. Aqueous work-up and flash chromatography (silica gel, 2% methanol, 98% ethyl acetate) afforded quinoxaline-2-carboxylic acid (4-(tert-butyl-dimethyl-silanyloxy)-2-{4-[2-(6,7-dimethoxy-3,4-dihydro-1H-isoquinolin-2-yl)-ethyl]-phenylcarbamoyl}-phenyl)-amide (183 mg) as a yellow foam.

Step (iv)

A solution of tetrabutyammonium fluoride in tetrahydrofuran (1.0M, 0.067 ml, 0.067 mmol) was added to a solution of quinoxaline-2-carboxylic acid (4-(tert-butyl-dimethyl-silanyloxy)-2-{4-[2-(6,7-dimethoxy-3,4-dihydro-1H-isoquinolin-2-yl)-ethyl]-phenylcarbamoyl}-phenyl)-amide (150 mg, 0.21 mmol) in tetrahydrofuran (10 ml) while cooling in an ice/water bath. The mixture was stirred for 30 minutes, poured into saturated ammonium chloride solution (20 ml) and extracted with ethyl acetate (30 ml) twice. The combined organic phases were washed with water (30 ml), brine (30 ml), dried over dry magnesium sulphate and reduced in vacuo. Flash chromatography (silica gel, 2% methanol, 98% ethyl acetate) and trituration in diethyl ether gave 9554 (32 mg as a yellow solid.

(c) Quinoline-3-carboxylic acid (5-amino-2-{4-[2-(6,7-dimethoxy-3,4-dihydro-1H-isoquinolin-2-yl)-ethyl]-phenylcarbamoyl}-phenyl)-amide (9589) was prepared as shown in scheme 6.

Scheme 6

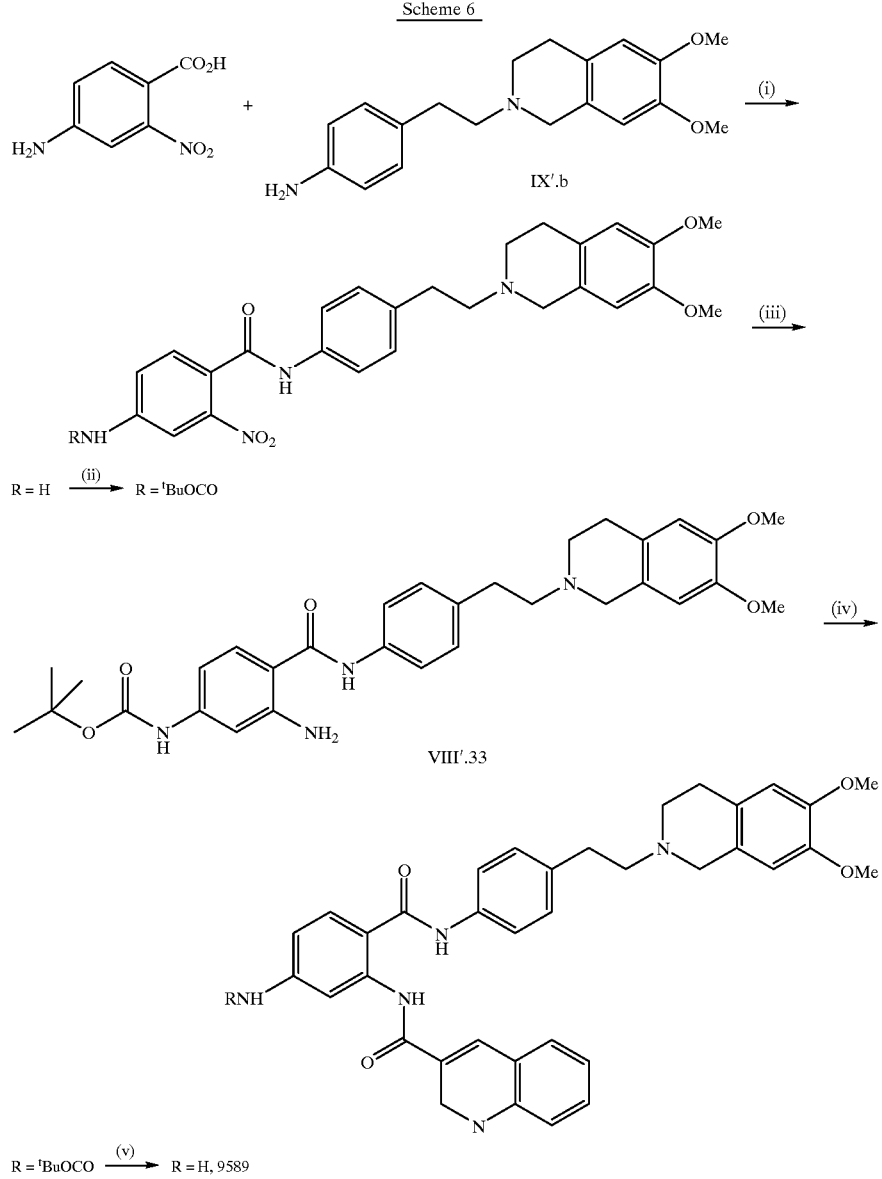

Step (i)

A solution of 4-amino-2-nitrobenzoic acid (0.96 g, 5.3 mmol), amine IX'.b (1.65 g, 5.3 mmol), hydroxybenzotriazole monohydrate (0.79 g, 5.8 mmol), N-cyclohexyl-N-(2-morpholinoethyl)carbodiimide methyl-p-toluene sulphonate (2.46 g, 5.8 mmol) in anhydrous dichloromethane (15 ml) was stirred at 20–25 C. for 18 hours. Water (15 ml) was added and the mixture extracted with dichloromethane (15 ml) three times. The combined organic extracts were dried over dry magnesium sulphate and reduced in vacuo. Trituration in diethylether and flash column chromatography (10% methanol, 90% dichloromethane) afforded the intermediate nitroamine (0.42 g) as an orange solid.

Step (ii)

A solution of the product of Step (i) (0.42 g, 0.88 mmol), di-tert-butyl dicarbonate (0.24 g, 1.10 mmol) and N,N-dimethylaminopyridine (5 mg, 0.04 mmol) in anhydrous dichloromethane (15 ml) was stirred in an ice/water bath for one hour, allowed to warm to room temperature and stirred for a further three days. Potassium carbonate solution (15 ml) was added and the mixture extracted with dichloromethane (15 ml) three times. The combined organic layers were dried over magnesium sulphate and dried in vacuo. Chromatography (2.5% methanol, 97.5% dichloromethane, silica gel) afforded the intermediate protected nitroamine (0.37 g).

Step (iii)

To a solution of this product (0.35 g, 0.61 mmol) in ethanol (5 ml) and dichloromethane (5 ml) was added 10% palladium on cabon (35 mg). The mixture was stirred under hydrogen gas at atmospheric pressure for eighteen hours. The mixture was filtered through Celite™ and reduced until crystallisation was initiated. After cooling the product, amine VIII'.32 (0.19 g), was isolated as a yellow crystalline solid.

Step (iv)

Amine VIII'.32 (192 mg, 0.35 mmol) was added to a suspension of quinoline-3-carboxylic acid chloride (82 mg, 0.43 mmol) in anhydrous dichloromethane (3 ml) while cooling in an ice/water bath. The resulting solution was stirred for one hour, allowed to warm to room temperature and stirred for a further eighteen hours. Dilute potassium carbonate solution (30 ml) was added and the mixture was extracted with chloroform (30 ml). The organic phase was washed with water four times, dried over anhydrous magnesium sulphate and reduced in vacuo. Trituration with dry diethyl ether and recrystallisation (methanol, dichloromethane) gave the product, Boc-protected 9589, as a cream solid (0.19 g).

Step (v)

A solution of the above compound (78 mg, 0.11 mmol) was stirred in a mixture of 5N hydrochloric acid (20 ml) and ethanol (25 ml) for three days. The mixture was basified with saturated potassium carbonate solution and extracted with dichloromethane (50 ml) three times. The combined organic phases were dried over dry magnesium sulphate and reduced in vacuo. Flash chromatography (2.5% methanol, 97.5% dichloromethane) and recrystallisation from methanol/dichloromethane) afforded the title compound, 9589, as a pale brown solid (15 mg).

Example 7

Preparation of Compounds of Formula Ia Prepared from Methyl Anthranilate (Process Variant (b'))

The route to compounds of formula (Ia) via the intermediate of formula XII' is shown in scheme 7:

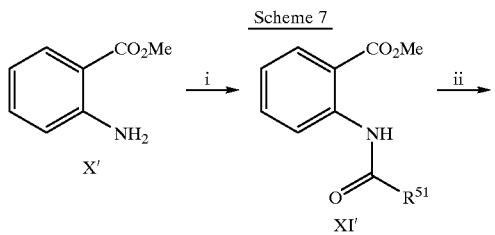

Scheme 7

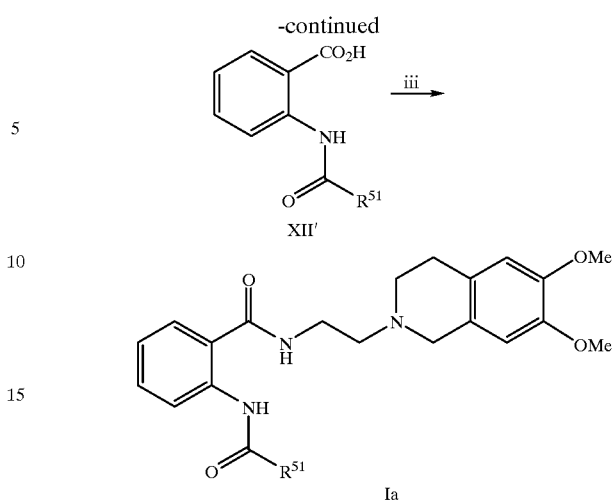

Reaction of commercially available methyl anthranilate X' with an acid chloride of formula $R^{51}$—COCl in the presence of triethylamine using dichloromethane as solvent, at room temperature for 1–14 hours yielded the intermediate of general formula XI'. Hydrolysis of the intermediate ester XI' was achieved by treating it with sodium hydroxide in methanol/water at reflux for 1–5 hours. Acidification of the mixture with HCl followed by work up furnished intermediate acid XII'.

Preparation of the final product of formula Ia was achieved by coupling this acid with amine IX'.a. To a solution of the intermediate acid in THF was added 1,1-carbonyldiimidazole (1.1 equivalents) and the mixture was stirred for one hour at room temperature. To this mixture was added amine IX'.a (1.0 equivalents) and pyridinium p-toluene sulphonate (2.6 equivalents). The resulting mixture was refluxed for 56 hours and cooled. After solvent removal and work-up the product was purified by flash column chromatography over silica gel. The compounds prepared by this general route are summarised in Table 13.

TABLE 13

| $R^{51}$ | Compound of Formula Ia |
|---|---|
| 2 group) | ![structure] 9304 |

TABLE 13-continued

| R⁵¹ | Compound of Formula Ia | |
|---|---|---|
| 4-methylbiphenyl | [structure with biphenyl carbonyl] | 9294 |
| methylenedioxyphenyl (methyl-benzodioxole) | [structure with benzodioxole carbonyl] | 9302 |
| 6-methylnaphthalen-2-yl | [structure with naphthalene-2-carbonyl] | 9295 |

Example 8

Preparation of Compounds of Formula Ia Via Azalactones of General Formula XIII' (Process Variant (c'))

Scheme 8

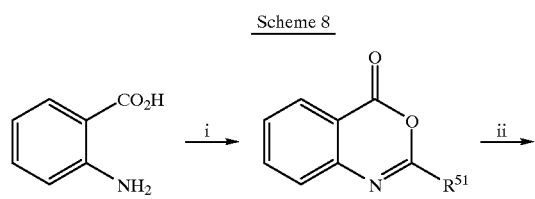

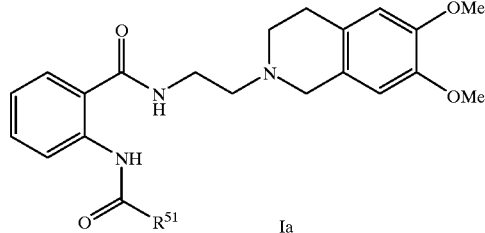

Ia

Reaction of commercially available anthranilic acid with an acid chloride of general formula R⁵¹—COCl in pyridine or pyridine/dichloromethane mixture at 0° C. for 3–8 hours, gives rise to the azalactone intermediates of formula XIII'. Treatment of this intermediate with amine IX'.a in refluxing toluene in the presence of p-toluene sulphonic acid or camphor sulphonic acid for 14–24 hours gives rise to compounds of general formula Ia. Final products were purified by flash column chromatography over silica gel. The following compounds of formula Ia were prepared via this route:

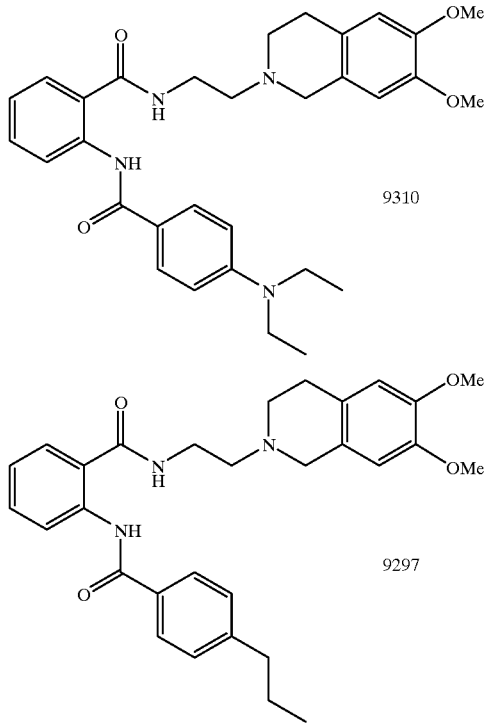

9310

9297

Example 9

Preparation of Salts

The hydrochloride salts of compounds of formula (I) were prepared by treatment of a solution of the compounds in THF with 2 molar hydrochloric acid followed by sonication until a clear solution was obtained. The solvent was then removed in vacuo and the residual solution was freeze-dried to give the hydrochloride salt.

In an alternative method, hydrochloride salts were prepared by bubbling HCl gas through a solution of the corresponding free base in THF, followed by evaporation to dryness.

Example 10

Pharmaceutical Composition

Tablets, each weighing 0.15 g and containing 25 mg of a compound of the invention can be manufactured as follows:

Composition for 10,000 tablets compound of the invention (250 g)

lactose (800 g)

corn starch (415 g)

talc powder (30 g)

magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium stearate is added, carefully mixed and processed into tablets.

Example 11

Characterisation of compounds of formula (I)

The compounds prepared in Examples 2 to 9 were characterised by mass spectroscopic, microanalytical, proton n.m.r. and, in some cases, infra-red techniques. The results are set out in the following tables.

|  |  | Mass spec data |  |  | $^1$H NMR data |
| --- | --- | --- | --- | --- | --- |
| No. | Molecular formula | mass (intensity) | mode | solvent/field | d |
| 9304 | $C_{30}H_{35}N_3O_4$ 501 | MH$^+$ 502 (70%) | CI | CDCl$_3$/400 MHz | 1.29 (6H, 2xd), 2.86 (6H, br.m), 3.0 (1H, septet), 3.68 (4H, m), 3.83 (3H, s), 3.86 (3H, s), 6.54 (1H, s), 6.62 (1H, s), 7.08 (1H, t), 7.16 (1H, br.s), 7.38 (2H, d), 7.51 (2H, t), 7.99 (2H, d), 8.82 (1H, d), 12.22 (1H, br.s). |
| 9405 | $C_{30}H_{34}N_3O_4Cl$ 535/537 | MH$^+$ 536 (15%), 206 (100%) | EI | CDCl$_3$/400 MHz | 1.28 (6H, d), 2.74–2.80 (6H, m), 2.95–3.04 (1H, m, CH), 3.60 (2H, br.s) 3.65–3.70 (2H, m), 3.81 (3H, s, OMe), 3.83 (3H, s, OMe), 6.49 (1H, s), 6.58 (1H, s), 7.10 (2H, d, J = 8 Hz), 7.32–7.40 (3H, m), 7.88 (2H, d, J = 7 Hz), 8.44 (1H, d, J = 8 Hz), 10.36 (1H, br.s, NH) |
| 9354 | $C_{30}H_{34}N_3O_4Cl$ 535/537 | MH$^+$ 536 (30%) | CI | CDCl$_3$/400 MHz | 1.28 (6H, d, J = 7 Hz), 2.75–2.85 (6H, m), 2.95–3.02 (1H, m, CH), 3.62–3.66 (4H, m), 3.84 (3H, s, OMe), 3.86 (3H, s, OMe), 6.54 (1H, s), 6.62 (1H, s), 7.00 (1H, br.s, NH), 7.37 (2H, d, J = 7 Hz), 7.44–7.47 (2H, m), 7.95 (2H, d, J = 7 Hz), 8.80 (1H, d, J = 8 Hz), 12.01 (1H, br.s, NH) |

| | | | | | |
|---|---|---|---|---|---|
| 9350 | C$_{30}$H$_{34}$ClN$_3$O$_4$ 535.5 | MH$^+$ 536:538 - 3:1 ratio Φ Cl cpd (100%). | ESI | CDCl$_3$/400 MHz | 1.29 (6H, d), 2.90–3.42 (8H, m), 3.78–3.98 (9H, m), 6.55 (1H, s), 6.64 (1H, s), 7.12 (1H, d), 7.34 (2H, d), 7.84 (1H, dd), 7.96 (2H, d), 7.92–8.06 (1H, br.m), 8.95 (1H, s), 12.48 (1H, s). |
| 9401 | C$_{30}$H$_{34}$ClN$_3$O$_4$ 535.5 g | MH$^+$ 536/538 [⁻3:1 intensity, Cl cpd] (47%) Base Peak 192 (100%) | EI | CDCl$_3$/400 MHz | 1.30 (6H, d), 2.75–3.03 (7H, m), 3.58–3.68 (2H, m), 3.72 (2H, br.s), 3.82 (3H, s), 3.83 (3H, s), 6.50 (1H, s), 6.59 (1H, s), 7.20 (1H, t), 7.34 (2H, d), 7.28–7.48 (IH, br.m), 7.50 (1H, d), 7.54 (1H, d), 7.92 (2H, d), 9.25 (1H, s) |
| 9394 | C$_{30}$H$_{34}$N$_3$O$_4$Br 579/581 | MH$^+$ 580 (15%), 206 (70%) | EI | CDCl$_3$/400 MHz | 1.28 (6H, d, J = 7 Hz), 2.78–2.87 (6H, m), 2.95–3.02 (1H, m, CH), 3.60–3.65 (4H, m), 3.83 (3H, s, OMe), 3.85 (3H, s, OMe), 6.54 (1H, s), 6.62 (1H, s), 6.90 (1H, br.s, NH), 7.36 (2H, d, J = 7 Hz), 7.55–7.60 (2H, m). 7.94 (2H, d, J = 7 Hz), 8.74 (1H, d, J = 8 Hz), 11.99 (1H, br.s, NH) |
| 9349 | C$_{31}$H$_{34}$FN$_3$O$_4$ 519 | MH$^+$ 520 (100%) | ESI | CDCl$_3$/400 MHz | 1.29 (6H, d), 2.80–3.10 (7H, m), 3.65–3.90 (10H, m), 6.54 (1H, s), 6.62 (1H, s), 6.77 (1H, t), 7.38 (2H, d), 7.67 (1H, br.s), 7.98 (2H, d), 8.67 (1H, dd), 12.53 (1H, s) and one unobserved NH signal. |
| 9398 | C$_{31}$H$_{37}$N$_3$O$_4$ 515 | MH$^+$ 516 (24%) Base peak 206 (100%) | EI | CDCl$_3$/400 MHz | 1.28 (6H, d), 2.32 (3H, s), 2.66–2.84 (6H, m), 2.97 (1H, septet), 3.55 (2H, dd), 3.62 (2H, s), 3.83 (3H, s), 3.84 (3H, s), 6.51 (1H, s), 6.59 (1H, s), 6.95 (1H, br.s), 7.15 (1H, t), 7.28–7.40 (4H, m), 7.95 (2H, d), 10.12 (1H, s). |
| 9399 | C$_{31}$H$_{37}$N$_3$O$_5$ 531 | MH$^+$ 532 (10%) Base peak 192 (100%) | CI$^+$ | CDCl$_3$/400 MHz | 1.28 (6H, d), 2.60–2.82 (6H, m), 2.97 (1H, septet), 3.50–3.60 (4H, m), 3.83 (3H, s), 3.84 (3H, s), 3.86 (3H, s), 6.48 (1H, s), 6.58 (1H, s), 6.93 (1H, br.s), 7.02 (1H, d), 7.12 (1H, d), 7.20 (1H, d), 7.32 (2H, d), 7.90 (2H, d), 8.94 (1H, s). |
| 9424 | C$_{30}$H$_{35}$N$_3$O$_5$ 517 | MH$^+$ 518 (100%) | CI$^+$ | CDCl$_3$/400 MHz | 1.28 ppm (6H, s), 2.78–3.04 (6H, m), 2.98 (1H, septet), 3.60–3.86 (4H, m), 3.82 (3H, s), 3.83 (3H, s), 6.52 (1H, s), 6.60 (1H, s), 7.10–7.28 (3H, m), 7.38 (2H, d), 7.40–7.64 (1H, br.s), 8.02 (2H, d), 10.18 (1H, s), 12.32 (1H, s) |
| 9420 | C$_{30}$H$_{34}$N$_4$O$_6$ | MH$^+$, 547 (100%) | CI$^+$ | CDCl$_3$/400 MHz | 12.20 (1H, s), 9.68 (1H, d, J = 1 Hz), 7.96 (2H, d, J = 8 Hz), 7.84 (1H, dd, J = 8 Hz, 1 Hz), 7.52 (1H, d, J = 8 Hz), 7.48 (2H, d, J = 8 Hz), 7.38 (1H, br.s), 6.62 (1H, s), 6.54 (1H, s), 3.86 (3H, s), 3.82 (3H, s), 3.72–3.54 (4H, m), 3.02 (1H, septet, J = 7 Hz), 2.90–2.78 (6H, m), 1.30 (6H, d, J = 7 Hz). |
| 9435 | C$_{30}$H$_{36}$N$_4$O$_4$ | MH$^+$, 517 (100%) | CI$^+$ | CDCl$_3$%400 MHz | 12.70 (1H, s), 8.28 (1H, d, J = 1 Hz), 8.00 (2H, d, J = 8 Hz), 7.36 (2H, d, J = 8 Hz), 7.28 (1H, d, J = 8 Hz), 6.88 (1H, br.s), 6.64 (1H, s), 6.56 (1H, s), 6.30 (1H, dd, J = 8 Hz, 1 Hz), 4.06 (2H, br.s), 3.88 (3H, s), 3.86 (3H, s), 3.68–3.58 (4H, m), 3.00 (1H, septet, J = 7 Hz), 2.90–2.74 (6H, m), 1.30 (6H, d, J = 7 Hz). |
| 9432 | C$_{36}$H$_{39}$N$_3$O$_4$ 577 | MH$^+$, 578 (20%) | CI | CDCl$_3$/400 MHz | 1.28 (6H, 2xd, J = 7 Hz), 2.80–2.85 (6H, m) 2.94–3.02 (1H, m CH), 3.62–3.70 (4H, m), 3.80 (3H, s, OMe), 3.82 (3H, s, OMe), 6.52 (1H, s) 6.60 (1H, s), 7.20 (1H, br.s, NH), 7.30–7.40 (5H, m), 7.46 (2H, d, J = 7 Hz), 7.65–7.75 (2H, m), 8.00 (2H, d, J = 7 Hz), 8.87 (1H, d, J = 8 Hz), 12.12 (1H, br.s, NH). |
| 9410 | C$_{34}$H$_{37}$N$_3$O$_4$ 551 | MH$^+$ 552 (6%) Base peak 316 (100%) | EI | CDCl$_3$/400 MHz | 1.30 (6H, d), 2.88–3.12 (7H, m), 3.70–3.89 (10H, m), 6.55 (1H, s), 6.62 (1H, s), 7.26 (1H, s), 7.33–7.43 (3H, m), 7.52 (1H, t), 7.82 (2H, t), 8.03 (2H, d), 8.32 (1H, br.s), 9.27 (1H, s), 12.08 (1H, s) |
| 9256.0 | C$_{29}$H$_{34}$O$_4$N$_4$ = SO$_2$Da | SO$_3$ Da MH$^+$ 20% 148 Da 100% 267 Da 20% 192 Da 45% | DCI$^+$ | CDCl$_3$/400 MHz | 2.76–2.87d (6H, m), 3.05 (6H, 2xs), 3.61–3.68 (4H, m), 3.83 (3H, s), 3.86 (3H, s), 6.55 (1H, s), 6.62 (1H, s), 6.77 (2H, d), 6.95–7.04 (2H, overlapping t |

-continued

| | | | | | |
|---|---|---|---|---|---|
| 9297.00 | C$_{30}$H$_{35}$N$_3$O$_5$, 501 | MH$^+$ 502 (100%) | CI | CDCl$_3$/400.134 MHz | and br.s), 7.43–7.50 (2H, m), 7.77 (2H, d), 8.80 (1H, d). 11.99 (1H, br.s). 0.98 (3H, t), 1.68 (2H, sextet), 2.68 (2H, t), 2.74–2.85 (6H, m), 3.62 (4H, s and t), 3.81 (3H, s), 3.86 (3H, s), 6.54 (1H, s), 6.62 (1H, s), 7.02 (1H, br.s), 7.05 (1H, t), 7.31 (2H, d), 7.48 (1H, d), 7.5 (1H, t), 7.98 (2H, d), 8.8 (1H, d), 12.20 (1H, br.s). t is not clear |
| 9395 | C$_{32}$H$_{39}$O$_4$N$_3$ 529 Da | MH$^+$ 530 Da 100% | DCI$^+$/NH$_3$ | CDCl$_3$/400 MHz | 0.92 (3H, t), 1.30–1.40 (4H, m), 1.42–1.69 (2H, overlapping water and sample signals), 2.68 (2H, t), 2.85–2.97 (6H, m), 3.67–3.79 (4H, m), 3.82 (3H, s), 3.87 (3H, s), 6.53 (1H, s), 6.62 (1H, s), 7.08 (1H, t), 7.32 (2H, d), 7.5–7.65 (2H, m), 7.98 (2H, d), 8.82 (1H, d), 12.24 (1H br.s). |
| 9331.0 | C$_{33}$H$_{39}$O$_4$N$_3$ 541 Da | MH$^+$ 542 Da 25% 192 Da 100% 102 Da 100% | DCI$^+$ | CDCl$_3$/400 MHz | 1.20–1.33 (1H, br.m), 1.42 (4H, br.m), 1.78 (1H, br.d), 1.89 (4H, br.m), 2.59 (1H, br.m), 2.89 (6H, m), 3.64–3.75 (4H, overlapping signals), 3.82 (3H, s), 3.86 (3H, s), 6.55 (1H, s), 6.63 (1H, s), 7.09 (1H, t), 7.35 (2H, d), 7.48–7.61 (2H, m), 7.99 (2H, d), 8.82 (1H, d), 12.21 (1H, br.s). NB: other NH signal not seen. |
| 9294.00 | C$_{33}$H$_{33}$N$_3$O$_4$ 535 | MH$^+$ 536 (100%) | CI | 400.134 MHz CDCl$_3$ | 2.82 (6H, m), 3.65 (2H, s), 3.68 (2H, t), 3.82 (3H, s), 3.85 (3H, s), 6.52 (1H, s), 6.62 (1H, s), 7.08 (1H, br.s), 7.09 (1H, t), 7.4 (1H, t), 7.46 (3H, m), 7.52 (1H, t), 7.64 (2H, d), 7.74 (2H, d), 8.12 (2H, d), 8.85 (1H, d), 12.34 (1H, s). |
| 9295.00 | C$_{31}$H$_{31}$N$_3$O$_4$ 509 | MH$^+$ 510 (100%) | ESI | 400.134 MHz, CDCl$_3$ | 2.81 (6H, m), 3.65 (2H, s), 3.66 (2H, t), 3.82 (3H, s), 3.86 (3H, s), 6.54 (1H, s), 6.62 (1H, s), 7.06 (1H, br.s), 7.1 (1H, t), 7.48–7.61 (4H, m), 7.89 (1H, d), 7.96 (1H, d), 8.04 (1H, d), 8.12 (1H, d), 8.6 (1H, s), 8.8 (1H, d), 12.42 (1H, s). |
| 9302 | C$_{28}$H$_{29}$N$_3$O$_6$ 503 | MH$^+$ and (M-H)$^+$ 50:50 502 (100%) | ESI | 400 13 MHz | 2.86 (6H, br.m), 3.7 (4H, t and s), 3.86 (3H, s), 3.88 (3H, s), 6.05 (2H, s), 6.55 (1H, s), 6.61 (1H, s), 6.91 (1H, d), 7.08 (1H, t), 7.5 (2H, t) 7.53 (1H, d), 7.61 (1H, d), 8.79 (1H, d) 12.2 (1H, br.s). |
| 9310.00 | C$_{31}$H$_{38}$N$_4$O$_4$ 530 | MH$^+$ (>>30%) | CI | 400.134 MHz | 1.21 (6H, t), 2.85 (6H, m)$^+$, 3.42 (4H, q), 3.68 (4H, m)$^x$, 3.82 (3H, s), 3.86 (3H, s), 6.52 (1H, s), 6.61 (1H, s), 6.71 (2H, d), 7.01 (1H, t), 7.11 (1H, br.s), 7.48 (2H, 1H t + d)*, 7.94 (2H, d), 8.82 (1H, d), 11.98 (1H, br.s). $^+$almost looks like triplet $^x$should be triplet and singlet *possible overlapping triplet and doublet. |
| 9334 | C$_{31}$H$_{37}$O$_4$N$_3$ 515 | MH$^+$ 516 (100%) | CI | CDCl$_3$/400 MHz | 1.39 (9H, s), 2.79–2.91 (8H, m), 3.61–3.71 (2H, br.s), 3.81 (3H, s), 3.86 (3H, s), 6.54 (1H, s), 6.62 (1H, s), 7.04–7.11 (1H, m), 7.46–7.56 (4H, m), 8.01 (2H, d), 8.82 (1H, d) both NH protons not observed poor spectra. |
| 9351 | C$_{27}$H$_{29}$N$_3$O$_4$ 459 | MH$^+$, 460 (100%) | ESI | CDCl$_3$/400 MHz | 2.75–2.85 (6H, m), 3.62–3.65 (4H, m), 3.82 (3H, s, OMe), 3.85 (3H, s, OMe), 6.53 (1H, s), 6.60 (1H, s), 7.04–7.10 (2H, m), 7.45–7.55 (5H, m), 8.03–8.06 (2H, m), 8.84 (1H, d, J = 8 Hz). 12.25 (1H, br.s, NH). |
| 9380 | C$_{27}$H$_{28}$O$_4$N$_3$ Br 538 | MH$^+$, 538/540 1.1 (100%) | DCI +/− | CDCl$_3$/400 MHz | 2.95–3.07 (6H, m), 3.74–3.86 (10H, m), 6.54 (1H, s), 6.63 (1H, s), 7.63 (1H, t), 7.93 (2H, d), 8.79 (1H, d), 12.47 (1H, br.s). NH proton not observed. |
| 9381 | C$_{27}$H$_{28}$O$_6$N$_4$ SO$_4$ Da | MH$^+$ 505 Da (100%) | DCI$^+$ | CDCl$_3$/400 MHz | 2.89–3.07 (6H, m), 3.71–3.89 (10H, m), 6.55 (1H, s), 6.66 (1H, s) 7.19 (1H, t), 7.51–7.60 (2H, m), 7.74 (1H, br.s), 8.22 (2H, d), 8.37 (2H, d), 8.84 (1H, d), 12.77 (1H, br.s). |
| 9426 | C$_{33}$H$_{33}$N$_3$O$_5$ 551 | MH$^+$ 552 (8%) Base peak 69 (100%) | CI$^+$ | CDCl$_3$/400 MHz | 2.80–3.00 (6H, br.m), 3.60–3.90 (10H, m), 6.53 (1H, s), 6.62 (1H, s), |

-continued

| | | | | | |
|---|---|---|---|---|---|
| | | | | | 7.06–7.12 (6H, m), 7.18 (1H, t), 7.38 (2H, t), 7.50 (1H, t), 7.62 (1H, br.d), 8.03 (2H, d), 8.81 (1H, d), 12.31 (1H, s). |
| 9427 | C$_{34}$H$_{33}$N$_3$O$_5$ 563 | MH$^+$ 564 (32%) Base peak 328 (100%) | CI$^+$ | CDCl$_3$/400 MHz | 2.70–2.98 (6H, br.m), 3.62–3.80 (4H, m), 3.84 (3H, s), 3.85 (3H, s), 6.54 (1H, s), 6.62 (1H, s), 7.12 (1H, t), 7.41 (1H, br.s), 7.47–7.67 (5H, m), 7.82 (2H, d), 7.92 (2H, d), 8.14 (2H, d), 8.85 (1H, d), 12.54 (1H, s). |
| 9442 | C$_{34}$H$_{35}$N$_3$O$_4$ 549 | MH$^+$ 550 (100%) | CI$^+$ | CDCl$_3$/400 MHz | 2.78–3.02 (6H, br.), 3.60–3.78 (4H, m), 3.86 (3H, s), 3.87 (3H, s), 4.06 (2H, s), 6.53 (1H, s) 6.62 (1H, s), 7.08 (1H, t), 7.12–7.65 (10H, m), 7.97 (2H, d), 8.82 (1H, d), 12.25 (1H, s) |
| 9459 | C$_{33}$H$_{39}$N$_3$O$_5$ 557 | MH$^+$ 558 (100%) | CI$^+$ | CDCl$_3$/400 MHz | 1.28–2.08 (10H, m), 2.72–2.94 (6H, m), 3.60–3.76 (4H, m), 3.87 (3H, s), (3H, s), 4.35 (1H, m), 6.53 (1H, s), 6.61 (1H, s), 6.98 (2H, d), 7.05 (1H, t), 7.45–7.60 (2H, m), 7.98 (2H, d), 8.30 (1H, d), 12.16 (1H, s). |
| 9460 | C$_{34}$H$_{35}$N$_3$O$_5$ 565 | MH$^+$ 566 (100%) | CI$^+$ | CDCl/400 MHz | 2.70–2.88 (6H, m), 3.58–3.68, (4H, m), 3.85 (3H, s), 3.86 (3H, s), 5.15 (2H, s), 6.54 (1H, s), 6.62 (1H, s), 6.95–7.55 (11H, m), 8.04 (2H, d), 8.80 (1H, d), 12.18 (1H, s). |
| 9377 | C$_{26}$H$_{28}$N$_4$O$_4$ 460 | MH$^+$ 461 (77%) Base peak 206 (100%) | CI$^+$ | CDCl$_3$/400 MHz | 2.70–2.95 (6H, m), 3.62–3.90 (10H, m), 6.52 (1H, s), 6.60 (1H, s), 7.10 (1H, t), 7.14–7.28 (1H, br.m), 7.40–7.62 (3H, m), 7.88 (1H, t), 8.28 (1H, d), 8.78 (1H, d), 8.86 (1H, d), 12.94 (1H, s). |
| 9359 | C$_{26}$H$_{28}$N$_4$O$_4$ 460 | MH$^+$ 461 (32%) Base peak 356 (100%) | CI$^+$ | CDCl$_3$/400 MHz | 2.75–2.95 (6H, m), 3.60–3.77 (4H, m), 3.84 (3H, s), 3.85 (3H, s), 6.55 (1H, s), 6.62 (1H, s), 7.12 (1H, t), 7.40–7.62 (4H, m), 8.32 (1H, dt), 8.78 (1H, dd), 8.82 (1H, d), 9.29 (1H, s), 12.56 (1H, s). |
| 9384 | C$_{26}$H$_{28}$N$_4$O$_4$ 460 | MH$^+$ 461 (100%) | ESI | CDCl$_3$/400 MHz | 2.76–2.94 (6H, m), 3.60–3.72 (4H, m), 3.85 (3H, s), 3.86 (3H, s), 6.53 (1H, s), 6.61 (1H, s), 7.11 (1H, t), 7.33 (1H, br. s), 7.50–7.60 2H, m), 7.89 (2H, d), 8.75–8.95 (3H, m), 12.67 (1H, s). |
| 9391 | C$_{28}$H$_{27}$N$_5$O$_4$ | M$^+$ 461 (8%) Base peak 206 (100%) | EI | CDCl$_3$/400 MHz | 2.75–2.90 (6H, m), 3.60–3.24 (4H, m), 3.84 (3H, s), 3.85 (3H, s), 6.53 (1H, s), 6.60 (1H, s), 7.07–7.20 (2H, m), 7.47–7.59 (2H, m), 8.75 (2H, dd), 8.85 (1H, d), 9.49 (1H, s), 12.98 (1H, s). |
| 9347 | C$_{29}$H$_{29}$N$_5$O$_4$ 511 | MH$^+$ 512 (100%) | CI$^+$ | CDCl$_3$/400 MHz | 2.75–3.00 (6H, m), 3.70–3.90 (10H, m), 6.52 (1H, s), 6.60 (1H, s), 7.10–7.52 (1H, br.m), 7.15 (1H, t), 7.56 (1H, t), 7.65 (1H, br.d), 8.82–8.94 (2H, m), 8.15–8.40 (2H, m), 8.88 (1H, d), 9.74 (1H, s), 13.14 (1H, s). |
| 9383 | C$_{30}$H$_{30}$N$_4$O$_4$ 510 | MH$^+$ 511 (100%) | ESI | CDCl$_3$/400 MHz | 2.80–2.95 (6H, m), 3.66–3.80 (4H, br.m), 3.83 (3H, s), 3.84 (3H, s), 6.51 (1H, s), 6.59 (1H, s), 7.12 (1H, t), 7.55 (1H, t), 7.60 (1H, br.d), 7.71 (2H, m), 7.83 (1H, d), 7.88 (1H, d), 8.69 (1H, d), 8.90 (1H, d), 9.53 (1H, d), 12.89 (1H, s). One NH signal not observed. |
| 9385 | C$_{30}$H$_{30}$N$_4$O$_4$ 510 | MH$^+$ 511 (100%) | CI$^+$ | CDCl$_3$ | 2.70–3.05 (6H, m), 3.70–3.90 (10H, m), 6.45 (1H, s), 6.53 (1H, s), 7.08 (1H, t), 7.45 (1H, br.s), 7.51 (1H, t), 7.60–7.70 (2H, m), 7.80 (1H, t), 7.90 (1H, d), 8.32–8.42 (3H, m), 8.87 (1H, d), 13.13 (1H, s). |
| 9389 | C$_{30}$H$_{30}$N$_4$O$_4$ 510 | MH$^+$ 511 (100%) | EI | CDCl$_3$/400 MHz | 2.88 (6H, br.s), 3.63–3.79 (4H, m), 3.83 (3H, s), 3.84 (3H, s), 6.51 (1H, s), 6.61 (1H, s), 7.11 (1H, t), 7.16–7.26 (1H, m), 7.53 (1H, t), 7.60 (1H, br.d), 7.70–7.82 (2H, m), 8.02 (1H, d), 8.08 (1H, d), 8.71 (1H, s), 8.92 (1H, d), 9.37 (1H, s), 13.07 (1H, s) |
| 9397 | C$_{30}$H$_{30}$N$_4$O$_4$ 510 | MH$^+$ 511 (14%) Base peak 207 (100%) | EI | CDCl$_3$/400 MHz | 2.77–2.93 (6H, m), 3.60–3.75 (4H, m), 3.82 (3H, s), 3.83 (3H, s), 6.53 (1H, s), 6.62 (1H, s), 7.12 (1H, t), 7.31 (1H, br.s), 7.50–7.68 (3H, m), 7.83 (1H, t), 8.03 (1H, d), 8.19 (1H, d), 8.80–8.90 (2H, m), 9.55 (1H, s), 12.72 (1H, s). |

-continued

| | | | | | |
|---|---|---|---|---|---|
| 9365 | $C_{25}H_{27}N_3O_4S$ 465 | MH⁺ 466 (100%) | CI | CDCl₃/400 MHz | 2.77–2.85 (6H, m), 3.63–3.68 (4H, m), 3.84 (3H, s, OMe), 3.86 (3H, s, OMe), 6.53 (1H, s), 6.60 (1H, s), 7.04–7.10 (2H, m), 7.36–7.38 (1H, m), 7.45–7.51 (2H, m), 7.63–7.65 (1H, m), 8.10–8.12 (1H, m), 8.77 (1H, d, J = Hz), 12.21 (1H, br.s, NH). |
| 9367 | $C_{29}H_{30}N_4O_4$ 498 | MH⁺ 499 (100%) | CI | CDCl₃/400 MHz | 2.80–2.86 (6H, m), 3.64–3.73 (4H, m), 3.84 (3H, s, OMe), 3.86 (3H, s, OMe), 6.55 (1H, s), 6.62 (1H, s), 7.05–7.10 (2H, m), 7.15–7.20 (1H, m), 7.25–7.34 (2H, m, obscured by CHCl₃), 7.44–7.55 (3H, m), 7.74 (1H, d, J = 8 Hz), 8.77 (1H, d, J = 7 Hz), 9.09 (1H, br.s, NH), 12.47 (1H, br.s, NH) |
| 9531 | $C_{35}H_{33}N_5O_4$ 587 | MH⁺ 588 (100%) | ESI | CDCl₃/400 MHz | 2.72–2.98 (8H, m), 3.68 (2H, s), 3.84 (3H, s), 3.85 (3H, s), 6.53 (1H, s), 6.60 (1H, s), 7.16–7.34 (3H, m), 7.55–7.64 (3H, m), 7.68 (1H, d), 7.80–7.94 (3H, m), 8.14–8.34 (2H, d), 8.86 (1H, d), 9.75 (1H, s), 12.65 (1H, br.s). |
| 9542 | $C_{35}H_{34}N_6O_5$ | MH⁺ 619 (100%) | ESI | d₆ DMSO/400 MHz | 11.40 (1H, s), 10.16 (1H, s), 9.60 (1H, s), 8.98 (1H, s), 8.66 (1H, s), 8.36 (1H, s), 8.28–8.20 (1H, m), 8.18–8.10 (1H, m), 8.06–7.96 (2H, m), 7.84 (1H, d, J = 8 Hz), 7.68 (2H, d, J = 8 Hz), 7.28 (2H, d, J = 8 Hz), 6.70–6.60 (3H, m), 3.71 (3H, s), 3.70 (3H, s), 3.58 (2H, s), 2.88–2.80 (2H, m), 2.78–2.66 (6H, m). |
| 9543 | $C_{36}H_{35}N_5O_4$ 601 | MH⁺ 602 (100%) | ESI | CDCl₃/400 MHz | 2.41 (3H, s), 2.70–2.98 (8H, m), 3.68 (2H, s), 3.85 (3H, s), 3.86 (3H, s), 6.54 (1H, s), 6.60 (1H, s), 7.28 (2H, d), 7.40 (1H, d), 7.48 (1H, s), 7.62 (2H, d), 7.80–7.95 (3H, m), 8.12–8.32 (2H, m), 8.70 (1H, d) 9.74 (1H, s), 12.49 (1H, br.s). |
| 9554 | $C_{35}H_{33}N_5O_5$ 603 | MH⁺ 604 (100%) | ESI | DMSO/400 MHz | 2.55–2.87 (8H, m), 3.45–3.77 (8H, m), 6.63 (2H, d), 7.07 (1H, d), 7.21–7.31 (3H, m), 7.49 (2H, d), 7.94–8.24 (4H, m), 8.44 (1H, d), 9.57 (1H, s), 9.87 (1H, s), 10.48 (1H, hr.s), 2.08 (1H, br.s). |
| 9541 | $C_{35}H_{32}N_6O_6$ | MH⁺ 663 (100%) | ESI | d₆ DMSO/400 MHz | 11.98 (1H, s), 10.84 (1H, s), 9.4 (1H, s), 9.56 (1H, d, J = 2 Hz), 8.28–8.00 (6H, m), 7.74 (2H, d, J = 8 Hz), 7.32 (2H, d, J = 8 Hz), 6.66 (1H, s), 6.64 (1H, s), 3.72 (3H, s), 3.71 (3H, s), 3.58 (2H, s), 2.90–2.80 (2H, m), 2.76–2.66 (6H, m). |
| 9561 | $C_{36}H_{32}F_3N_5O_4$ | MH⁺ 656 (100%) | ESI | d₆ DMSO/400 MHz | 12.00 (1H, s), 10.74 (1H, s), 9.60 (1H, s), 9.08 (1H, s), 8.24 (1H, d, J = 8 Hz), 8.18–8.08 (2H, m), 8.06–7.96 (2H, m), 7.76–7.54 (3H, m), 7.30 (2H, d, J = 8 Hz), 6.66 (1H, s), 6.64 (1H, s), 3.69 (3H, s), 3.68 (3H, s), 3.54 (2H, s), 2.88–2.78 (2H, m), 2.76–2.62 (6H, m). |
| 9562 | $C_{35}H_{32}FN_5O_4$ | MH⁺ 606 (100%) | ESI | d₆ DMSO/400 MHz | 11.70 (1H, s), 10.50 (1H, s), 9.60 (1H, s), 8.58 (1H, dd, J = 2, 12 Hz), 8.24 (1H, d, J = 8 Hz), 8.18–8.10 (1H, m), 8.08–7.98 (3H, m), 7.70 (2H, d, J =8 Hz), 7.28 (2H, d, J = 8 Hz), 7.24–7.14 (1H, m), 6.66 (1H, s), 6.64 (1H, s), 3.71 (3H, s), 3.70 (3H, s), 3.56 (2H, s), 2.88–2.78 (2H, m), 2.76–2.64 (6H, m). |
| 9564 | $C_{35}H_{32}FN_5O_4$ | MH⁺ 606 (100%) | ESI | CDCl₃/400 MHz | 2.72–2.98 (8H, m), 3.65 (2H, s), 3.85 (3H, s), 3.86 (3H, s), 6.54 (1H, s), 6.60 (1H, s), 6.98 (1H, dd), 7.30 (2H, d), 7.54 (1H, dd), 7.64 (2H, d) 7.82–7.94 (2H, m), 8.16–8.36 (3H, m), 8.71 (1H, d), 9.73 (1H, s) 12.98 (1H, br.s). |
| 9568 | $C_{38}H_{32}FN_5O_4$ 605 | MH⁺ 606 (100%) | ESI | CDCl₃/400 MHz | 2.70–3.00 (8H, m), 3.65 (2H, s), 3.85 (3H, s), 3.86 (3H, s), 6.54 (1H, s), 6.61 (1H, s), 7.20–7.45 (4H, m), 7.60 (2H, d), 7.80–7.95 (3H, m), 8.12–8.32 (2H, m), 8.73–8.83 (1H, m), 9.72 (1H, s), 12.51 (1H, br.s). |
| 9573 | $C_{37}H_{37}N_5O_6$ 647 | MH⁺ 648 (100%) | CI⁺ | CDCl₃/400 MHz | 2.70–3.00 (8H, m), 3.65 (2H, s), 3.85 |

-continued

| | | | | | |
|---|---|---|---|---|---|
| | | | | | (3H, s), 3.86 (3H, s) 3.94 (3H, s), 4.02 (3H, s), 6.54 (1H, s), 6.61 (1H, s), 7.13 (1H, s), 7.28 (2H, d), 7.59 (2H, d), 7.78–7.92 (3H, m), 8.19 (1H, d), 8.28 (1H, d), 8.10 (1H, s), 9.72 (1H, s), 12.79 (1H, br.s). |
| 9544 | $C_{36}H_{34}N_4O_4$ 586 | MH$^+$ 587 (100%) | ESI | CDCl$_3$/400 MHz | 2.73–3.05 (8H, m), 3.66 (2H, s), 3.86 (3H, s), 3.87 (3H, s), 6.53 (1H, s), 6.61 (1H, s), 7.20 (1H, t), 7.23–7.37 (2H, m), 7.52–7.74 (5H, m), 7.83 (1H, t), 7.97 8.07 (2H, m), 8.18 (1H, d), 8.80 (1H, s), 8.85 (1H, d), 9.54 (1H, s), 12.24 (1H, br.s). |
| 9571 | $C_{36}H_{33}FN_4O_4$ | MH$^+$ 605 (100%) | CI$^+$ | d$_6$ DMSO/400 MHz | 12.24 (1H, s), 10.51 (1H, s), 9.32 (1H, d, J = 2 Hz), 8.90 (1H, d, J = 2 Hz), 8.38 (1H, dd, J = 3, 12 Hz), 8.18 (1H, d, J = 8 Hz), 8.14 (1H, d, J = 8 Hz), 8.08 (1H, dd, J = 7, 9 Hz); 7.92 (1H, t, J = 8 Hz), 7.74 (1H, t, J = 8H), 7.64 (2H, d, J = 8 Hz), 7.26 (2H, d, J = 8 Hz), 7.24–7.18 (1H, m), 6.64 (1H, s), 6.62 (1H, s), 3.69 (3H, s), 3.68 (3H, s), 3.53 (2H, s), 2.86–2.78 (2H, m), 2.76–2.52 (6H, m). |
| 9574 | $C_{36}H_{33}FN_4O_4$ 604 | MH$^+$ 605 (100%) | CI$^+$ | CDCl$_3$/400 MHz | 2.70–3.05 (8H, m), 3.67 (2H, s), 3.85 (3H, s), 3.86 (3H, s), 6.53 (1H, s), 6.10 (1H, s), 7.15–7.45 (4H, m), 7.52–7.70 (3H, m), 7.84 (1H, t), 8.00 (1H, d), 8.18 (1H, d), 8.27 (1H, br.s), 8.70–8.82 (2H, m), 9.51 (1H, s), 11.98 (1H, br.s). |
| 9581 | $C_{36}H_{33}N_5O_6$ | MH$^+$ 632 (100%) | ESI | d$_6$ DMSO/400 MHz | 11.70 (1H, s), 10.72 (1H, s), 9.33 (1H, s), 9.14 (1H, s), 8.90 (1H, d, J = 8 Hz), 8.20–8.10 (4H, m), 7.91 (1H, t, J = 8 Hz), 7.72 (1H, t, J = 8 Hz), 7.64 (2H, d, J = 8 Hz), 7.24 (2H, d, J = 8 Hz), 6.64 (1H, s), 6.62 (1H, s), 3.69 (3H, s), 3.68 (3H, s), 3.53 (2H, s), 2.84–2.76 (2H, m), 2.74–2.64 (6H, m). |
| 9545 | $C_{36}H_{34}N_4O_4$ 586 | MH$^+$ 587 (100%) | ESI | CDCl$_3$/400 MHz | 2.68–2.98 (8H, m), 3.66 (2H, s), 3.86 (3H, s), 3.87 (3H, s), 6.54 (1H, s), 6.60 (1H, s), 7.15 (1H, t), 7.38 (2H, d), 7.55 (1H, t), 7.58–7.72 (4H, m), 7.80 (1H, t), 7.89 (1H, d), 8.02 (1H, br.s), 8.28 (1H, d), 8.32–8.40 (2H, m), 8.83 (1H, d), 12.72 (1H, br.s). |
| 9472 | $C_{32}H_{32}N_4O_4$ 536 | MH$^+$ 537 (15%) 190 (100%) | CI$^+$ | d$_6$ DMSO/400 MHz | 12.26 (1H, s), 10.48 (1H, s); 8.74–8.70 (1H, m), 8.68 (1H, d, J = 8 Hz), 8.18 (1H, d, J = 8 Hz), 8.08 (1H, t, J = 8 Hz), 7.88 (1H, d, J = 8 Hz), 7.68–7.58 (4H, m), 7.30–7.22 (3H, m), 6.68 (1H, s), 6.66 (1H, s), 3.72 (3H, s), 3.71 (3H, s), 3.54 (2H, s), 2.86–2.78 (2H, m), 2.76–2.64 (6H, m). |
| 9482 | $C_{32}H_{32}N_4O_4$ 536 | MH$^+$ 537 (100%) | ESI | CDCl$_3$/400 MHz | 2.75–2.95 (8H, m), 3.65 (2H, s), 3.84 (6H, 2xs, 2xOMe), 6.54 (1H, s), 6.60 (1H, s), 7.15–7.20 (1H, m), 7.28 (2H, d, J = 7 Hz), 7.41–7.46 (1H, m), 7.52–7.68 (4H, m), 7.97 (1H, NH), 8.26–8.30 (1H, m), 8.77–8.84 (2H, m), 9.29 (1H, s), 12.06 (1H, br.s, NH). |
| 9483 | $C_{32}H_{32}N_4O_4$ 536 | MH$^+$ 537 (100%) | ESI | CDCl$_3$/400 MHz | 2.76–2.95 (8H, m), 3.65 (2H, s), 3.83 (6H, 2xs, 2xOMe), 6.52 (1H, s), 6.59 (1H, s), 7.07–7.12 (1H, m), 7.28 (2H, d, J = 7 Hz), 7.48–7.55 (3H, m), 7.65 (1H, d, J = 7 Hz), 7.84 (2H, d, J = 7 Hz), 8.27 (1H, br.s, NH), 8.74 (1H, d, J = 8 Hz), 8.82 (2H, d, J = 7 Hz), 12.10 (1H, br.s, NH). |
| 9493 | $C_{31}H_{31}N_5O_4$ 537 | MH$^+$ 538 (100%) | ESI | CDCl$_3$/400 MHz | 2.73–2.93 (8H, m), 3.64 (2H, s), 3.83 (6H, 2xs, 2xOMe), 6.53 (1H, s), 6.60 (1H, s) 7.20–7.28 (3H, m), 7.52–7.63 (3H, m), 7.67 (1H, d, J = 8 Hz), 7.82 (1H, s), 8.69–8.71 (H, m), 8.75–8.77 (1H, m), 8.83 (1H, d, J = 8 Hz), 9.49 (1H, s) 12.48 (1H, br.s, NH). |
| 9527 | $C_{32}H_{33}N_5O_4$ 551 | MH$^+$ 552 (100%) | ESI | CDCl$_3$/400 MHz | 2.65 (3H, s, Me), 2.75–2.94 (8H, m), 3.65 (2H, s), 3.84 (6H, 2xs, 2xOMe), 6.54 (1H, s), 6.60 (1H, s), 7.15–7.20 |

| | | | | | |
|---|---|---|---|---|---|
| | | | | | (1H, m), 7.24–7.28 (2H, m, obscured by CHCl₃), 7.54–7.60 (3H, m), 7.66 (1H, d, J = 8 Hz), 7.90 (1H, s), 8.54 (1H, s), 8.78 (1H, d, J = 8 Hz), 9.34 (1H, s), 12.39 (1H, br.s, NH). |
| 9557 | C₃₃H₃₄N₄O₄ 550 | MH⁺ 551 (100%) | DCI | CDCl₃/400 MHz | 2.65 (3H, s), 2.73–2.99 (8H, m), 3.64 (2H, s), 3.84 (3H, s), 3.85 (3H, s), 6.55 (1H, s), 6.62 (1H, s), 7.25–7.35 (4H, m), 7.53 (2H, d), 7.60 (1H, t), 7.69 (1H, d), 7.89 (1H, s), 8.18 (1H, d), 8.84 (1H, d), 9.17 (1H, s), 12.03 (1H, s). |
| 9582 | C₃₃H₃₄N₄O₅ 566 | MH⁺ 567 (100%) | ESI | D₆ DMSO/400 MHz | 11.70 (1H, br.s), 10.45 (1H, br.s), 9.73 (1H, d), 8.45 (1H, d), 8.15 (1H, dd), 7.95 (1H, d), 7.63–7.59 (3H, m), 7.30–7.20 (3H, m), 7.00 (H, d), 6.67 (1H, s), 6.64 (1H, s), 3.92 (3H, s), 3.70 (3H, s), 3.69 (3H, s), 3.55 (2H, s), 2.85–2.80 (2H, m), 2.72–2.65 (6H, m). |
| 9569 | C₃₄H₃₅N₅O₅ 593 | MH⁺ 594 (50%) | CI | CDCl₃/400 MHz | 1.22–1.27 (3H, t, Me), 2.75–2.95 (8H, m), 3.25 (2H, q, J = 8 Hz, COCH₂), 3.66 (2H, s), 3.84 (3H, s, OMe), 3.85 (3H, s, OMe), 6.55 (1H, s) 6.62 (1H, s), 7.25–7.31 (3H, m, obscured by CHCl₃), 7.53–7.65 (3H, m), 7.69 (1H, d, J = 8 Hz), 7.82 (1H, br.s, NH), 8.83 (1H, d, J = 8 Hz), 9.31 (1H, s), 9.48 (1H, s), 12.62 (1H, br.s, NH). |
| 9456 | C₃₃H₃₃N₃O₄ 535 | M⁺ 536 (100%) | CI | DMSO/400 MHz | 2.63–2.75 (6H, m), 2.78–2.85 (2H, m), 3.54 (2H, s), 3.68 (6H, 2xs), 6.63 (2H, d), 7.21–7.3 (3H, m), 7.52–7.64 (6H, m), 7.88–7.97 (3H, m), 8.52 (1H, d), 10.44 (1H, s), 11.78 (1H, s). |
| 9510 | C₃₄H₃₅N₃O₄ 549 | MH⁺ 550 (100%) | ESI | CDCl₃/400 MHz | 2.31 (3H, s), 2.70–2.98 (8H, m), 3.67 (2H, s), 3.84 (3H, s), 3.85 (3H, s), 6.55 (1H, s), 6.60 (1H, s), 6.81 (1H, d), 7.28 (2H, d) ,7.42–7.62 (6H, m), 7.98–8.04 (2H, m), 8.26 (1H, s), 8.57 (1H, s), 11.80 (1H, s). |
| 9511 | C₃₄H₃₅N₃O₄ 549 | MH⁺ 550 (100%) | CI⁺ | CDCl₃/400 MHz | 2.25 (3H, s), 2.70–2.98 (8H, m), 3.67 (2H, s), 3.85 (3H, s), 3.86 (3H, s), 6.53 (1H, s), 6.60 (1H, s) 7.22–7.34 (3H, m), 7.39 (1H, s), 7.45–7.63 (5H, m), 8.02 (2H, d), 8.22 (1H, s) 8.49 (H, d), 11.61 (1H, br.s). |
| 9512 | C₃₄H₃₅N₃O₄ 549 | MH⁺ 550 (100%) | CI⁺ | CDCl₃/400 MHz | 2.50 (3H, s), 2.65–2.98 (8H, m), 3.66 (2H, s), 3.82 (3H, s), 3.83 (3H, s), 6.52 (1H, s), 6.60 (1H, s), 7.01 (1H, d), 7.23 (2H, d), 7.32 (1H, t), 7.40–7.60 (5H, m), 7.80–7.90 (3H, m), 8.06 (1H, d), 9.32 (1H, s). |
| 9489 | C₃₃H₃₂FN₃O₄ | MH⁺ 554 (26%) Fragment 435 (100%) | CI⁺ | CDCl₃/400 MHz | 2.70–2.98 (8H, m), 3.63 (2H, s), 3.84 (3H, s), 3.85 (3H, s), 6.53 (1H, s), 6.60 (1H, s), 7.10 (1H, t), 7.17 (1H, dd), 7.20–7.64 (8H, m), 8.03 (1H, t), 8.12 (1H, s), 8.63 (1H, d), 11.37 (1H, br.d). |
| 9500 | C₃₃H₃₂N₃FO₄ 553 | MH⁺ 554 (100%) | CI⁺ | CDCl₃/400 MHz | 2.70–2.98 (8H, m), 3.65 (2H, s), 3.83 (3H, s), 3.84 (3H, s), 6.53 (1H, s), 6.60 (1H, s), 7.11 (1H, t), 7.20–7.32 (3H, m), 7.40–7.80 (7H, m), 8.09 (1H, s), 8.72 (1H, d), 11.85 (1H, s). |
| 9501 | C₃₃H₃₂N₃FO₄ 553 | MH⁺ 554 (100%) | CI⁺ | CDCl₃/400 MHz | 2.70–3.00 (8H, m), 3.68 (2H, s), 3.84 (3H, s), 3.85 (3H, s), 5.54 (H, s), 6.60 (1H, s), 7.05 (1H, t), 7.18 (2H, t), 7.30 (2H, d), 7.48 (1H, t), 7.53–7.63 (3H, m), 9.02 (2H, q), 8.26 (1H, s), 8.68 (1H, d), 11.78 (1H, s). |
| 9513 | C₃₃H₃₁F₂N₃O₄ | MH⁺ 572 (100%) | ESI | d₆ DMSO/400 MHz | 11.38 (1H, s), 10.44 (1H, s), 8.42 (1H, d, J = 8 Hz), 8.00–7.94 (1H, m), 7.88 (1H, d, J = 8 Hz), 7.64–7.56 (3H, m), 7.48–7.40 (1H, m), 7.34–7.20 (4H, m), 6.66 (1H, s), 6.64 (1H, s), 3.79 (3H, s), 3.71 (3H, s), 3.54 (2H, s), 2.84–2.76 (2H, m), 2.74–2.52 (6H, m). |
| 9514 | C₃₃H₃₁F₂N₃O₄ | MH⁺ 572 (100%) | ESI | d₆ DMSO/400 MHz | 11.28 (1H, s), 10.38 (1H, s), 8.30 (1H, d, J = 8 Hz), 7.84 (1H, d, J = 8 Hz), 7.62–7.52 (4H, m), 7.32 (1H, t, J = 8 Hz), 7.26–7.18 (4H, m), 6.66 (1H, s), 6.64 (1H, s), 3.72 (3H, s), 3.71 (3H, s), 3.54 (2H, s), 2.84–2.78 (2H, m), 2.76–2.62 |

-continued

| | | | | | |
|---|---|---|---|---|---|
| | | | | | (6H, m). |
| 9494 | C$_{33}$H$_{32}$ClN$_3$O$_4$ | MH$^+$ 570, 572 (100%; 3:1) | CI$^+$ | d$_6$ DMSO/400 MHz | 11.14 (1H, s), 10.38 (1H, s), 8.32 (1H, d, J = 8 Hz), 7.86 (1H, d, J = 8 Hz), 7.68–7.42 (7H, m), 7.32 (1H, t, J = 8 Hz), 7.22 (2H, d, J = 8 Hz), 6.66 (1H, s), 6.64 (1H, s), 3.68 (3H, s), 3.67 (3H, s), 3.52 (2H, s), 2.82–2.76 (2H, m), 2.74–2.50 (6H, m). |
| 9495 | C$_{33}$H$_{32}$ClN$_3$O$_4$ | MH$^+$ 570, 572 (100%; 3:1) | CI$^+$ | d$_6$ DMSO/400 MHz | 11.68 (1H, s), 10.44 (1H, s), 8.38 (1H, d, J = 8 Hz), 7.92–7.80 (3H, m), 7.68–7.56 (5H, m), 7.36–7.20 (3H, m), 6.66 (1H, s), 6.64 (1H, s), 3.72 (3H, s), 3.71 (3H, s), 3.54 (2H, s), 2.84–2.76 (2H, m), 2.74–2.52 (6H, m). |
| 9496 | C$_{33}$H$_{32}$ClN$_3$O$_4$ | MH$^+$ 570, 572 (100%; 3:1) | CI$^+$ | d$_6$ DMSO/400 MHz | 11.78 (1H, s), 10.46 (1H, s), 8.46 (1H, d, J = 8 Hz), 7.96–7.88 (3H, m), 7.68–7.56 (5H, m), 7.32–7.20 (3H, s), 6.66 (1H, s), 6.64 (1H, s), 3.72 (3H, s), 3.71 (3H, s), 3.54 (2H, s), 2.86–2.78 (2H, m), 2.76–2.64 (6H, m). |
| 9497 | C$_{34}$H$_{35}$N$_3$O$_4$ | MH$^+$ 550 (100%) | ESI | d$_6$ DMSO/400 MHz | 11.06 (1H, s), 10.38 (1H, s), 8.38 (1H, d, J = 8 Hz), 7.86 (1H, d, J = 8 Hz), 7.62–7.56 (3H, m), 7.52 (1H, d, J = 8 Hz), 7.40 (1H, t, J = 8 Hz), 7.34–7.26 (3H, m), 7.22 (2H, d, J = 8 Hz), 6.66 (1H, s), 6.64 (1H, s), 3.72 (3H, s), 3.71 (3H, s), 3.52 (2H, s), 2.80–2.74 (2H, m), 2.72–2.60 (6H, m), 2.40 (3H, s). |
| 9503 | C$_{34}$H$_{35}$N$_3$O$_4$ | MH$^+$ 550 (100%) | ESI | d$_6$ DMSO/400 MHz | 11.68 (1H, s), 10.44 (1H, s), 8.48 (1H, d, J = 8 Hz), 7.90 (1H, d, J = 8 Hz), 7.76 (1H, s), 7.70 (1H, d, J = 8 Hz), 7.66–7.58 (3H, m), 7.48–7.38 (2H, m), 7.30–7.22 (3H, m), 6.66 (1H, s), 6.64 (1H, s), 3.72 (3H, s), 3.71 (3H, s), 3.54 (2H, s), 2.84–2.78 (2H, m), 2.76–2.62 (6H, m), 2.38 (3H, s). |
| 9504 | C$_{34}$H$_{35}$N$_3$O$_4$ | MH$^+$ 550 (100%) | ESI | d$_6$ DMSO/400 MHz | 11.78 (1H, s), 10.46 (1H, s), 8.52 (1H, d, J = 8 Hz), 7.92 (1H, d, J = 8 Hz), 7.82 (2H, d, J = 8 Hz), 7.64–7.56 (3H, m), 7.38 (2H, d, J = 8 Hz), 7.30–7.22 (3H, m), 6.66 (1H, s), 6.64 (1H, s), 3.72 (3H, s), 3.71 (3 Hz), 3.54 (2H, s), 2.86–2.78 (2H, m), 2.76–2.64 (6H, m), 2.38 (3H, s). |
| 9477 | C$_{34}$H$_{35}$N$_3$O$_5$ 565 | MH$^+$ 566 (100%) | CI$^+$ | CDCl$_3$ | 2.70–2.98 (8H, m), 3.65 (2H, s), 3.85 (3H, s), 3.86 (3H, s), 4.02 (3H, s), 6.55 (1H, s), 6.60 (1H, s), 6.98 (1H, d), 7.02–7.12 (2H, m), 7.20–7.32 (2H, m), 7.42–7.50 (2H, m), 7.55 (1H, d), 7.60 (2H, d), 8.06 (1H, s), 8.22 (1H, d), 8.65 (1H, d), 11.54 (1H, s). |
| 9517 | C$_{34}$H$_{35}$N$_3$O$_5$ 565 | MH$^+$ 566 (100%) | ESI | CDCl$_3$/400 MHz | 2.76–2.95 (8H, m), 3.65 (2H, s), 3.84 (6H, 2xs, 2xOMe), 3.89 (3H, s, OMe), 6.54 (1H, s), 6.61 (1H, s), 7.05–7.10 (1H, m), 7.14–7.19 (1H, m), 7.26–7.30 (2H, m, obscured by CHCl$_3$), 7.38–7.42 (1H, m), 7.52–7.60 (5H, m), 7.66 (1H, d, J = 8 Hz), 7.92 (1H, s, NH), 8.80 (1H, d, J = 8 Hz), 11.80 (1H, br.s, NH). |
| 9518 | C$_{34}$H$_{35}$N$_3$O$_5$ 565 | MH$^+$ 566 (100%) | ESI | CDCl$_3$/400 MHz | 2.75–2.95 (8H, m), 3.64 (2H, s), 3.83 (6H, 2xs, 2xOMe), 3.87 (3H, s, OMe), 6.53 (1H, s) 6.60 (1H, s), 6.98 (2H, d, J = 7 Hz), 7.04–7.09 (1H, m), 7.28 (2H, d, J = 7 Hz), 7.48–7.63 (4H, m), 7.99 (2H, d, J = 7 Hz), 8.09 (1H, s, NH), 8.75 (1H, d, J = 8 Hz), 11.65 (1H, br.s, NH). |
| 9535 | C$_{33}$H$_{33}$N$_3$O$_5$ 551 | MH$^+$ 552 (100%) | CI | CDCl$_3$/400 MHz | 2.74–2.94 (8H, m), 3.65 (2H, s), 3.83 (6H, 2xs, 2xOMe), 6.54 (1H, s), 6.60 (1H, s), 6.91–7.00 (2H, m), 7.20–7.30 (3H, m), 7.407.44 (1H, m), 7.53 (2H, d, J = 7 Hz), 7.59–7.63 (1H, m), 7.70 (1H, d, J = 8 Hz), 7.78 (1H, d, J = 8 Hz), 7.85 (1H, s), 8.71 (1H, d, J = 8 Hz), 12.08 (1H, br.s), 12.22 (1H, s). |
| 9549 | C$_{33}$H$_{33}$N$_3$O$_5$ 551 | MH$^+$ 552 (100%) | ESI | CDCl$_3$/400 MHz | 2.74–2.95 (8H, m) 3.64 (2H, s), 3.83 (3H, s, OMe), 3.85 (3H, s, OMe), 6.52 |

-continued

| | | | | | |
|---|---|---|---|---|---|
| | | | | | (1H, s), 6,59 (1H, s), 6.98–7.01 (1H, m), 7.14–7.17 (1H, m), 7.23–7.28 (2H, m), 7.34–7.38 (1H, s), 7.42–7.60 (6H, m), 7.65 (1H, d, J = 8 Hz), 7.87 (1H, s), 8.81 (1H, d, J = 8 Hz), 11.74 (1H, br.s, NH). |
| 9559 | $C_{33}H_{33}N_3O_5$ 551 | MH+ 552 (100%) | ESI | CDCl$_3$/DMSO/ 400 MHz | 2.76–2.94 (8H, m), 3.65 (2H, s), 3.83 (6H, 2xs, 2xOMe), 6.55 (1H, s), 6.62 (1H, s), 6.93 (2H, d, J = 7 Hz), 7.12–7.16 (1H, m), 7.26 (2H, d, J = 7 Hz), 7.50–7.57 (1H, m), 7.60 (2H, d, J = 7 Hz), 7.73–7.76 (1H, m), 7.90 (2H, d, J = 8 Hz), 8.78 (1H, d, J = 8 Hz), 8.93 (1H, s), 9.10 (1H, br.s), 11.69 (1H, s, NH). |
| 9534 | $C_{35}H_{35}N_3O_6$ 593 | MH+ 594 (100%) | ESI | CDCl$_3$/400 MHz | 2.31 (3H, s, Ac), 2.73–2.93 (8H, m), 3.64 (2Hs), 3.84 (6H, 2xs, 2xOMe), 6.53 (1H, s), 6.60 (1H, s), 7.14–7.19 (2H, m), 7.24–7.27 (2H, m, obscured by CHCl$_3$), 7.32–7.36 (1H, m), 7.49–7.58 (4H, m), 7.63 (1H, d, J = 8 Hz), 7.85–7.92 (2H, m), 8.69 (1H, d, J = 8 Hz), 11.29 (1H, br.s, NH). |
| 9540 | $C_{35}H_{35}N_3O_6$ 593 | MH+ 594 (100%) | ESI | CDCl$_3$/400 MHz | 2.32 (3H, s, Ac), 2.76–2.96 (8H, m), 3.65 (2H, s), 3.83 (6H, 2xs, 2xOMe), 6.53 (1H, s), 6.60 (1H, s), 6.98–7.01 (1H, m), 7.27–7.31 (3H, m), 7.39–7.45 (1H, m), 7.49–7.64 (4H, m), 7.77–7.79 (1H, m), 7.84 (1H, d, J = 7 Hz), 8.45 (1H, s, NH), 8.62 (1H, d, J = 8 Hz), 11.72 (1H, s, NH). |
| 9548 | $C_{35}H_{35}N_3O_6$ 593 | MH+ 594 (100%) | ESI | CDCl$_3$/400 MHz | 2.32 (3H, s, OAc), 2.75–2.95 (8H, m), 3.65 (2H, s), 3.84 (6H, 2xs, OMe), 6.53 (1H, s), 6.60 (1H, s), 7.10–7.15 (1H, m), 7.20–7.30 (4H, m), 7.52–7.56 (3H, m), 7.64 (1H, d, J = 8 Hz), 8.00–8.06 (3H, m), 8.77 (1H, d, J = 8 Hz), 11.82 (1H, s, NH). |
| 9523 | $C_{34}H_{32}F_3N_3O_4$ | MH+ 604 (100%) | ESI | d$_6$ DMSO/400 MHz | 11.10 (1H, s), 10.48 (1H, s), 8.26 (1H, d, J = 8 Hz), 7.86 (2H, d, J = 8 Hz), 7.84–7.68 (3H, m), 7.64–7.54 (3H, m), 7.34 (1H, t, J = 8 Hz), 7.22 (2H, d, J = 8 Hz), 6.66 (1H, s), 6.64 (1H, s), 3.72 (3H, s), 3.71 (3H, s), 3.54 (2H, s), 2.84–2.76 (2H, m), 2.74–2.52 (6H, m). |
| 9524 | $C_{34}H_{32}F_3N_3O_4$ | MH+ 604 (100%) | ESI | d$_6$ DMSO/400 MHz | 11.70 (1H, s), 10.42 (1H, s), 8.36 (1H, d, J = 8 Hz), 8.24 (1H, s), 8.18 (1H, d, J = 8 Hz), 7.98 (1H, d, J = 8 Hz), 7.90 (1H, d, J = 8 Hz), 7.84 (1H, t, J = 8 Hz), 7.66–7.58 (3H, m), 7.34 (1H, t, J = 8 Hz), 7.24 (2H, d, J = 8 Hz), 6.66 (1H, s), 6.64 (1H, s), 3.72 (3H, s), 3.71 (3H, s), 3.56 (2H, s), 2.86–2.78 (2H, m), 2.76–2.54 (6H, m). |
| 9556 | $C_{35}H_{37}N_4O_4$ | MH+ 579 (32%) | ESI | CDCl$_3$/400 MHz | 2.70–2.98 (8H, m), 3.03 (6H, two coincident singlets), 3.66 (2H, s), 3.85 (3H, s), 3.86 (3H, s), 6.54 (1H, s), 6.60 (1H, s), 6.89 (1H, d), 7.08 (1H, t) 7.20–7.42 (4H, m), 7.49 (1H, t), 7.52–7.64 (3H, m), 8.15 (1H, s), 8.74 (1H, d), 11.65 (1H, br.s). |
| 9447 | $C_{36}H_{39}N_3O_4$ 577 | MH+ 578 (100%) | CI | CDCl$_3$/400 MHz | 1.28 (6H, 2xd, J = 7 Hz), 2.74–3.01 (9H, m), 3.65 (2H, br.s), 3.84 (6H, 2xs, 2xOMe), 6.53 (1H, s), 6.60 (1H, s), 7.05–7.10 (1H, m), 7.25–7.35 (4H, m), 7.48–7.65 (4H, m), 7.93 (2H, d, J = 7 Hz), 8.08 (1H, s), 8.75 (1H, d, J = 8 Hz), 11.68 (1H, br.s, NH). |
| 9461 | $C_{39}H_{43}N_3O_4$ 617 | MH+ 618 | CI | CDCl$_3$/400 MHz | 1.34–1.93 (10H, m), 2.52–2.62 (1H, m, CH), 2.76–2.95 (8H, m), 3.65 (2H, s) 3.83 (6H, 2xs, 2xOMe), 6.55 (1H, s), 6.59 (1H, s), 6.95–7.00 (1H, m), 7.25–7.35 (4H, m), 7.40–7.45 (1H, m), 7.55–7.62 (3H, m), 7.90 (2H, d, J = 7 Hz), 8.37 (1H, s, NH), 8.65 (1H, d, J = 8 Hz), 11.60 (1H, br.s, NH). |
| 9470 | $C_{37}H_{35}N_3O_4$ 585 | MH+ 586 (100%) | CI+ | CDCl$_3$/400 MHz | 2.66–2.94 (8H, m), 3.62 (2H, s), 3.82 (3H, s), 3.83 (3H, s), 6.52 (1H, s), 6.59 (1H, s), 7.10–7.70 (10H, m), 7.86 (2H, dd), 7.95 (2H, s), 8.53 (1H, d), |

-continued

| | | | | | |
|---|---|---|---|---|---|
| 9476 | $C_{37}H_{35}N_3O_4$ 585 | MH+ 586 (15%) | CI | $CDCl_3$/400 MHz | 8.87 (1H, d), 11.33 (1H, s). 2.77–2.97 (8H, m), 3.63 (2H, s), 3.84 (6H, 2xs, 2xOMe), 6.53 (1H, s), 6.60 (1H, s), 7.10–7.16 (1H, m) 7.29 (2H, d, J = 7 Hz), 7.54–7.61 (5H, m), 7.67 (1H, d, J = 8HZ), 7.87–8.09 (5H, m), 8.55 (1H, br.s, NH), 8.83 (1H, d, J = 8 Hz), 11.95 (1H, br.s, NH). |
| 9536 | $C_{33}H_{31}Cl_2N_3O_4$ 603 | MH+ 604/606/608 (100%) 9:6:1 intensity Φ $Cl_2$ cpd) | ESI | $CDCl_3$ | 2.70–2.98 (8H, m), 3.66 (2H, s), 3.87 (3H, s), 3.88 (3H, s), 6.55 (1H, s), 6.60 (1H, s), 7.17 (1H, t), 7.30 (2H, d), 7.48–7.60 (4H, m), 7.65 (1H, d), 7.80 (1H, d), 8.02 (1H, br.s), 8.13 (1H, d), 8.74 (1H, d), 11.95 (1H, br.s). |
| 9538 | $C_{35}H_{37}N_3O_4$ 563 | MH+ 564 (100%) | ESI | $CDCl_3$ | 2.34 (3H, s), 2.36 (3H, s), 2.72–2.98 (8H, m), 3.66 (2H, s), 3.83 (3H, s), 3.84 (3H, s), 6.55 (1H, s), 6.61 (1H, s), 7.03 (1H, t), 7.20–7.34 (3H, m), 7.45 (1H, t), 7.54–7.62 (3H, m), 7.70 (1H, d), 7.80 (1H, s), 8.25 (1H, s), 8.68 (1H, s), 11.59 (1H, s). |
| 9471 | $C_{31}H_{31}N_3O_4S$ | MH+ 542 (6%) 230 (100%) | CI+ | $d_6$ DMSO/400 MHz | 11.68 (1H, s), 10.46 (1H, s), 8.40 (1H, d, J = 8 Hz), 7.96 (1H, d, J = 8 Hz), 7.88 (1H, d, J = 3 Hz), 7.74 (1H, d, J = 2 Hz), 7.66–7.56 (3H, m), 7.30–7.70 (4H, m), 6.66 (1H, s), 6.64 (1H, s), 3.72 (3H, s), 3.71 (3H, s), 3.56 (2H, s), 2.86–2.78 (2H, m), 2.76–2.64 (6H, m). |
| 9492 | $C_{31}H_{31}N_3O_4S$ 541 | MH+ 542 (100%) | ESI | $CDCl_3$/400 MHz | 2.75–2.95 (8H, m), 3.65 (2H, s), 3.83 (6H, 2xs, 2xOMe), 6.53 (1H, s), 6.60 (1H, s), 7.10–7.15 (1H, m), 7.29 (2H, d, J = 7 Hz), 7.36–7.39 (1H, m), 7.51–7.66 (5H, m), 7.94 (1H, s, NH), 8.09–8.11 (1H, m), 8.79 (1H, d, J = 8 Hz), 11.74 (1H, br.s, NH). |
| 9526 | $C_{31}H_{31}N_3O_5$ 525 | MH+ 526 (100%) | CI+ | $CDCl_3$/400 MHz | 2.72–2.98 (8H, m), 3.67 (2H, s), 3.85 (3H, s), 3.86 (3H, s), 6.55 (1H, s), 6.62 (1H, s), 6.86 (1H, s), 7.60 (1H, t), 7.28 (2H, d), 7.42–7.62 (5H, m), 8.08 (2H, d), 8.70 (1H, d), 11.55 (1H, br.s). |
| 9515 | $C_{35}H_{34}N_4O_4$ | MH+ 575 (100%) | ESI | $d_6$ DMSO/400 MHz | 11.76 (1H, s), H.34 (1H, s), 10.44 (1H, s), 8.58 (1H, d, J = 8 Hz), 8.18 (1H, d, J = 8 Hz), 7.98 (1H, s), 7.90 (1H, d, J = 8 Hz), 7.64 (2H, d, J = 8 Hz), 7.58 (1H, t, J = 8 Hz), 7.50 (1H, d, J = 8 Hz), 7.30–7.16 (5H, m), 6.66 (1H, s), 6.64 (1H, s), 3.72 (3H, s), 3.71 (3H, s), 3.54 (2H, s), 2.86–2.78 (2H, m), 2.74–2.64 (6H, m). |
| 9539 | $C_{35}H_{33}N_3O_5$ 575 | MH+ 576 (100%) | CI+ | $CDCl_3$/400 MHz | 2.70–3.00 (8H, m), 3.67 (2H, s), 3.83 (3H, s), 3.84 (3H, s), 6.54 (1H, s), 6.61 (1H, s), 7.15 (1H, t), 7.22–7.37 (3H, m), 7.43 (1H, t), 7.48–7.74 (7H, m), 8.02 (1H, br.s), 8.74 (1H, d), 11.89 (1H, br.s). |
| 9466 | $C_{34}H_{41}N_3O_4$ 555 | MH+ 556 (100%) | ESI | $CDCl_3$/400 MHz | 1.24–1.51 (5H, m), 1.75–1.95 (7H, m), 2.52–2.60 (1H, m, CH), 2.78–2.83 (6H, m), 3.59–3.67 (4H, m), 3.83 (3H, s, OMe), 3.89 (3H, s, OMe), 6.24–6.27 (1H, m), 6.54 (1H, s), 6.63 (1H, s), 7.03 (1H, d, J = 8 Hz), 7.27–7.34 (3H, m), 7.96 (2H, d, J = 7 Hz), 8.74 (1H, d, J = 8 Hz), 9.36 (1H, br.s, NH), 12.62 (1H, br.s, NH). |
| 9479 | $C_{32}H_{35}N_3O_2$ 481 | MH+ 482 (100%) | CI+ | $CDCl_3$/400 MHz | 1.20–2.00 (10H, m), 2.50–2.62 (1H, m), 2.70–2.98 (6H, m), 3.65 (2H, q), 3.72 (2H, s), 6.95–7.55 (10H, m), 7.98 (2H, d), 8.80 (1H, d), 12.18 (1H, s). |
| 9567 | $C_{36}H_{35}N_5O_4$ 601 | MH+ 602 (100%) | CI+ | $CDCl_3$/400 MHz | 1.85–2.00 (2H, m), 2.55 (2H, t), 2.60–2.88 (6H, m), 3.54 (2H, s), 3.82 (3H, s), 3.83 (3H, s), 6.52 (1H, s), 6.60 (1H, s), 7.18–7.32 (3H, m), 7.56–6.65 (3H, m), 7.60 (1H, d) 7.82–7.94 (3H, m), 8.14–8.36 (2H, m), 8.85 (1H, d), 9.73 (1H, s), 12.67 (1H, br.s), |
| 9572 | $C_{34}H_{31}N_3O_4$ 573 | MH+ 574 (100%) | CI+ | $CDCl_3$/400 MHz | 2.70–2.90 (4H, m), 3.55 (2H, s), 3.69 (2H, s), 3.79 (3H, s), 3.83 (3H, s), 6.49 (1H, s), 6.61 (1H, s), 7.22 (1H, t), 7.45 |

-continued

| No | Molecular formula | Mass spec data mass (intensity) | mode | ¹H NMR data solvent/field | δ |
|---|---|---|---|---|---|
| | | | | | (2H, d), 7.60 (1H, t), 7.64–7.74 (3H, m), 7.80–7.92 (2H, m), 8.01 (1H, br.s), 8.12–8.34 (2H, m), 8.85 (1H, d), 9.74 (1H, s), 12.72 (1H, br.s). |
| 9577 | $C_{34}H_{30}N_4O_2$ 526 | MH⁺ 527 (100%) | CI⁺/ NH₃ | CDCl₃/400 MHz | 12.25 (1H, s), 9.55 (1H, d), 8.85 (1H, d), 8.81 (1H, d), 8.20 (1H, d), 8.05–8.00 (2H, m), 7.85–7.81 (1H, m), 7.71–7.60 (3H, m), 7.57 (2H, d), 7.31 (2H, d), 7.19 (1H, t), 7.14–7.09 (3H, m), 7.05–7.02 (1H, m), 3.75 (2H, s), 2.98–2.92 (4H, m) 2.85–2.77 (4H, m). |
| 9576 | $C_{38}H_{38}N_4O_6$ 646 | MH⁺ 647 (100%) | ESI | CDCl₃/400 MHz | 2.75–3.05 (8H, m), 3.70 (2H, s), 3.86 (3H, s), 3.87 (3H, s), 3.94 (3H, s), 4.03 (3H, s), 6.54 (1H, s), 6.61 (1H, s), 7.12 (1H, s), 7.29 (2H, d), 7.55 (2H, d), 7.64 (1H, t), 7.84 (1H, t), 7.88 (1H, s), 7.99 (1H, d), 8.18 (1H, d), 8.66 (1H, s), 8.78 (1H, s), 9.55 (1H, s), 12.50 (1H, s). |
| 9578 | $C_{37}H_{34}N_4O_6$ | MH⁺ 631 (100%) | ESI | d₆ DMSO/400 MHz | 12.25 (1H, s), 10.37 (1H, s), 9.32 (1H, s), 8.88 (1H, s), 8.18–8.08 (3H, s), 7.90 (1H, t), 7.72 (1H, t), 7.62 (2H, d), 7.58 (1H, s), 7.24 (2H, d), 6.64 (1H, s), 6.62 (1H, s), 6.16 (2H, s), 3.69 (3H, s), 3.68 (3H, s), 3.52 (2H, s), 2.82–2.58 (8H, m). |
| 9584 | $C_{37}H_{36}N_4O_4$ | MH⁺ 601 (100%) | ESI | d₆ DMSO/400 MHz | 11.68 (1H, s), 10.44 (1H, s), 9.30 (1H, s), 8.86 (1H, s), 8.26 (1H, d), 8.16 (1H, d), 8.12 (1H, d), 7.90 (1H, t), 7.74 (1H, s), 7.72 (1H, t), 7.64 (2H, d), 7.46 (1H, d), 7.24 (2H, d), 6.66 (1H, s), 6.64 (1H, s), 3.70 (3H, s), 3.69 (3H, s), 3.52 (2H, s), 2.82–2.76 (2H, m), 2.74–2.62 (6H, m), 2.40 (3H, s). |
| 9585 | $C_{35}H_{32}N_4O_4$ | MH⁺ 573 (100%) | ESI | d₆ DMSO/400 MHz | 11.74 (1H, s), 10.56 (1H, s), 9.36 (1H, s), 8.90 (1H, s), 8.36 (1H, d), 8.20–8.06 (2H, m),7.96–7.84 (2H, m), 7.78–7.58 (4H, m), 7.40–7.28 (3H, m), 6.68 (1H, s), 6.60 (1H, s), 3.70 (3H, s), 3.68 (3H, s), 3.60–3.20 (4H, m), 2.82–2.64 (4H, m). |
| 9586 | $C_{36}H_{33}ClN_4O_4$ | MH⁺ 621/623 (100%, 3:1) | ESI | d₆ DMSO/400 MHz | 11.99 (1H, s), 10.55 (1H, s), 9.32 (1H, s), 8.89 (1H, s), 8.52 (1H, s), 8.20–8.06 (2H, m), 8.00–7.86 (2H, m), 7.73 (1H, t), 7.63 (2H, d), 7.43 (1H, d), 7.25 (2H, d), 6.66 (1H, s), 6.64 (1H, s), 3.70 (3H, s), 3.69 (3H, s), 3.63 (2H, s), 2.88–2.66 (8H, m). |
| 9588 | $C_{37}H_{36}N_4O_4$ | MH⁺ 601 (100%) | CI⁺ | CDCl₃/400 MHz | 12.34 (1H, s), 9.54 (1H, s), 8.80 (1H, s), 8.68 (1H, s), 8.22 (1H, s), 8.20 (1H, d), 8.02 (1H, d), 7.84 (1H, t), 7.66 (1H, t), 7.62 (2H, d), 7.56 (1H, d), 7,30 (2H, d), 6.92 (1H, d), 6.62 (1H, s), 6,56 (1H, s), 3.85 (3H, s), 3.84 (3H, s), 3.68 (2H, s), 2.98–2.74 (8H, m, 2.38 (3H, s). |
| 9589 | $C_{36}H_{35}N_4O_4$ | MH⁺ 602 (100%) | ESI | d₆ DMSO/400 MHz | 10.12 (1H, br.s), 9.80 (1H, s), 9.44 (1H, s), 9.04 (1H, s), 8.16–8.08 (2H, m), 7.94 (1H, s), 7.90 (1H, t), 7.78–7.66 (4H, m), 7.20 (2H, d), 6.86 (1H, d), 6.66 (1H, s), 6.64 (1H, s), 5.70 (2H, br.s), 3.70 (3H, s), 3.69 (3H, s), 3.52 (2H, s), 2.86–2.52 (8H, m). |
| 9590 | $C_{36}H_{38}N_4O_4$ 590 | MH⁺ 591 | ESI | d₆ DMSO/400 MHz | 11.65 (1H, s), 10.45 (1H, s), 8.80 (1H, s), 8.38 (1H, d), 7.95–7.90 (2H, m), 7.67–7.61 (3H, m), 7.30 (1H, t), 7.27 (2H, d), 6.67 (1H, s), 6.65 (1H, s), 3.82 (3H, s), 3.81 (3H, s), 3.56 (2H, br.s), 2.91–2.70 (12H, m), 1.92–1.88 (2H, m), 1.85–1.78 (2H, m). |
| 9593 | $C_{35}H_{33}N_4O_4Cl$ | MH⁺ 621 (60%) 311 (100%) | ESI | CDCl₃/400 MHz | |
| 9591 | $C_{36}H_{33}N_4O_4$ Cl | MH⁺ (100%) - 621 and 623 (higher chlorine isotope) | ESI | d₆ - DMSO/ 400 MHz | 11.17 (s, 1H), 10.40 (s, 1H), 8.70 (s, 1H), 8.20 (d, 1H), 8.07 (d, 1H), 8.00 (d, 1H), 7.92 (t, 1H), 7.82 (d, 1H), 7.72 (t, 1H), 7.60 (d, 3H), 7.45 (t, 1H), 7.20 (d, 2H), 6.65 |

-continued

| | | | | | |
|---|---|---|---|---|---|
| | | | | | (s, 1H), 6.62 (s, 1H), 3.70 (s, 6H), 3.52 (s, 2H), 2.80–2.60 (m, 8H) |
| 9592 | $C_{33}H_{33}N_4O_5F_3$ | MH+ (100%) – 671 | ESI | $d_6$ – DMSO/ 400 MHz | 12.50 (s, 1H), 10.35 (s, 1H), 8.95 (s, 1H), 8.42 (d, 1H), 8.35 (d, 1H), 8.20 (s, 1H), 7.70 (d, 1H), 7.65 (d, 2H), 7.58 (d, 1H), 7.59 (t, 1H), 7.23 (d, 2H), 7.22 (t, 1H), 6.65 (s, 1H), 6.60 (s, 1H), 3.70 (s, 6H), 3.55 (s, 2H), 2.80–2.60 (m, 8H) Phenolic OH not visible |
| 9594 | $C_{34}H_{32}N_4O_4S$ | MH+ (90%) – 593 and 208 (100%) | DCI/NH$_3$ | CDCl$_3$/ 400 MHz | 12.24 (s, 1H, br), 9.57 (d, 1H), 8.82 (d, 1H), 8.45 (d, 1H), 8.20 (d, 1H), 8.02 (d, 1H), 7.86–7.84 (m, 1H), 7.68–7.62 (m, 1H), 7.53 (d, 2H), 7.51 (d, 1H), 7.41 (s, 1H, br), 7.30 (d, 2H), 6.61 (s, 1H), 6.53 (s, 1H), 3.86 (s, 3H), 3.85 (s, 3H), 3.67 (s, 2H), 2.95–2.75 (m, 8H) |
| 9595 | $C_{38}H_{39}N_5O_4$ | MH+ (100%) – 630 | ESI | CDCl$_3$/ 400 MHz | 11.48 (s, 1H), 9.51 (s, 1H), 8.75 (s, 1H), 8.60 (d, 1H), 8.16 (d, 1H), 7.98 (d, 1H), 7.89 (s, 1H), 7.86–7.80 (m, 1H), 7.67–7.62 (m, 1H), 7.58–7.52 (m, 2H), 7.29 (d, 2H), 7.00 (s, 1H), 6.90 (s, 1H), 6.61 (s, 1H), 6.55 (s, 1H), 3.87 (s, 6H), 3.68 (s, 2H), 3.05 (s, 6H), 2.98–2.78 (m, 8H) |
| 9596 | $C_{37}H_{38}N_6O_4$ | MH+ (100%) – 631 | ESI | CDCl$_3$/400 MHz | 11.83 (s, 1H), 9.60 (s, 1H), 8.50 (d, 1H), 8.25 (d, 1H), 8.17 (d, 1H), 8.60 (s, 1H), 7.86–7.82 (m, 2H), 7.61 (d, 2H), 7.28 (d, 2H), 6.95–6.92 (m, 2H), 6.60 (s, 1H), 6.52 (s, 1H), 3.85 (s, 6H), 3.62 (s, 2H), 3.00 (s, 6H), 2.95–2.75 (m, 8H) |
| 9597 | $C_{33}H_{31}N_5O_4S$ | MH+ (100%) – 594 | DCI/NH$_3$ | CDCl$_3$/ 400 MHz | 12.95 (s, 1H, br), 9.75 (s, 1H), 8.50 (d, 1H), 8.40–8.37 (m, 1H), 8.23–8.20 (m, 1H), 7.93–7.87 (m, 2H), 7.58 (d, 2H), 7.52 (d, 1H), 7.42 (s, 1H, br), 7.32 (d, 2H), 6.62 (s, 1H), 6.55 (s, 1H), 3.86 (s, 3H), 3.85 (s, 3H), 3.68 (s, 2H), 3.00–2.79 (m, 8H) |
| 9600 | $C_{34}H_{32}N_6O_4$ | MH+ (84%) – 589 "M$^{2+}$" m/2 (100%) – 295 | ESI | CDCl$_3$/ 400 MHz | 12.05 (s, 1H, br), 9.75 (s, 1H), 8.87–8.47 (m, 1H), 8.29 (d, 1H), 8.21 (d, 1H), 8.04 (s, 1H, br), 7.94–7.82 (m, 3H), 7.71 (s, 2H, br), 7.29 (d, 2H), 7.06 ( s, 1H, br), 6.60 (s, 1H), 6.55 (s, 1H), 3.84 (s, 3H), 3.83 (s, 3H), 3.69 (s, 2H), 3.00–2.70 (m, 8H) |
| 9606 | $C_{36}H_{34}N_4O_5$ | MH+ (100%) – 602.7 | CI | $d_6$ – DMSO/ 400 MHz | 12.60 (s, 1H), 10.35 (s, 1H), 8.80 (s, 1H), 8.39 (d, 1H), 8.25 (d, 1H), 7.80–7.45 (m, 8H), 7.25 (m, 3H), 6.65 (d, 2H), 3.70 (s, 6H), 3.55 (s, 2H), 2.85–2.65 (m, 8H) |
| 9608 | $C_{34}H_{33}N_5O_4S$ | MH+ (100%) – 608 | ESI | CDCl$_3$/ 400 MHz | 13.62 (s, 1H, br), 9.75 (s, 1H), 8.38–8.34 (m, 1H), 8.22–8.18 (m, 1H), 7.94–7.85 (m, 2H), 7.72 (s, 1H, br), 7.61 (d, 2H), 7.32 (d, 2H), 6.68 (s, 1H), 6.62 (s, 1H), 6.54 (s, 1H), 3.85 (s, 6H), 3.68 (s, 2H), 2.97–2.79 (m, 8H), 2.65 (s, 3H) |
| 9609 | $C_{35}H_{34}N_4O_4S$ | MH+ (100%) – 607 and 304 (80%) | ESI | CDCl$_3$/400 MHz | 13.42 (s, 1H, br), 9.56 (d, 1H), 8.79 (d, 1H), 8.19 (d, 1H), 8.01 (d, 1H), 7.85–7.82 (m, 1H), 7.77 (s, 1H, br), 7.68–7.62 (m, 1H), 7.55 (d, 2H), 7.32 (d, 2H), 6.62–6.60 (m, 2H), 6.53 (s, 1H), 3.84 (s, 6H), 3.68 (s, 2H), 2.96–2.76 (m, 8H), 2.65 (s, 3H) |
| 9612 | $C_{34}H_{33}N_5O_4$ | MH+ (100%) – 576 | ESI | CDCl$_3$/ 400 MHz | 12.67 (s, 1H), 9.75 (s, 1H), 8.87 (d, 1H), 8.34–8.14 (m, 2H), 7.92–7.82 (m, 3H), 7.70 (d, 1H), 7.63–7.53 (m, 3H), 7.30–7.16 (m, 3H), 6.90–6.75 (m, 3H), 3.88 (s, 3H), 3.87 (s, 3H), 3.52 (s, 2H), 2.92–2.78 (m, 2H), 2.72– |

-continued

| | | | | | |
|---|---|---|---|---|---|
| | | | | | 2.62 (m, 2H), 2.30 (s, 3H) |
| 9613 | $C_{35}H_{34}N_4O_4$ | MH+ (100%) - 575 | ESI | CDCl$_3$/ 400 MHz | 12.25 (s, 1H), 9.55 (s, 1H), 8.83 (d, 1H), 8.70 (s, 1H), 8.19 (d, 7.83 (t, 1H), 7.70–7.52 (m, 5H), 7.24 (d, 2H), 7.16 (t, 1H), 6.90–6.78 (m, 3H), 3.87 (s, 3H), 3.86 (s, 3H), 3.50 (s, 2H), 2.90–2.80 (m, 2H), 2.70–2.60 (m, 2H), 2.21 (s, 3H) |
| 9614 | $C_{34}H_{31}N_5O_4$ | MH+ (100%) - 574 | ESI | d$_6$ - DMSO/ 400 MHz | 12.55 (s, 1H), 10.48 (s, 1H), 9.59 (s, 1H), 8.69 (d, 1H), 8.22 (d, 1H), 8.09 (d, 1H), 8.05–7.95 (m, 2H), 7.93 (d, 1H), 7.64 (t, 1H), 7.51 (d, 1H), 7.45 (s, 1H), 7.30 (t, 1H), 7.10 (d, 1H), 6.93 (s, 1H), 6.90–6.82 (m, 2H), 3.74 (s, 6H), 3.60–3.50 (m, 4H), 2.85–2.64 (m, 4H) |
| 9615 | $C_{37}H_{36}N_4O_4S$ | MH+ (100%) - 633 and 317 (80%) | ESI | CDCl$_3$/400 MHz | 11.95 (s, 1H, br), 9.46 (d, 1H), 8.72 (d, 1H), 8.65 (d, 1H), 8.15 (s, 1H, br), 8.1 0 (d, 1H), 7.93 (d, 1H), 7.78–7.72 (m, 1H), 7.58–7.49 (m, 4H), 7.35 (dd, 1H), 7.22 (d, 2H), 6.55 (s, 1H), 6.49 (s, 1H), 3.78 (s, 6H), 3.60 (s, 2H), 2.87–2.68 (m, 8H), 2.39 (s, 3H) |
| 9616 | $C_{34}H_{32}N_4O_4S$ | MH+ (100%) - 593 and 297 (95%) | ESI | CDCl$_3$/400 MHz | 11.81 (s, 1H), 9.47 (d, 1H), 8.68 (d, 1H), 8.28 (d, 1H), 8.12 (d, 1H), 7.95 (d, 1H), 7.85 (s, 1H, br), 7.80–7.75 (m, 2H), 7.60–7.55 (m, 1H), 7.48 (d, 2H), 7.28 (d, 2H), 6.55 (s, 1H), 6.49 (s, 1H), 3.78 (s, 6H), 3.60 (s, 2H), 2.87–2.69 (m, 8H) |
| 9617 | $C_{31}H_{32}N_4O_4S$ | MH+ (90%) - 557 and 279 (100%) | ESI | CDCl$_3$/400 MHz | 11.65 (s, 1H), 9.16 (d, 1H), 8.28 (d, 1H), 8.15 (dd, 1H), 7.83–7.80 (m, 2H), 7.52 (d, 2H), 7.30–7.28 (m, 3H), 6.6 1(s, 1H), 6.55 (s, 1H), 3.85 (s, 6H), 3.69 (s, 2H), 2.95–2.75 (m, 8H), 2.65 (s, 3H) |
| 9621 | $C_{36}H_{34}N_4O_4S$ | MH+ (60%) - 619, 310 (50%) and 250 (100%) | ESI | CDCl$_3$/400 MHz | 12.12 (s, 1H, br), 9.55 (d, 1H), 8.80 (d, 1H), 8.75 (d, 1H), 8.39 (s, 1H, br), 8.20 (d, 1H), 8.02 (d, 1H), 787–7.82 (m, 1H), 7.69–7.62 (m, 4H), 7.55–7.50 (m, 1H), 7.45 (d, 2H), 7.10–7.07 (m, 1H), 6.58 (s, 1H), 6.52 (s, 1H), 3.83 (s, 3H), 3.81 (s, 3H), 3.62 (s, 2H), 3.20–3.15 (m, 2H), 2.85–2.75 (m, 6H) |
| 9622 | $C_{34}H_{32}N_6O_4$ | MH+ (100%) - 589 and 295 (60%) | ESI | CDCl$_3$/400 MHz | 13.18 (s, 1H, br), 10.04 (s, 1H, br), 9.63 (d, 1H), 8.91 (d, 1H), 8.74 (d, 1H), 8.35 (d, 1H), 8.21 (d, 1H), 8.05 (d, 1H), 7.88–7.83 (m, 1H), 7.71–7.65 (m, 3H), 7.32 (d, 2H), 6.6 1 (s, 1H), 6.55 (s, 1H), 3.85 (2 singlets, 6H), 3.68 (s, 2H), 2.96–2.78 (m, 8H) |
| 9623 | $C_{36}H_{34}N_4O_5$ | MH+ (100%) - 603 | ESI | CDCl$_3$/400 MHz | 12.32 (s, 1H, br), 9.52 (s, 1H), 8.88 (d, 1H), 8.81 (s, 1H), 8.19 (d, 1H), 8.01 (d, 1H), 7.90 (s, 1H, br), 7.88–7.80 (m, 1H), 7.72 (d, 1H), 7.67–7.61 (m, 2H), 7.56 (d, 2H), 7.23–7.20 (m, 1H), 6.98 (d, 2H), 6.60 (s, 1H), 6.55 (s, 1H), 4.24 (t, 2H), 3.85 (s, 6H), 3.71 (s, 2H), 3.00 (t, 2H), 2.90–2.88 (m, 4H) |
| 9625 | $C_{37}H_{36}N_4O_4$ | MH+ (100%) - 601 (M+H)$^{2+}$, "m$^{2+}$" (58%) 301 | ESI | CDCl$_3$/400 MHz | 12.22 (s, 1H), 9.52 (s, 1H), 8.84–8.74 (m, 2H), 8.20–8.10 (m, 2H), 7.99 (d, 1H), 7.83 (t, 1H), 7.72–7.50 ( m, 5H), 7.32–7.24 (m, 2H), 7.14 (t, 1H), 6.59 (s, 1H), 6.55 (s, 1H), 3.95–3.75 (m, 7H), 3.20–3.07 (m, 1H), 2.95–2.75 (m, 6H), 2.71–2.59 (m, 1H), 1.38 (d, 3H) |
| 9626 | $C_{33}H_{28}N_4O_2$ | MH+ (100%) - 513.1 | ESI | CDCl$_3$/400 MHz | 12.25 (s, 1H), 9.55 (s, 1H), 8.86 (d, 1H), 8.80 (s, 1H), 8.20 (d, 1H), 8.04 (s, 1H), 8.01 (d, 1H), 7.84 (t, 1H), 7.71–7.54 (m, 5H), |

-continued

| | | | | | |
|---|---|---|---|---|---|
| | | | | | 7.32 (d, 2H), 7.24–7.18 (m, 5H), 4.03 (s, 4H), 3.06–2.97 (m, 2H), 3.05–2.89 (m, 2H) |
| 9628 | $C_{34}H_{28}N_4O_2Cl_2$ | MH$^+$ (100%) - 595, 597 (50%), 599 (10%), and 475 (90%) | ESI | CDCl$_3$/400 MHz | 12.22 (s, 1H, br), 9.55 (d, 1H), 8.86–8.81 (m, 2H), 8.21–8.15 (m, 2H), 8.00 (d, 1H), 7.85–7.81 (m, 1H), 7.70–7.52 (m, 5H), 7.29 (d, 2H), 7.20 (s, 1H), 7.18–7.16 (m, 1H), 7.12 (s, 1H), 3.64 (s, 2H), 2.93–2.75 (m, 8H) |
| 9629 | $C_{34}H_{28}N_4O_2Cl_2$ | MH$^+$ (80%) - 595, 597 (50%), 599 (10%), 399 (70%) and 298 (100%) | ESI | CDCl$_3$/400 MHz | 12.25 (s, 1H, br), 9.55 (d, 1H), 8.83 (d, 1H), 8.79 (d, 1H), 8.19 (d, 1H), 8.11 (s, 1H, br), 8.02 (d, 1H), 7.85–7.80 (m, 1H), 7.70–7.55 ( m, 5H), 7.31 (d, 2H), 7.25 (d, 1H), 7.20–7.15 (m, 1H), 6.98 (d, 1H), 3.85 (s, 2H), 2.95–2.75 (m, 8H) |
| 9630 | $C_{36}H_{36}N_4O_4$ | MH$^+$ (100%) - 589 | ESI | CDCl$_3$/400 MHz | 12.25 (s, 1H, br), 9.55 (d, 1H), 8.85 (d, 1H), 8.80 (d, 1H), 8.19 (d, 1H), 8.11 (s, 1H, br), 8.02 (d, 1H), 7.85–7.80 (m, 1H), 7.73–7.55 (m, 5H), 7.25 (d, 2H), 7.20–7.16 (m, 1H), 6.80–6.72 (m, 3H), 3.87 (s, 3H), 3.85 (s, 3H), 2.85–2.68 (m, 8H), 2.39 (s, 3H) |
| 9631 | $C_{35}H_{34}N_4O_2$ | MH$^+$ (100%) - 543 | DCI/NH$_3$ | CDCl$_3$/400 MHz | 12.23 (s, 1H, br), 9.55 (d, 1H), 8.81 (d, 1H), 8.79 (s, 1H), 8.19 (d, 1H), 8.10 (s, 1H, br), 8.02 (d, 1H), 7.85–7.80 (m, 1H), 7.70–7.58 ( m, 3H), 7.55 (d, 2H), 7.22 (d, 2H), 7.18–7.12 (m, 1H), 7.08–7.00 (m, 3H), 3.52 (s, 2H), 2.86–2.81 (m, 2H), 2.69–2.62 (m, 2H), 2.28 (s, 3H), 2.25 (s, 3H), 2.24 (s, 3H) |
| 9632 | $C_{35}H_{33}N_5O_5$ | MH$^+$ (100%) - 604 | ESI | CDCl$_3$/400 MHz | 12.63 (s, 1H), 9.68 (s, 1H), 8.78 (d, 1H), 8.21(d, 1H), 8.10 (d, 1H), 7.86 (s, 1H), 7.80–7.77 (m, 2H), 7.60 (d, 1H), 7.55–7.50 (m, 3H), 7.16–7.H (m, 1H), 6.90 (d, 2H), 6.53 (s, 1H), 6.48 (s, 1H), 4.17 (t, 2H), 3.78 (s, 6H), 3.63 (s, 2H), 2.97 (t, 2H), 2.80–2.78 (m, 4H) |
| 9633 | $C_{36}H_{34}N_4O_4$ | MH$^+$ (100%) - 587 | ESI | CDCl$_3$/400 MHz | 12.21 (s, 1H), 9.53 (s, 1H), 8.87 (d, 1H), 8.82 (s, 1H), 8.18 (d, 1H), 8.00 (m, 2H), 7.85–7.80 (m, 1H), 7.70 (d, 1H), 7.65–7.60 (m, 2H), 7.50 (m, 2H), 7.37–7.30 (m, 1H), 7.25–7.20 (m, 1H), 7.11 (d, 1H), 6.61 (s, 1H), 6.55 (s, 1H), 3.87 (s, 6H), 3.70 (s, 2H), 3.00–2.94 (m, 2H), 2.89–2.82 (m, 6H) |
| 9634 | $C_{34}H_{29}N_5O_4$ | MH$^+$ (100%) - 572 | ESI | d$_6$ - DMSO/ 400 MHz | 11.78 (s, 1H, br), 10.48 (s, 1H, br), 9.33 (d, 1H), 8.99 (d, 1H), 8.39 (d, 1H), 8.15 (d, 1H), 8.13 (d, 1H), 7.99 (s, 1H), 7.97 (s, 1H), 7.95–7.88 (m, 2H), 7.85–7.07 (m, 6H), 7.71 (t, 1H), 7.66–7.60 (m, 3H), 7.40–7.30 (m, 2H), 7.24 (d, 2H), 3.75 (s, 2H), 2.91 (t, 2H) |
| 9635 | $C_{31}H_{32}N_4O_4S$ | MH$^+$ (100%) - 557.3 | ESI | CDCl$_3$/400 MHz | 11.90 (s, 1H), 8.70 (d, 1H), 8.05 (s, 1H), 7.97 (s, 1H), 7.65 (d, 1H), 7.58 (d, 2H), 7.53 (s, 1H), 7.25 (d, 2H), 7.16 (t, 1H), 6.62 (s, 1H), 6.54 (s, 1H), 3.85 (s, 6H), 3.75 (s, 2H), 3.05–2.83 (m, 8H), 2.79 (s, 3H) |
| 9636 | $C_{36}H_{36}N_4O_4$ | MH$^+$ (100%) - 589 | ESI | CDCl$_3$/400 MHz | 12.27 (s, 1H), 9.55 (s, 1H), 8.88 (d, 1H), 8.80 (s, 1H), 8.9 (d, 1H), 8.00 (d, 1H), 7.95 (s, 1H, br), 7.88–7.81 (m, 1H), 7.70 (d, 1H), 7.69–7.60 (m, 2H), 7.52 (d, 2H), 7.25–7.20 (m, 3H), 6.90 (s, 1H, br), 6.84–6.78 (m, 2H), 3.88 (s, 6H), 3.60 (s, 2H, br), 2.82–2.71 (m, 4H, |

| | | | | | |
|---|---|---|---|---|---|
| 9638 | $C_{31}H_{32}N_4O_5$ | MH+ (100%) - 541 | ESI | CDCl$_3$/400 MHz | br), 2.61 (q, 2H, br), 1.07 (t, 3H, br) 11.69 (s, 1H), 8.73 (d, 1H), 8.17 (s, 1H), 7.87 (s, 1H), 7.65 (d, 1H), 7.60–7.50 (m, 3H), 7.32–7.23 (m, 3H), 7.18 (t, 1H), 6.62 (s, 1H), 6.55 (s, 1H), 3.87 (s, 3H), 3.86 (s, 3H), 3.69 (s, 3H), 3.00–2.74 (m, 8H), 2.54 (s, 3H) |
| 9639 | $C_{31}H_{38}N_4O_4$ | MH+ (100%) - 603 | ESI | CDCl$_3$/400 MHz | 12.20 (s, 1H, br), 9.55 (d, 1H), 8.80–8.75 (m, 2H), 8.35 (s, 1H, br), 8.20 (d, 1H), 8.02 (d, 1H), 7.78–7.72 (m, 1H), 7.68–7.58 (m, 4H), 7.52 (t, 1H), 7.23 (d, 2H), 7.10 (m, 1H), 6.92 (s, 1H), 6.83 (s, 2H), 4.53 (septet, 1H), 3.85 (s, 3H), 3.48 (s, 2H), 2.87–2.81 (m, 2H), 2.68–2.62 (m, 2H), 2.30 (s, 3H), 1.35 (d, 6H) |
| 9640 | $C_{36}H_{36}N_4O_5$ | MH+ (100%) - 605.3 | ESI | CDCl$_3$/400 MHz | 12.25 (s, 1H), 9.55 (s, 1H), 8.85 (d, 1H), 8.80 (s, 1H), 8.20 (d, 1H), 8.07–8.00 (m, 2H), 7.84 (t, 1H), 7.70–7.53 (m, 5H), 7.30–7.18 (m, 3H), 6.54 (s, 2H), 3.85 (s, 9H), 3.50 (s, 2H), 2.83 (t, 2H), 2.66 (t, 2H), 2.33 (s, 3H) |
| 9641 | $C_{38}H_{40}N_4O_4$ | MH+ (100%) - 617 | ESI | CDCl$_3$/400 MHz | 12.25 (s, 1H), 9.55 (d, 1H), 8.85 (d, 1H), 8.80 (d, 1H), 8.20 (d, 1H), 8.05 (s, 1H, br), 8.02 (d, 1H), 7.88–7.81 (m, 1H), 7.70–7.57 (m, 3H), 7.53 (d, 2H), 7.21–7.15 (m, 3H), 6.88 (s, 1H), 6.83–6.78 (m, 2H), 3.86 (s, 3H), 3.85 (s, 3H), 3.58 (s, 2H), 2.81–2.68 (m, 4H), 2.51(t, 2H), 1.52–1.47 (m, 2H), 1.35–1.25 (m, 2H), 0.90 (t, 3H) |
| 9642 | $C_{38}H_{40}N_4O_4$ | MH+ (100%) - 617 | ESI | CDCl$_3$/400 MHz | 12.25 (s, 1H, br), 9.55 (d, 1H), 8.85 (d, 1H), 8.80 (d, 1H), 8.19 (d, 1H), 8.03 (s, 1H, br), 8.01 (d, 1H), 7.85–7.80 (m, 1H), 7.71–7.58 (m, 3H), 7.55 (d, 2H), 7.22 (d, 2H), 7.20–7.18 (m, 1H), 6.85 (s, 1H), 6.82–6.78 (m, 2H), 4.02 (t, 2H), 3.85 (s, 3H), 3.50 (s, 2H), 2.85 (t, 2H), 2.65 (t, 2H), 2.31(s, 3H), 1.85–1.79 (m, 2H), 1.55–1.45 (m, 2H), 0.96 (t, 3H) |
| 9643 | $C_{35}H_{28}N_4O_2F_2$ | MH+ (100%) - 551 | ESI | CDCl$_3$/400 MHz | 12.22 (s, 1H, br), 9.55 (d, 1H), 8.81–8.75 (m, 2H), 8.21 (s, 1H, br), 8.19 (d, 1H), 8.02 (d, 1H), 7.85–7.81 (m, 1H), 7.68–7.52 (m, 5H), 7.22 (d, 2H), 7.17–7.02 (m, 3H), 6.97–6.92 (m, 1H), 3.50 (s, 2H), 2.85 (t, 2H), 2.65 (t, 2H), 2.28 (s, 3H) |
| 9645 | $C_{31}H_{32}N_4O_4$ | MH+ (100%) - 573 | ESI | CDCl$_3$/400 MHz | 12.18 (s, 1H, br), 9.50 (s, 1H), 8.78 (d, 1H), 8.72 (s, 1H), 8.11 (d, 1H), 7.95 (d, 1H), 7.92 (s, 1H), 7.78–7.72 (m, 1H), 7.62–7.50 (m, 5H), 7.18–7.10 (m, 3H), 6.75–6.70 (m, 3H), 4.18 (s, 4H), 3.40 (s, 2H), 2.78 (t, 2H), 2.58 (t, 2H), 2.20 (s, 3H) |
| 9646 | $C_{37}H_{38}N_4O_4$ | MH+ (100%) - 603 | ESI | CDCl$_3$/400 MHz | 12.15 (s, 1H, br), 9.45 (s, 1H), 8.72 (s, 1H), 8.70 (d, 1H), 8.25 (s, 1H), 8.10 (d, 1H), 7.90 (d, 1H), 7.78–7.72 (m, 1H), 7.60–4.41 (m, 5H), 7.13 (d, 2H), 7.04–7.00 (m, 1H), 6.79–6.68 (m, 3H), 4.45–4.39 (m, 1H), 3.78 (s, 3H), 3.40 (s, 2H), 2.78–2.72 (m, 21.1), 2.60–2.56 (m, 2H), 2.23 (s, 3H), 1.30 (s, 3H), 1.28 (s, 3H) |
| 9647 | $C_{34}H_{32}N_4O_4$ | MH+ (100%) - 561 | ESI | CDCl$_3$/400 MHz | 12.23 (s, 1H, br), 9.54 (s, 1H), 8.88 (d, 1H), 8.80 (s, 1H), 8.19 (d, 1H), 8.10 (s, 1H, br), 8.00 (d, 1H), 7.85–7.80 (m, 1H), 7.70 (d, 1H), 7.65–7.55 (m, 4H), 7.22 (d, 2H), 7.20–7.15 (m, 1H), 6.88 (s, |

-continued

| | | | | | |
|---|---|---|---|---|---|
| | | | | | 1H), 6.80–6.78 (m, 2H), 3.88 (s, 3H), 3.50 (s, 2H), 2.85 (t, 2H), 2.65 (t, 2H), 2.29 (s, 3H) OH proton not visible |
| 9648 | $C_{37}H_{36}N_4O_6$ | MH$^+$ (40%) - 633 "M$^{2+}$" 317 (100%) | ESI | CDCl$_3$/400 MHz | 12.29 (s, 1H), 9.55 (s, 1H), 8.87 (d, 1H), 8.81 (s, 1H), 8.18 (d, 1H), 8.02–7.96 (m, 2H), 7.85–7.80 (m, 1H), 7.72–7.50 (m, 5H), 7.26–7.18 (m, 1H), 6.98 (d, 2H), 6.61 (s, 1H), 6.54 (s, 1H), 4.31–4.24 (m, 1H), 4.10 (d, 2H), 3.87 (s, 3H), 3.86 (s, 3H), 3.82 (d, 1H), 3.64 (d, 1H), 3.04–2.72 (m, 6H) OH proton not visible |
| 9649 | $C_{34}H_{32}N_4O_4$ | MH$^+$ (50%) - 425 | ESI | CDCl$_3$/400 MHz | 12.25 (s, 1H), 9.55 (d, 1H), 8.82 (d, 1H), 8.75 (d, 1H), 8.43 (s, 1H), 8.22 (d, 1H), 7.98 (d, 1H), 7.81 (t, 1H), 7.67–7.54 (m, 4H), 7.50–7.43 (m, 1H), 7.29 (d, 2H), 7.07 (t, 1H), 6.88–6.81 (m, 2H), 6.73–6.68 (m, 1H), 3.82 (s, 3H), 3.50 (s, 2H), 2.89–2.82 (m, 2H), 2.70–2.63 (m, 2H), 2.34 (s, 3H) OH proton not visible |
| 9650 | $C_{37}H_{36}N_4O_4$ | MH$^+$ (100%) - 601 "M$^{2+}$" 301 (86%) | ESI | CDCl$_3$/400 MHz | 12.33 (s, 1H), 9.53 (s, 1H), 8.90 (d, 1H), 8.77 (s, 1H), 8.17 (d, 1H), 7.99 (d, 1H), 7.88–7.58 (m, 6H), 7.30–7.12 (m, 3H), 6.62 (s, 1H), 6.55 (s, 1H), 3.85 (s, 3H), 3.84 (s, 3H), 3.70 (s, 2H), 3.00–2.75 (m, 8H), 2.35 (s, 3H) |
| 9651 | $C_{37}H_{36}N_4O_5$ | MH$^+$ (100%) - 617 "M$^{2+}$" 309 (58%) | ESI | CDCl$_3$/400 MHz | 12.48 (s, 1H), 9.57 (s, 1H), 8.91 (d, 1H), 8.84 (s, 1H), 8.61 (s, 1H), 8.39 (d, 1H), 8.19 (d, 1H), 8.02 (d, 3H), 7.84 (t, 1H), 7.73 (d, 1H), 7.65–7.60 (m, 2H), 7.65–7.60 (m, 2H), 7.30–7.20 (m, 1H), 7.03 (d, 1H), 6.85 (s, 1H), 6.61 (s, 1H), 6.55 (s, 1H), 3.92 (s, 3H), 3.87 (s, 3H), 3.86 (s, 3H), 3.70 (s, 2H), 3.00–2.70 (m, 8H) |
| 9652 | $C_{36}H_{36}N_4O_4$ | MH$^+$ (100%) - 589 | ESI | CDCl$_3$/400 MHz | 12.18 (s, 1H, br), 9.55 (d, 1H), 8.80 (d, 1H), 8.75 (d, 1H), 8.39 (s, 1H, br), 8.20 (d, 1H), 8.02 (d, 1H), 7.86–7.82 (m, 1H), 7.68–7.62 (m, 4H), 7.52–7.49 (m, 1H), 7.41 (d, 2H), 7.10–7.05 (m, 1H), 6.98(d, 1H), 6.91–6.83 (m, 2H), 4.55 (septet, 1H), 3.83 (s, 3H), 3.51 (s, 2H), 3.48 (s, 2H), 2.20 (s, 3H), 1.36 (d, 6H) |
| 9653 | $C_{32}H_{33}N_5O_4$ | MH$^+$ (100%) - 552 | ESI | CDCl$_3$/400 MHz | 12.33 (s, 1H), 9.31 (s, 1H), 8.78 (d, 1H), 8.50 (s, 1H), 8.00 (s, 1H), 7.65 (d, 1H), 7.6 1(t, 1H), 7.55–7.46 (m, 2H), 7.32 (t, 1H), 7.20 (t, 1H), 7.08 (d, 1H), 6.52 (s, 1H), 6.45 (s, 1H), 3.79 (s, 6H), 3.60 (s, 2H), 2.92–2.88 (m, 2H), 2.80–2.70 (m, 6H), 2.65 (s, 3H) |
| 9654 | $C_{31}H_{36}N_4O_4$ | MH$^+$ (100%) - 601 | ESI | d$_6$ - DMSO/ 400 MHz | 11.80 (s, 1H), 10.47 (s, 1H), 9.34 (s, 1H), 8.88 (s, 1H), 8.38 (d, 1H), 8.17–8.97 (m, 2H), 7.94–7.87 (m, 2H), 7.72 (t, 1H), 7.66–7.60 (m, 3H), 7.34 (t, 1H), 7.23 (d, 2H), 6.63 (s, 1H), 6.59 (s, 1H), 3.68 (s, 6H), 3.55–3.35 (m, 2H), 3.08–2.95 (m, 1H), 2.70–2.40 (m, 6H), 1.19 (d, 3H) |
| 9655 | $C_{35}H_{35}N_5O_2$ | MH$^+$ (100%) - 558 | ESI | CDCl$_3$/400 MHz | 10.26 (s, 1H, br), 9.53 (d, 1H), 8.85 (d, 1H), 8.80 (d, 1H), 8.20 (d, 1H), 8.10 (s, 1H), 8.00 (d, 1H), 7.82 (t, 1H), 7.70 (d, 1H), 7.68–7.52 (m, 3H), 7.55 (d, 2H), 7.38–7.29 (m, 4H), 6.80 (d, 2H), 3.62 (s, 2H, br), 2.94 (s, 6H), 2.93–2.90 (m, 2H, br), 2.80–2.74 (m, 2H, br), 2.36 (s, 3H, br) |
| 9656 | $C_{40}H_{44}N_4O_6$ | MH$^+$ (100%) - 677 | ESI | CDCl$_3$/400 MHz | 12.45 (s, 1H), 9.50 (s, 1H), 8.71 |

-continued

| | | | | | (s, 1H), 8.54 (s, 1H), 8.50 (s, 1H), 8.15 (d, 1H), 7.98 (d, 1H), 7.81–7.79 (m, 1H), 7.60–7.55 (m, 3H), 7.20 (d, 2H), 7.10 (s, 1H), 6.85 (s, 1H), 6.78 (s, 2H), 3.97 (t, 2H), 3.88 (s, 3H), 3.81 (s, 3H), 3.68 (s, 3H), 3.47 (s, 2H), 2.80 (t, 2H), 2.62 (t, 2H), 2.28 (s, 3H), 1.81–1.75 (t, 2H), 1.50–1.42 (m, 2H), 0.92 (t, 3H). |
|---|---|---|---|---|---|
| 9657 | $C_{33}H_{35}N_5O_5$ | MH$^+$ (100%) - 582 | ESI | $d_6$ - DMSO/ 400 MHz | 12.65 (s, 1H, br), 9.93 (s, 1H), 9.35 (s, 1H), 8.89–8.78 (m, 2H), 7.94 (d, 1H), 7.76 (t, 1H), 7.48 (d, 1H), 7.58 (t, 1H), 7.05 (s, 1H), 6.77 (d, 1H), 6.45 (s, 1H), 6.30 (s, 1H), 3.63 (s, 3H), 3.71 (s, 3H), 3.70 (s, 3H), 3.58 (s, 2H, br), 2.89–2.33 (m, 2H), 2.70 (m, 6H), 2.59 (s, 3H). |
| 9658 | $C_{32}H_{33}N_5O_4$ | MH$^+$ (100%) - 568 | ESI | $d_6$ - DMSO/ 400 MHz | 12.62 (s, 1H, br), 9.27 (s, 1H), 9.32 (s, 1H), 8.90 (m, 1H), 8.80 (m, 1H, 8.71 (s, 1H), 8.70 (s, 1H), 7.97 (d, 1 tI), 7.65 (t, 1H), 7.47 (d, 1H), 7.30 (t, 1H), 7.02 (s, 1H), 6.68 (d, 1H), 6.67 (s, 1H), 6.65 (s, 1H), 3.77 (s, 3H), 3.70 (s, 3H), 3.69 (s, 3H), 3.56 (s, 2H), 2.87–2.82 (m, 2H), 2.75–2.68 (m, 6H) |
| 9659 | $C_{32}H_{33}N_5O_5$ | MH$^+$ (100%) - 552 | ESI | $d_6$ - DMSO/ 400 MHz | 10.15 (s, 1H), 9.34 (s, 1H), 8.90 (d, 1H), 8.80–8.77 (m, 1H), 8.74 (d, 1H), 8.02 (d, 1H), 7.65 (t, 1H), 7.33 (t, 1H), 7.23–7.17 (m, 2H), 7.15–7.08 (m, 1H), 6.66 (s, 1H), 6.64 (s, 1H), 3.655 (s, 3H), 3.65 (s, 3H), 3.57 (s, 2H), 2.85–2.78 (m, 2H), 2.75–2.26 (m, 6H), 2.21 (s, 3H) |
| 9660 | $C_{37}H_{36}N_4O_4$ | MH$^+$ (100%) - 601 | ESI | CDCl$_3$/400 MHz | 12.16 (s, 1H), 9.48 (d, 1H), 8.76–8.72 (m, 2H), 8.12–8.07 (m, 2H), 7.92 (d, 2H), 7.86–7.50 (m, 1H), 7.63–7.44 (m, 4H), 7.40 (s, 1H), 7.28–7.23 (m, 1H), 7.11–7.04 (m, 1H), 7.00 (d, 1H), 6.49 (s, 1H), 6.43 (s, 1H), 3.76 (s, 3H), 3.72 (s, 3H), 3.48 (s, 2H), 2.76–2.61 (m, 6H), 2.50–2.44 (m, 2H), 1.94–1.84 (m, 2H). |
| 9661 | $C_{32}H_{34}N_4O_4$ | MH$^+$ (100%) - 539.4 | DCI/NH$_3$ | CDCl$_3$/400 MHz | 12.01 (s, 1H), 9.27 (s, 1H), 8.81–8.76 (m, 1H), 8.71 (d, 1H), 8.34–8.26 (m, 2H), 7.67–7.58 (m, 3H), 7.52–7.37 (m, 4H), 7.11–7.03 (m, 1H), 6.98 (d, 1H), 6.89–6.82 (m, 2H), 4.55 (septet, 1H), 3.85 (s, 3H), 3.50 (s, 2H), 3.48 (s, 2H), 2.21 (s, 3H), 1.38 (d, 6H). |
| 9663 | $C_{35}H_{33}N_4O_4Cl$ | MH$^+$ (62%) - 609<br>M$^+$Na$^+$ (100%) - 631 | ESI | $d_6$ - DMSO/ 400 MHz | 12.00 (s, 1H), 9.34 (s, 1H), 8.89 (s, 1H), 8.54 (s, 1H), 8.18–8.08 (m, 2H), 7.97 (d, 1H), 7.91 (t, 1H), 7.71 (t, 1H), 7.61 (d, 2H), 7.42 (d, 1H), 7.19 (d, 2H), 6.86–6.78 (m, 2H), 6.77–6.71 (m, 1H), 3.70 (s, 3H), 3.68 (s, 3H), 3.43 (s, 2H), 2.78–2.70 (m, 2H), 2.59–2.52 (m, 2H), 2.17 (s, 3H). |
| 9664 | $C_{35}H_{30}N_4O_4$ | MH$^+$ (100%) - 571 | ESI | $d_6$ - DMSO/ 400 MHz | 11.80 (s, 1H), 10.46 (s, 1H), 9.33 (s, 1H), 8.89 (s, 1H), 8.38 (d, 1H), 8.18–8.08 (m, 2H), 7.95–7.87 (m, 2H), 7.72 (t, 1H), 7.67–7.60 (m, 3H), 7.34 (t, 1H), 7.22 (d, 2H), 6.62 (s, 1H), 6.60 (s, 1H), 5.90 (s, 2H), 3.50 (s, 2H), 2.83–2.75 (m, 2H), 2.72–2.60 (m, 6H). |
| 9665 | $C_{38}H_{38}N_4O_4$ | MH$^+$ (100%) - 615 | ESI | $d_6$ - DMSO/ 400 MHz | 11.80 (s, 1H), 10.46 (s, 1H), 9.33 (s, 1H), 8.88 (s, 1H), 8.38 (d, 1H), 8.17–8.07 (m, 2H), 7.97–7.87 (m, 2H), 7.71 (t, 1H), 7.67–7.58 (m, 3H), 7.32 (t, 1H), 7.22 (d, 2H), 6.62 (s, 1H), 6.60 (s, |

-continued

| | | | | | |
|---|---|---|---|---|---|
| | | | | | 1H), 3.83 (q, 4H), 3.50 (s, 2H), 2.82–2.74 (m, 2H), 2.72–2.60 (m, 6H), 1.27 (t, 6H). |
| 9666 | $C_{36}H_{32}N_6O_4S$ | MH+ (60%) - 645 | ESI | $CDCl_3$/400 MHz | 9.75 (s, 1H, br), 9.55 (d, 1H), 9.27 (s, 1H, br), 8.90 (d, 1H), 8.73 (d, 1H), 8.63 (d, 1H), 8.21 (d, 1H), 8.00 (d, 1H), 7.90–7.85 (m, 1H), 7.71–7.66 (m, 1H), 7.55 (d, 2H), 7.21 (d, 2H), 6.55 (s, 1H), 6.50 (s, 1H), 3.83 (s, 3H), 3.82 (s, 3H), 3.62 (s, 2H), 2.90–2.70 (m, 8H). |
| 9667 | $C_{31}H_{32}N_4O_4F_2$ | MH+ (100%) - 611.5 | $DCI/NH_3$ | $CDCl_3$/400 MHz | 12.35 (s, 1H), 9.51 (s, 1H), 8.93–8.88 (m, 1H), 8.78 (s, 1H), 8.20 (d, 1H), 8.00 (d, 1H), 7.83 (t, 1H), 7.78 (s, 1H), 7.64 (t, 1H), 7.56–7.49 (m, 3H), 7.23 (d, 2H), 6.88 (s, 1H), 6.80 (s, 2H), 3.88 (s, 6H), 3.50 (s, 2H), 2.86–2.80 (m, 2H), 2.68–2.63 (m, 2H), 2.31 (s, 3H). |
| 9668 | $C_{36}H_{36}N_4O_4$ | MH+ (100%) - 589 | ESI | $CDCl_3$/400 MHz | 12.32 (s, 1H), 9.55 (d, 1H), 8.78 (d, 1H), 8.65 (s, 1H), 8.21 (s, 1H), 8.19 (d, 1H), 8.02 (d, 1H), 7.85 (t, 1H), 7.65 (t, 1H), 7.60 (d, 2H), 7.55 (d, 1H), 7.23 (d, 2H), 6.90 (d, 1H), 6.89 (s, 1H), 6.85–6.80 (m, 2H), 3.86 (s, 6H), 3.50 (s, 2H), 2.85–2.81 (m, 2H), 2.70–2.65 (m, 2H), 2.35 (s, 3H), 2.28 (s, 3H). |
| 9669 | $C_{37}H_{38}N_4O_4$ | MH+ (100%) - 603 | ESI | $CDCl_3$/400 MHz | 12.20 (s, 1H), 9.53 (d, 1H), 8.80 (d, 1H), 8.75 (d, 1H), 8.35 (s, 1H), 8.19 (d, 1H), 8.01 (d, 1H), 7.85–7.81 (m, 1H), 7.65–7.60 (m, 2H), 7.55 (d, 2H), 7.48 (t, 1H), 7.17 (d, 2H), 7.05 (t, 1H), 6.91 (s, 1H), 6.85–6.75 (m, 2H), 3.86 (s, 3H), 3.85 (s, 3H), 3.59 (s, 2H), 2.99 (septet, 1H), 2.69 (s, 4H), 1.00 (d, 6H). |
| 9677 | $C_{35}H_{33}N_5O_6$ | MH+ (35%) - 620 | ESI | $d_6$ - DMSO/ 400 MHz | 11.72 (s, 1H), 10.72 (s, 1H), 9.35 (s, 1H), 9.14 (s, 1H), 8.90 (s, 1H), 8.24–8.06 (m, 4H), 7.94 (t, 1H), 7.72 (t, 1H), 7.65 (d, 2H), 7.20 (d, 2H), 6.88–6.70 (m, 3H), 3.69 (s, 3H), 3.68 (s, 3H), 3.44 (s, 2H), 2.78–2.68 (m, 2H), 262–2.50 (m, 2H), 2.17 (s, 3H) |

What is claimed is:

1. A compound which is an anthranilic acid of formula (I):

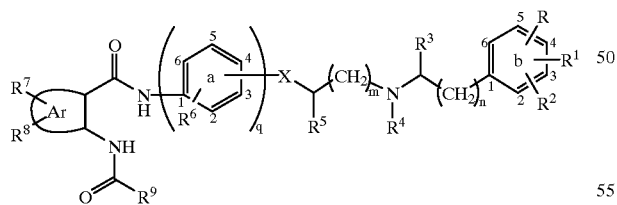

(I)

wherein each of R, $R^1$ and $R^2$, which are the same or different, is H, $C_1$–$C_6$ alkyl, OH, $C_1$–$C_6$ alkoxy, halogen, nitro, or $N(R^{10}R^{11})$ wherein each of $R^{10}$ and $R^{11}$, which are the same or different, is H or $C_1$–$C_6$ alkyl, or $R^1$ and $R^2$, being attached to adjacent positions of ring b, together form a methylenedioxy or ethylenedioxy group;

$R^3$ is H or $C_1$–$C_6$ alkyl;

$R^4$ is $C_1$–$C_6$ alkyl or $R^4$ represents —$CH_2$— or —$CH_2CH_2$— which is attached either (i) to position 2 of ring b to complete a saturated 5- or 6-membered nitrogen-containing ring fused to ring b, or (ii) to the position in ring a adjacent to that to which X, being a single bond, is linked, thereby completing a saturated 5- or 6-membered nitrogen-containing ring fused to ring a;

$R^5$ is H, OH or $C_1$–$C_6$ alkyl;

X is a direct bond, O, S, —S—$(CH_2)_p$— or —O—$(CH_2)_p$— wherein p is an integer of 1 to 6;

$R_6$ is H, $C_1$–$C_6$ alkyl or $C_1$–$C_6$ alkoxy;

q is 0 or 1;

Ar is an unsaturated carbocyclic or heterocyclic group;

each of $R^7$ and $R^8$, which are the same or different, is H, $C_1$–$C_6$ alkyl which is unsubstituted or substituted, $C_1$–$C_6$ alkoxy, hydroxy, halogen, phenyl, —NHOH, nitro, a group $N(R^{10}R^{11})$ as defined above or a group $SR^{12}$ wherein $R^{12}$ is H or $C_1$–$C_6$ alkyl; or $R^7$ and $R^8$, when situated on adjacent carbon atoms, form together with the carbon atoms to which they are attached a benzene ring or a methylenedioxy substituent;

$R^9$ is phenyl or an unsaturated heterocyclic group, each of which is unsubstituted or substituted by $C_1$–$C_6$ alkyl, OH, $C_1$–$C_6$ alkoxy, halogen, $C_3$–$C_6$ cycloalkyl, phenyl, benzyl, trifluoromethyl, nitro, acetyl, benzoyl or N(R$^{10}$R$^{11}$) as defined above, or two substituents on adjacent ring positions of the said phenyl or heterocyclic group together complete a saturated or unsaturated 6-membered ring or form a methylenedioxy group;

n is 0 or 1; and m is 0 or an integer of 1 to 6;

or a pharmaceutically acceptable salt thereof.

2. A compound according to claim 1 wherein the anthranilic acid has the following structure (A):

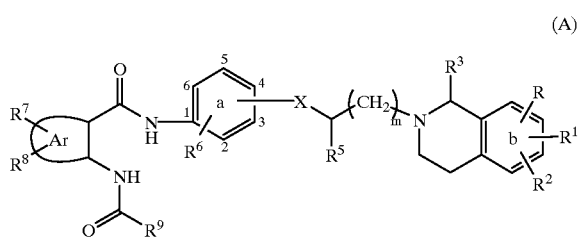

(A)

wherein (a) each of R, R$^1$ and R$^2$, which are the same or different, is H, OH, NO$_2$, N(R$^{10}$R$^{11}$), halogen or C2–C6 alkoxy, or R is H and R$^1$ and R$^2$ form, together with the carbon atoms to which they are attached, a methylenedioxy or ethylenedioxy group, provided R$^1$ and R$^2$ are not both H;

R$^3$ is H or C$_1$–C$_6$ alkyl;

R$^5$ is H, OH or C$_1$–C$_6$ alkyl;

X is a direct bond, O, S, —S—(CH$_2$)p— or —O—(CH$_2$) p— wherein p is an integer of 1 to 6;

R$^6$ is H, C$_1$–C$_6$ alkyl or C$_1$–C$_6$ alkoxy;

Ar is an unsaturated carbocyclic or heterocyclic group;

each of R$^7$ and R$^8$, which are the same or different, is H, C$_1$–C$_6$ alkyl which is unsubstituted or substituted, C$_1$–C$_6$ alkoxy, hydroxy, halogen, phenyl, —NHOH, nitro, a group N(R$^{10}$R$^{11}$) as defined above or a group SR$^{12}$ wherein R$^{12}$ is H or C$_1$–C$_6$ alkyl; or R$^7$ and R$^8$, when situated on adjacent carbon atoms, form together with the carbon atoms to which they are attached a benzene ring or a methylenedioxy substituent;

R$^9$ is phenyl or an unsaturated heterocyclic group, each of which is unsubstituted or substituted by C$_1$–C$_6$ alkyl, OH, C$_1$–C$_6$ alkoxy, halogen, C$_3$–C$_6$ cycloalkyl, phenyl, benzyl, trifluoromethyl, nitro, acetyl, benzoyl or N(R$^{10}$R$^{11}$) as defined above, or two substituents on adjacent ring positions of the phenyl or heterocyclic group together complete a saturated or unsaturated 6-membered ring or form a methylenedioxy group; and m is 0 or an integer of 1 to 6; or (b) each of R, R$^1$ and R$^2$, which are the same or different, is H or OMe and each of R$^3$, R$^5$, R$^6$, R$^7$, R$^8$, R$^9$, Ar, X and m is as defined above.

3. A compound according to claim 1 wherein the anthranilic acid has the following structure (B)

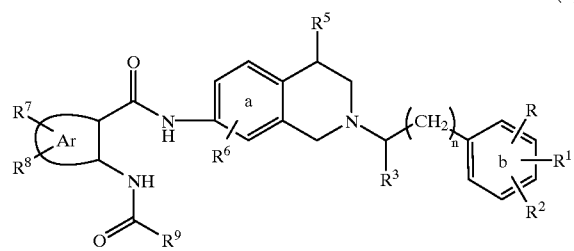

(B)

wherein each of R, R$^1$ and R$^2$, which are the same or different, is H, C$_1$–C$_6$ alkyl, OH, C$_1$–C$_6$ alkoxy, halogen, nitro, or N(R$^{10}$R$^{11}$) wherein each of R$^{10}$ and R$^{11}$, which are the same or different, is H or C$_1$–C$_6$ alkyl; or R$^1$ and R$^2$, being attached to adjacent positions of ring b, together form a methylenedioxy or ethylenedioxy group;

R$^3$ is H or C$_1$–C$_6$ alkyl

R$^5$ is H, OH or C$_1$–C$_6$ alkyl;

R$^6$ is H, C$_1$–C$_6$ alkyl or C$_1$–C$_6$ alkoxy;

Ar is an unsaturated carbocyclic or heterocyclic group;

each of R$^7$ and R$^8$, which are the same or different, is H, C$_1$–C$_6$ alkyl which is unsubstituted or substituted, C$_1$–C$_6$ alkoxy, hydroxy, halogen, phenyl, —NHOH, nitro, a group N(R$^{10}$R$^{11}$) as defined above or a group SR$^{12}$ wherein R$^{12}$ is H or C$_1$–C$_6$ alkyl; or R$^7$ and R$^8$, when situated on adjacent carbon atoms, form together with the carbon atoms to which they are attached a benzene ring or a methylenedioxy substituent;

R$^9$ is phenyl or an unsaturated heterocyclic group, each of which is unsubstituted or substituted by C$_1$–C$_6$ alkyl, OH, C$_1$–C$_6$ alkoxy, halogen, C$_3$–C$_6$ cycloalkyl, phenyl, benzyl, trifluoromethyl, nitro, acetyl, benzoyl or N(R$^{10}$R$^{11}$) as defined above, or two substituents on adjacent ring positions of the phenyl or heterocyclic group together complete a saturated or unsaturated 6-membered ring or form a methylenedioxy group; and n is 0 or 1.

4. A compound according to claim 1 wherein the anthranilic acid has the following structure (C):

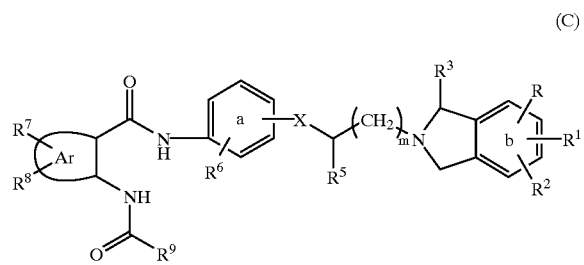

(C)

wherein each of R, R$^1$ and R$^2$, which are the same or different, is H, C$_1$–C$_6$ alkyl, OH, C$_1$–C$_6$ alkoxy, halogen, nitro, or N(R$^{10}$R$^{11}$) wherein each of R$^{10}$ and R$^{11}$, which are the same or different, is H or C$_1$–C$_6$ alkyl; or R$^1$ and R$^2$, being attached to adjacent positions of ring b, together form a methylenedioxy or ethylenedioxy group;

R$^3$ is H or C$_1$–C$_6$ alkyl

R$^5$ is H, OH or C$_1$–C$_6$ alkyl;

X is a direct bond, O, S, —S—(CH$_2$)p— or —O—(CH$_2$) p— wherein p is an integer of 1 to 6;

R⁶ is H, $C_1$–$C_6$ alkyl or $C_1$–$C_6$ alkoxy;

Ar is an unsaturated carbocyclic or heterocyclic group;

each of R⁷ and R⁸, which are the same or different, is H, $C_1$–$C_6$ alkyl which is unsubstituted or substituted, $C_1$–$C_6$ alkoxy, hydroxy, halogen, phenyl, —NHOH, nitro, a group N($R^{10}R^{11}$) as defined above or a group $SR^{12}$ wherein $R^{12}$ is H or $C_1$–$C_6$ alkyl; or R⁷ and R⁸, when situated on adjacent carbon atoms, form together with the carbon atoms to which they are attached a benzene ring or a methylenedioxy substituent;

R⁹ is phenyl or an unsaturated heterocyclic group, each of which is unsubstituted or substituted by $C_1$–$C_6$ alkyl, OH, $C_1$–$C_6$ alkoxy, halogen, $C_3$–$C_6$ cycloalkyl, phenyl, benzyl, trifluoromethyl, nitro, acetyl, benzoyl or N($R^{10}R^{11}$) as defined above, or two substituents on adjacent ring positions of the phenyl or heterocyclic group together complete a saturated or unsaturated 6-membered ring or form a methylenedioxy group;

m is 0 or an integer of 1 to 6.

5. A compound according to claim 1 wherein the anthranilic acid has the following structure (D)

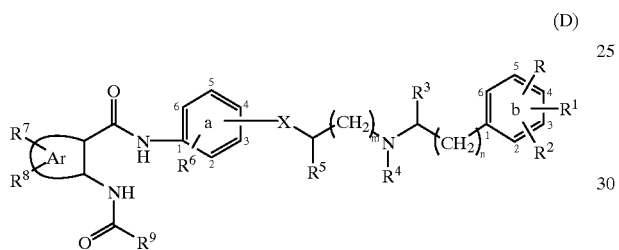

(D)

wherein
each of R, R¹ and R², which are the same or different, is H, $C_1$–$C_6$ alkyl, OH, $C_1$–$C_6$ alkoxy, halogen, nitro, or N($R^{10}R^{11}$) wherein each of $R^{10}$ and $R^{11}$, which are the same or different, is H or $C_1$–$C_6$ alkyl; or R¹ and R², being attached to adjacent positions of ring b, together form a methylenedioxy or ethylenedioxy group;

R³ is H or $C_1$–$C_6$ alkyl

R⁴ is $C_1$–$C_6$ alkyl or R⁴ represents —CH₂— or —CH₂CH₂— which is attached either (i) to position 2 of ring b to complete a saturated 5- or 6-membered nitrogen-containing ring fused to ring b, or (ii) to the position in ring a adjacent to that to which X, being a single bond, is linked, thereby completing a saturated 5- or 6-membered nitrogen-containing ring fused to ring a;

R⁵ is H, OH or $C_1$–$C_6$ alkyl;

R⁶ is H, $C_1$–$C_6$ alkyl or $C_1$–$C_6$ alkoxy;

Ar is an unsaturated carbocyclic or heterocyclic group;

each of R⁷ and R⁸, which are the same or different, is H, C1–C6 alkyl which is unsubstituted or substituted, $C_1$–$C_6$ alkoxy, hydroxy, halogen, phenyl, —NHOH, nitro, a group N($R^{10}R^{11}$) as defined above or a group $SR^{12}$ wherein $R^{12}$ is H or $C_1$–$C_6$ alkyl; or R⁷ and R⁸, when situated on adjacent carbon atoms, form together with the carbon atoms to which they are attached a benzene ring or a methylenedioxy substituent;

R⁹ is phenyl or an unsaturated heterocyclic group, each of which is unsubstituted or substituted by $C_1$–$C_6$ alkyl, OH, $C_1$–$C_6$ alkoxy, halogen, $C_3$–$C_6$ cycloalkyl, phenyl, benzyl, trifluoromethyl, nitro, acetyl, benzoyl or N($R^{10}R^{11}$) as defined above, or two substituents on adjacent ring positions of the phenyl or heterocyclic group together complete a saturated or unsaturated 6-membered ring or form a methylenedioxy group;

n is 0 or 1; and m is 0 or an integer of 1 to 6.

6. A compound which is an anthranilic acid of formula (Ia):

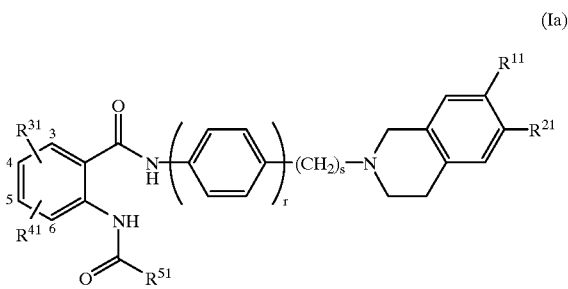

(Ia)

wherein $R^{11}$ and $R^{21}$, which may be the same or different, are each hydrogen or methoxy; $R^{31}$ and $R^{41}$, which may be the same or different, are each independently selected from H, $CH_3$, $CF_3$, F, Cl, Br, $NH_2$, $NO_2$, NHOH, methoxy, hydroxy and phenyl; or $R^{31}$ and $R^{41}$, when situated on adjacent carbon atoms, form together with the carbon atoms to which they are attached a benzene ring or a methylenedioxy substituent; $R^{51}$ is 2-furanyl, 3-furanyl, 2-thiophene, 3-thiophene, 2-indolyl or 2-benzofuranyl or a ring of one of the following formulae (II'), (III') or (IV'):

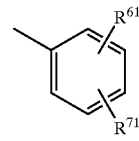

(II')

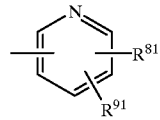

(III')

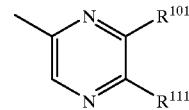

(IV')

wherein
$R^{61}$ and $R^{71}$, which may be the same or different, are selected from hydrogen, $C_1$–$C_6$ alkyl which is linear or branched, $C_3$–$C_6$ cycloalkyl, phenyl, benzyl, trifluoromethyl, F, Cl, Br, $OR^{12}$, $NO_2$, dimethylamino, diethylamino, acetyl and benzoyl, or $R^{61}$ and $R^{71}$ when situated on adjacent carbon atoms, form together with the carbon atoms to which they are attached a benzene ring or a methylenedioxy substituent;

$R^{81}$ and $R^{91}$, which may be the same or different, are each hydrogen, methyl or methoxy, or $R^{81}$ and $R^{91}$, when situated on adjacent carbon atoms, form together with the pyridine to which they are attached a quinoline or 5,6,7,8-tetrahydroquinoline ring system;

$R^{101}$ and $R^{111}$, which may be the same or different, are each hydrogen, methyl or propionyl; or $R^{101}$ and $R^{111}$, when situated on adjacent carbon atoms, form together with the carbon atoms to which they are attached a benzene ring, $R^{121}$ is H, $C_1$–$C_6$ alkyl, $C_3$–$C_6$ cycloalkyl, phenyl, benzyl or acetyl;

r is 0 or 1, and s is 1, 2 or 3;

or a pharmaceutically acceptable salt thereof.

7. A compound according to claim 6 wherein, in formula (Ia), r is 1, s is 2, $R^{11}$ and $R^{21}$ are both methoxy and $R^{51}$ is a 2-quinoxaline group, a 3-quinoline group, a 2-pyrazine group or a 3-pyridine group, all of which groups are unsubstituted or substituted.

8. A compound which is 2-chloro-quinoline-3-carboxylic acid (2-{4-[2-(6,7-dimethoxy-3,4-dihydro-1H-isoquinolin-2-yl)-ethyl]-phenylcarbamoyl}-phenyl)-amide 4-Hydroxy-7-trifluoromethyl-quinoline-3-carboxylic acid (2-{4-[2-(6,7-dimethoxy-3,4-dihydro-1H-isoquinolin-2-yl)-ethyl]-phenylcarbamoyl}-phenyl)-amide Quinoline-3-carboxylic acid (2-{4-[2-(6,7-dimethoxy-3,4-dihydro-1H-isoquinolin-2-yl)-ethyl]-phenylcarbamoyl}-thiophen-3-yl)-amide Quinoline-3-carboxylic acid (2-{4-[2-(6,7-dimethoxy-3,4-dihydro-1H-isoquinolin-2-yl)-ethyl]-phenylcarbamoyl}-4-dimethylamino-phenyl)-amide Quinoxaline-2-carboxylic acid (2-{4-[2-(6,7-dimethoxy-3,4-dihydro-1H-isoquinolin-2-yl)-ethyl]-phenylcarbamoyl}-4-dimethylamino-phenyl)-amide Quinoxaline-2-carboxylic acid (2-{4-[2-(6,7-dimethoxy-3,4-dihydro-1H-isoquinolin-2-yl)-ethyl]-phenylcarbamoyl}-thiophen-3-yl)-amide Quinoxaline-2-carboxylic acid (3-{4-[2-(6,7-dimethoxy-3,4-dihydro-1H-isoquinolin-2-yl)-ethyl]-phenylcarbamoyl}-pyridin-2-yl)-amide 4-Hydroxy-quinoline-3-carboxylic acid (2-{4-[2-(6,7-dimethoxy-3,4-dihydro-1H-isoquinolin-2-yl)-ethyl]-phenylcarbamoyl}-phenyl)-amide Quinoxaline-2-carboxylic acid (3-{4-[2-(6,7-dimethoxy-3,4-dihydro-1H-isoquinolin-2-yl)-ethyl]-phenylcarbamoyl}-4-methyl-thiophen-2-yl)-amide Quinoline-3-carboxylic acid (3-{4-[2-(6,7-dimethoxy-3,4-dihydro-1H-isoquinolin-2-yl)-ethyl]-phenylcarbamoyl}-4-methyl-thiophen-2-yl)-amide Quinoxaline-2-carboxylic acid [2-(4-{2-[(3,4-dimethoxy-benzyl)-methyl-amino]-ethyl}-phenylcarbamoyl)-phenyl]-amide Quinoline-3-carboxylic acid [2-(4-{2-[(3,4-dimethoxy-benzyl)-methyl-amino]-ethyl}-phenylcarbamoyl)-phenyl]-amide Quinoxaline-2-carboxylic acid {2-[2-(3,4-dimethoxy-benzyl)-1,2,3,4-tetrahydro-isoquinolin-7-ylcarbamoyl]-phenyl}-amide Quinoline-3-carboxylic acid (2-{4-[2-(6,7-dimethoxy-3,4-dihydro-7H-isoquinolin-2-yl)-ethyl]-phenylcarbamoyl}-4-methylsulfanyl-phenyl)-amide Quinoline-3-carboxylic acid (4-{4-[2-(6,7-dimethoxy-3,4-dihydro-1H-isoquinolin-2-yl)-ethyl]-phenylcarbamoyl}-thiophen-3-yl)-amide N-(4-{4-[2-(6,7-Dimethoxy-3,4-dihydro-1H-isoquinolin-2-yl)-ethyl]-phenylcarbamoyl}-thiophen-3-yl)-6-methyl-nicotinamide Quinoline-3-carboxylic acid (2-{4-[2-(6,7-dimethoxy-3,4-dihydro-1H-isoquinolin-2-yl)-ethylsulfanyl]-phenylcarbamoyl}-phenyl)-amide Quinoline-3-carboxylic acid (3-{4-[2-(6,7-dimethoxy-3,4-dihydro-1H-isoquinolin-2-yl)-ethyl]-phenylcarbamoyl}-pyrazin-2-yl)-amide Quinoline-3-carboxylic acid (2-{4-[2-(6,7-dimethoxy-3,4-dihydro-1H-isoquinolin-2-yl)-ethoxy]-phenylcarbamoyl}-phenyl)-amide Quinoline-3-carboxylic acid (2-{4-[2-(6,7-dimethoxy-1-methyl-3,4-dihydro-1H-isoquinolin-2-yl)-ethyl]-phenylcarbamoyl}-phenyl)-amide Quinoline-3-carboxylic acid (2-{4-[2-(1,3-dihydro-isoindol-2-yl)-ethyl]-phenylcarbamoyl}-phenyl)-amide Quinoline-3-carboxylic acid (2-{4-[2-(6,7-dichloro-3,4-dihydro-1H-isoquinolin-2-yl)-ethyl]-phenylcarbamoyl}-phenyl)-amide Quinoline-3-carboxylic acid (2-{4-[2-(7,8-dichloro-3,4-dihydro-1H-isoquinolin-2-yl)-ethyl]-phenylcarbamoyl}-phenyl)-amide Quinoline-3-carboxylic acid {2-[4-(2-{[2-(3,4-dimethoxy-phenyl)-ethyl]-methyl-amino}-ethyl)-phenylcarbamoyl]-phenyl}-amide Quinoline-3-carboxylic acid [2-(4-{2-[(3,4-dimethyl-benzyl)-methyl-amino]-ethyl}-phenylcarbamoyl)-phenyl]-amide Quinoxaline-2-carboxylic acid (2-{4-[2-(6,7-dimethoxy-3,4-dihydro-1H-isoquinolin-2-yl)-ethoxy]-phenylcarbamoyl}-phenyl)-amide Quinoline-3-carboxylic acid (2-{3-[2-(6,7-dimethoxy-3,4-dihydro-1H-isoquinolin-2-yl)-ethyl]-phenylcarbamoyl}-phenyl)-amide Quinoline-3-carboxylic acid (2-{4-[2-(7-nitro-3,4-dihydro-1H-isoquinolin-2-yl)-ethyl]-phenylcarbamoyl}-phenyl)-amide 2-Methyl-thiazole-4-carboxylic acid (2-{4-[2-(6,7-dimethoxy-3,4-dihydro-1H-isoquinolin-2-yl)-ethyl]-phenylcarbamoyl}-phenyl)-amide Quinoline-3-carboxylic acid [2-(4-{2-[(3,4-dimethoxy-benzyl)-ethyl-amino]-ethyl}-phenylcarbamoyl)-phenyl]-amide 2-Methyl-oxazole-4-carboxylic acid (2-{4-[2-(6,7-dimethoxy-3,4-dihydro-1H-isoquinolin-2-yl)-ethyl]-phenylcarbamoyl)-phenyl)-amide Quinoline-3-carboxylic acid [2-(4-{2-[(3-isopropoxy-4-methoxy-benzyl)-methyl-amino]-ethyl}-phenylcarbamoyl)-phenyl]-amide Quinoline-3-carboxylic acid [2-(4-{2-[methyl-(3,4,5-trimethoxy-benzyl)-amino]-ethyl}-phenylcarbamoyl)-phenyl]-amide Quinoline-3-carboxylic acid [2-(4-{2-[butyl-(3,4-dimethoxy-benzyl)-amino]-ethyl}-phenylcarbamoyl)-phenyl]-amide Quinoline-3-carboxylic acid [2-(4-{2-[(4-butoxy-3-methoxy-benzyl)-methyl-amino]-ethyl}-phenylcarbamoyl)-phenyl]-amide Quinoline-3-carboxylic acid [2-(4-{2-[(3,4-difluoro-benzyl)-methyl-amino]-ethyl}-phenylcarbamoyl)-phenyl]-amide Quinoline-3-carboxylic acid [2-(4-{2-[(2,3-dihydro-benzo[1,4]dioxin-6-ylmethyl)-methyl-amino]-ethyl}-phenylcarbamoyl)-phenyl]-amide Quinoline-3-carboxylic acid [2-(4-{2-[(4-isopropoxy-3-methoxy-benzyl)-methyl-amino]-ethyl}-phenylcarbamoyl)-phenyl]-amide Quinoline-3-carboxylic acid [2-(4-{2-[(3-hydroxy-4-methoxy-benzyl)-methyl-amino]-ethyl}-phenylcarbamoyl)-phenyl]-amide Quinoline-3-carboxylic acid (2-{4-[3-(6,7-dimethoxy-3,4-dihydro-1H-isoquinolin-2-yl)-2-hydroxy-propoxy]-phenylcarbamoyl}-phenyl)-amide Quinoline-3-carboxylic acid [2-(4-{2-[(4-hydroxy-3-methoxy-benzyl)-methyl-amino]-ethyl}-phenylcarbamoyl)-phenyl]-amide Quinoline-3-carboxylic acid (2-{4-[2-(6,7-dimethoxy-3,4-dihydro-1H-isoquinolin-2-yl)-ethyl]-2-methyl-phenylcarbamoyl}-phenyl)-amide
Quinoline-3-carboxylic acid (2-{4-[2-(6,7-dimethoxy-3,4-dihydro-1H-isoquinolin-2-yl)-ethyl]-2-methoxy-phenylcarbamoyl}-phenyl)-amide
Quinoline-3-carboxylic acid [2-(4-{[(3-isopropoxy-4-methoxy-benzyl)-methyl-amino]-methyl}-phenylcarbamoyl)-phenyl]-amide
5-Methyl-pyrazine-2-carboxylic acid (2-{3-[2-(6,7-dimethoxy-3,4-dihydro-1H-isoquinolin-2-yl)-ethyl]-phenylcarbamoyl}-phenyl)-amide
Quinoline-3-carboxylic acid (2-{4-[2-(6,7-dimethoxy-3,4-dihydro-1H-isoquinolin-2-yl)-1-methyl-ethyl]-phenylcarbamoyl}-phenyl)-amide
Quinoline-3-carboxylic acid [2-(4-{2-[(4-dimethylamino-benzyl)-methyl-amino]-ethyl}-phenylcarbamoyl)-phenyl]-amide
Quinoline-3-carboxylic acid [2-(4-{2-[(3-butoxy-4-methoxy-benzyl)-methyl-amino]-ethyl}-phenylcarbamoyl)-4,5-dimethoxy-phenyl]-amide
5-Methyl-pyrazine-2-carboxylic acid (2-{4-[2-(6,7-dimethoxy-3,4-dihydro-1H-isoquinolin-2-yl)-ethyl]-2-methoxy-phenylcarbamoyl}-phenyl)-amide
Pyrazine-2-carboxylic acid (2-{4-[2-(6,7-dimethoxy-3,4-dihydro-1H-isoquinolin-2-yl)-ethyl]-2-methyl-phenylcarbamoyl}-phenyl)-amide
Pyrazine-2-carboxylic acid (2-{4-[2-(6,7-dimethoxy-3,4-dihydro-1H-isoquinolin-2-yl)-ethyl]-2-methoxy-phenylcarbamoyl}-phenyl)-amide
Quinoline-3-carboxylic acid (2-{3-[3-(6,7-dimethoxy-3,4-dihydro-1H-isoquinolin-2-yl)-propyl]-phenylcarbamoyl}-phenyl)-amide
N-[2-(4-{[(3-Isopropoxy-4-methoxy-benzyl)-methyl-amino]-methyl}-phenylcarbamoyl)-phenyl]-nicotinamide
Quinoline-3-carboxylic acid [5-chloro-2-(4-{2-[(3,4-dimethoxy-benzyl)-methyl-amino]-ethyl}-phenylcarbamoyl)-phenyl]-amide
Quinoline-3-carboxylic acid (2-{4-[2-(7,8-dihydro-5H-[1,3]dioxolo[4,5-g]isoquinolin-6-yl)-ethyl]-phenylcarbamoyl}-phenyl)-amide
Quinoline-3-carboxylic acid (2-{4-[2-(6,7-diethoxy-3,4-dihydro-1H-isoquinolin-2-yl)-ethyl]-phenylcarbamoyl}-phenyl)-amide
Quinoline-3-carboxylic acid (6-{4-[2-(6,7-dimethoxy-3,4-dihydro-1H-isoquinolin-2-yl)-ethyl]-phenylcarbamoyl}-thieno[2,3-b]pyrazin-7-yl)-amide
Quinoline-3-carboxylic acid [2-(4-{2-[(3,4-dimethoxy-benzyl)-methyl-amino]-ethyl}-phenylcarbamoyl)-4,5-difluoro-phenyl]-amide
Quinoline-3-carboxylic acid [2-(4-{2-[(3,4-dimethoxy-benzyl)-methyl-amino]-ethyl}-phenylcarbamoyl)-5-methyl-phenyl]-amide
Quinoline-3-carboxylic acid [2-(4-{2-[(3,4-dimethoxy-benzyl)-isopropyl-amino]-ethyl}-phenylcarbamoyl)-phenyl]-amide
Quinoline-3-carboxylic acid [2-(4-{2-[(3,4-dimethoxy-benzyl)-methyl-amino]-ethyl}-phenylcarbamoyl)-5-nitro-phenyl]-amide
2-(4-Isopropyl-benzoylamino)-N-[2-(6,7-dimethoxy-3,4-dihydro-1H-isoquinolin-2-yl)-ethyl]-benzamide
2-(4-Isopropyl-benzoylamino)-N-[2-(6,7-dimethoxy-3,4-dihydro-1H-isoquinolin-2-yl)-ethyl]-6-chloro-benzamide
2-(4-Isopropyl-benzoylamino)-N-[2-(6,7-dimethoxy-3,4-dihydro-1H-isoquinolin-2-yl)-ethyl]-5-chloro-benzamide
2-(4-Isopropyl-benzoylamino)-N-[2-(6,7-dimethoxy-3,4-dihydro-1H-isoquinolin-2-yl)-ethyl]-4-chloro-benzamide
2-(4-Isopropyl-benzoylamino)-N-[2-(6,7-dimethoxy-3,4-dihydro-1H-isoquinolin-2-yl)-ethyl]-3-chloro-benzamide
2-(4-Isopropyl-benzoylamino)-N-[2-(6,7-dimethoxy-3,4-dihydro-1H-isoquinolin-2-yl)-ethyl]-5-bromo-benzamide
2-(4-Isopropyl-benzoylamino)-N-[2-(6,7-dimethoxy-3,4-dihydro-1H-isoquinolin-2-yl)-ethyl]-4-fluoro-benzamide
2-(4-Isopropyl-benzoylamino)-N-[2-(6,7-dimethoxy-3,4-dihydro-1H-isoquinolin-2-yl)-ethyl]-3-methyl-benzamide
2-(4-Isopropyl-benzoylamino)-N-[2-(6,7-dimethoxy-3,4-dihydro-1H-isoquinolin-2-yl)-ethyl]-3-methoxy-benzamide
2-(4-Isopropyl-benzoylamino)-N-[2-(6,7-dimethoxy-3,4-dihydro-1H-isoquinolin-2-yl)-ethyl]-3-hydroxy-benzamide
2-(4-Isopropyl-benzoylamino)-N-[2-(6,7-dimethoxy-3,4-dihydro-1H-isoquinolin-2-yl)-ethyl]-4-nitro-benzamide
2-(4-Isopropyl-benzoylamino)-N-[2-(6,7-dimethoxy-3,4-dihydro-1H-isoquinolin-2-yl)-ethyl]-4-amino-benzamide
2-(4-Isopropyl-benzoylamino)-N-[2-(6,7-dimethoxy-3,4-dihydro-1H-isoquinolin-2-yl)-ethyl]-5-phenyl-benzamide
3-(4-Isopropyl-benzoylamino)-naphthalene-2-carboxylic acid [2-(6,7-dimethoxy-3,4-dihydro-1H-isoquinolin-2-yl)-ethyl]-amide
2-(4-Dimethylamino-benzoylamino)-N-[2-(6,7-dimethoxy-3,4-dihydro-1H-isoquinolin-2-yl)-ethyl]-benzamide
2-(4-Propyl-benzoylamino)-N-[2-(6,7-dimethoxy-3,4-dihydro-1H-isoquinolin-2-yl)-ethyl]-benzamide
2-(4-Pentyl-benzoylamino)-N-[2-(6,7-dimethoxy-3,4-dihydro-1H-isoquinolin-2-yl)-ethyl]-benzamide
2-(4-Cyclohexyl-benzoylamino)-N-[2-(6,7-dimethoxy-3,4-dihydro-1H-isoquinolin-2-yl)-ethyl]-benzamide
Biphenyl-4-carboxylic acid {2-[2-(6,7-dimethoxy-3,4-dihydro-1H-isoquinolin-2-yl)-ethylcarbamoyl]-phenyl}-amide
Naphthalene-2-carboxylic acid {2-[2-(6,7-dimethoxy-3,4-dihydro-1H-isoquinolin-2-yl)-ethylcarbamoyl]-phenyl}-amide
Benzo[1,3]dioxole-5-carboxylic acid {2-[2-(6,7-dimethoxy-3,4-dihydro-1H-isoquinolin-2-yl)-ethylcarbamoyl]-phenyl}-amide
2-(4-Diethylamino-benzoylamino)-N-[2-(6,7-dimethoxy-3,4-dihydro-1H-isoquinolin-2-yl)-ethyl]-benzamide
2-(4-tert-Butyl-benzoylamino)-N-[2-(6,7-dimethoxy-3,4-dihydro-1H-isoquinolin-2-yl)-ethyl]-benzamide
2-Benzoylamino-N-[2-(6,7-dimethoxy-3,4-dihydro-1H-isoquinolin-2-yl)-ethyl]-benzamide
2-(4-Bromo-benzoylamino)-N-[2-(6,7-dimethoxy-3,4-dihydro-1H-isoquinolin-2-yl)-ethyl]-benzamide
2-(4-Nitro-benzoylamino)-N-[2-(6,7-dimethoxy-3,4-dihydro-1H-isoquinolin-2-yl)-ethyl]-benzamide
2-(4-Phenoxy-benzoylamino)-N-[2-(6,7-dimethoxy-3,4-dihydro-1H-isoquinolin-2-yl)-ethyl]-benzamide
2-(4-Benzoyl-benzoylamino)-N-[2-(6,7-dimethoxy-3,4-dihydro-1H-isoquinolin-2-yl)-ethyl]-benzamide
2-(4-Benzyl-benzoylamino)-N-[2-(6,7-dimethoxy-3,4-dihydro-1H-isoquinolin-2-yl)-ethyl]-benzamide
2-(4-Cyclohexyloxy-benzoylamino)-N-[2-(6,7-dimethoxy-3,4-dihydro-1H-isoquinolin-2-yl)-ethyl]-benzamide
2-(4-Benzyloxy-benzoylamino)-N-[2-(6,7-dimethoxy-3,4-dihydro-1H-isoquinolin-2-yl)-ethyl]-benzamide
Pyridine-2-carboxylic acid {2-[2-(6,7-dimethoxy-3,4-dihydro-1H-isoquinolin-2-yl)-ethylcarbamoyl]-phenyl}-amide
N-{2-[2-(6,7-Dimethoxy-3,4-dihydro-1H-isoquinolin-2-yl)-ethylcarbamoyl]-phenyl}-nicotinamide
N-{2-[2-(6,7-Dimethoxy-3,4-dihydro-1H-isoquinolin-2-yl)-ethylcarbamoyl]-phenyl}-isonicotinamide Pyrazine-2-carboxylic acid {2-[2-(6,7-dimethoxy-3,4-dihydro-1H-isoquinolin-2-yl)-ethylcarbamoyl]-phenyl}-amide
Quinoxaline-2-carboxylic acid {2-[2-(6,7-dimethoxy-3,4-dihydro-1H-isoquinolin-2-yl)-ethylcarbamoyl]-phenyl}-amide
Isoquinoline-1-carboxylic acid (2-[2-(6,7-dimethoxy-3,4-dihydro-1H-isoquinolin-2-yl)-ethylcarbamoyl]-phenyl}-amide
Quinoline-2-carboxylic acid {2-[2-(6,7-dimethoxy-3,4-dihydro-1H-isoquinolin-2-yl)-ethylcarbamoyl]-phenyl}-amide
Isoquinoline-3-carboxylic acid {2-[2-(6,7-dimethoxy-3,4-dihydro-1H-isoquinolin-2-yl)-ethylcarbamoyl]-phenyl}-amide
Quinoline-3-carboxylic acid {2-[2-(6,7-dimethoxy-3,4-dihydro-1H-isoquinolin-2-yl)-ethylcarbamoyl]-phenyl}-amide
Thiophene-3-carboxylic acid {2-[2-(6,7-dimethoxy-3,4-dihydro-1H-isoquinolin-2-yl)-ethylcarbamoyl]-phenyl}-amide
1H-Indole-2-carboxylic acid {2-[2-(6,7-dimethoxy-3,4-dihydro-1H-isoquinolin-2-yl)-ethylcarbamoyl]-phenyl}-amide
Quinoxaline-2-carboxylic acid (2-{4-[2-(6,7-dimethoxy-3,4-dihydro-1H-isoquinolin-2-yl)-ethyl]-phenylcarbamoyl}-phenyl)-amide
Quinoxaline-2-carboxylic acid (2-{4-[2-(6,7-dimethoxy-3,4-dihydro-1H-isoquinolin-2-yl)-ethyl]-phenylcarbamoyl}-5-hydroxyamino-phenyl)-amide
Quinoxaline-2-carboxylic acid (2-{4-[2-(6,7-dimethoxy-3,4-dihydro-1H-isoquinolin-2-yl)-ethyl]-phenylcarbamoyl}-4-methyl-phenyl)-amide
Quinoxaline-2-carboxylic acid (2-{4-[2-(6,7-dimethoxy-3,4-dihydro-1H-isoquinolin-2-yl)-ethyl]-phenylcarbamoyl}-4-hydroxy-phenyl)-amide
Quinoxaline-2-carboxylic acid (2-{4-[2-(6,7-dimethoxy-3,4-dihydro-1H-isoquinolin-2-yl)-ethyl]-phenylcarbamoyl}-5-nitro-phenyl)-amide
Quinoxaline-2-carboxylic acid (2-{4-[2-(6,7-dimethoxy-3,4-dihydro-1H-isoquinolin-2-yl)-ethyl]-phenylcarbamoyl}-5-trifluoromethyl-phenyl)-amide
Quinoxaline-2-carboxylic acid (2-{4-[2-(6,7-dimethoxy-3,4-dihydro-1H-isoquinolin-2-yl)-ethyl]-phenylcarbamoyl}-5-fluoro-phenyl)-amide
Quinoxaline-2-carboxylic acid (2-{4-[2-(6,7-dimethoxy-3,4-dihydro-1H-isoquinolin-2-yl)-ethyl]-phenylcarbamoyl}-3-fluoro-phenyl)-amide
Quinoxaline-2-carboxylic acid (2-{4-[2-(6,7-dimethoxy-3,4-dihydro-1H-isoquinolin-2-yl)-ethyl]-phenylcarbamoyl}-4-fluoro-phenyl)-amide
Quinoxaline-2-carboxylic acid (2-{4-[2-(6,7-dimethoxy-3,4-dihydro-1H-isoquinolin-2-yl)-ethyl]-phenylcarbamoyl}-4,5-dimethoxy-phenyl)-amide
Quinoline-3-carboxylic acid (2-{4-[2-(6,7-dimethoxy-3,4-dihydro-1H-isoquinolin-2-yl)-ethyl]-phenylcarbamoyl}-phenyl)-amide
Quinoline-3-carboxylic acid (2-{4-[2-(6,7-dimethoxy-3,4-dihydro-1H-isoquinolin-2-yl)-ethyl]-phenylcarbamoyl}-5-fluoro-phenyl)-amide
Quinoline-3-carboxylic acid (2-{4-[2-(6,7-dimethoxy-3,4-dihydro-1H-isoquinolin-2-yl)-ethyl]-phenylcarbamoyl}-4-fluoro-phenyl)-amide
Quinoline-3-carboxylic acid (2-{4-[2-(6,7-dimethoxy-3,4-dihydro-1H-isoquinolin-2-yl)-ethyl]-phenylcarbamoyl}-4,5-dimethoxy-phenyl)-amide
Quinoline-3-carboxylic acid (6-{4-[2-(6,7-dimethoxy-3,4-dihydro-1H-isoquinolin-2-yl)-ethyl]-phenylcarbamoyl}-benzo[1,3]dioxol-5-yl)-amide
Quinoline-3-carboxylic acid (2-{4-[2-(6,7-dimethoxy-3,4-dihydro-1H-isoquinolin-2-yl)-ethyl]-phenylcarbamoyl}-5-nitro-phenyl)-amide
Quinoline-3-carboxylic acid (2-{4-[2-(6,7-dimethoxy-3,4-dihydro-1H-isoquinolin-2-yl)-ethyl]-phenylcarbamoyl}-4-methyl-phenyl)-amide
Quinoline-3-carboxylic acid (2-{4-[2-(6,7-dimethoxy-3,4-dihydro-1H-isoquinolin-2-yl)-ethyl]-phenylcarbamoyl}-5-methyl-phenyl)-amide
Quinoline-3-carboxylic acid (2-{4-[2-(6,7-dimethoxy-3,4-dihydro-1H-isoquinolin-2-yl)-ethyl]-phenylcarbamoyl}-4-chloro-phenyl)-amide
Quinoline-3-carboxylic acid (2-{4-[2-(6,7-dimethoxy-3,4-dihydro-1H-isoquinolin-2-yl)-ethyl]-phenylcarbamoyl}-5-chloro-phenyl)-amide
Quinoline-3-carboxylic acid (2-{4-[2-(6,7-dimethoxy-3,4-dihydro-1H-isoquinolin-2-yl)-ethyl]-phenylcarbamoyl}-5-amino-phenyl)-amide
Quinoline-2-carboxylic acid (2-{4-[2-(6,7-dimethoxy-3,4-dihydro-1H-isoquinolin-2-yl)-ethyl]-phenylcarbamoyl}-phenyl)-amide
5,6,7,8-Tetrahydroquinoline-3-carboxylic acid (2-{4-[2-(6,7-dimethoxy-3,4-dihydro-1H-isoquinolin-2-yl)-ethyl]-phenylcarbamoyl}-phenyl)-amide
Pyridine-2-carboxylic acid (2-{4-[2-(6,7-dimethoxy-3,4-dihydro-1H-isoquinolin-2-yl)-ethyl]-phenylcarbamoyl}-phenyl)-amide
N-(2-{4-[2-(6,7-Dimethoxy-3,4-dihydro-1H-isoquinolin-2-yl)-ethyl]-phenylcarbamoyl}-phenyl)-nicotinamide
N-(2-{4-[2-(6,7-Dimethoxy-3,4-dihydro-1H-isoquinolin-2-yl)-ethyl]-phenylcarbamoyl}-phenyl)-isonicotinamide
Pyrazine-2-carboxylic acid (2-{4-[2-(6,7-dimethoxy-3,4-dihydro-1H-isoquinolin-2-yl)-ethyl]-phenylcarbamoyl}-phenyl)-amide
5-Methyl-pyrazine-2-carboxylic acid (2-{4-[2-(6,7-dimethoxy-3,4-dihydro-1H-isoquinolin-2-yl)-ethyl]-phenylcarbamoyl}-phenyl)-amide
N-(2-{4-[2-(6,7-Dimethoxy-3,4-dihydro-1H-isoquinolin-2-yl)-ethyl]-phenylcarbamoyl}-phenyl)-6-methyl-nicotinamide
N-(2-{4-[2-(6,7-Dimethoxy-3,4-dihydro-1H-isoquinolin-2-yl)-ethyl]-phenylcarbamoyl}-phenyl)-6-methoxy-nicotinamide
5-Propionyl-pyrazine-2-carboxylic acid (2-{4-[2-(6,7-dimethoxy-3,4-dihydro-1H-isoquinolin-2-yl)-ethyl]-phenylcarbamoyl}-phenyl)-amide
2-Benzoylamino-N-{4-[2-(6,7-dimethoxy-3,4-dihydro-1H-isoquinolin-2-yl)-ethyl]-phenyl}-benzamide
2-Benzoylamino-N-{4-[2-(6,7-dimethoxy-3,4-dihydro-1H-isoquinolin-2-yl)-ethyl]-phenyl}-5-methyl-benzamide
2-Benzoylamino-N-{4-[2-(6,7-dimethoxy-3,4-dihydro-1H-isoquinolin-2-yl)-ethyl]-phenyl}-4-methyl-benzamide
2-Benzoylamino-N-{4-[2-(6,7-dimethoxy-3,4-dihydro-1H-isoquinolin-2-yl)-ethyl]-phenyl}-6-methyl-benzamide
2-(2-Fluoro-benzoylamino)-N-{4-[2-(6,7-dimethoxy-3,4-dihydro-1H-isoquinolin-2-yl)-ethyl]-phenyl}-benzamide
2-(3-Fluoro-benzoylamino)-N-{4-[2-(6,7-dimethoxy-3,4-dihydro-1H-isoquinolin-2-yl)-ethyl]-phenyl}-benzamide
2-(4-Fluoro-benzoylamino)-N-{4-[2-(6,7-dimethoxy-3,4-dihydro-1H-isoquinolin-2-yl)-ethyl]-phenyl}-benzamide
2-(2,4-Difluoro-benzoylamino)-N-{4-[2-(6,7-dimethoxy-3,4-dihydro-1H-isoquinolin-2-yl)-ethyl]-phenyl}-benzamide
2-(2,6-Difluoro-benzoylamino)-N-{4-[2-(6,7-dimethoxy-3,4-dihydro-1H-isoquinolin-2-yl)-ethyl]-phenyl}-benzamide
2-(2-Chloro-benzoylamino)-N-{4-[2-(6,7-dimethoxy-3,4-dihydro-1H-isoquinolin-2-yl)-ethyl]-phenyl}-benzamide 2-(3-Chloro-benzoylamino)-N-{4-[2-(6,7-dimethoxy-3,4-dihydro-1H-isoquinolin-2-yl)-ethyl]-phenyl}-benzamide
2-(4-Chloro-benzoylamino)-N-{4-[2-(6,7-dimethoxy-3,4-dihydro-1H-isoquinolin-2-yl)-ethyl]-phenyl}-benzamide
2-(2-Methyl-benzoylamino)-N-{4-[2-(6,7-dimethoxy-3,4-dihydro-1H-isoquinolin-2-yl)-ethyl]-phenyl}-benzamide
2-(3-Methyl-benzoylamino)-N-{4-[2-(6,7-dimethoxy-3,4-dihydro-1H-isoquinolin-2-yl)-ethyl]-phenyl}-benzamide
2-(4-Methyl-benzoylamino)-N-{4-[2-(6,7-dimethoxy-3,4-dihydro-1H-isoquinolin-2-yl)-ethyl]-phenyl}-benzamide
2-(2-Methoxy-benzoylamino)-N-{4-[2-(6,7-dimethoxy-3,4-dihydro-1H-isoquinolin-2-yl)-ethyl]-phenyl}-benzamide
2-(3-Methoxy-benzoylamino)-N-{4-[2-(6,7-dimethoxy-3,4-dihydro-1H-isoquinolin-2-yl)-ethyl]-phenyl}-benzamide
2-(4-Methoxy-benzoylamino)-N-{4-[2-(6,7-dimethoxy-3,4-dihydro-1H-isoquinolin-2-yl)-ethyl]-phenyl}-benzamide
2-(2-Hydroxy-benzoylamino)-N-{4-[2-(6,7-dimethoxy-3,4-dihydro-1H-isoquinolin-2-yl)-ethyl]-phenyl}-benzamide
2-(3-Hydroxy-benzoylamino)-N-{4-[2-(6,7-dimethoxy-3,4-dihydro-1H-isoquinolin-2-yl)-ethyl]-phenyl}-benzamide
2-(4-Hydroxy-benzoylamino)-N-{4-[2-(6,7-dimethoxy-3,4-dihydro-1H-isoquinolin-2-yl)-ethyl]-phenyl}-benzamide
Acetic acid 2-(2-{4-[2-(6,7-dimethoxy-3,4-dihydro-1H-isoquinolin-2-yl)-ethyl]-phenylcarbamoyl}-phenylcarbamoyl)-phenyl ester
Acetic acid 3-(2-{4-[2-(6,7-dimethoxy-3,4-dihydro-1H-isoquinolin-2-yl)-ethyl]-phenylcarbamoyl}-phenylcarbamoyl)-phenyl ester
Acetic acid 4-(2-{4-[2-(6,7-dimethoxy-3,4-dihydro-1H-isoquinolin-2-yl)-ethyl]-phenylcarbamoyl}-phenylcarbamoyl)-phenyl ester
2-(2-Trifluoromethyl-benzoylamino)-N-{4-[2-(6,7-dimethoxy-3,4-dihydro-1H-isoquinolin-2-yl)-ethyl]-phenyl}-benzamide
2-(3-Trifluoromethyl-benzoylamino)-N-{4-[2-(6,7-dimethoxy-3,4-dihydro-1H-isoquinolin-2-yl)-ethyl]-phenyl}-benzamide
2-(3-Dimethylamino-benzoylamino)-N-{4-[2-(6,7-dimethoxy-3,4-dihydro-1H-isoquinolin-2-yl)-ethyl]-phenyl}-benzamide
2-(4-Isopropyl-benzoylamino)-N-{4-[2-(6,7-dimethoxy-3,4-dihydro-1H-isoquinolin-2-yl)-ethyl]-phenyl}-benzamide
2-(4-Cyclohexyl-benzoylamino)-N-{4-[2-(6,7-dimethoxy-3,4-dihydro-1H-isoquinolin-2-yl)-ethyl]-phenyl}-benzamide
Naphthalene-1-carboxylic acid (2-{4-[2-(6,7-dimethoxy-3,4-dihydro-1H-isoquinolin-2-yl)-ethyl]-phenylcarbamoyl}-phenyl)-amide
Naphthalene-2-carboxylic acid (2-{4-[2-(6,7-dimethoxy-3,4-dihydro-1H-isoquinolin-2-yl)-ethyl]-phenylcarbamoyl}-phenyl)-amide
2-(3,4-Dichloro-benzoylamino)-N-{4-[2-(6,7-dimethoxy-3,4-dihydro-1H-isoquinolin-2-yl)-ethyl]-phenyl}-benzamide
2-(3,4-Dimethyl-benzoylamino)-N-{4-[2-(6,7-dimethoxy-3,4-dihydro-1H-isoquinolin-2-yl)-ethyl]-phenyl}-benzamide
Thiophene-2-carboxylic acid (2-{4-[2-(6,7-dimethoxy-3,4-dihydro-1H-isoquinolin-2-yl)-ethyl]-phenylcarbamoyl}-phenyl)-amide
Thiophene-3-carboxylic acid (2-{4-[2-(6,7-dimethoxy-3,4-dihydro-1H-isoquinolin-2-yl)-ethyl]-phenylcarbamoyl}-phenyl)-amide
Furan-3-carboxylic acid (2-{4-[2-(6,7-dimethoxy-3,4-dihydro-1H-isoquinolin-2-yl)-ethyl]-phenylcarbamoyl}-phenyl)-amide
1H-Indole-2-carboxylic acid (2-{4-[2-(6,7-dimethoxy-3,4-dihydro-1H-isoquinolin-2-yl)-ethyl]-phenylcarbamoyl}-phenyl)-amide
Benzofuran-2-carboxylic acid (2-{4-[2-(6,7-dimethoxy-3,4-dihydro-1H-isoquinolin-2-yl)-ethyl]-phenylcarbamoyl}-phenyl)-amide
2-(4-Cyclohexyl-benzoylamino)-N-[3-(6,7-dimethoxy-3,4-dihydro-1H-isoquinolin-2-yl)-propyl]-benzamide
2-(4-Cyclohexyl-benzoylamino)-N-[2-(3,4-dihydro-1H-isoquinolin-2-yl)-ethyl]-benzamide
Quinoxaline-2-carboxylic acid (2-{4-[3-(6,7-dimethoxy-3,4-dihydro-1H-isoquinolin-2-yl)-propyl]-phenylcarbamoyl}-phenyl)-amide
Quinoxaline-2-carboxylic acid {2-[4-(6,7-dimethoxy-3,4-dihydro-1H-isoquinolin-2-ylmethyl)-phenylcarbamoyl]-phenyl}-amide
Quinoline-3-carboxylic acid (2-{4-[2-(3,4-dihydro-1H-isoquinolin-2-yl)-ethyl]-phenylcarbamoyl}-phenyl)-amide
Quinoline-3-carboxylic acid {2-[4-(6,7-dimethoxy-3,4-dihydro-1H-isoquinolin-2-ylmethyl)-phenylcarbamoyl]-phenyl}-amide or a pharmaceutically acceptable salt thereof.

9. A pharmaceutical or veterinary composition comprising a pharmaceutical or veterinary carrier or diluent and, as an active principle, a compound as defined in claim 1 or 6.

10. A method of modulating p-gp mediated MDR in the treatment of tumors, which method comprises administering to a patient harboring a tumor which expresses P-gp mediated MDR a therapeutically effective amount of a compound as defined in claim 1 or claim 8.

11. A method of potentiating the cytotoxicity of an agent which is cytotoxic to a tumor cell, which method comprises administering to a patient in need thereof a therapeutically effective amount of a compound as defined in claim 1 or claim 8.

12. A method according to claim 11 wherein the said agent is selected from the group consisting of anthracycline antibiotics, vinca alkaloids, mitoxantrone, actinomycin D, taxanes, epipodophyllotoxins and plicamycin.

13. A method according to claim 12 wherein the said agent is an anthracycline antibiotic.

14. A method according to claim 12 wherein the said agent is selected from the group consisting of doxorubicin, daunorubicin, vincristine, vinblastine, taxol, etoposide and plicamycin.

15. A method according to claim 11 which comprises administering the said compound to the patient whilst the tumor is exposed to the said agent.

16. A method of treating a disease in which the responsible pathogen exhibits multi-drug resistance, which method comprises administering to a patient in need thereof a therapeutically effective amount of a compound as defined in claim 1 or claim 8.

17. A method according to claim 16 wherein the said pathogen exhibits P-gp mediated multi-drug resistance.

18. A method according to claim 16 wherein the disease is selected from the group consisting of multi-drug resistant forms of malaria, tuberculosis, leishmaniasis and amoebic dysentery.

19. A method according to claim 16 which comprises administering, separately, simultaneously or sequentially, the said compound and a drug to which the said pathogen exhibits multi-drug resistance.

20. A method of enhancing a characteristic of a therapeutic agent, the said characteristic being selected from the group consisting of penetration, absorption, distribution, metabolism and elimination, which method comprises administering to a patient in need thereof, separately, simultaneously or sequentially, a therapeutically effective amount of a compound as defined in claim 1 or claim 8 and the said therapeutic agent.

21. A method according to claim 20 wherein the said characteristic is selected from the group consisting of penetration into the central nervous system and oral absorption.

22. A process for producing a compound which is an anthranilic acid derivative of formula (I):

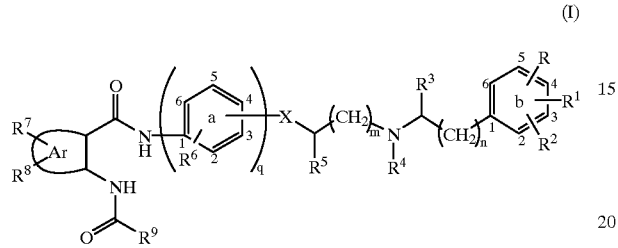

(I)

wherein
each of R, $R^1$ and $R^2$, which are the same or different, is H, $C_1$–$C_6$ alkyl, OH, $C_1$–$C_6$ alkoxy, halogen, nitro, or $N(R^{10}R^{11})$ wherein each of $R^{10}$ and $R^{11}$, which are the same or different, is H or $C_1$–$C_6$ alkyl; or $R^1$ and $R^2$, being attached to adjacent positions of ring b, together form a methylenedioxy or ethylenedioxy group;

$R^3$ is H or $C_1$–$C_6$ alkyl $R^4$ is $C_1$–$C_6$ alkyl or $R^4$ represents —$CH_2$— or —$CH_2CH_2$— which is attached either (i) to position 2 of ring b to complete a saturated 5- or 6-membered nitrogen-containing ring fused to ring b, or (ii) to the position in ring a adjacent to that to which X, being a single bond, is linked, thereby completing a saturated 5- or 6-membered nitrogen-containing ring fused to ring a;

$R^5$ is H, OH or $C_1$–$C_6$ alkyl;

X is a direct bond, O, S, —S—$(CH_2)p$— or —O—$(CH_2)p$— wherein p is an integer of 1 to 6;

$R^6$ is H, $C_1$–$C_6$ alkyl or $C_1$–$C_6$ alkoxy;

q is 0 or 1;

Ar is an unsaturated carbocyclic or heterocyclic group;

each of $R^7$ and $R^8$, which are the same or different, is H, $C_1$–$C_6$ alkyl which is unsubstituted or substituted, $C_1$–$C_6$ alkoxy, hydroxy, halogen, phenyl, —NHOH, nitro, a group $N(R^{10}R^{11})$ as defined above or a group $SR^{12}$ wherein $R^{12}$ is H or $C_1$–$C_6$ alkyl; or $R^7$ and $R^8$, when situated on adjacent carbon atoms, form together with the carbon atoms to which they are attached a benzene ring or a methylenedioxy substituent;

$R^9$ is phenyl or an unsaturated heterocyclic group, each of which is unsubstituted or substituted by $C_1$–$C_6$ alkyl, OH, $C_1$–$C_6$ alkoxy, halogen, $C_3$–$C_6$ cycloalkyl, phenyl, benzyl, trifluoromethyl, nitro, acetyl, benzoyl or $N(R^{10}R^{11})$ as defined above, or two substituents on adjacent ring positions of the said phenyl or heterocyclic group together complete a saturated or unsaturated 6-membered ring or form a methylenedioxy group;

n is 0 or 1; and m is 0 or an integer of 1 to 6;

or a pharmaceutically acceptable salt thereof;

which process comprises:
(a) treating an aminobenzamide of formula (VI)

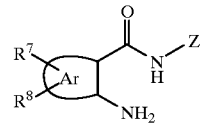

(VI)

wherein Ar, $R^7$ and $R^8$ are as defined above and Z is the moiety:

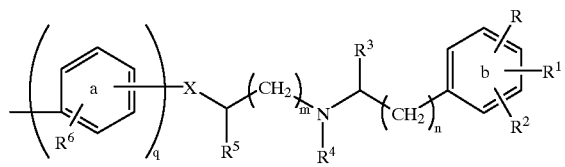

wherein m, n, q, R, $R^1$ to $R^6$ and X are as defined above, with a carboxylic acid of formula $R^9$—COOH, or an activated derivative thereof, wherein $R^9$ is as defined above; or (b) treating a compound of formula XII:

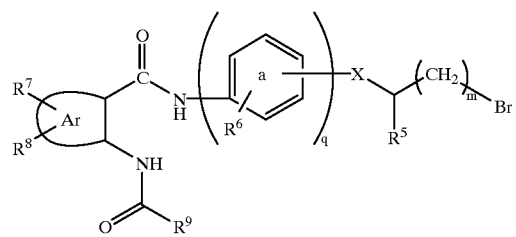

(XII)

wherein Ar, $R^5$, $R^6$ to $R^9$, X, q and m are as defined above, with an amine of formula XX:

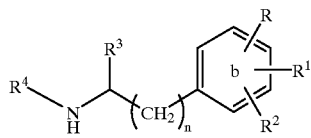

(XX)

wherein R, $R^1$ to $R^4$ and n are as defined above; and, if desired, removing any optional protecting groups present, and/or if desired, converting one compound of formula (I) into another compound of formula (I) and/or, if desired, converting one compound of formula (I) into a pharmaceutically acceptable salt thereof and/or, if desired, converting a salt into a free compound of formula (I).

23. A process for producing a compound which is an anthranilic acid of formula (Ia):

(Ia)

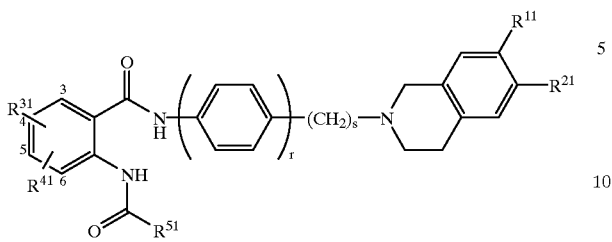

wherein $R^{11}$ and $R^{21}$, which may be the same or different, are each hydrogen or methoxy; R31 and R41, which may be the same or different, are each independently selected from H, $CH_3$ $CF_3$, F, Cl, Br, $NH_2$, $NO_2$, NHOH, methoxy, hydroxy and phenyl; or $R^{31}$ and $R^{41}$, when situated on adjacent carbon atoms, form together with the carbon atoms to which they are attached a benzene ring or a methylenedioxy substituent; $R^{51}$ is 2-furanyl, 3-furanyl, 2-thiophene, 3-thiophene, 2-indolyl or 2-benzofuranyl or a ring of one of the following formulae (II'), (III') or (IV'):

(II')

(III')

(IV')

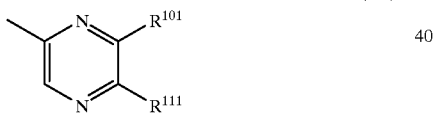

wherein $R^{61}$ and $R^{71}$, which may be the same or different, are selected from hydrogen, $C_1$–$C_6$ alkyl which is linear or branched, $C_3$–$C_6$ cycloalkyl, phenyl, benzyl, trifluoromethyl, F, Cl, Br, $OR^{12}$, $NO_2$, dimethylamino, diethylamino, acetyl and benzoyl, or $R^{61}$ and $R^{71}$ when situated on adjacent carbon atoms, form together with the carbon atoms to which they are attached a benzene ring or a methylenedioxy substituent;

$R^{81}$ and $R^{91}$, which may be the same or different, are each hydrogen, methyl or methoxy, or $R^{81}$ and $R^{91}$, when situated on adjacent carbon atoms, form together with the pyridine to which they are attached a quinoline or 5,6,7,8-tetrahydroquinoline ring system;

$R^{101}$ and $R^{111}$, which may be the same or different, are each hydrogen, methyl or propionyl; or $R^{101}$ and $R^{111}$, when situated on adjacent carbon atoms, form together with the carbon atoms to which they are attached a benzene ring, $R^{121}$ is H, $C_1$–$C_6$ alkyl, $C_3$–$C_6$ cycloalkyl, phenyl, benzyl or acetyl;

r is 0 or 1, and s is 1, 2 or 3; or a pharmaceutically acceptable salt thereof; which process comprises:

(a) treating an aminobenzamide of formula VIII'

(VIII')

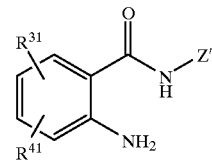

wherein $R^{31}$ and $R^{41}$ are as defined above and are optionally protected, and Z' is the moiety

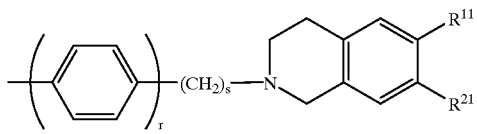

wherein r, s, $R^{11}$ and $R^{21}$ are as defined above, with a carboxylic acid of formula $R^{51}$—COOH or an activated derivative thereof, wherein $R^{51}$ is as defined above; or (b) treating a compound of formula XII':

(XII')

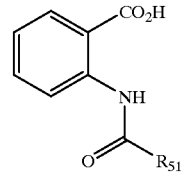

wherein $R^{51}$ is as defined above, with an amine of formula IX':

(IX')

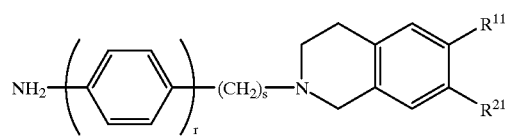

wherein r, s, $R^{11}$ and $R^{21}$ are as defined above; or (c) treating an azalactone of formula XIII':

(XIII')

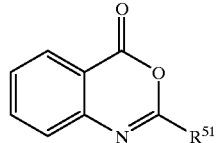

wherein $R^{51}$ is as defined above, with an amine of formula (IX')

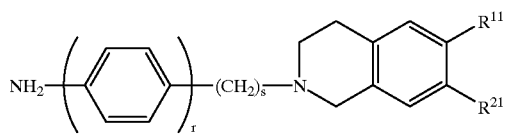

(IX')

wherein r, s, $R^{11}$ and $R^{21}$ are as defined above; and, if desired, removing any optional protecting groups present, and/or if desired, converting one compound of formula (Ia) into another compound of formula (Ia) and/or, if desired, converting a compound of formula (Ia) into a pharmaceutically acceptable salt thereof and/or, if desired, converting a salt into a free compound of formula (Ia).

* * * * *

UNITED STATES PATENT AND TRADEMARK OFFICE
CERTIFICATE OF CORRECTION

PATENT NO. : 6,218,393 B1
DATED : April 17, 2001
INVENTOR(S) : Ryder et al.

It is certified that error appears in the above-identified patent and that said Letters Patent is hereby corrected as shown below:

<u>Title page,</u>
Item [30], insert: -- Foreign Application Priority Data
        Aug. 19, 1997 (GB)    9717576
        Oct. 18, 1996          PCT/GB96/02552 --

Signed and Sealed this

Fifteenth Day of October, 2002

*Attest:*

*Attesting Officer*

JAMES E. ROGAN
*Director of the United States Patent and Trademark Office*